US011261495B2

(12) United States Patent
Van Ooijen et al.

(10) Patent No.: US 11,261,495 B2
(45) Date of Patent: Mar. 1, 2022

(54) ASSESSMENT OF THE PI3K CELLULAR SIGNALING PATHWAY ACTIVITY USING MATHEMATICAL MODELLING OF TARGET GENE EXPRESSION

(71) Applicant: KONINKLIJKE PHILIPS N.V., Eindhoven (NL)

(72) Inventors: Jan Hendrik Van Ooijen, Eindhoven (NL); Wilhelmus Franciscus Johannes Verhaegh, Eindhoven (NL); Anja Van De Stolpe, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/023,820

(22) PCT Filed: Dec. 30, 2014

(86) PCT No.: PCT/EP2014/079468
§ 371 (c)(1),
(2) Date: Mar. 22, 2016

(87) PCT Pub. No.: WO2015/101635
PCT Pub. Date: Jul. 9, 2015

(65) Prior Publication Data

US 2016/0298196 A1 Oct. 13, 2016

(30) Foreign Application Priority Data

Jan. 3, 2014 (EP) .................................... 14150145

(51) Int. Cl.
*G01N 33/48* (2006.01)
*C12Q 1/6886* (2018.01)
*G16B 25/00* (2019.01)
*G16C 99/00* (2019.01)
*G16B 25/10* (2019.01)

(52) U.S. Cl.
CPC ........... *C12Q 1/6886* (2013.01); *G16B 25/00* (2019.02); *G16B 25/10* (2019.02); *G16C 99/00* (2019.02); *C12Q 2600/106* (2013.01); *C12Q 2600/158* (2013.01)

(58) Field of Classification Search
None
See application file for complete search history.

(56) References Cited

U.S. PATENT DOCUMENTS

2011/0265197 A1* 10/2011 Depinho ........... A01K 67/0276 800/14
2013/0059859 A1 3/2013 Punnoose
2014/0156200 A1 6/2014 Verhaegh

FOREIGN PATENT DOCUMENTS

WO 2014102668 A2 7/2014
WO 2014174003 A1 10/2014

OTHER PUBLICATIONS

Kaarbo, Mari, et al, "PI3K-AKTmTOR pathway is dominant over androgen receptor signaling in prostate cancer cells", Cellular Oncology, vol. 32, No. 1-2, 2010, pp. 11 to 27.

Vogel, Charles L. et al, "Efficacy and Safety of Trastuzumab as a Single Agent in First-Line Treatment of HER2-Overexpressing Metastatic Breast Cancer", Journal of Clinical Oncology, vol. 20, No. 3, Feb. 2002, pp. 719 to 726.

Laprise, Patrick et al., "Phosphatidylinositol 3-kinase controls human intestinal epithelial cell differentiation by promoting adherens junction assembly and p38 MAPK activation", Journal of Biological 10 Chemistry, vol. 277, No. 10, Mar. 2002, pp. 8226 to 8234.

Philips, Wayne A. et al, "Increased levels of phosphatidylinositol 3-kinase activity in colorectal tumors", Cancer, vol. 83, No. 1, Jul. 1998, pp. 41 to 47.

Smith, Graham R. et al "Modelling the Response of FOXO Transcription Factors to Multiple Post-Translational Modifications made by Aging-Related Signalling Pathways", Plos One, vol. 5, No. 6, Jun. 2010.

Rogers, Simon et al. "Bayesian Model-Based Inference of Transcription Factor Activity", BMC Bioinformatics, Biomed Central, vol. 8, No. Suppl. 2, 2007.

Greer, Eric L. et al "FOXO Transcription Factors at the Interface Between Longevity and Tumor Suppression", oncogene. vol. 24, No. 50, 2005, pp. 7410-7425.

Ochs, Michael F. et al "Detection of Treatment-Induced Changes in Signalling Pathways in Gastrointestinal Stromal Tumors using Transcriptomic Data", Cancer Research, vol. 69, No. 23, 2009, pp. 9125-9132.

Su, Junjie et al "Accurate and Reliable Cancer Classification bsed on Probabilistic Inference of Pathway Activity", Plos One, vol. 4, No. 12, 2009.

(Continued)

*Primary Examiner* — Anna Skibinsky

(57) ABSTRACT

The present invention relates to a method comprising inferring activity of a PI3K cellular signaling pathway in a tissue and/or cells and/or a body fluid of a medical subject based at least on expression levels of one or more target gene(s) of the PI3K cellular signaling pathway measured in an extracted sample of the tissue and/or the cells and/or the body fluid of the medical subject. The present invention further relates to an apparatus comprising a digital processor configured to perform such a method, a non-transitory storage medium storing instructions that are executable by a digital processing device to perform such a method, and a computer program comprising program code means for causing a digital processing device to perform such a method.

13 Claims, 10 Drawing Sheets

Specification includes a Sequence Listing.

(56) References Cited

OTHER PUBLICATIONS

Engleman, Jeffrey A. "Targeting P13K Signalling in Cancer Opportunities, Challengesand Limitations", Nature Reviews, Cancer, vol. 9, No. 8, 2009.
Van De Stolpe, Anja et al "RNA Based Approaches to Profile Oncogenic Pathways from Low Quantity Samples to Drive Precision Oncology Strategies", Methods, Frontiers in Genetics, vol. 11, Feb. 2021.
Verhaegh, Wim et al "Knowledge-based Computational Models", Oncotarget, vol. 5, No. 14, 2014.
Verhaegh, Wim et al, "Selection of Personalized Patient Therapy through the use of Knowledge-Based Computational Models that Identify Tumor-Driving Signal Transduction Pathways", Cancer Research, Integrated Systems and Technologies: Mathematical Oncology, vol. 74, No. 11, Jun. 2014.
"Measuring Functional Activity of Signal Transduction Pathways from target Gene mRNA Levels", Philips Molecular Pathway DX, Oct. 2020.
Van Ooijen, Henk et al "Assessment of Functional Phosphatidylinositol 3-Kinase Pathway Activity in Cancer Tissue using Forkhead Box-0 Target Gene Expression in a Knowledge-Based Computational model", The Maerican Journal of Pathology, vol. 188, No. 9, Sep. 2018.

* cited by examiner

ASSESSMENT OF THE PI3K CELLULAR SIGNALING PATHWAY ACTIVITY USING MATHEMATICAL MODELLING OF TARGET GENE EXPRESSION

FIELD OF THE INVENTION

The present invention generally relates to the field of bioinformatics, genomic processing, proteomic processing, and related arts. More particularly, the present invention relates to a method comprising inferring activity of a PI3K cellular signaling pathway in a tissue and/or cells and/or a body fluid of a medical subject based at least on expression levels of one or more target gene(s) of the PI3K cellular signaling pathway measured in an extracted sample of the tissue and/or the cells and/or the body fluid of the medical subject. The present invention further relates to an apparatus comprising a digital processor configured to perform such a method, a non-transitory storage medium storing instructions that are executable by a digital processing device to perform such a method, and a computer program comprising program code means for causing a digital processing device to perform such a method.

BACKGROUND OF THE INVENTION

Genomic and proteomic analyses have substantial realized and potential promise for clinical application in medical fields such as oncology, where various cancers are known to be associated with specific combinations of genomic mutations/variations and/or high or low expression levels for specific genes, which play a role in growth and evolution of cancer, e.g., cell proliferation and metastasis.

For example, screening for an over-expression of the HER2 receptor on the membrane of cells in breast cancer samples is currently the standard test performed for identifying patients that are eligible to HER2 inhibitors such as Trastuzumab. Over-expression of the ERBB2 gene, which results in an over-expression of the HER2 receptor on the cell membrane, occurs in approximately 25% to 30% of all breast cancers and is associated with an increased disease recurrence and a poor prognosis. However, the expression of the HER2 receptor is by no means a conclusive indictor for driving tumor growth as the signaling initiated by the HER2 receptor can for instance be dampened by the downstream cellular signaling pathway. This also seems to be reflected in the initial response rate of 26% in HER2-positive breast cancer patients treated with Trastuzumab (Charles L. Vogel, et al., "Efficacy and Safety of Trastuzumab as a Single Agent in First-Line Treatment of HER2-Overexpressing Metastatic Breast Cancer", Journal of Clinical Oncology, Vol. 20, No. 3, February 2002, pages 719 to 726). Besides that, the cellular signaling pathway downstream of the HER2 receptor can also be activated by mutations/over-expression in proteins downstream of the HER2 receptor, resulting in (a) relatively aggressive tumor type(s) that will not be detected by measuring HER2 expression levels. It is therefore desirable to be able to improve the possibilities of characterizing patients that have a tumor, e.g., breast cancer, which is at least partially driven by effects occurring in the cellular signaling pathway downstream of the HER2 receptor.

SUMMARY OF THE INVENTION

The present invention provides new and improved methods and apparatuses as disclosed herein.

In accordance with a main aspect of the present invention, the above problem is solved by a method for inferring activity of a PI3K cellular signaling pathway using mathematical modelling of target gene expressions, namely a method comprising:

inferring activity of a PI3K cellular signaling pathway in a tissue and/or cells and/or a body fluid of a medical subject based at least on expression levels of one or more target gene(s) of the PI3K cellular signaling pathway measured in an extracted sample of the tissue and/or the cells and/or the body fluid of the medical subject, wherein the inferring comprises:

determining a level of a FOXO transcription factor (TF) element in the extracted sample of the tissue and/or the cells and/or the body fluid of the medical subject, the FOXO TF element controlling transcription of the one or more target gene(s) of the PI3K cellular signaling pathway, the determining being based at least in part on evaluating a mathematical model relating expression levels of the one or more target gene(s) of the PI3K cellular signaling pathway to the level of the FOXO TF element;

inferring the activity of the PI3K cellular signaling pathway in the tissue and/or the cells and/or the body fluid of the medical subject based on the determined level of the FOXO TF element in the extracted sample of the tissue and/or the cells and/or the body fluid of the medical subject, wherein the inferring is performed by a digital processing device using the mathematical model.

The present invention is based on the realization of the inventors that a suitable way of identifying effects occurring in the cellular signaling pathway downstream of the HER2 receptor, herein, the PI3K cellular signaling pathway, can be based on a measurement of the signaling output of the cellular signaling pathway, which is—amongst others—the transcription of the target genes by a transcription factor (TF), herein, the FOXO TF element, controlled by the cellular signaling pathway. The PI3K cellular signaling pathway targeted herein is not only linked to breast cancer, but is known to be inappropriately activated in many types of cancer (Jeffrey A. Engelman, "Targeting PI3K signalling in cancer: opportunities, challenges and limitations", Nature Reviews Cancer, No. 9, August 2009, pages 550 to 562). It is thought to be regulated by the RTK receptor family, which also includes the HER-family. Subsequently, the PI3K cellular signaling pathway passes on its received signal(s) via a multitude of processes, of which the two main branches are the activation of the mTOR complexes and the inactivation of a family of transcription factors often referred to as FOXO (cf. the figure showing the PI3K cellular signaling pathway in the above article from Jeffrey A. Engelman). The present invention concentrates on the PI3K cellular signaling pathway and the FOXO TF family, the activity of which is substantially negatively correlated with the activity of the PI3K cellular signaling pathway, i.e., activity of FOXO is substantially correlated with inactivity of the PI3K cellular signaling pathway, whereas inactivity of FOXO is substantially correlated with activity of the PI3K cellular signaling pathway. The present invention makes it possible to determine the activity of the PI3K cellular signaling pathway in a tissue and/or cells and/or a body fluid of a medical subject by (i) determining a level of a FOXO TF element in the extracted sample of the tissue and/or the cells and/or the body fluid of the medical subject, wherein the determining is based at least in part on evaluating a mathematical model relating expression levels of one or more target gene(s) of the PI3K cellular signaling pathway, the transcription of which is controlled by the FOXO TF element, to the level of the FOXO TF element, and by (ii) inferring the activity of the PI3K cellular signaling pathway in the tissue and/or the cells and/or the body fluid of the medical subject based on the determined level of the FOXO TF element in the extracted sample of the tissue and/or the cells and/or the body fluid of the medical subject. This preferably allows improving the possibilities of characterizing patients that have a tumor, e.g., breast cancer, which is at least partially driven by a deregulated PI3K cellular signaling pathway, and that are therefore likely to respond to inhibitors of the PI3K cellular signaling pathway.

Herein, a FOXO transcription factor (TF) element is defined to be a protein complex containing at least one of the FOXO TF family members, i.e., FOXO1, FOXO3A, FOXO4 and FOXO6, which is capable of binding to specific DNA sequences, thereby controlling transcription of target genes.

The mathematical model may be a probabilistic model, preferably a Bayesian network model, based at least in part on conditional probabilities relating the FOXO TF element and expression levels of the one or more target gene(s) of the PI3K cellular signaling pathway measured in the extracted sample of the tissue and/or the cells and/or the body fluid of the medical subject, or the mathematical model may be based at least in part on one or more linear combination(s) of expression levels of the one or more target gene(s) of the PI3K cellular signaling pathway measured in the extracted sample of the tissue and/or the cells and/or the body fluid of the medical subject. In particular, the inferring of the activity of the PI3K cellular signaling pathway may be performed as disclosed in the published international patent application WO 2013/011479 A2 ("Assessment of cellular signaling pathway activity using probabilistic modeling of target gene expression") or as described in the published international patent application WO 2014/102668 A2 ("Assessment of cellular signaling pathway activity using linear combination (s) of target gene expressions"), the contents of which are herewith incorporated in their entirety.

The medical subject may be a human or an animal. Moreover, the tissue and/or the cells and/or the body fluid of the medical subject may be from a cell line and/or a tissue culture derived from a medical subject and, if applicable, cultivated in vitro in the lab (e.g., for regenerative purposes). Furthermore, the "target gene(s)" may be "direct target genes" and/or "indirect target genes" (as described herein).

Particularly suitable target genes are described in the following text passages as well as the examples below (see, e.g., Tables 1 to 3).

Thus, according to a preferred embodiment the target gene(s) is/are selected from the group consisting of the target genes listed in Table 3.

Particularly preferred is a method wherein the inferring comprises:

inferring the activity of the PI3K cellular signaling pathway in the tissue and/or the cells and/or the body fluid of the medical subject based at least on expression levels of one or more, preferably at least three, target gene(s) of the PI3K cellular signaling pathway measured in the extracted sample of the tissue and/or the cells and/or the body fluid of the medical subject selected from the group consisting of: AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2 and TNFSF10.

Further preferred is a method, wherein the inferring is further based on expression levels of at least one target gene of the PI3K cellular signaling pathway measured in the extracted sample of the tissue and/or the cells and/or the body fluid of the medical subject selected from the group consisting of: ATP8A1, C10orf10, CBLB, DDB1, DYRK2, ERBB3, EREG, EXT1, FGFR2, IGF1R, IGFBP1, IGFBP3, LGMN, PPM1D, SEMA3C, SEPP1, SESN1, SLC5A3, SMAD4 and TLE4.

Further preferred is a method, wherein the inferring is further based on expression levels of at least one target gene of the PI3K cellular signaling pathway measured in the extracted sample of the tissue and/or the cells and/or the body fluid of the medical subject selected from the group consisting of: ATG14, BIRC5, IGFBP1, KLF2, KLF4, MYOD1, PDK4, RAG1, RAG2, SESN1, SIRT1, STK11 and TXNIP.

If the inferring is further based both on expression levels of at least one target gene selected from the group specified in the preceding paragraph and on expression levels of at least one target gene selected from the group specified in the paragraph preceding the preceding paragraph, the target genes IGFBP1 and SESN1, which are mentioned above with respect to both groups, may only be contained in one of the groups.

Another aspect of the present invention relates to a method (as described herein), further comprising:

determining whether the PI3K cellular signaling pathway is operating abnormally in the tissue and/or the cells and/or the body fluid of the medical subject based on the inferred activity of the PI3K cellular signaling pathway in the tissue and/or the cells and/or the body fluid of the medical subject.

The present invention also relates to a method (as described herein) further comprising:

recommending prescribing a drug for the medical subject that corrects for abnormal operation of the PI3K cellular signaling pathway, wherein the recommending is performed only if the PI3K cellular signaling pathway is determined to be operating abnormally in the tissue and/or the cells and/or the body fluid of the medical subject based on the inferred activity of the PI3K cellular signaling pathway.

The present invention also relates to a method (as described herein), wherein the inferring comprises:

inferring the activity of the PI3K cellular signaling pathway in the tissue and/or the cells and/or the body fluid of the medical subject based at least on expression levels of two, three or more target genes of a set of target genes of the PI3K cellular signaling pathway measured in the extracted sample of the tissue and/or the cells and/or the body fluid of the medical subject.

Preferably, the set of target genes of the PI3K cellular signaling pathway includes at least nine, preferably all target genes selected from the group consisting of: AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2 and TNFSF10.

A method, wherein the set of target genes of the PI3K cellular signaling pathway further includes at least one target gene selected from the group consisting of: ATP8A1, C10orf10, CBLB, DDB1, DYRK2, ERBB3, EREG, EXT1, FGFR2, IGF1R, IGFBP1, IGFBP3, LGMN, PPM1D, SEMA3C, SEPP1, SESN1, SLC5A3, SMAD4 and TLE4, is particularly preferred.

A method, wherein the set of target genes of the PI3K cellular signaling pathway further includes at least one target gene selected from the group consisting of: ATG14, BIRC5, IGFBP1, KLF2, KLF4, MYOD1, PDK4, RAG1, RAG2, SESN1, SIRT1, STK11 and TXNIP, is also particularly preferred.

If the set of target genes further includes both at least one target gene selected from the group specified in the preceding paragraph and at least one target gene selected from the group specified in the paragraph preceding the preceding paragraph, the target genes IGFBP1 and SESN1, which are mentioned above with respect to both groups, may only be contained in one of the groups.

The sample(s) to be used in accordance with the present invention can be, e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, preferably via a biopsy procedure or other sample extraction procedure. The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, the body fluid of which a sample is extracted may be urine, gastrointestinal contents, or an extravasate. The term "extracted sample", as used herein, also encompasses the case where tissue and/or cells and/or body fluid of the subject have been taken from the subject and, e.g., have been put on a microscope slide, and where for performing the claimed method a portion of this sample is extracted, e.g., by means of Laser Capture Microdissection (LCM), or by scraping off the cells of interest from the slide, or by fluorescence-activated cell sorting techniques.

In accordance with another disclosed aspect, an apparatus comprises a digital processor configured to perform a method according to the present invention as described herein.

In accordance with another disclosed aspect, a non-transitory storage medium stores instructions that are executable by a digital processing device to perform a method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, a computer program comprises program code means for causing a digital processing device to perform a method according to the present invention as described herein. The digital processing device may be a handheld device (e.g., a personal data assistant or smartphone), a notebook computer, a desktop computer, a tablet computer or device, a remote network server, or so forth.

The present invention as described herein can, e.g., also advantageously be used in connection with:

diagnosis based on the inferred activity of the PI3K cellular signaling pathway in the tissue and/or the cells and/or the body fluid of the medical subject;

prognosis based on the inferred activity of the PI3K cellular signaling pathway in the tissue and/or the cells and/or the body fluid of the medical subject;

drug prescription based on the inferred activity of the PI3K cellular signaling pathway in the tissue and/or the cells and/or the body fluid of the medical subject;

prediction of drug efficacy based on the inferred activity of the PI3K cellular signaling pathway in the tissue and/or the cells and/or the body fluid of the medical subject;

prediction of adverse effects based on the inferred activity of the PI3K cellular signaling pathway in the tissue and/or the cells and/or the body fluid of the medical subject;

monitoring of drug efficacy;

drug development;

assay development;

pathway research;

cancer staging;

enrollment of the medical subject in a clinical trial based on the inferred activity of the PI3K cellular signaling pathway in the tissue and/or the cells and/or the body fluid of the medical subject;

selection of subsequent test to be performed; and selection of companion diagnostics tests.

Further advantages will be apparent to those of ordinary skill in the art upon reading and understanding the attached figures, the following description and, in particular, upon reading the detailed examples provided herein below.

It shall be understood that the method of claim 1, the apparatus of claim 13, the non-transitory storage medium of claim 15, and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
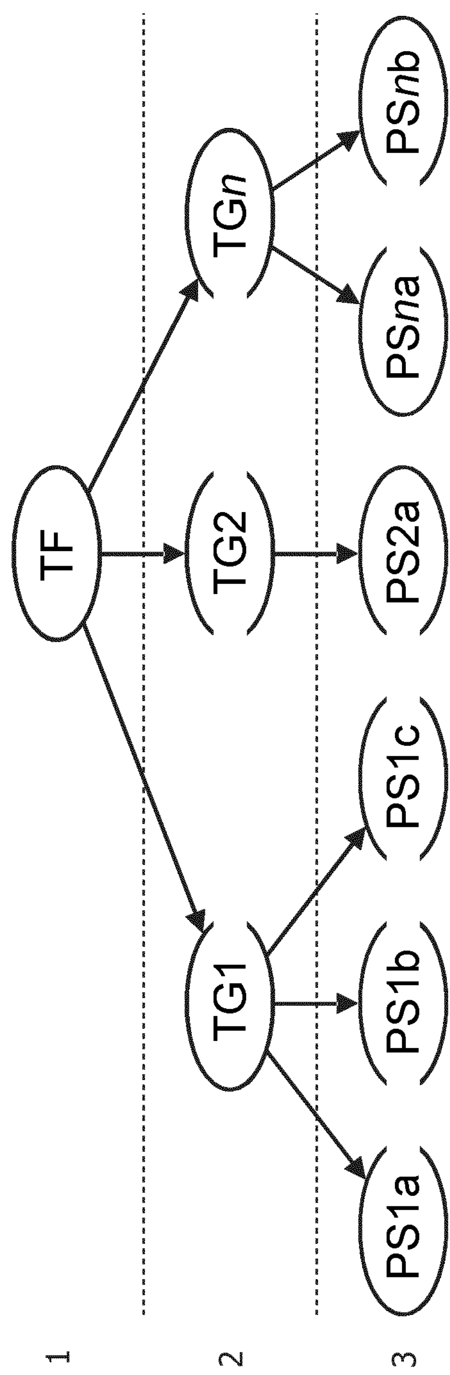
FIG. 1 shows schematically and exemplarily a mathematical model, herein, a Bayesian network model, used to model the transcriptional program of the PI3K cellular signaling pathway.

The following examples merely illustrate particularly preferred methods and selected aspects in connection therewith. The teaching provided therein may be used for constructing several tests and/or kits, e.g., to detect, predict and/or diagnose the abnormal activity of one or more cellular signaling pathways. Furthermore, upon using methods as described herein drug prescription can advantageously be guided, drug prediction and monitoring of drug efficacy (and/or adverse effects) can be made, drug resistance can be predicted and monitored, e.g., to select subsequent test(s) to be performed (like a companion diagnostic test). The following examples are not to be construed as limiting the scope of the present invention.

Example 1

Mathematical Model Construction

As described in detail in the published international patent application WO 2013/011479 A2 ("Assessment of cellular signaling pathway activity using probabilistic modeling of target gene expression"), by constructing a probabilistic model, e.g., a Bayesian network model, and incorporating conditional probabilistic relationships between expression levels of one or more target gene(s) of a cellular signaling pathway, herein, the PI3K cellular signaling pathway, and the level of a transcription factor (TF) element, herein, the FOXO TF element, the TF element controlling transcription of the one or more target gene(s) of the cellular signaling pathway, such a model may be used to determine the activity of the cellular signaling pathway with a high degree of accuracy. Moreover, the probabilistic model can be readily updated to incorporate additional knowledge obtained by later clinical studies, by adjusting the conditional probabilities and/or adding new nodes to the model to represent additional information sources. In this way, the probabilistic model can be updated as appropriate to embody the most recent medical knowledge.

In another easy to comprehend and interpret approach described in detail in the published international patent application WO 2014/102668 A2 ("Assessment of cellular signaling pathway activity using linear combination(s) of target gene expressions"), the activity of a cellular signaling pathway, herein, the PI3K cellular signaling pathway, may be determined by constructing and evaluating a linear or (pseudo-) linear model incorporating relationships between expression levels of one or more target gene(s) of the cellular signaling pathway and the level of a transcription factor (TF) element, herein, the FOXO TF element, the TF element controlling transcription of the one or more target gene(s) of the cellular signaling pathway, the model being based at least in part on one or more linear combination(s) of expression levels of the one or more target gene(s).

In both approaches, the expression levels of the one or more target gene(s) may preferably be measurements of the level of mRNA, which can be the result of, e.g., (RT)-PCR and microarray techniques using probes associated with the target gene(s) mRNA sequences, and of RNA-sequencing. In another embodiment the expression levels of the one or more target gene(s) can be measured by protein levels, e.g., the concentrations of the proteins encoded by the target genes.

The aforementioned expression levels may optionally be converted in many ways that might or might not suit the application better. For example, four different transformations of the expression levels, e.g., microarray-based mRNA levels, may be:

- "continuous data", i.e., expression levels as obtained after preprocessing of microarrays using well known algorithms such as MAS5.0 and fRMA,
- "z-score", i.e., continuous expression levels scaled such that the average across all samples is 0 and the standard deviation is 1,
- "discrete", i.e., every expression above a certain threshold is set to 1 and below it to 0 (e.g., the threshold for a probeset may be chosen as the median of its value in a set of a number of positive and the same number of negative clinical samples),
- "fuzzy", i.e., the continuous expression levels are converted to values between 0 and 1 using a sigmoid function of the following format: 1/(1+exp((thr−expr)/se)), with expr being the continuous expression levels, thr being the threshold as mentioned before and se being a softening parameter influencing the difference between 0 and 1.

One of the simplest linear models that can be constructed is a model having a node representing the transcription factor (TF) element, herein, the FOXO TF element, in a first layer and weighted nodes representing direct measurements of the target gene(s) expression intensity levels, e.g., by one probeset that is particularly highly correlated with the particular target gene, e.g., in microarray or (q)PCR experiments, in a second layer. The weights can be based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is particularly simple. A specific way of selecting the one expression level that is used for a particular target gene is to use the expression level from the probeset that is able to separate active and passive samples of a training data set the best. One method to determine this probeset is to perform a statistical test, e.g., the t-test, and select the probeset with the lowest p-value. The training data set's expression levels of the probe with the lowest p-value is by definition the probe with the least likely probability that the expression levels of the (known) active and passive samples overlap. Another selection method is based on odds-ratios. In such a model, one or more expression level(s) are provided for each of the one or more target gene(s) and the one or more linear combination(s) comprise a linear combination including for each of the one or more target gene(s) a weighted term, each weighted term being based on only one expression level of the one or more expression level(s) provided for the respective target gene. If the only one expression level is chosen per target gene as described above, the model may be called a "most discriminant probesets" model.

In an alternative to the "most discriminant probesets" model, it is possible, in the case where possibly multiple expression levels are measured per target gene, to make use of all the expression levels that are provided per target gene. In such a model, one or more expression level(s) are provided for each of the one or more target gene(s) and the one or more linear combination(s) comprise a linear combination of all expression levels of the one or more expression level(s) provided for the one or more target gene(s). In other words, for each of the one or more target gene(s), each of the one or more expression level(s) provided for the respective target gene may be weighted in the linear combination by its own (individual) weight. This variant may be called an "all probesets" model. It has an advantage of being relatively simple while making use of all the provided expression levels.

Both models as described above have in common that they are what may be regarded as "single-layer" models, in which the level of the TF element is calculated based on a linear combination of expression levels.

After the level of the TF element, herein, the FOXO TF element, has been determined by evaluating the respective model, the determined TF element level can be thresholded in order to infer the activity of the cellular signaling pathway, herein, the PI3K cellular signaling pathway. A method to calculate such an appropriate threshold is by comparing the determined TF element level wlc of training samples known to have a passive pathway and training samples with an active pathway. A method that does so and also takes into account the variance in these groups is given by using a threshold $$thr = \frac{\sigma_{wlc_{pas}}\mu_{wlc_{act}} + \sigma_{wlc_{act}}\mu_{wlc_{pas}}}{\sigma_{wlc_{pas}} + \sigma_{wlc_{act}}} \quad (1)$$

where σ and μ are the standard deviation and the mean of the training samples. In case only a small number of samples are available in the active and/or passive training samples, a pseudocount may be added to the calculated variances based on the average of the variances of the two groups:

$$\tilde{v} = \frac{v_{wlc_{act}} + v_{wlc_{pas}}}{2} \quad (2)$$

$$\tilde{v}_{wlc_{act}} = \frac{x\tilde{v} + (n_{act} - 1)v_{wlc_{act}}}{x + n_{act} - 1}$$

$$\tilde{v}_{wlc_{pas}} = \frac{x\tilde{v} + (n_{pas} - 1)v_{wlc_{pas}}}{x + n_{pas} - 1}$$

where v is the variance of the groups and x a positive pseudocount. The standard deviation σ can next be obtained by taking the square root of the variance v.

The threshold can be subtracted from the determined level of the TF element wlc for ease of interpretation, resulting in the cellular signaling pathway's activity score, such that negative values corresponds to a passive cellular signaling pathway and positive values to an active cellular signaling pathway.

As an alternative to the above-described "single-layer" models, a "two-layer" model may also be used in an example. In such a model, a summary value is calculated for every target gene using a linear combination based on the measured intensities of its associated probesets ("first (bottom) layer"). The calculated summary value is subsequently combined with the summary values of the other target genes of the cellular signaling pathway using a further linear combination ("second (upper) layer"). Again, the weights can be either learned from a training data set or based on expert knowledge or a combination thereof. Phrased differently, in the "two-layer" model, one or more expression level(s) are provided for each of the one or more target gene(s) and the one or more linear combination(s) comprise for each of the one or more target gene(s) a first linear combination of all expression levels of the one or more expression level(s) provided for the respective target gene ("first (bottom) layer"). The model is further based at least in part on a further linear combination including for each of the one or more target gene(s) a weighted term, each weighted term being based on the first linear combination for the respective target gene ("second (upper) layer"

The calculation of the summary values can, in a preferred version of the "two-layer" model, include defining a threshold for each target gene using the training data and subtracting the threshold from the calculated linear combination, yielding the target gene summary. Here the threshold may be chosen such that a negative target gene summary value corresponds to a down-regulated target gene and that a positive target gene summary value corresponds to an up-regulated target gene. Also, it is possible that the target gene summary values are transformed using, e.g., one of the above-described transformations (fuzzy, discrete, etc.), before they are combined in the "second (upper) layer". Next the determined target genes summary values are summed to get the TF summary level.

After the level of the TF element has been determined by evaluating the "two-layer" model, the determined TF element level can be thresholded in order to infer the activity of the cellular signaling pathway, as described above.

In the following, the models described above are collectively denoted as "(pseudo-) linear" models. A more detailed description of the training and use of probabilistic models, e.g., a Bayesian network model, and of (pseudo-)linear models is provided in Example 3 below.

Example 2

Selection of Target Genes

A transcription factor (TF) is a protein complex (i.e., a combination of proteins bound together in a specific structure) or a protein that is able to regulate transcription from target genes by binding to specific DNA sequences, thereby controlling the transcription of genetic information from DNA to mRNA. The mRNA directly produced due to this action of the transcription complex is herein referred to as a "direct target gene" (of the transcription factor). Cellular signaling pathway activation may also result in more secondary gene transcription, referred to as "indirect target genes". In the following, Bayesian network models (as exemplary mathematical models) comprising or consisting of direct target genes as direct links between cellular signaling pathway activity and mRNA level, are preferred, however the distinction between direct and indirect target genes is not always evident. Herein, a method to select direct target genes using a scoring function based on available scientific literature data is presented. Nonetheless, an accidental selection of indirect target genes cannot be ruled out due to limited information as well as biological variations and uncertainties. In order to select the target genes, two repositories of currently available scientific literature were employed to generate two lists of target genes.

The first list of target genes was generated based on scientific literature retrieved from the MEDLINE database of the National Institute of Health accessible at "www.ncbi.nlm.nih.gov/pubmed" and herein further referred to as "Pubmed". Publications containing putative FOXO target genes were searched for by using queries such as (FOXO AND "target gene") in the period of the first quarter of 2013. The resulting publications were further analyzed manually following the methodology described in more detail below.

Specific cellular signaling pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a target gene, like for example an mRNA increasing on an microarray of an cell line in which it is known that the PI3K cellular signaling axis is active, other evidence can be very strong, like the combination of an identified cellular signaling pathway TF binding site and retrieval of this site in a chromatin immunoprecipitation (ChIP) assay after stimulation of the specific cellular signaling pathway in the cell and increase in mRNA after specific stimulation of the cellular signaling pathway in a cell line.

Several types of experiments to find specific cellular signaling pathway target genes can be identified in the scientific literature:

1. ChIP experiments in which direct binding of a cellular signaling pathway-TF to its binding site on the genome is shown. Example: By using chromatin immunoprecipitation (ChIP) technology subsequently putative functional FOXO TF binding sites in the DNA of cell lines with and without active induction of the PI3K cellular signaling pathway were identified, as a subset of the binding sites recognized purely based on nucleotide sequence. Putative functionality was identified as ChIP-derived evidence that the TF was found to bind to the DNA binding site.
2. Electrophoretic Mobility Shift (EMSA) assays which show in vitro binding of a TF to a fragment of DNA containing the binding sequence. Compared to ChIP-based evidence EMSA-based evidence is less strong, since it cannot be translated to the in vivo situation.
3. Stimulation of the cellular signaling pathway and measuring mRNA profiles on a microarray or using RNA sequencing, using cellular signaling pathway-inducible cell lines and measuring mRNA profiles measured several time points after induction—in the presence of cycloheximide, which inhibits translation to protein, thus the induced mRNAs are assumed to be direct target genes.
4. Similar to 3, but using quantitative PCR to measure the amounts of mRNAs.
5. Identification of TF binding sites in the genome using a bioinformatics approach. Example for the FOXO TF element: Using the conserved FOXO binding motif 5'-TTGTTTAC-3', a software program was run on the human genome sequence, and potential binding sites were identified, both in gene promoter regions and in other genomic regions.
6. Similar as 3, only in the absence of cycloheximide.
7. Similar to 4, only in the absence of cycloheximide.
8. mRNA expression profiling of specific tissue or cell samples of which it is known that the cellular signaling pathway is active, however in absence of the proper negative control condition.

In the simplest form one can give every potential target mRNA 1 point for each of these experimental approaches in which the target mRNA was identified.

Alternatively, points can be given incrementally, meaning one technology 1 point, a second technology adds a second point, and so on. Using this relatively ranking strategy, one can make a list of most reliable target genes.

Alternatively, ranking in another way can be used to identify the target genes that are most likely to be direct target genes, by giving a higher number of points to the technology that provides most evidence for an in vivo direct target gene, in the list above this would mean 8 points for experimental approach 1), 7 for 2), and going down to 1 point for experimental approach 8). Such a list may be called a "general target gene list".

Despite the biological variations and uncertainties, the inventors assumed that the direct target genes are the most likely to be induced in a tissue-independent manner. A list of these target genes may be called an "evidence curated list of target genes". Such an evidence curated list of target genes has been used to construct computational models of the PI3K cellular signaling pathway that can be applied to samples coming from different tissue sources.

The following will illustrate exemplary how the selection of an evidence curated target gene list specifically was constructed for the PI3K cellular signaling pathway.

For the purpose of selecting PI3K target genes used as input for the "model", the following three criteria were used:

1. Gene promoter/enhancer region contains a FOXO binding motif:
   a. The FOXO binding motif should be proven to respond to an activity of the PI3K cellular signaling pathway, e.g., by means of a transient transfection assay in which the specific FOXO motif is linked to a reporter gene, and
   b. The presence of the FOXO motif should be confirmed by, e.g., an enriched motif analysis of the gene promoter/enhancer region.
2. FOXO (differentially) binds in vivo to the promoter/enhancer region of the gene in question, demonstrated by, e.g., a ChIP/CHIP experiment or another chromatin immunoprecipitation technique:
   a. FOXO is proven to bind to the promoter/enhancer region of the gene when the PI3K cellular signaling pathway is not active, and
   b. (preferably) does not bind (or weakly binds) to the gene promoter/enhancer region of the gene when the PI3K cellular signaling pathway is active.
3. The gene is differentially transcribed when the activity of the PI3K cellular signaling pathway is changed, demonstrated by, e.g.,
   a. fold enrichment of the mRNA of the gene in question through real time PCR, or microarray experiment, or
   b. the demonstration that RNA Pol II binds to the promoter region of the gene through an immunoprecipitation assay.

The selection was performed by defining as target genes of the PI3K cellular signaling pathway the genes for which enough and well documented experimental evidence was gathered proving that all three criteria mentioned above were met. A suitable experiment for collecting evidence of PI3K differential binding is to compare the results of, e.g., a ChIP/CHIP experiment in a cancer cell line that expresses activity of the PI3K cellular signaling pathway in response to tamoxifen (e.g., a cell line transfected with a tamoxifen-inducible FOXO construct, such as FOXO.A3.ER), when exposed or not exposed to tamoxifen. The same holds for collecting evidence of mRNA transcription.

The foregoing discusses the generic approach and a more specific example of the target gene selection procedure that has been employed to select a number of target genes based upon the evidence found using the above mentioned approach. The lists of target genes used in the Bayesian network models for the PI3K cellular signaling pathway is shown in Table 1.

TABLE 1

Evidence curated list of target genes of the PI3K cellular signaling pathway used in the Bayesian network models and associated probesets used to measure the mRNA expression level of the target genes.

| Target gene | Probeset |
|---|---|
| ATP8A1 | 1569773_at |
| | 210192_at |
| | 213106_at |
| BCL2L11 | 1553088_a_at |
| | 1553096_s_at |
| | 1555372_at |
| | 1558143_a_at |
| | 208536_s_at |
| | 222343_at |
| | 225606_at |
| BNIP3 | 201848_s_at |
| | 201849_at |
| BTG1 | 1559975_at |
| | 200920_s_at |
| | 200921_s_at |
| C10orf10 | 209182_s_at |
| | 209183_s_at |
| CAT | 201432_at |
| | 211922_s_at |
| | 215573_at |
| CBLB | 208348_s_at |
| | 209682_at |
| CCND1 | 208711_s_at |
| | 208712_at |
| | 214019_at |
| CCND2 | 200951_s_at |
| | 200952_s_at |
| | 200953_s_at |
| | 231259_s_at |
| | 1555056_at |
| | 202769_at |
| | 202770_s_at |
| | 211559_s_at |
| CDKN1B | 209112_at |
| DDB1 | 208619_at |
| DYRK2 | 202968_s_at |
| | 202969_at |
| | 202970_at |
| | 202971_s_at |
| ERBB3 | 1563252_at |
| | 1563253_s_at |
| | 202454_s_at |
| | 215638_at |
| | 226213_at |
| EREG | 1569583_at |
| | 205767_at |
| ESR1 | 205225_at |
| | 211233_x_at |
| | 211234_x_at |
| | 211235_s_at |
| | 211627_x_at |
| | 215551_at |
| | 215552_s_at |
| | 217190_x_at |

TABLE 1-continued

Evidence curated list of target genes of the PI3K cellular signaling pathway used in the Bayesian network models and associated probesets used to measure the mRNA expression level of the target genes.

| Target gene | Probeset |
|---|---|
| | 207672_at |
| EXT1 | 201995_at |
| FASLG | 210865_at |
| | 211333_s_at |
| FGFR2 | 203638_s_at |
| | 203639_s_at |
| | 208225_at |
| | 208228_s_at |
| | 208229_at |
| | 208234_x_at |
| | 211398_at |
| | 211399_at |
| | 211400_at |
| | 211401_s_at |
| | 240913_at |
| GADD45A | 203725_at |
| IGF1R | 203627_at |
| | 203628_at |
| | 208441_at |
| | 225330_at |
| | 243358_at |
| IGFBP1 | 205302_at |
| IGFBP3 | 210095_s_at |
| | 212143_s_at |
| INSR | 207851_s_at |
| | 213792_s_at |
| | 226212_s_at |
| | 226216_at |
| | 226450_at |
| LGMN | 201212_at |
| MXI1 | 202364_at |
| PPM1D | 204566_at |
| | 230330_at |
| SEMA3C | 203788_s_at |
| | 203789_s_at |
| SEPP1 | 201427_s_at |
| | 231669_at |
| SESN1 | 218346_s_at |
| SLC5A3 | 1553313_s_at |
| | 212944_at |
| | 213167_s_at |
| | 213164_at |
| SMAD4 | 1565702_at |
| | 1565703_at |
| | 202526_at |
| | 202527_s_at |
| | 235725_at |
| SOD2 | 215078_at |
| | 215223_s_at |
| | 216841_s_at |
| | 221477_s_at |
| TLE4 | 204872_at |
| | 214688_at |
| | 216997_x_at |
| | 233575_s_at |
| | 235765_at |
| TNFSF10 | 202687_s_at |
| | 202688_at |
| | 214329_x_at |

The second list of target genes was generated using the manually-curated database of scientific publications provided within Thomson-Reuters' Metacore (last accessed: 14$^{th}$ May, 2013). The database was queried for genes that are transcriptionally regulated directly downstream of the family of human FOXO transcription factors (i.e., FOXO1, FOXO3A, FOXO4 and FOXO6). This query resulted in 336 putative FOXO target genes that were further analyzed as follows. First all putative FOXO target genes that only had one supporting publication were pruned. Next a scoring function was introduced that gave a point for each type of experimental evidence, such as ChIP, EMSA, differential expression, knock down/out, luciferase gene reporter assay, sequence analysis, that was reported in a publication. The same experimental evidence is sometimes mentioned in multiple publications resulting in a corresponding number of points, e.g., two publications mentioning a ChIP finding results in twice the score that is given for a single ChIP finding. Further analysis was performed to allow only for genes that had diverse types of experimental evidence and not only one type of experimental evidence, e.g., differential expression. Finally, an evidence score was calculated for all putative FOXO target genes and all putative FOXO target genes with an evidence score of 6 or more were selected (shown in Table 2). The cut-off level of 6 was chosen heuristically as it was previously shown that approximately 30 target genes suffice largely to determine pathway activity.

A list of these target genes may be called a "database-based list of target genes". Such a curated target gene list has been used to construct computational models that can be applied to samples coming from different tissue sources.

TABLE 2

Database-based list of target genes of the PI3K cellular signaling pathway used in the Bayesian network models and associated probesets used to measure the mRNA expression level of the target genes.

| Target gene | Probeset |
|---|---|
| AGRP | 207193_at |
| ATG14 | 204568_at |
| BCL2L11 | 1553088_a_at |
| | 1553096_s_at |
| | 1555372_at |
| | 1558143_a_at |
| | 208536_s_at |
| | 222343_at |
| | 225606_at |
| BCL6 | 203140_at |
| | 215990_s_at |
| BIRC5 | 202094_at |
| | 202095_s_at |
| | 210334_x_at |
| BNIP3 | 201848_s_at |
| | 201849_at |
| CAT | 201432_at |
| | 211922_s_at |
| | 215573_at |
| CAV1 | 203065_s_at |
| | 212097_at |
| CCNG2 | 1555056_at |
| | 202769_at |
| | 202770_s_at |
| | 211559_s_at |
| | 228081_at |
| CDKN1A | 1555186_at |
| | 202284_s_at |
| CDKN1B | 209112_at |
| FASLG | 210865_at |
| | 211333_s_at |
| FBXO32 | 225801_at |
| | 225803_at |
| | 225345_s_at |
| | 225328_at |
| GADD45A | 203725_at |
| IGFBP1 | 205302_at |
| KLF2 | 219371_s_at |
| | 226646_at |
| KLF4 | 220266_s_at |
| | 221841_s_at |
| MYOD1 | 206656_s_at |
| | 206657_s_at |
| NOS3 | 205581_s_at |
| PCK1 | 208383_s_at |
| PDK4 | 1562321_at |

TABLE 2-continued

Database-based list of target genes of the PI3K cellular signaling pathway used in the Bayesian network models and associated probesets used to measure the mRNA expression level of the target genes.

| Target gene | Probeset |
|---|---|
| | 205960_at |
| | 225207_at |
| POMC | 205720_at |
| PPARGC1A | 1569141_a_at |
| | 219195_at |
| PRDX3 | 201619_at |
| | 209766_at |
| RAG1 | 1554994_at |
| | 206591_at |
| RAG2 | 215117_at |
| RBL2 | 212331_at |
| | 212332_at |
| SESN1 | 218346_s_at |
| SIRT1 | 218878_s_at |
| SOD2 | 215078_at |
| | 215223_s_at |
| | 216841_s_at |
| | 221477_s_at |
| STK11 | 204292_x_at |
| | 231017_at |
| | 41657_at |
| TNFSF10 | 202687_s_at |
| | 202688_at |
| | 214329_x_at |
| TXNIP | 201008_s_at |
| | 201009_s_at |
| | 201010_s_at |

The third list of target genes was generated on the basis of the two aforementioned lists, i.e., the evidence curated list (cf. Table 1) and the database-based list (cf. Table 2). Three criteria have been used to further select genes from these two lists. The first criterion is related to the function attributed to the target genes. Functions attributed to genes can be found in scientific literature, but are often available in public databases such as the OMIM database of the NIH (accessible via "http://www.ncbi.nlm.nih.gov/omim"). Target genes from the evidence curated list in Table 1 and the database-based list in Table 2 that were found to be attributed to be involved in processes essential to cancer, such as apoptosis, cell cycle, tumor suppression/progression, DNA repair, differentiation, were selected in the third list. Lastly, target genes that were found to have a high differential expression in cell line experiments with known high PI3K/low FOXO activity versus known low PI3K/high FOXO activity were selected. Herein, target genes that had a minimum expression difference of $2^{0.5}$ (herein: on a probeset level) between the "on" and "off" state of FOXO transcription averaged over multiple samples were included in the third list. The third criterion was especially aimed at selecting the most discriminative target genes. Based on the expression levels in cell line experiments with multiple samples with known high PI3K/low FOXO activity and multiple samples with known low PI3K/high FOXO activity, an odds ratio (OR) was calculated. Herein, the odds ratio was calculated per probeset using the median value as a cut-off and a soft boundary representing uncertainty in the measurement. Target genes from the evidence curated list and the database-based list were ranked according to the "soft" odds ratio and the highest ranked (OR>2) and lowest ranked (OR<1/2, i.e., negatively regulated target genes) target genes were selected for the third list of target genes.

Taking into account the function of the gene, the differential expression in "on" versus "off" signaling and a higher odds ratio, a set of target genes was found (shown in Table 3) that was considered to be more probative in determining the activity of the PI3K signaling pathway. Such a list of target genes may be called a "shortlist of target genes". Hence, the target genes reported in Table 3 are particularly preferred according to the present invention. Nonetheless, given the relative ease with which acquisition technology such as microarrays can acquire expression levels for large sets of genes, it is contemplated to utilize some or all of the target genes of Table 3, and optionally additionally use on, two, some, or all of the remaining target genes of Table 1 and Table 2.

TABLE 3

Shortlist of target genes of the PI3K cellular signaling pathway based on the evidence curated list of target genes and the database-based list of target genes.

| Target gene |
|---|
| AGRP |
| BCL2L11 |
| BCL6 |
| BNIP3 |
| BTG1 |
| CAT |
| CAV1 |
| CCND1 |
| CCND2 |
| CCNG2 |
| CDKN1A |
| CDKN1B |
| ESR1 |
| FASLG |
| FBXO32 |
| GADD45A |
| INSR |
| MXI1 |
| NOS3 |
| PCK1 |
| POMC |
| PPARGC1A |
| PRDX3 |
| RBL2 |
| SOD2 |
| TNFSF10 |

Example 3

Training and Using the Mathematical Model

Before the mathematical model can be used to infer the activity of the cellular signaling pathway, herein, the PI3K cellular signaling pathway, in a tissue and/or cells and/or a body fluid of a medical subject, the model must be appropriately trained.

If the mathematical model is a probabilistic model, e.g., a Bayesian network model, based at least in part on conditional probabilities relating the FOXO TF element and expression levels of the one or more target gene(s) of the PI3K cellular signaling pathway measured in the extracted sample of the tissue and/or the cells and/or the body fluid of the medical subject, the training may preferably be performed as described in detail in the published international patent application WO 2013/011479 A2 ("Assessment of cellular signaling pathway activity using probabilistic modeling of target gene expression").

If the mathematical model is based at least in part on one or more linear combination(s) of expression levels of the one or more target gene(s) of the PI3K cellular signaling pathway measured in the extracted sample of the tissue and/or the cells and/or the body fluid of the medical subject, the training may preferably be performed as described in detail in the published international patent application WO 2014/102668 A2 ("Assessment of cellular signaling pathway activity using linear combination(s) of target gene expressions").

a) Exemplary Bayesian Network Model

Herein, an exemplary Bayesian network model as shown in FIG. 1 was first used to model the transcriptional program of the PI3K cellular signaling pathway in a simple manner. The model consists of three types of nodes: (a) a transcription factor (TF) element in a first layer 1; (b) target gene(s) TG1, TG2, TGn in a second layer 2, and, in a third layer 3; (c) measurement nodes linked to the expression levels of the target gene(s). These can be microarray probesets PS1a, PS1b, PS1c, PS2a, PSna, PSnb, as preferably used herein, but could also be other gene expression measurements such as RNAseq or RT-qPCR.

A suitable implementation of the mathematical model, herein, the exemplary Bayesian network model, is based on microarray data. The model describes (i) how the expression levels of the target gene(s) depend on the activation of the TF element, and (ii) how probeset intensities, in turn, depend on the expression levels of the respective target gene(s). For the latter, probeset intensities may be taken from fRMA pre-processed Affymetrix HG-U133Plus2.0 microarrays, which are widely available from the Gene Expression Omnibus (GEO, www.ncbi.nlm.nih.gov/geo) and ArrayExpress (www.ebi.ac.uk/arrayexpress).

As the exemplary Bayesian network model is a simplification of the biology of a cellular signaling pathway, herein, the PI3K cellular signaling pathway, and as biological measurements are typically noisy, a probabilistic approach was opted for, i.e., the relationships between (i) the TF element and the target gene(s), and (ii) the target gene(s) and their respective probesets, are described in probabilistic terms. Furthermore, it was assumed that the activity of the oncogenic cellular signaling pathway which drives tumor growth is not transiently and dynamically altered, but long term or even irreversibly altered. Therefore the exemplary Bayesian network model was developed for interpretation of a static cellular condition. For this reason complex dynamic cellular signaling pathway features were not incorporated into the model.

Once the exemplary Bayesian network model is built and calibrated (see below), the model can be used on microarray data of a new sample by entering the probeset measurements as observations in the third layer 3, and inferring backwards in the model what the probability must have been for the TF element to be "present". Here, "present" is considered to be the phenomenon that the TF element is bound to the DNA and is controlling transcription of the cellular signaling pathway's target genes, and "absent" the case that the TF element is not controlling transcription. This latter probability is hence the primary read-out that may be used to indicate activity of the cellular signaling pathway, herein, the PI3K cellular signaling pathway, which can next be translated into the odds of the cellular signaling pathway being active by taking the ratio of the probability of being active vs. being inactive (i.e., the odds are given by $p/(1-p)$ if p is the predicted probability of the cellular signaling pathway being active).

In the exemplary Bayesian network model, the probabilistic relations have been made quantitative to allow for a quantitative probabilistic reasoning. In order to improve the generalization behavior across tissue types, the parameters describing the probabilistic relationships between (i) the TF element and the target gene(s) have been carefully hand-picked. If the TF element is "absent", it is most likely that the target gene is "down", hence a probability of 0.95 is chosen for this, and a probability of 0.05 for the target gene being "up". The latter (non-zero) probability is to account for the (rare) possibility that the target gene is regulated by other factors or accidentally observed "up" (e.g. because of measurement noise). If the TF element is "present", then with a probability of 0.70 the target gene is considered "up", and with a probability of 0.30 the target gene is considered "down". The latter values are chosen this way, because there can be several reasons why a target gene is not highly expressed even though the TF element is present, for instance, because the gene's promoter region is methylated. In the case that a target gene is not up-regulated by the TF element, but down-regulated, the probabilities are chosen in a similar way, but reflecting the down-regulation upon presence of the TF element. The parameters describing the relationships between (ii) the target gene(s) and their respective probesets have been calibrated on experimental data. For the latter, in this example, microarray data was used from cell line experiments with defined active and inactive pathway settings, but this could also be performed using patient samples with known cellular signaling pathway activity status.

Herein, publically available data on the expression of a HUVEC cell line with a stable transfection of a FOXO construct that is inducible upon stimulation with 4OHT (GSE16573 available from the Gene Expression Omnibus) was used as an example.

The cell lines with the inducible FOXO construct that were stimulated for 12 hours with 4OHT were considered as the FOXO active samples (n=3), whereas the passive FOXO samples were the cell lines with the construct without 4OHT stimulation (n=3).

Figure 2:
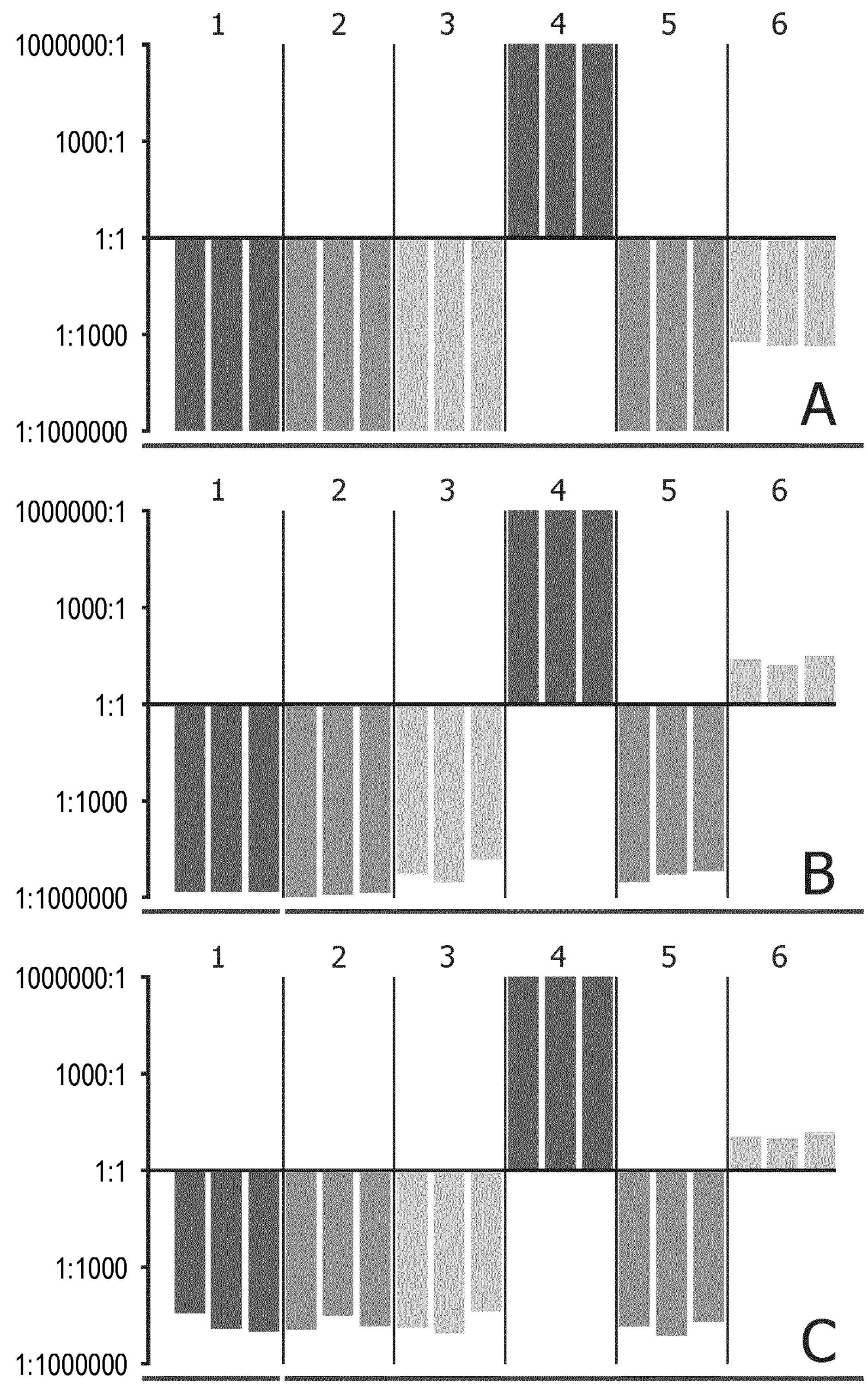
FIG. 2 shows training results of the exemplary Bayesian network model based on (A.) the evidence curated list of target genes of the PI3K cellular signaling pathway (cf. Table 1), (B.) the database-based list of target genes of the PI3K cellular signaling pathway (cf. Table 2), and (C.) the shortlist of target genes of the PI3K cellular signaling pathway (cf. Table 3).

FIG. 2 shows training results of the exemplary Bayesian network model based on (A.) the evidence curated list of target genes of the PI3K cellular signaling pathway (cf. Table 1), (B.) the database-based list of target genes of the PI3K cellular signaling pathway (cf. Table 2), and (C.) the shortlist of target genes of the PI3K cellular signaling pathway (cf. Table 3). In the diagram, the vertical axis indicates the odds that the FOXO TF element is "present" resp. "absent", which corresponds to the PI3K cellular signaling pathway being inactive resp. active, wherein values above the horizontal axis correspond to the FOXO TF element being more likely "present"/active and values below the horizontal axis indicate that the odds that the FOXO TF element is "absent"/inactive are larger than the odds that it is "present"/active.

The third group 3 of three samples encompassing the cell lines that were not stimulated with tamoxifen and that are thus FOXO inactive was assigned a passive FOXO label, whereas the fourth group 4 encompassing the samples stimulated with 4OHT, which are thus FOXO active, was assigned an active label. In the same dataset, the first, second and fifth group 1, 2, 5 were correctly predicted to have a passive PI3K cellular signaling pathway. The last group 6 consists of cell lines transfected with a mutation variant of the FOXO that is expected to be insensitive towards 4OHT stimulation. Nevertheless, some activity was found in the second model (B.) and in the third model (C.). The model based on the evidence curated list of target genes of the PI3K cellular signaling pathway correctly predicts the PI3K cellular signaling pathway to be passive in the last group 6, whereas the other two lists predicted it to be active with a relative low probability. (Legend: 1—Primary HUVECs infected with empty vector; 2—Primary HUVECs with empty vector+12 h stimulation with OHT; 3—Primary HUVECs infected with FOXO.A3.ER vector; 4—Primary HUVECs with FOXO.A3.ER vector+12 h stimulation with OHT; 5—Primary HUVECs infected with FOXO.A3.ER.H212R vector, 6—Primary HUVECs with FOXO.A3.ER.H212R vector+12 h stimulation with OHT)

In the following, test results of the exemplary Bayesian network model are shown in FIGS. 3 to 6.

Figure 3:
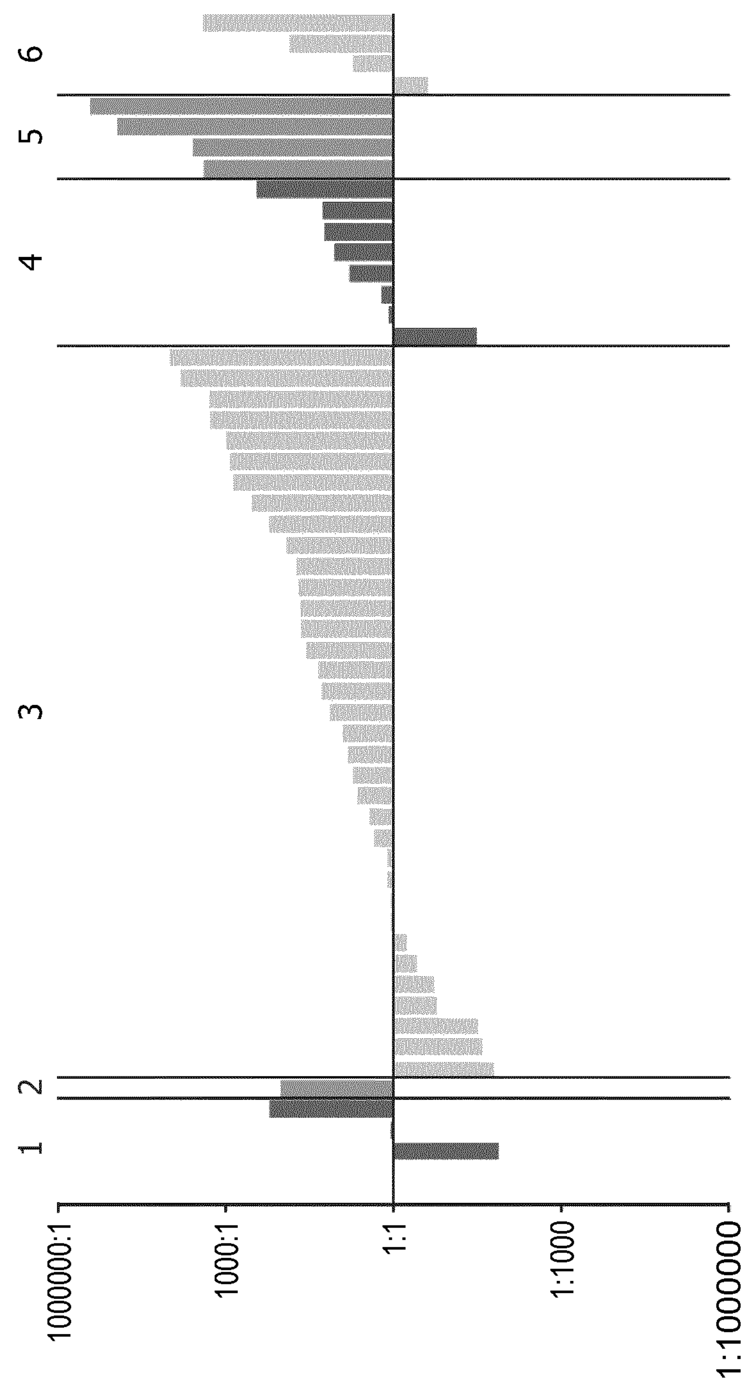
FIG. 3 shows test results of the exemplary Bayesian network model based on the shortlist of target genes of the PI3K cellular signaling pathway (cf. Table 3) for breast (cancer) samples of GSE17907.

FIG. 3 show test results of the exemplary Bayesian network model based on the shortlist of target genes of the PI3K cellular signaling pathway (cf. Table 3) for breast (cancer) samples of GSE17907. In the diagram, the vertical axis indicates the odds that the FOXO TF element is "present" resp. "absent", which corresponds to the PI3K cellular signaling pathway being inactive resp. active, wherein values above the horizontal axis correspond to the FOXO TF element being more likely "present"/active and values below the horizontal axis indicate that the odds that the FOXO TF element is "absent"/inactive are larger than the odds that it is "present"/active. The model correctly predicts an active FOXO TF element in the normal breast samples (group 5) as it is known from the literature. The majority of the samples predicted to have a passive FOXO TF element are found in the ERBB2/HER2 subgroup (group 3), which is not unexpectedly as an over-amplification of the ERBB2 gene, which encodes for HER2, is scientifically linked to an activity of the PI3K cellular signaling pathway and, consequently, in the translocation of FOXO out of the nucleus resulting in inhibition of FOXO-regulated transcription. The breast cancer sample with the molecular subtype basal (group 2) is, as expected, predicted to have an inactive FOXO TF element, since it is known that basal breast cancers typically lack HER2 expression and are therefore not likely to have an active PI3K cellular signaling pathway. (Legend: 1—Unknown, 2—Basal, 3—ERBB2/HER2, 4—Luminal A, 5—Normal breast, 6—Normal like).

Figure 4:
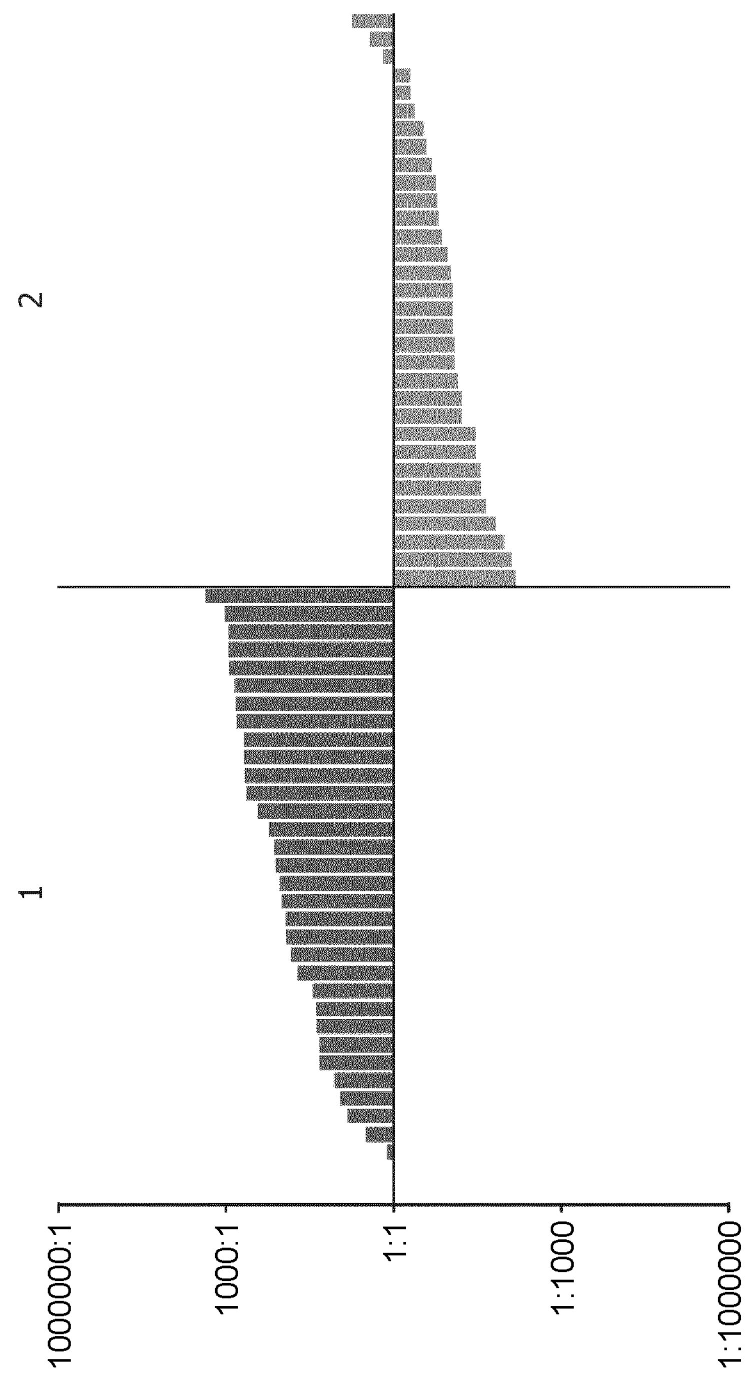
FIG. 4 shows test results of the exemplary Bayesian network model based on the shortlist of target genes of the PI3K cellular signaling pathway (cf. Table 3) for a number of healthy colon samples (group 1) and adenomatous polyps (group 2) published as the GSE8671 dataset.

FIG. 4 shows test results of the exemplary Bayesian network model based on the shortlist of target genes of the PI3K cellular signaling pathway (cf. Table 3) for a number of healthy colon samples (group 1) and adenomatous polyps (group 2) published as the GSE8671 dataset. In the diagram, the vertical axis indicates the odds that the FOXO TF element is "present" resp. "absent", which corresponds to the PI3K cellular signaling pathway being inactive resp. active, wherein values above the horizontal axis correspond to the FOXO TF element being more likely "present"/active and values below the horizontal axis indicate that the odds that the FOXO TF element is "absent"/inactive are larger than the odds that it is "present"/active. The model correctly predicts an active PI3K cellular signaling pathway in the normal samples (group 1), where the PI3K cellular signaling pathway is expected to be working normally. With respect to the adenomatous polyps (group 2), it is known from the literature that they express an increased activity of the PI3K cellular signaling pathway as a result of mutation therein. Philips and colleagues have shown that up to 86% of the colorectal tumors in their study had an increased activity of the PI3K cellular signaling pathway (Wayne A. Philips, et al., "Increased levels of phosphatidylinositol 3-kinase activity in colorectal tumors", Cancer, Vol. 83, No. 1, July 1998, pages 41 to 47). All but three of the adenoma samples were predicted by the model as being FOXO passive, and, hence, PI3K active, which nicely correlates with the number found in the literature. (Legend: 1—Normal, 2—Adenoma).

Figure 5:
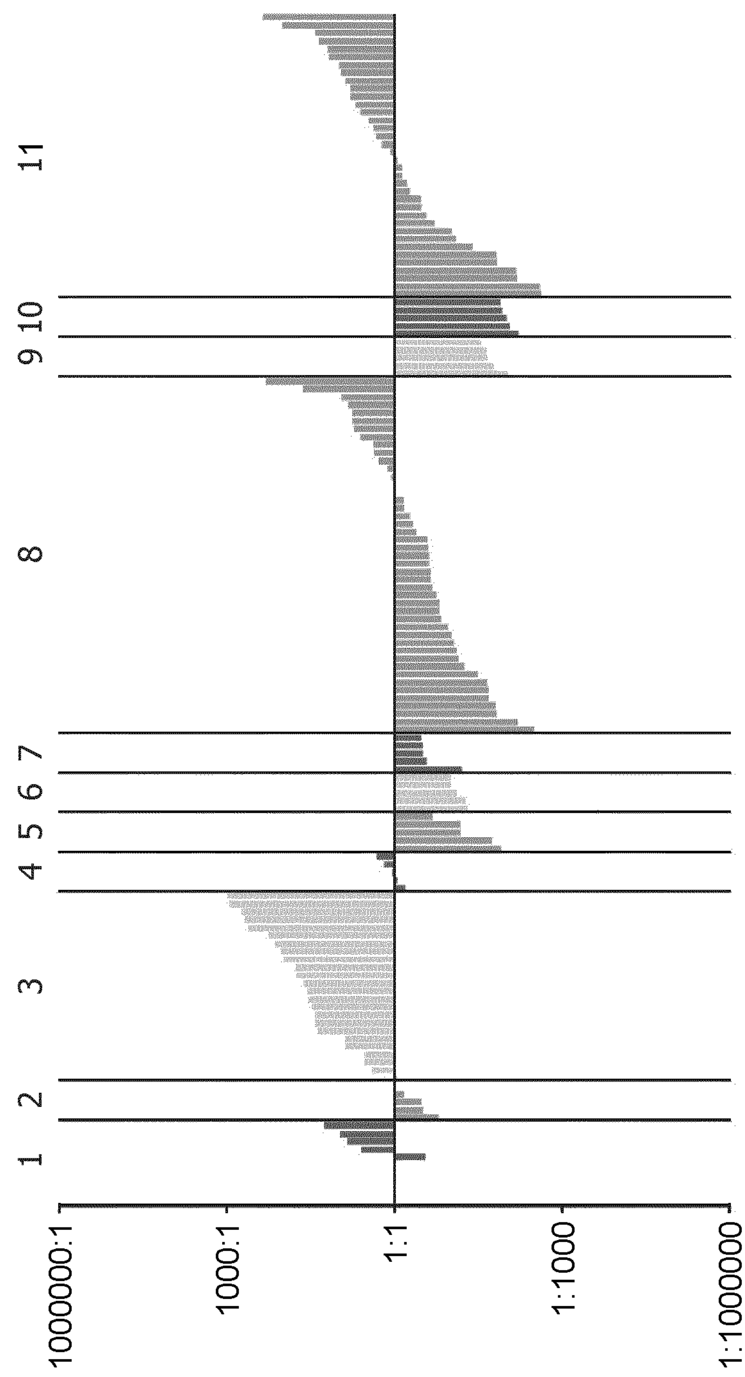
FIG. 5 shows test results of the exemplary Bayesian network model based on the shortlist of target genes of the PI3K cellular signaling pathway (cf. Table 3) for colon (cancer) samples of GSE20916.

FIG. 5 shows test results of the exemplary Bayesian network model based on the shortlist of target genes of the PI3K cellular signaling pathway (cf. Table 3) for colon (cancer) samples of GSE20916. In the diagram, the vertical axis indicates the odds that the FOXO TF element is “present” resp. “absent”, which corresponds to the PI3K cellular signaling pathway being inactive resp. active, wherein values above the horizontal axis correspond to the FOXO TF element being more likely “present”/active and values below the horizontal axis indicate that the odds that the FOXO TF element is “absent”/inactive are larger than the odds that it is “present”/active. The model, again, correctly predicts the normal samples to have an active FOXO TF element (groups 1 and 3), with the exception of the micro-dissected samples of the crypt epithelial cells (group 2), which likely have an active PI3K cellular signaling pathway and a passive FOXO TF element as a result of their continuous proliferation and more stem cell-like behaviour (Patrick Laprise, et al., “Phosphatidylinositol 3-kinase controls human intestinal epithelial cell differentiation by promoting adherens junction assembly and p38 MAPK activation”, Journal of Biological Chemistry, Vol. 277, No. 10, March 2002, pages 8226 to 8234). Unsurprisingly other FOXO passive samples are found in cancerous tissue (adenomas and carcinomas; groups 8 to 11). (Legend: 1—Normal colon (mucosa), 2—Normal colon (crypt), 3—Normal colon (surgery), 4—Distant normal colon (mucosa), 5—Distant normal colon (crypt), 6—Adenoma (mucosa), 7—Adenoma (crypt), 8—Adenocarcinoma (surgery), 9—Carcinoma (mucosa), 10—Carcinoma (crypt), 11—Carcinoma (surgery))

Figure 6:
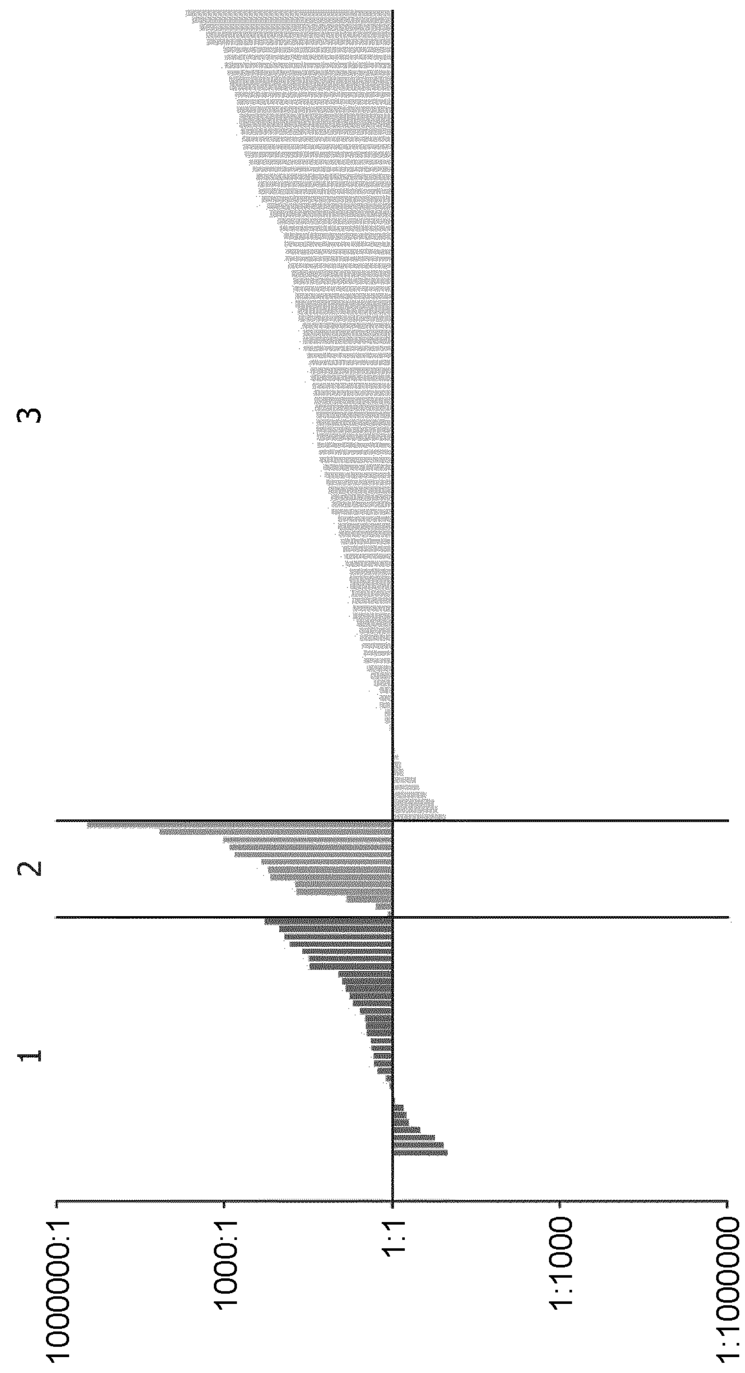
FIG. 6 shows test results of the exemplary Bayesian network model based on the shortlist of target genes of the PI3K cellular signaling pathway (cf. Table 3) for prostate (cancer) cells published in the GSE17951 dataset.

FIG. 6 shows test results of the exemplary Bayesian network model based on the shortlist of target genes of the PI3K cellular signaling pathway (cf. Table 3) for prostate (cancer) cells published in the GSE17951 dataset. In the diagram, the vertical axis indicates the odds that the FOXO TF element is “present” resp. “absent”, which corresponds to the PI3K cellular signaling pathway being inactive resp. active, wherein values above the horizontal axis correspond to the FOXO TF element being more likely “present”/active and values below the horizontal axis indicate that the odds that the FOXO TF element is “absent”/inactive are larger than the odds that it is “present”/active. All normal cells of the control group (group 2) are predicted to have an active FOXO TF element, whereas a small fraction of the samples in the tumour group (group 3) and the biopsy group (group 1) are predicted to have FOXO transcription silenced. In the literature, activity of the PI3K cellular signaling pathway in prostate cancer is reported (e.g., Mari Kaarbo, et al., “PI3K-AKT-mTOR pathway is dominant over androgen receptor signaling in prostate cancer cells”, Cellular Oncology, Vol. 32, No. 1-2, 2010, pages 11 to 27). (Legend: 1—Biopsy, 2—Control, 3—Tumor)

Figure 7:
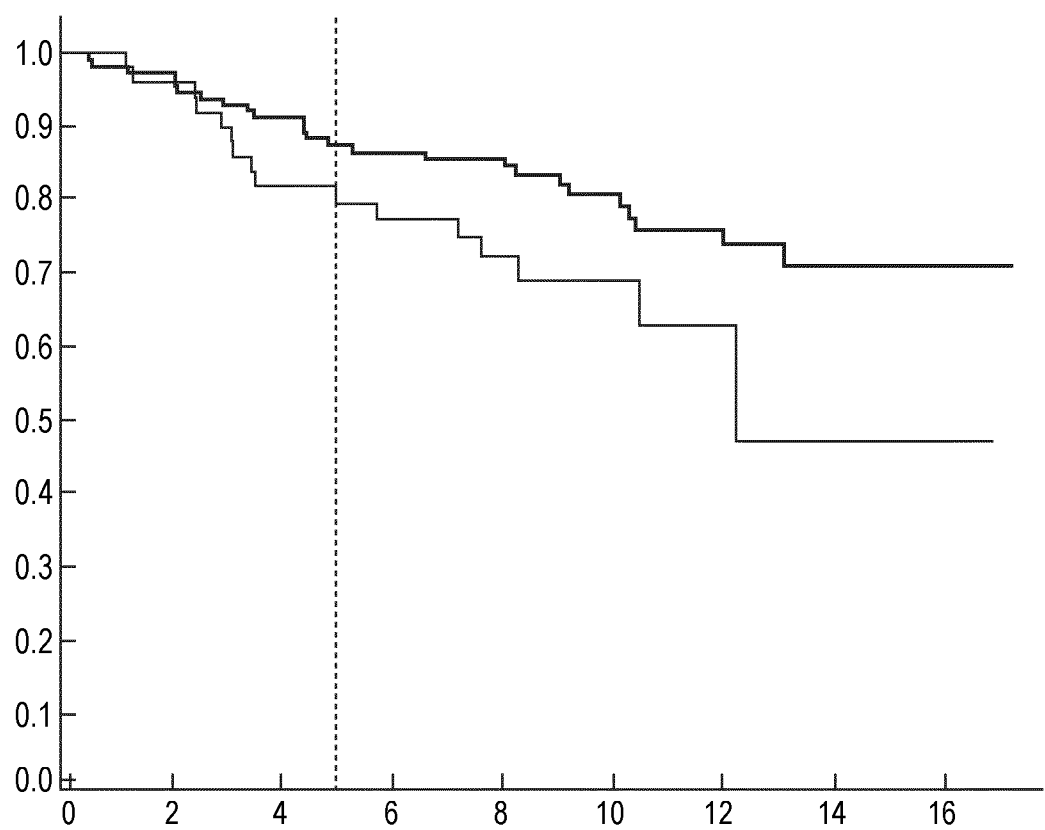
FIG. 7 illustrates a prognosis of ER+ breast cancer patients (GSE6532 & GSE9195) depicted in a Kaplan-Meier plot.

FIG. 7 illustrates a prognosis of ER+ breast cancer patients (GSE6532 & GSE9195) depicted in a Kaplan-Meier plot. In the diagram, the vertical axis indicates the recurrence free survival as a fraction of the patient group and the horizontal axis indicates a time in years. The plot indicates that an active FOXO TF element (indicated by the less steep slope of the curve that the curve ending above the other curve on the right side of the plot), which correlates with a passive PI3K cellular signaling pathway, is protective for recurrence, whereas having a passive FOXO TF element and, thus, an abnormally active PI3K cellular signaling pathway, is associated with a high risk of recurrence. (The patient group with a predicted active FOXO TF element consisted of 114 patients, whereas the patient group with a predicted passive FOXO TF element consisted of 50 patients). This result is also demonstrated in the hazard ratio of the predicted probability of FOXO transcription activity (using the probability of FOXO activity based on the shortlist of target genes of the PI3K cellular signaling pathway (cf. Table 3) as predictor): 0.45 (95% CI: 0.20-1.0, $p<0.03$).

b) Exemplary (Pseudo-)Linear Model

Before the (pseudo-)linear models as exemplary described herein can be used to infer pathway activity in a test sample the weights indicating the sign and magnitude of the association between the nodes and a threshold to call whether a node is either “absent” or present” need to be determined. One can use expert knowledge to fill in the weights and threshold a priori, but typically models are trained using a representative set of training samples, of which preferably the ground truth is known. E.g. expression data of probesets in samples with a known present transcription factor complex (=active pathway) or absent transcription factor complex (=passive pathway). However, it is impractical to obtain training samples from many different kinds of cancers, of which it is known what the activation status of the pathway to be modeled is. As a result, available training sets consist of a limited number of samples, typically from one type of cancer only. Herein a method is described to determine the parameters necessary to classify test samples as having an active or passive pathway.

Known in the field are a multitude of training algorithms (e.g. regression) that take into account the model topology and changes the model parameters, here weight and threshold, such that the model output, here weighted linear score, is optimized. Herein we demonstrate two exemplary methods that can be used to calculate the weights directly from the expression levels without the need of an optimization algorithm.

The first method, defined here as “black and white”-method boils down to a ternary system with the weighting factors being an element of $\{-1, 0, 1\}$. If we would put this in the biological context, the $-1$ and 1 corresponds to genes or probes that are down- and upregulated in case of PI3K cellular signaling pathway activity, respectively. In case a probe or gene cannot be statistically proven to be either up- or downregulated, it receives a weight of 0. Here one can use a left-sided and right-sided, two sample t-test of the expression levels of the active PI3K cellular signaling pathway samples versus the expression levels of the samples with a passive PI3K cellular signaling pathway to determine whether a probe or gene is up- or downregulated given the used training data. In cases where the average of the active samples is statistically larger than the passive samples, i.e. the p-value is below a certain threshold, e.g. 0.3, the probeset or target gene is determined to be upregulated. Conversely, in cases where the average of the active samples is statistically lower than the passive samples this probeset or target gene is determined to be downregulated upon activation of the PI3K cellular signaling pathway. In case the lowest p-value (left- or right-sided) exceeds the aforementioned threshold, the weight of this probe or gene can be defined to be 0.

An alternative method to come to weights and threshold(s) is based on the logarithm (e.g. base e) of the odds ratio, and therefore called “log odds”-weights. The odds ratio for each probe or gene is calculated based on the number of positive and negative training samples for which the probe/gene level is above and below a corresponding threshold, e.g. the median of all training samples (equation 3 in WO 2014/102668 A2). A pseudo-count can be added to circumvent divisions by zero (equation 4 in WO 2014/102668 A2). A further refinement is to count the samples above/below the threshold in a somewhat more probabilistic manner, by assuming that the probe/gene levels are e.g. normally distributed around its observed value with a certain specified standard deviation (e.g. 0.25 on a 2-log scale), and counting the probability mass above and below the threshold (equation 5 in WO 2014/102668 A2).

Alternatively, one can employ optimization algorithms known in the field such as regression to determine the weights and the threshold(s) of the (pseudo-)linear models described herein.

One has to take special attention to the way the parameters are determined for the (pseudo-)linear models to generalize well. Alternatively, one can use other machine learning methods such as Bayesian networks that are known in the field to be able to generalize quite well by taking special measures during training procedures.

Figure 8:
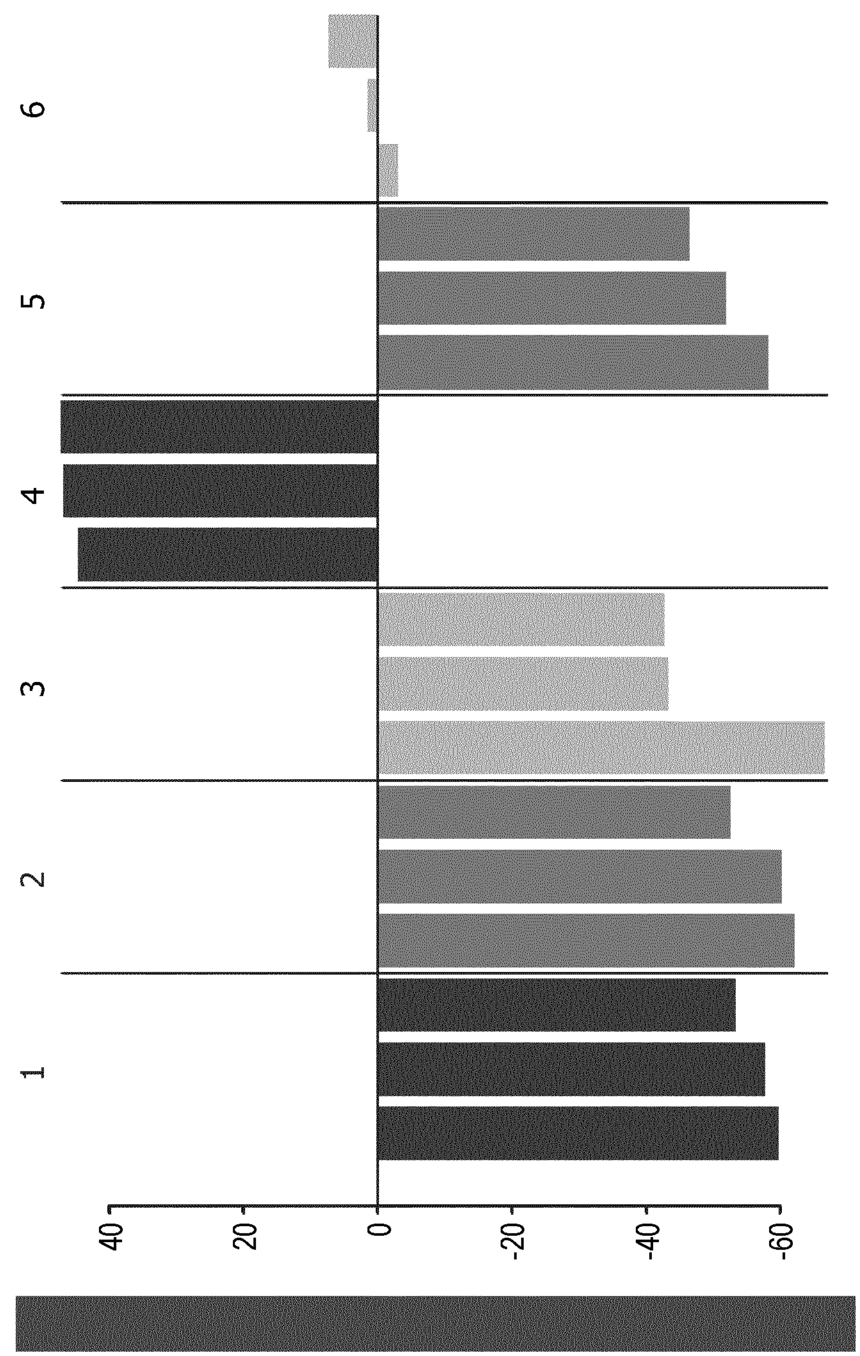
FIG. 8 shows training results of the exemplary linear model based on the shortlist of target genes of the PI3K cellular signaling pathway (cf. Table 3).

With reference to FIG. 8, an exemplary "two-layer" (pseudo-)linear model of the PI3K cellular signaling pathway using all target genes from the shortlist of target genes of the PI3K cellular signaling pathway (cf. Table 3) and all probesets of these target genes on the first and second layer, respectively, was trained using continuous data on the expression of a HUVEC cell line with a stable transfection of a FOXO construct that is inducible upon stimulation with 4OHT (GSE16573 available from the Gene Expression Omnibus) (cf. also the above description for the exemplary Bayesian network model). The cell lines with the inducible FOXO construct that were stimulated for 12 hours with 4OHT were considered as the FOXO active samples (n=3), whereas the passive FOXO samples were the cell lines with the construct without 4OHT stimulation (n=3). The training encompassed calculating the weights of the connections between the target genes expression levels, here represented by means of probeset intensities, and the target genes nodes using the "log odds"-method with a pseudocount of 10, as described herein. Subsequently, the activity score of the FOXO TF element was calculated by summation of the calculated target genes expression scores multiplied by either 1 or −1 for upregulated or downregulated target genes, respectively.

In the diagram shown in FIG. 8, the vertical axis shows the weighted linear score, wherein a positive resp. negative score indicates that the FOXO TF element is "present" resp. "absent", which corresponds to the PI3K cellular signaling pathway being inactive resp. active. The third group 3 of three samples encompassing the cell lines that were not stimulated with tamoxifen and that are thus FOXO inactive was assigned a passive FOXO label, whereas the fourth group 4 encompassing the samples stimulated with 4OHT, which are thus FOXO active, was assigned an active label. In the same dataset, the first, second and fifth group 1, 2, 5 were correctly predicted to have a passive PI3K cellular signaling pathway. The last group 6 consists of cell lines transfected with a mutation variant of the FOXO that is expected to be insensitive towards 4OHT stimulation. Nevertheless, some activity was also found in the sixth group using the trained (pseudo-) linear model. (Legend: 1—Primary HUVECs infected with empty vector, 2—Primary HUVECs with empty vector+12 h stimulation with OHT, 3—Primary HUVECs infected with FOXO.A3.ER vector, 4—Primary HUVECs with FOXO.A3.ER vector+12 h stimulation with OHT, 5—Primary HUVECs infected with FOXO.A3.ER. H212R vector, 6—Primary HUVECs with FOXO.A3.ER.H212R vector+12 h stimulation with OHT)

Figure 9:
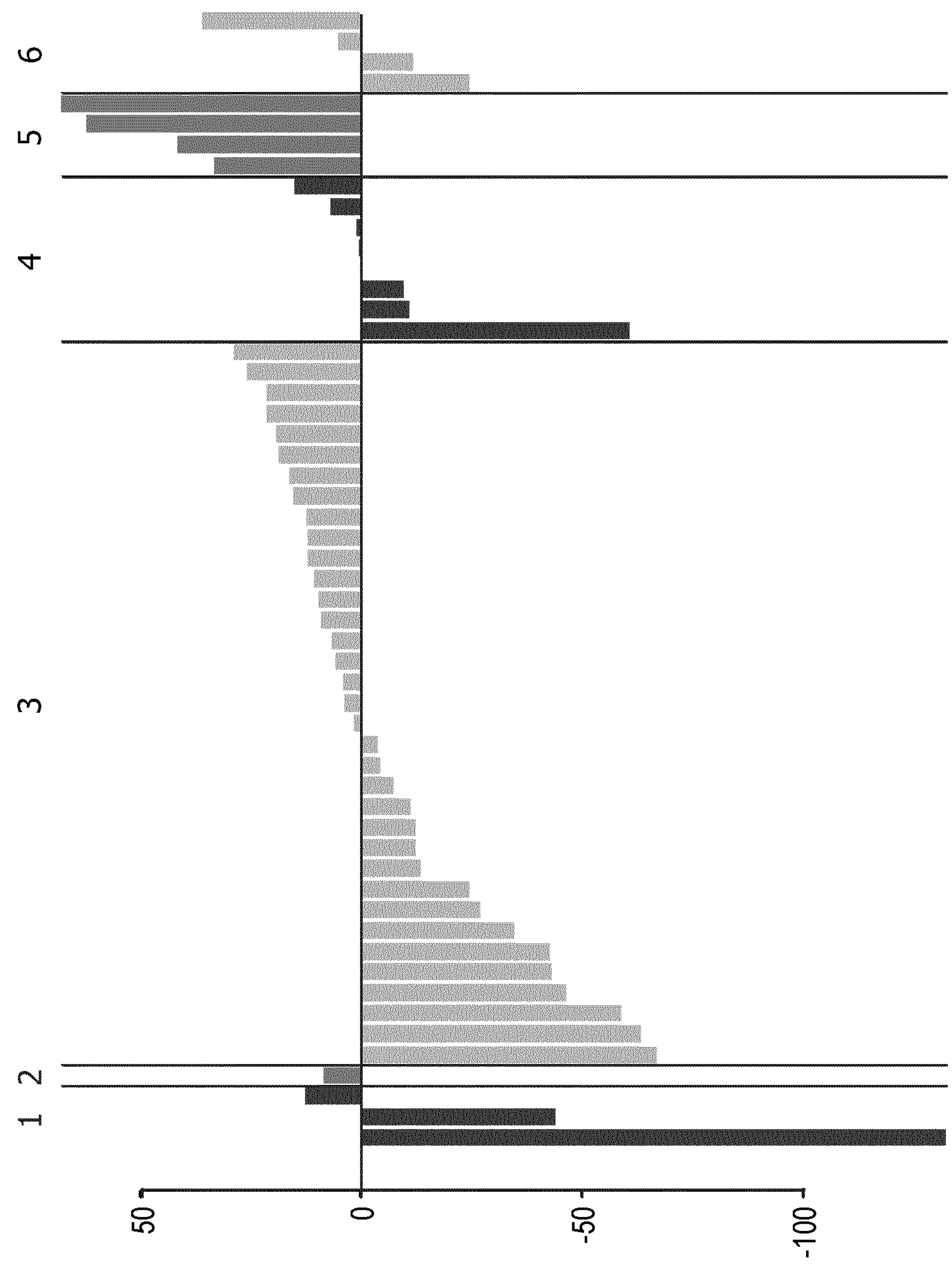
FIG. 9 shows test results of the exemplary linear model based on the shortlist of target genes of the PI3K cellular signaling pathway (cf. Table 3) for breast (cancer) samples of GSE17907.
Figure 10:
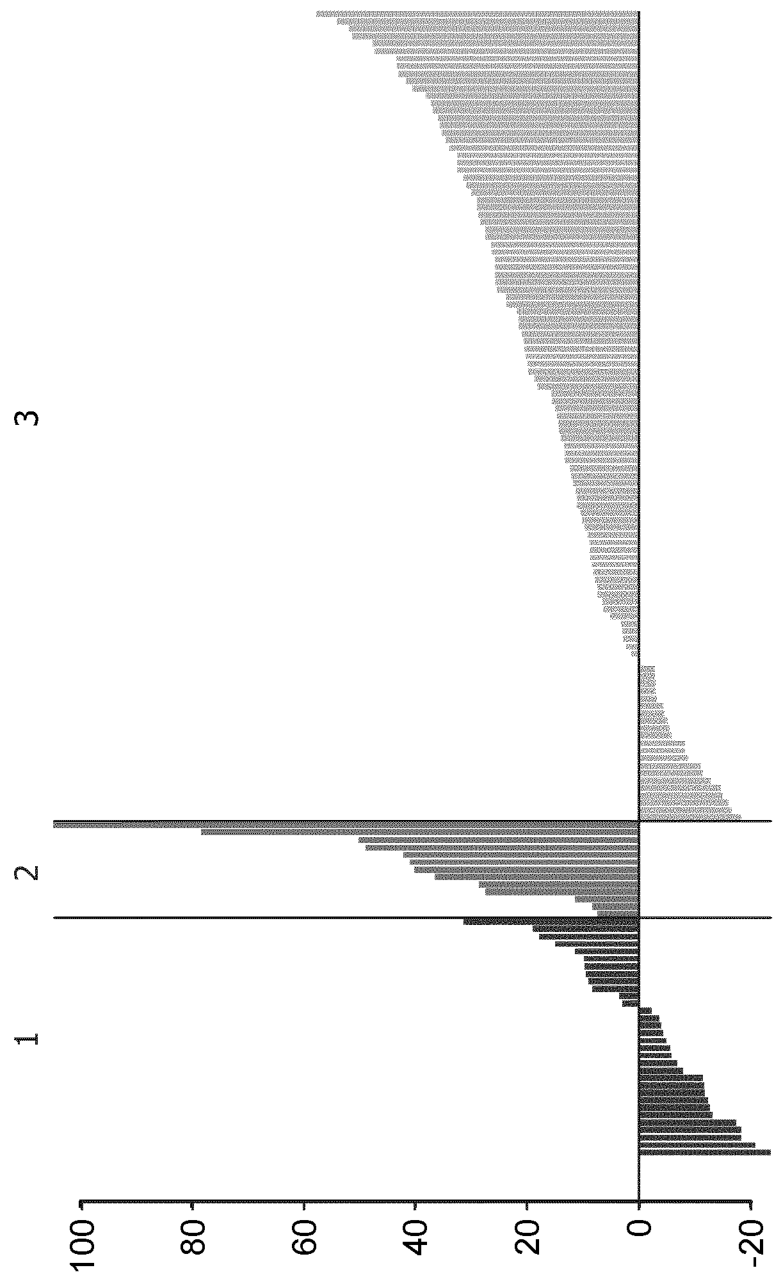
FIG. 10 shows test results of the exemplary linear model based on the shortlist of target genes of the PI3K cellular signaling pathway (cf. Table 3) for prostate (cancer) samples of GSE17951.

In the following, test results of the exemplary (pseudo-) linear model are shown in FIGS. 9 and 10.

FIG. 9 shows test results of the exemplary (pseudo-)linear model based on the shortlist of target genes of the PI3K cellular signaling pathway (cf. Table 3) for breast (cancer) samples of GSE17907. In the diagram, the vertical axis indicates the score that the FOXO TF element is "present" resp. "absent", which corresponds to the PI3K cellular signaling pathway being inactive resp. active, wherein values above the horizontal axis correspond to the FOXO TF element being more likely "present"/active and values below the horizontal axis indicate that the odds that the FOXO TF element is "absent"/inactive are larger than the odds that it is "present"/active. The model correctly predicts an active FOXO TF element in the normal breast samples (group 5), as it is known from the literature. The majority of the samples predicted to have a passive FOXO TF element are found in the ERBB2/HER2 group (group 3), which is not unexpectedly, as an over-amplification of the ERBB2 gene, which encodes for HER2, is scientifically linked to an activity of the PI3K cellular signaling pathway and, consequently, in the translocation of FOXO out of the nucleus resulting in inhibition of FOXO-regulated transcription. (Legend: 1—Unknown, 2—Basal, 3—ERBB2/HER2, 4—Luminal A, 5—Normal breast, 6—Normal like)

FIG. 10 shows test results of the exemplary (pseudo-) linear model based on the shortlist of target genes of the PI3K cellular signaling pathway (cf. Table 3) for prostate (cancer) samples of GSE17951. In the diagram, the vertical axis indicates the score that the FOXO TF element is "present" resp. "absent", which corresponds to the PI3K cellular signaling pathway being inactive resp. active, wherein values above the horizontal axis correspond to the FOXO TF element being more likely "present"/active and values below the horizontal axis indicate that the odds that the FOXO TF element is "absent"/inactive are larger than the odds that it is "present"/active. All normal cells of the control group (group 2) are predicted to have an active FOXO TF element, whereas a small fraction of the samples in the tumor group (group 3) and a larger fraction in the biopsy group (group 1) are predicted to have FOXO transcription silenced, corresponding to an increased activity of the PI3K cellular signaling pathway. In the literature, activity of the PI3K cellular signaling pathway in prostate cancer is reported (e.g., Mari Kaarbo, et al., "PI3K-AKT-mTOR pathway is dominant over androgen receptor signaling in prostate cancer cells", Cellular Oncology, Vol. 32, No. 1-2, 2010, pages 11 to 27) which is confirmed in these results. (Legend: 1—Biopsy, 2—Control, 3—Tumor)

Instead of applying the mathematical model, e.g., the exemplary Bayesian network model or the (pseudo-)linear model, on mRNA input data coming from microarrays or RNA sequencing, it may be beneficial in clinical applications to develop dedicated assays to perform the sample measurements, for instance on an integrated platform using qPCR to determine mRNA levels of target genes. The RNA/DNA sequences of the disclosed target genes can then be used to determine which primers and probes to select on such a platform.

Validation of such a dedicated assay can be done by using the microarray-based mathematical model as a reference model, and verifying whether the developed assay gives similar results on a set of validation samples. Next to a dedicated assay, this can also be done to build and calibrate similar mathematical models using mRNA-sequencing data as input measurements.

The set of target genes which are found to best indicate specific pathway activity, based on microarray/RNA sequencing based investigation using the mathematical model, e.g., the exemplary Bayesian network model or the (pseudo-)linear model, can be translated into a multiplex quantitative PCR assay to be performed on an extracted sample of the tissue and/or the cells and/or the body fluid of the medical subject and/or a computer to interpret the expression measurements and/or to infer the activity of the PI3K cellular signaling pathway. To develop such a test (e.g., FDA-approved or a CLIA waived test in a central service lab) for cellular signaling pathway activity, development of a standardized test kit is required, which needs to be clinically validated in clinical trials to obtain regulatory approval.

The present invention relates to a method comprising inferring activity of a PI3K cellular signaling pathway in a tissue and/or cells and/or a body fluid of a medical subject based at least on expression levels of one or more target gene(s) of the PI3K cellular signaling pathway measured in an extracted sample of the tissue and/or the cells and/or the body fluid of the medical subject. The present invention further relates to an apparatus comprising a digital processor configured to perform such a method, a non-transitory storage medium storing instructions that are executable by a digital processing device to perform such a method, and a computer program comprising program code means for causing a digital processing device to perform such a method.

The method may be used, for instance, in diagnosing an (abnormal) activity of the PI3K cellular signaling pathway, in prognosis based on the inferred activity of the PI3K cellular signaling pathway, in the enrollment of a medical subject in a clinical trial based on the inferred activity of the PI3K cellular signaling pathway, in the selection of subsequent test(s) to be performed, in the selection of companion diagnostics tests, in clinical decision support systems, or the like. In this regard, reference is made to the published international patent application WO 2013/011479 A2 ("Assessment of cellular signaling pathway activity using probabilistic modeling of target gene expression") and to the published international patent application WO 2014/102668 A2 ("Assessment of cellular signaling pathway activity using linear combination(s) of target gene expressions"), which describe these applications in more detail.

SEQUENCE LISTING:

| Seq. No.: | Gene: |
|---|---|
| Seq. 1 | AGRP |
| Seq. 2 | ATG14 |
| Seq. 3 | ATP8A1 |
| Seq. 4 | BCL2L11 |
| Seq. 5 | BCL6 |
| Seq. 6 | BIRC5 |
| Seq. 7 | BNIP3 |
| Seq. 8 | BTG1 |
| Seq. 9 | C10orf10 |
| Seq. 10 | CAT |
| Seq. 11 | CAV1 |
| Seq. 12 | CBLB |
| Seq. 13 | CCND1 |
| Seq. 14 | CCND2 |
| Seq. 15 | CCNG2 |
| Seq. 16 | CDKN1A |
| Seq. 17 | CDKN1B |
| Seq. 18 | DDB1 |
| Seq. 19 | DYRK2 |
| Seq. 20 | ERBB3 |
| Seq. 21 | EREG |
| Seq. 22 | ESR1 |
| Seq. 23 | EXT1 |
| Seq. 24 | FASLG |
| Seq. 25 | FBXO32 |
| Seq. 26 | FGFR2 |
| Seq. 27 | GADD45A |
| Seq. 28 | IGF1R |
| Seq. 29 | IGFBP1 |
| Seq. 30 | IGFBP3 |
| Seq. 31 | INSR |
| Seq. 32 | KLF2 |
| Seq. 33 | KLF4 |
| Seq. 34 | LGMN |
| Seq. 35 | MXI1 |
| Seq. 36 | MYOD1 |
| Seq. 37 | NOS3 |
| Seq. 38 | PCK1 |
| Seq. 39 | PDK4 |
| Seq. 40 | POMC |
| Seq. 41 | PPARGC1A |
| Seq. 42 | PPM1D |
| Seq. 43 | PRDX3 |
| Seq. 44 | RAG1 |
| Seq. 45 | RAG2 |
| Seq. 46 | RBL2 |
| Seq. 47 | SEMA3C |
| Seq. 48 | SEPP1 |
| Seq. 49 | SESN1 |
| Seq. 50 | SIRT1 |
| Seq. 51 | SLC5A3 |
| Seq. 52 | SMAD4 |
| Seq. 53 | SOD2 |
| Seq. 54 | STK11 |
| Seq. 55 | TLE4 |
| Seq. 56 | TNFSF10 |
| Seq. 57 | TXNIP |

The invention claimed is:

1. A method for correcting abnormal activity of a PI3K cellular signaling pathway in a subject, the method comprising:

physically measuring expression levels of three or more target genes of the PI3K cellular signaling pathway derived from a sample extracted from the subject, wherein the genes comprise three or more of AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2 and TNFSF10; and determining, by processor circuitry, activity of the PI3K cellular signaling pathway in the tissue and/or cells and/or the body fluid of the subject based on the expression levels of the three or more target genes of the PI3K cellular signaling pathway measured in the extracted sample of the tissue and/or the cells and/or the body fluid of the subject, wherein the determining comprises:

determining a level of a FOXO transcription factor (TF) element in the extracted sample of the tissue and/or the cells and/or the body fluid of the subject based on the expression levels of the three or more target genes of the PI3K cellular signaling pathway, the FOXO TF element controlling transcription of the three or more target genes of the PI3K cellular signaling pathway; and determining the activity of the PI3K cellular signaling pathway in the tissue and/or the cells and/or the body fluid of the subject based on the level of the FOXO TF element in the extracted sample of the tissue and/or the cells and/or the body fluid of the subject;

determining that the PI3K cellular signaling pathway is operating abnormally in the subject based on the determined activity of the PI3K cellular signaling pathway;

selecting, based on the determined abnormal operation of the PI3K cellular signaling pathway, a specific treatment configured to remedy the determined abnormal operation of the PI3K cellular signaling pathway; and administering, in response to the determined abnormal operation of the PI3K cellular signaling pathway and the selection of a specific treatment configured to remedy said determined abnormal operation, the selected specific treatment, wherein the determined abnormal operation of the PI3K cellular signaling pathway is overactive and the selected specific treatment inhibits or deregulates the activity of the PI3K cellular signaling pathway.

2. The method of claim 1, wherein the determining is further based on expression levels of at least one target gene of the PI3K cellular signaling pathway measured in the extracted sample of the tissue and/or the cells and/or the body fluid of the subject selected from the group consisting of: ATP8A1, C10orf10, CBLB, DDB1, DYRK2, ERBB3, EREG, EXT1, FGFR2, IGF 1R, IGFBP1, IGFBP3, LGMN, PPM1D, SEMA3C, SEPP1, SESN1, SLC5A3, SMAD4 and TLE4.

3. The method of claim 1, wherein the determining is further based on expression levels of at least one target gene of the PI3K cellular signaling pathway measured in the extracted sample of the tissue and/or the cells and/or the body fluid of the subject selected from the group consisting of: ATG14, BIRCS, IGFBP1, KLF2, KLF4, MYOD1, PDK4, RAG1, RAG2, SESN1, SIRT1, STK11 and TXNIP.

4. The method of claim 1, wherein the method is further used in at least one of the following forms of medical intervention:

diagnosis based on the determined activity of the PI3K cellular signaling pathway in the tissue and/or the cells and/or the body fluid of the subject;

prognosis based on the determined activity of the PI3K cellular signaling pathway in the tissue and/or the cells and/or the body fluid of the subject;

drug prescription based on the determined activity of the PI3K cellular signaling pathway in the tissue and/or the cells and/or the body fluid of the subject;

prediction of drug efficacy based on the determined activity of the PS3K cellular signaling pathway in the tissue and/or the cells and/or the body fluid of the subject;

prediction of adverse effects based on the determined activity of the PI3K cellular signaling pathway in the tissue and/or the cells and/or the body fluid of the subject;

monitoring of drug efficacy;

drug development;

assay development;

pathway research;

cancer staging;

enrollment of the subject in a clinical trial based on the determined activity of the PI3K cellular signaling pathway in the tissue and/or the cells and/or the body fluid of the subject;

selection of subsequent test to be performed; and selection of companion diagnostics tests.

5. The method of claim 1, wherein the set of target genes of the PI3K cellular signaling pathway includes at least nine target genes selected from the group comprising: AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXIL NOS3, PCK1, POMC, PPARGC1A, PRDX3, RBL2, SOD2 and TNFSF10.

6. The method of claim 5, wherein the set of target genes of the PI3K cellular signaling pathway further includes at least one target gene selected from the group consisting of: ATP8A1, C10orf10, CBLB, DDB1, DYRK2, ERBB3, EREG, EXT1, FGFR2, IGF1R, IGFBP1, IGFBP3, LGMN, PPM1D, SEMA3C, SEPP1, SESN1, SLC5A3, SMAD4 and TLE4.

7. The method of claim 5, wherein the set of target genes of the PI3K cellular signaling pathway further includes at least one target gene selected from the group consisting of: ATG14, BIRC5, IGFBP1, KLF2, KLF4, MYOD1, PDK4, RAG1, RAG2, SESN1, SIRT1, STK11 and TXNIP.

8. The method of claim 1, further comprising:

providing, based on the determined abnormal operation of the PI3K cellular signaling pathway, a recommendation for medical intervention configured to remedy the determined abnormal operation of the PI3K cellular signaling pathway.

9. The method of claim 1, further comprising determining that a tumor afflicting the subject is at least partially driven by deregulation of the PI3K cellular signaling pathway.

10. The method of claim 8, wherein the medical intervention comprises prescribing an inhibitor of the PI3K cellular signaling pathway to the subject.

11. The method of claim 1, wherein the obtaining of the expression levels of the three or more target genes includes measuring the expression levels of the three or more target genes.

12. The method of claim 1, wherein the target genes are mRNA direct target genes, and wherein the method further comprises:

constructing a network between the expression levels of the three or more mRNA direct target genes and the activity of the cellular signaling pathway, and training the network by:

determining the level of the FOXO TF element in the extracted sample of the tissue and/or the cells and/or the body fluid of the subject, the FOXO TF element controlling transcription of the three or more mRNA direct target genes of the PI3K cellular signaling pathway;

determining the activity of the PI3K cellular signaling pathway in the tissue and/or cells and/or the body fluid of the subject; and measuring the nodes representing corresponding probe set nodes of the corresponding three or more mRNA direct target genes.

13. The method of claim 1, wherein selecting a specific treatment configured to remedy the determined abnormal operation of the PI3K cellular signaling pathway comprises recommending or selecting a drug that downregulates the activity of the PI3K cellular signaling pathway.

* * * * *

SEQUENCE LISTING

<160> NUMBER OF SEQ ID NOS: 57

<210> SEQ ID NO 1
<211> LENGTH: 783
<212> TYPE: DNA
<213> ORGANISM: Homo sapiens

<400> SEQUENCE: 1
agctcctagg tccctgtcct gtggaaattt gtggaccctg ggcaccctct cttgctccca 60
aattttaatc ggctcctgga aacctcaccc caaattggag ataggcactc ctcttgtaga 120
acaaaaggct caggttcagg gagtgagggc ctgaactgtg cccccaccct ccaggaaggg 180
tccttcacgg cctggctgca gggatcagtc acgtgtggcc cttcattagg ccctgccata 240

```
taagccaagg gcacggggtg gccgggaact ctctaggcaa gaatcccgga ggcagaggcc    300

atgctgaccg cagcggtgct gagctgtgcc ctgctgctgg cactgcctgc cacgcgagga    360

gcccagatgg gcttggcccc catggagggc atcagaaggc ctgaccaggc cctgctccca    420

gagctcccag gcctgggcct gcgggcccca ctgaagaaga caactgcaga acaggcagaa    480

gaggatctgt tgcaggaggc tcaggccttg gcagaggtac tagacctgca ggaccgcgag    540

ccccgctcct cacgtcgctg cgtaaggctg catgagtcct gcctgggaca gcaggtgcct    600

tgctgtgacc catgtgccac gtgctactgc cgcttcttca atgccttctg ctactgccgc    660

aagctgggta ctgccatgaa tccctgcagc cgcacctagc tggccaacgt cagggtcggg    720

gctagggtag gggcaaggaa actcgaataa aggatgggac caacaaaaaa aaaaaaaaaa    780

aaa                                                                783
```

<210> SEQ ID NO 2
<211> LENGTH: 4760
<212> TYPE: DNA
<213> ORGANISM: Homo sapiens

<400> SEQUENCE: 2

```
aaaatcccac gtgactggct ctcctctcag gccatcatgg cgtctcccag tgggaaggga     60

gcccgggcgc tggaggctcc tggctgcggg ccccggccgc tcgcccggga cctggtggac    120

tccgtggacg atgcggaggg gctgtacgtg gctgtggagc gctgcccgct gtgcaacact    180

acccgccggc ggctgacctg cgccaaatgc gttcagagcg gcgatttcgt ctacttcgac    240

ggccgcgacc gggagaggtt tatcgacaag aaggaaaggt taagccgact taagagcaag    300

caagaagaat ttcagaaaga agtgttaaaa gctatggaag gaaaatggat aacagatcag    360

ttgagatgga aaataatgtc ctgcaagatg aggattgaac agttaaaaca aacaatatgt    420

aaaggaaatg aagaaatgga gaaaaattct gaaggccttc tcaaaaccaa ggaaaagaat    480

cagaagcttt acagtcgagc acaacggcac caagagaaaa aggagaagat tcagaggcat    540

aatcgcaaac ttggtgacct ggtagaaaaa aagaccattg acttaagaag tcattatgag    600

cgtctggcaa atcttcgacg atcccatata ttagagctca cctctgtcat tttccaatc     660

gaggaagtaa agacgggtgt gagagacccc gcagatgtgt cttcagagag tgacagtgcc    720

atgacctcca gcactgtgag caagcttgct gaagcccgga ggacaactta cctctcagga    780

cgatgggtct gtgacgatca caacggagac accagcatta gcattacagg gccttggatt    840

agcctcccta acaatgggga ctactctgcc tactacagct gggtggagga gaagaaaaca    900

acccaggggc ctgacatgga gcagagtaac cctgcctaca ccatcagtgc tgcgctgtgc    960

tatgcaactc agctggtcaa cattctgtct catatacttg atgtaaatct tcccaaaaag   1020

ctctgcaaca gtgaattttg tggcgaaaat ctaagcaagc agaaatttac tcgagcagtg   1080

aagaaactga atgcaaatat tctttacctt tgtttttctc agcatgtaaa tttagatcaa   1140

ttacaaccac tgcataccct caggaatcta atgtacctgg tcagtccaag ctctgaacac   1200

ctaggcaggt cagggccctt tgaagtacga gcagaccttg aggagtccat ggaatttgtg   1260

gatcccggag ttgctggaga atcagatgag agcggagatg agcgcgtcag cgatgaagaa   1320

accgacctgg gcacagactg ggagaacttg cctagtcccc ggttttgtga tatcccttcc   1380

cagtctgtgg aagtctccca gagtcagagc acccaggcgt ccccacccat cgcgagcagc   1440

agtgcaggtg ggatgatctc ctctgcagca gcctcggtga cctcctggtt taaagcttac   1500
```

-continued

```
actggacacc gttaacgagc atggaccaaa acataccaaa tctgcatcaa gaaagttctt   1560
ctcccactac actctagtaa acattttctg tttaagttaa gatagtgtct ggaacaaaga   1620
ggttaaagtg ttgttttgtt ttgtcttttt aagcagggag acaaacattt ctatttgcca   1680
agtggcctgt gatggtgacc aacatgctta tgataattaa gagaacaggg gtcgaaggtc   1740
tttctaccca gaccagtgct ggtggaagga ggacctgtgc gtgtggccag ttctgccaag   1800
gaagcagttg atttgggttc cctctgggcc cgggccaccg ggcccacaga tatgggtcag   1860
tgtgctggtc cttgcggtgc tgagactgtt cctgacactt taagttttag aggttggttg   1920
aatcacaaga ggtgattctt gattattagg acatgaaaga taaaagctct ttaataagag   1980
tttttctgcc attgtttttt gtatgagaac cagcaggcaa tttaaaattt ctaatttggt   2040
cctttgattt tgtttgggag gggtgagtta cacgtatttt attcatgctg ctctgtcgta   2100
gtttgtcaga cattcctgtt tttctttccc ccacacacca aagaaaatga aagtcttttt   2160
ctttaggacc cacatccata aatggaagaa atcctggctg caataatgtc tagagagttt   2220
ttaactattt tcttgtattc tgaggggaat taagcttatt cttacctagt tgaattcctg   2280
ccatccacac tatgagcatt ttgaaattga acttatattt tctgggtgaa aataagtcat   2340
gaaggtcatt cccttatgta agctcaatgc ctgcctgggc acaggggaaa agccacttag   2400
ttaagtggcc tctggtcatt cttgtggtgt ccactttctt tctatgggat tgagtaggtg   2460
gcaggtgttt tcaggggaaa ccatcctact tgtttccccg aactctttgt tgctctgagg   2520
acacagcttt gctcagaaat gcagcgcaga tccttacggc tgatgctact ctgctctgtt   2580
ctggggaaag cacaatataa agaaagaatt tcccagccag gcgcagtggc tcacgcctgt   2640
aatcccagca ctttaggagg ccgaggcagg cggatcactt gaggtcagga gtttgagagc   2700
agcctggcta acatggtgaa accctgtttc tactaaaaat acaaaaaatt accgggtgtg   2760
gtggcgcacg cctgtaatcc cagctactcg ggaggctgcg gcaggagaat cgcttgaacc   2820
gggaggcaga ggttgcagtg agccgagatt gtgccattgc actccagcct gggcaacaag   2880
agcgaaactc cgtctcaaaa aaaaaaagaa tttccctcag caggagatca ttttcagctc   2940
acgtgtcttg tcattctttt agtgacaatc ttacaagaaa actataatga gagaggcatt   3000
atgtacaaat atgtaagtag tttattttta ataactgcaa aaaaatccta tgtaacaact   3060
accaaaagaa atcctatgaa agagtcctaa caggcattat taccatatct tatgtgattg   3120
gcatgatagc acctctgata aatcattcag aggtttgcca tgccccagct tcttttctca   3180
tcataataat tgtagttgat actttgcctc caagtccgag gtgctatata gcttttgcta   3240
atggtatatt tggtgttttg tatagttttg ggtagagttg cagaacggag tttatttcta   3300
tccggtagtc acaaattcct tggctctatg aattttccat gaaaggagga agtaggcttt   3360
tctcgttgtg ggtggtcttt tttttttttg gagacggagt ctcactcagc tgcccaggct   3420
ggagtgtagt ggcaccatct ccgctcactg caaccaccat ctcctgggtt caagcaattc   3480
ttccatctca acctcccgag tagctgggat tataggcacc tgccatcatg cccagctaat   3540
ttttgtattt tagtaaagac gggggttttc accatgttgg ccaggctggt cttgaactcc   3600
tgacttcagg tgatccgctt gccttggcct cctaaagtgc taggattaca ggcctgagcc   3660
accgcgcccg gccccttatg ggttcttcta cactgctggg atctctgttt taagtgctca   3720
gcttcatgat tgattgctgg gcttccattt tcccatccag ttctggagtt cgtagagagt   3780
gaagatggta gacttgaaca gataaataaa cttaacgatc ttgtaagagt tgtctagcta   3840
cttaaaaccc tcagaagtaa gagcttagtc tcacgagttg taagagtggg atttggagct   3900
```

```
tggtggtgga gactgacttc agctgagaga tgcacaacag tcatggtttt cttaagcctc   3960
ttatgaaacc atgaatgaga gatgaagcta aagaatagaa tccagagatc acaaactcat   4020
ctagagtact tccacaaaat ttacaaagat gtgggaactt tatggatagg atatattttg   4080
tttgttgttg ttaatatcaa ctagaggcac tttacatagg gttaagtgat cgaacccttt   4140
tgtggttttg aacaccaaca tactggctta cactgctgaa atattttggg tttcattatt   4200
ttgcactgga tccaccctgt aaatactctt aagtatacat ttcaaccact gtttttttcta   4260
ctctttttgc tgctcattaa aatctttcat gtaggtgcca gaaccatatg taaacagctt   4320
tttaaaaaat tgaagctggt attttgttta aacaaaaagc catagaactt ggtcatgttt   4380
tccattttaa aatgatttac tgaaacaaag taatactaat aaaaacccac aggcaccaaa   4440
caggctgctt aaaatggtct gttaaagaca ttttttggtt atggaatata agaaaagttt   4500
tgcacatctg taagggggaa aaacagtata tcaccattgg gtagagtgga cgggactcat   4560
gtaaggactc aatttgggga agagcattca gtggcatgct gttagaggac tagtgtccga   4620
gaatctcctc acagtatcat gttgcaggaa ttccccattg ctctgcaact tccaaaccag   4680
tttgagtcat acaaatgttt tctaaacttt tattgtatta ctgcaataaa tcttttaaca   4740
gtaaaaaaaa aaaaaaaaaa                                               4760
```

```
<210> SEQ ID NO 3
<211> LENGTH: 8270
<212> TYPE: DNA
<213> ORGANISM: Homo sapiens

<400> SEQUENCE: 3

aagagctcgc ccagctctgc gggcgccgcc accttcgccg ccaccgctgc ctttctcctc     60
ctcctgtcgg cgtgcggggg ccgcgcccgg cggcagctct gccctaggtg ggcggcggcg    120
cggcccaggc tgcagctgag cgctctgcgc ggcgcagccg ggtctcccgc gtgtaccacg    180
ccgtgacagg tgcagagtcc gggctgagga cccacctgca gccgccgccg cgatgcccac    240
catgcggagg accgtgtcgg agatccgctc gcgcgccgaa ggttatgaga agacagatga    300
tgtttcagag aagacctcac tggctgacca ggaggaagta aggactattt tcatcaacca    360
gccccagctg acaaaattct gcaataacca tgtcagcact gcaaaataca acataatcac    420
attccttcca agatttctct actctcagtt cagaagagct gctaattcat tttttctctt    480
tattgcactg ctgcagcaaa tacctgatgt gtcaccaaca ggtcgttata caacactggt    540
tcctctctta tttattttag ctgtggcagc tatcaaagag ataatagaag atattaaacg    600
acataaagct gataatgcag tgaacaagaa acaaacgcaa gttttgagaa atggtgcttg    660
ggaaattgtc cactgggaaa aggtggcagt aggggagata gtgaaagtga ccaatgggga    720
acatctccca gcagatctca tcagtctgtc ctcaagtgag ccccaagcca tgtgctacat    780
tgaaacatcc aacttagatg gtgaaacaaa cttgaaaatt agacagggct taccagcaac    840
atcagatatc aaagacgttg acagtttgat gaggatttct ggcagaattg agtgtgaaag    900
tccaaacaga catctctacg attttgttgg aaacataagg cttgatggac atggcaccgt    960
tccactggga gcagatcaga ttcttcttcg aggagctcag ttgagaaata cacagtgggt   1020
tcatggaata gttgtctaca ctggacatga caccaagctg atgcagaatt caacaagtcc   1080
accacttaag ctctcaaatg tggaacggat tacaaatgta caaattttga ttttattttg   1140
tatcttaatt gccatgtctc ttgtctgttc tgtgggctca gccatttgga atcgaaggca   1200
```

-continued

```
ttctggaaaa gactggtatc tcaatctaaa ctatggtggc gctagtaatt ttggactgaa   1260

tttcttgacc ttcatcatcc ttttcaacaa tctcattcct atcagcttat tggttacatt   1320

agaagttgtg aaatttaccc aggcatactt cataaattgg gatcttgaca tgcactatga   1380

acccacagac actgctgcta tggctcgaac atctaatctg aatgaggaac ttggccaggt   1440

taaatacata ttttctgaca aaactggtac tctgacatgc aatgtaatgc agtttaagaa   1500

gtgcaccata gcgggagttg cttatggcca tgtccctgaa cctgaggatt atggctgctc   1560

tcctgatgaa tggcagaact cacagtttgg agatgaaaaa acatttagtg attcatcatt   1620

gctggaaaat ctccaaaata atcatccaac tgcacctata atatgtgaat ttcttacaat   1680

gatggcagtc tgtcacacag cagtgccaga gcgagaaggt gacaagatta tttatcaagc   1740

agcatctcca gatgagggag cattggtcag agcagccaag caattgaatt ttgttttcac   1800

tggaagaaca cccgactcgg tgattataga ttcactgggg caggaagaaa gatatgaatt   1860

gctcaatgtc ttggagttta ccagtgctag gaaaagaatg tcagtgattg ttcgcactcc   1920

atctggaaag ttacgactct actgcaaagg agctgacact gtaatttatg atcgactggc   1980

agagacgtca aaatacaaag aaattaccct aaaacattta gagcagtttg ctacagaagg   2040

gttaagaact ttatgttttg ctgtggctga gatttcagag agcgactttc aggagtggcg   2100

agcagtctat cagcgagcat ctacatctgt gcagaacagg ctactcaaac tcgaagagag   2160

ttatgagttg attgaaaaga atcttcagct acttggagca acagccattg aggataaatt   2220

acaagatcaa gtgcctgaaa ccatagaaac gctaatgaaa gcagacatca aaatctggat   2280

ccttacaggg gacaagcaag aaactgccat taacatcgga cactcctgca aactgttgaa   2340

gaagaacatg ggaatgattg ttataaatga aggctctctt gatggaacaa gggaaactct   2400

cagtcgtcac tgtactaccc ttggtgatgc tctccggaaa gagaatgatt ttgctcttat   2460

aattgatggg aaaaccctca aatatgcctt aacctttgga gtacgacagt atttcctgga   2520

cttagctttg tcatgcaaag ctgtcatttg ctgtcgggtt tctcctcttc aaaaatctga   2580

agttgttgag atggttaaga aacaagtcaa agtcgtaacg cttgcaatcg gtgatggagc   2640

aaatgatgtc agcatgatac agacagcgca cgttggtgtt ggtatcagtg gcaatgaagg   2700

cctgcaggca gctaattcct ctgactactc catagctcag ttcaaatatt tgaagaattt   2760

actgatgatt catggtgcct ggaactataa cagagtctcc aagtgcatct tatactgctt   2820

ctacaagaat atagtgctct atattatcga gatctggttt gcctttgtta atggcttttc   2880

tggacagatc ctctttgaaa gatggtgtat aggtctctat aacgtgatgt ttacagcaat   2940

gcctccttta actcttggaa tatttgagag atcatgcaga aaagagaaca tgttgaagta   3000

ccctgaatta tacaaaacat ctcagaatgc cctggacttc aacaccaagg ttttctgggt   3060

tcattgttta aatggcctct tccactcagt tattctgttt tggtttccac taaaagccct   3120

tcagtatggt actgcatttg gaaatgggaa aacctcggat tatctgctac tgggaaactt   3180

tgtgtacact tttgtggtga taactgtgtg tttgaaagct ggattggaga catcatattg   3240

gacatggttc agccacatag cgatatgggg gagcatcgca ctctgggtgg tgtttttggg   3300

aatctactca tctctgtggc ctgccattcc gatggcccct gatatgtcag gagaggcagc   3360

catgttgttc agttctggag tcttttggat gggcttgtta ttcatccctg tggcatctct   3420

gctccttgat gtggtgtaca aggttatcaa gaggactgct tttaaaacat tggtcgatga   3480

agttcaggag ctggaggcaa aatctcaaga cccaggagca gttgtacttg gaaaaagcct   3540

gaccgagagg gcgcaactgc tcaagaacgt ctttaagaag aaccacgtga acttgtaccg   3600
```

```
ctctgaatcc ttgcaacaaa atctgctcca tgggtatgcg ttctctcaag atgaaaatgg   3660
aatcgtttca cagtctgaag tgataagagc atatgatacc acgaaacaga ggcccgacga   3720
atggtgatgg ggagagcctg aaaggcaggc tctgttacct ctctaaggag agctaccagg   3780
ttgtcaccgc agtctgctaa ccaattccag tctggtccat gaagaggaaa ggtagatctg   3840
agctcatctc gctgatggac attcagattc atgtatatta tagacataag cactgtgcaa   3900
ctgtactgta acaccatctc ttttggattt ttttaaggta tttgctaagt ctttgtaaac   3960
ggaaattgaa aatgacctgg tatcttgcca gagggctttc ttaaacggag aataagtcag   4020
tattcttatg ccattactgt ggggctgtaa ctgactgtca gtttattggc tgtaccacaa   4080
ggtaaccaac cattaaaaaa ctctaaatga tatttagtta aagggactct tggtatccag   4140
acttagattt caggatatgc tgaaacaaac cagcattctt aaggaactga ctcaccttcc   4200
tgagcaaaat ttctaaacaa gcatttgtgt ccaaaattgt cttgataaat gtttgccaaa   4260
gaggttcagt aagtgttttt ctagttcagt agtcatatgc ccagaaatgt aagagaaagt   4320
ttacttccag ttccgctgta agatctgcat gcctgacttt ccaaatgtaa gagtgattta   4380
caaaaatgaa tatttcaagg catttgctac taaaatcggt gatgttgcac ctttggcctt   4440
acaaatgctt ctttgttgtt tgtcgtgttt atttgttaga ggacacacgt gttaatgtga   4500
ctctgttgtt atgacactga tttttcaaac tatgtatgtt tcaggtattt ctgatgaagt   4560
ttcatcatca tttagatttt tctaaaaatc tggctaatgc agtagattga gtgatgtcat   4620
tttgtcttaa agtttttcct cttaagaaac atatgctacg tatttacgtg ggatttccaa   4680
agcttctgtt gcaatatttg gaataacatg tcagataaat gcatgggctt ttgtcctgtg   4740
ttccagttcc cactagagat gcctgtgtct tgtgtagcac acccagtgtt atggtgactg   4800
ccccctatac tgaagactga aaattatttc acagttcact catcaaatag ttcccaaaat   4860
tcgtcacatg ctgcttattg ggacaaatag gtagtacatt ttccccattt aaaaaatgcg   4920
gattttactc aggccggtaa ctttacagtc agaggacacg ttcatcatga gtagcttttg   4980
ttagtatgtt ttaaaatgta tcttcagttc aattattttc agcatttaca agacatctga   5040
aaatggctat tttgctacca acagtaaatg aaggggctgt ttaaaaacca caaccagttt   5100
tctacactat tttttaaata atactttcat ttgaaaaaaa ggaattagtt ttcagataca   5160
cttcagagat tgaagcaaac tatttgcctt ttactcaaaa gcctgcttgc ctttacatgg   5220
acttaccagc aaaataggta gaactttctc ttttaaaaaa agtcaactag aattgagaag   5280
aggtgatttt ttttcagatc gcttctcgag tttaatattt tcacattctt ttcacccttt   5340
ttctcaatct agatttaaaa ttaggatata tgtcatttcc ttgtctgtat ttgtagctcc   5400
ttagttacca gtatgcctct ccattttcta caaataagag gttataacac atatacataa   5460
ttctaacctt aagggaacac acgtttacat actttacttc ccaagcccct cctgtttggg   5520
gtacagattg agagagtcat gaatcaacac atctagcaag accacaggtg taagagtcta   5580
agatcgtctt caaaattctg aagtcccagt ctttacctgt ccagtgaatg aatattcaga   5640
gcagcttttc ctgggcttcc cagtggtgat agctgaggtc aaaccacaaa aaataagaaa   5700
gcaagagtga aatgcacccc tccagagaaa cactttgtag tgtttaattc tgttaataga   5760
gaagagctgc ttctgtttgc gctcacttca tcagtggcac ccttctgcag aattttaata   5820
taaaaacatt atggatataa tagaactgga ttttctgact taaaaatgta agttttattt   5880
taatcttgaa acgtggattg tttctgtgga gctcttaaac atgagaagaa tacttacggt   5940
```

-continued

```
tgataatgtg taacatgatc tgaaatgtga ctaatttgag cctctttgtc ccatcgtcct   6000
gtttttgaat tattgacatt gtcagtctct ttgcttcctg ggtgagactt ggggtttgag   6060
ggacagggaa tgaccttctt ggtgaaactt aaaatataac attgcaattg cagtgacttt   6120
acagtgttaa attagagaaa atagtctgat tttttaaacc ttccttaact ggaaaaaagt   6180
cacatggttt taccaggatt gaaataaaca gtcaatgtga cttttaacat gtgttttttt   6240
gaaataaagg gcacgtactc ttcaattaaa aagttcctta tagggactct ggcaaatgct   6300
aacacagttg ctttacaatg tttacaattc agacaatacg acttataata gaaaatcctc   6360
attcatttag cattgaaaag ctggaagttg cttctttaat gttgaatagt atacagtggt   6420
attgagcatg gactttctaa atgttttata tatacatata aaaatatatt ggtgtctcac   6480
acccagaaag atgttatatt gtagatatta ttaggaaaac agtgtttctc aggaacgttg   6540
taaattttaa atgatatatg tacttcccgt cctcccacct ccactctgtg ctctaatgtg   6600
agactgcttc agcagtgttg ctaagttaat ggaaaacttt ttctaatcaa gtcaggtgaa   6660
tgtgtattct gctaaataat gttagccatt tacatgaatt gtatggtcat taaatggaat   6720
cagtgattcc tctttaattt ccagagggga aatgaattat ggaaatcagt cagcattctg   6780
atcattaaat tttatacttt aattttgccg ttcagcattc taaatatcca atgtgaaagt   6840
cacatgataa tttgttttgc attgcgtgca ctgtacaaca cttacaactt gtcatttaaa   6900
atgttttctc gggaaatgaa tgctagtcag aaagtaatag attgtattat tcatagtttt   6960
aaaattatga caatgtcata attactacaa agctaaataa tcgtgtttat ttttgtgcag   7020
ttgccctttg atagttcctg gttttaaaac ctattaagtg tataatctta caaatagtca   7080
tctacaaaat ttatggagaa agtgcccagc ccattcacat cacatggacc aggaattctt   7140
ttgtaaatga cttaaggtaa catcatgcag ttcagtgcct aataaatgct ttttaatgat   7200
gaacatttct ataatgactc gtaagatacc atagtctgat tttctcaca ttaaaataac   7260
tgaagtcact tgtgtaacgt agttatactt tgctgcattt taattaacct tcaacagcta   7320
ttaaagtgga atgtaagtta aattttgaag gaaaggaaat aaatgtttc catatttcgt   7380
cttgatttac tttctgtatg agaacagctg tgtttttgat aggtttatgg tttgcatgag   7440
ttcatattta aagtgatcca ggccaatgca tggctattgc tgtaaatctt gatgtttatt   7500
tctgccttgt aaagttctat cacggcctac ctggaattta aaattcagta gacaaattaa   7560
ttggtcctct gcacaacttt tttaataagt agattatttt acaaagaaat ttgaacaaat   7620
ttaattgaat cttttgttta gcttgcctct aagaactttt cttaataaag ctcccaaaac   7680
ttctcagcaa ataaatctcc cttaagtagg aaagctagat ttcatatttg cttactttga   7740
attaacagca actttccaca ggtaaatctg ttcttgcaaa gatgtgagca gaatagttaa   7800
aaataatatt tttatgtttc atggttctaa atggaagcca taaatgcagt aaatactatc   7860
tgttgtttaa ctactttaat cgtcattttt tacattttca agtttattag gttaagaaaa   7920
acagggcagc cttggaaggc agctactaca gaaaactgca gttttgcgtt aaagataaag   7980
tagtattttc agctccctga aaaaccattc ctgctgaaac tgctgtagaa attgtgaagc   8040
tgcatgagtg gagagtattg aatctgtggt tatagtagtt ttctcaggtt tgtttatctt   8100
gatgtttgat gcactgtgtt ttatagttat taaaattgag taatattatt tctatgcagt   8160
gttatgtgtc attggccttt tgtgaatgtg catgttttaa actgcaaatt ttaaacattt   8220
tgtcctctaa ttgttattaa aaatgaaata aactttacca ttacttaaaa              8270
```

<210> SEQ ID NO 4
<211> LENGTH: 417
<212> TYPE: DNA
<213> ORGANISM: Homo sapiens

<400> SEQUENCE: 4
atggcaaagc aaccttctga tgtaagttct gagtgtgacc gagaaggtag acaattgcag 60
cctgcggaga ggcctcccca gctcagacct ggggcccta cctccctaca gacagagcca 120
caagacagga gcccagcacc catgagttgt gacaaatcaa cacaaacccc aagtcctcct 180
tgccaggcct tcaaccacta tctcagtgca atggcttcca tgaggcaggc tgaacctgca 240
gatatgcgcc cagagatatg gatcgcccaa gagttgcggc gtatcggaga cgagtttaac 300
gcttactatg caaggagggt atttttgaat aattaccaag cagccgaaga ccacccacga 360
atggttatct tacgactgtt acgttacatt gtccgcctgg tgtggagaat gcattga 417

<210> SEQ ID NO 5
<211> LENGTH: 3575
<212> TYPE: DNA
<213> ORGANISM: Homo sapiens

<400> SEQUENCE: 5
accatcgtct tgggcccggg gagggagagc caccttcagg cccctcgagc ctcgaaccgg 60
aacctccaaa tccgagacgc tctgcttatg aggacctcga aatatgccgg ccagtgaaaa 120
aatcttgtgg ctttgagggc ttttggttgg ccaggggcag taaaaatctc ggagagctga 180
caccaagtcc tcccctgcca cgtagcagtg gtaaagtccg aagctcaaat tccgagaatt 240
gagctctgtt gattcttaga actggggttc ttagaagtgg tgatgcaaga agtttctagg 300
aaaggccgga caccaggttt tgagcaaaat tttggactgt gaagcaaggc attggtgaag 360
acaaaatggc ctcgccggct gacagctgta tccagttcac ccgccatgcc agtgatgttc 420
ttctcaacct taatcgtctc cggagtcgag acatcttgac tgatgttgtc attgttgtga 480
gccgtgagca gtttagagcc cataaaacgg tcctcatggc ctgcagtggc ctgttctata 540
gcatctttac agaccagttg aaatgcaacc ttagtgtgat caatctagat cctgagatca 600
accctgaggg attctgcatc ctcctggact tcatgtacac atctcggctc aatttgcggg 660
agggcaacat catggctgtg atggccacgg ctatgtacct gcagatggag catgttgtgg 720
acacttgccg gaagtttatt aaggccagtg aagcagagat ggtttctgcc atcaagcctc 780
ctcgtgaaga gttcctcaac agccggatgc tgatgcccca agacatcatg gcctatcggg 840
gtcgtgaggt ggtggagaac aacctgccac tgaggagcgc ccctgggtgt gagagcagag 900
cctttgcccc cagcctgtac agtggcctgt ccacaccgcc agcctcttat tccatgtaca 960
gccacctccc tgtcagcagc ctcctcttct ccgatgagga gtttcgggat gtccggatgc 1020
ctgtggccaa ccccttcccc aaggagcggg cactcccatg tgatagtgcc aggccagtcc 1080
ctggtgagta cagccggccg actttggagg tgtcccccaa tgtgtgccac agcaatatct 1140
attcacccaa ggaaacaatc ccagaagagg cacgaagtga tatgcactac agtgtggctg 1200
agggcctcaa acctgctgcc ccctcagccc gaaatgcccc ctacttccct tgtgacaagg 1260
ccagcaaaga agaagagaga ccctcctcgg aagatgagat tgccctgcat ttcgagcccc 1320
ccaatgcacc cctgaaccgg aagggtctgg ttagtccaca gagcccccag aaatctgact 1380
gccagcccaa ctcgcccaca gagtcctgca gcagtaagaa tgcctgcatc ctccaggctt 1440
ctggctcccc tccagccaag agccccactg accccaaagc ctgcaactgg aagaaataca 1500

-continued

```
agttcatcgt gctcaacagc ctcaaccaga atgccaaacc agaggggcct gagcaggctg   1560
agctgggccg cctttcccca cgagcctaca cggccccacc tgcctgccag ccacccatgg   1620
agcctgagaa ccttgacctc cagtccccaa ccaagctgag tgccagcggg gaggactcca   1680
ccatcccaca agccagccgg ctcaataaca tcgttaacag gtccatgacg ggctctcccc   1740
gcagcagcag cgagagccac tcaccactct acatgcaccc cccgaagtgc acgtcctgcg   1800
gctctcagtc cccacagcat gcagagatgt gcctccacac cgctggcccc acgttccctg   1860
aggagatggg agagacccag tctgagtact cagattctag ctgtgagaac ggggccttct   1920
tctgcaatga gtgtgactgc cgcttctctg aggaggcctc actcaagagg cacacgctgc   1980
agacccacag tgacaaaccc tacaagtgtg accgctgcca ggcctccttc cgctacaagg   2040
gcaacctcgc cagccacaag accgtccata ccggtgagaa accctatcgt tgcaacatct   2100
gtggggccca gttcaaccgg ccagccaacc tgaaaaccca cactcgaatt cactctggag   2160
agaagcccta caaatgcgaa acctgcggag ccagatttgt acaggtggcc cacctccgtg   2220
cccatgtgct tatccacact ggtgagaagc cctatccctg tgaaatctgt ggcacccgtt   2280
tccggcacct tcagactctg aagagccacc tgcgaatcca cacaggagag aaaccttacc   2340
attgtgagaa gtgtaacctg catttccgtc acaaaagcca gctgcgactt cacttgcgcc   2400
agaagcatgg cgccatcacc aacaccaagg tgcaataccg cgtgtcagcc actgacctgc   2460
ctccggagct ccccaaagcc tgctgaagca tggagtgttg atgctttcgt ctccagcccc   2520
ttctcagaat ctacccaaag gatactgtaa cactttacaa tgttcatccc atgatgtagt   2580
gcctctttca tccactagtg caaatcatag ctggggggttg gggtggtgg gggtcggggc   2640
ctgggggact gggagccgca gcagctcccc ctcccccact gccataaaac attaagaaaa   2700
tcatattgct tcttctccta tgtgtaaggt gaaccatgtc agcaaaaagc aaaatcattt   2760
tatatgtcaa agcaggggag tatgcaaaag ttctgacttg actttagtct gcaaaatgag   2820
gaatgtatat gttttgtggg aacagatgtt tcttttgtat gtaaatgtgc attcttttaa   2880
aagacaagac ttcagtatgt tgtcaaagag agggctttaa tttttttaac caaaggtgaa   2940
ggaatatatg gcagagttgt aaatatataa atatatatat atataaaata aatatatata   3000
aacctaaaaa agatatatta aaaatataaa actgcgttaa aggctcgatt ttgtatctgc   3060
aggcagacac ggatctgaga atctttattg agaaagagca cttaagagaa tattttaagt   3120
attgcatctg tataagtaag aaaatatttt gtctaaaatg cctcagtgta tttgtatttt   3180
tttgcaagtg aaggtttaca atttacaaag tgtgtattaa aaaaaacaaa aagaacaaaa   3240
aaatctgcag aaggaaaaat gtgtaatttt gttctagttt tcagtttgta tatacccgta   3300
caacgtgtcc tcacggtgcc ttttttcacg gaagttttca atgatgggcg agcgtgcacc   3360
atccctttttt gaagtgtagg cagacacagg gacttgaagt tgttactaac taaactctct   3420
ttgggaatgt ttgtctcatc ccattctgcg tcatgcttgt gttataacta ctccggagac   3480
agggtttggc tgtgtctaaa ctgcattacc gcgttgtaaa atatagctgt acaaatataa   3540
gaataaaatg ttgaaaagtc aaactggaaa aaaaa                              3575
```

<210> SEQ ID NO 6
<211> LENGTH: 2655
<212> TYPE: DNA
<213> ORGANISM: Homo sapiens

<400> SEQUENCE: 6

```
cccagaaggc cgcggggggt ggaccgccta agagggcgtg cgctcccgac atgccccgcg     60
```

```
gcgcgccatt aaccgccaga tttgaatcgc gggacccgtt ggcagaggtg gcggcggcgg    120
catgggtgcc ccgacgttgc cccctgcctg gcagcccttt ctcaaggacc accgcatctc    180
tacattcaag aactggccct tcttggaggg ctgcgcctgc accccggagc ggatggccga    240
ggctggcttc atccactgcc ccactgagaa cgagccagac ttggcccagt gtttcttctg    300
cttcaaggag ctggaaggct gggagccaga tgacgacccc atagaggaac ataaaaagca    360
ttcgtccggt tgcgctttcc tttctgtcaa gaagcagttt gaagaattaa cccttggtga    420
atttttgaaa ctggacagag aaagagccaa gaacaaaatt gcaaaggaaa ccaacaataa    480
gaagaaagaa tttgaggaaa ctgcggagaa agtgcgccgt gccatcgagc agctggctgc    540
catggattga ggcctctggc cggagctgcc tggtcccaga gtggctgcac cacttccagg    600
gtttattccc tggtgccacc agccttcctg tgggcccctt agcaatgtct taggaaagga    660
gatcaacatt ttcaaattag atgtttcaac tgtgctcttg ttttgtcttg aaagtggcac    720
cagaggtgct tctgcctgtg cagcgggtgc tgctggtaac agtggctgct tctctctctc    780
tctctctttt ttgggggctc atttttgctg ttttgattcc cgggcttacc aggtgagaag    840
tgagggagga agaaggcagt gtcccttttg ctagagctga cagctttgtt cgcgtgggca    900
gagccttcca cagtgaatgt gtctggacct catgttgttg aggctgtcac agtcctgagt    960
gtggacttgg caggtgcctg ttgaatctga gctgcaggtt ccttatctgt cacacctgtg   1020
cctcctcaga ggacagtttt tttgttgttg tgtttttttg tttttttttt tttggtagat   1080
gcatgacttg tgtgtgatga gagaatggag acagagtccc tggctcctct actgtttaac   1140
aacatggctt tcttattttg tttgaattgt taattcacag aatagcacaa actacaatta   1200
aaactaagca caaagccatt ctaagtcatt ggggaaacgg ggtgaacttc aggtggatga   1260
ggagacagaa tagagtgata ggaagcgtct ggcagatact ccttttgcca ctgctgtgtg   1320
attagacagg cccagtgagc cgcggggcac atgctggccg ctcctccctc agaaaaaggc   1380
agtggcctaa atcctttta aatgacttgg ctcgatgctg tgggggactg gctgggctgc    1440
tgcaggccgt gtgtctgtca gcccaacctt cacatctgtc acgttctcca cacgggggag   1500
agacgcagtc cgcccaggtc cccgctttct ttggaggcag cagctcccgc agggctgaag   1560
tctggcgtaa gatgatggat ttgattcgcc ctcctccctg tcatagagct gcagggtgga   1620
ttgttacagc ttcgctggaa acctctggag gtcatctcgg ctgttcctga gaaataaaaa   1680
gcctgtcatt tcaaacactg ctgtggaccc tactgggttt ttaaaatatt gtcagttttt   1740
catcgtcgtc cctagcctgc caacagccat ctgcccagac agccgcagtg aggatgagcg   1800
tcctggcaga gacgcagttg tctctgggcg cttgccagag ccacgaaccc cagacctgtt   1860
tgtatcatcc gggctccttc cgggcagaaa caactgaaaa tgcacttcag acccacttat   1920
ttctgccaca tctgagtcgg cctgagatag acttttccct ctaaactggg agaatatcac   1980
agtggttttt gttagcagaa aatgcactcc agcctctgta ctcatctaag ctgcttattt   2040
ttgatatttg tgtcagtctg taaatggata cttcacttta ataactgttg cttagtaatt   2100
ggctttgtag agaagctgga aaaaaatggt tttgtcttca actcctttgc atgccaggcg   2160
gtgatgtgga tctcggcttc tgtgagcctg tgctgtgggc agggctgagc tggagccgcc   2220
cctctcagcc cgcctgccac ggcctttcct taaaggccat ccttaaaacc agaccctcat   2280
ggctaccagc acctgaaagc ttcctcgaca tctgttaata aagccgtagg cccttgtcta   2340
agtgcaaccg cctagacttt ctttcagata catgtccaca tgtccatttt tcaggttctc   2400
```

```
taagttggag tggagtctgg gaagggttgt gaatgaggct tctgggctat gggtgaggtt   2460

ccaatggcag gttagagccc ctcgggccaa ctgccatcct ggaaagtaga gacagcagtg   2520

cccgctgccc agaagagacc agcaagccaa actggagccc ccattgcagg ctgtcgccat   2580

gtggaaagag taactcacaa ttgccaataa agtctcatgt ggttttatct aaaaaaaaaa   2640

aaaaaaaaaa aaaaa                                                    2655
```

<210> SEQ ID NO 7
<211> LENGTH: 789
<212> TYPE: DNA
<213> ORGANISM: Homo sapiens

<400> SEQUENCE: 7

```
gccaccgccc gcagctgaag cacatccgca gcccggcgcg actccgatcg ccgcagttgc     60

cctctggcgc catgtccgag aacggagcgc ccgggatgca ggaggagagc ctgcagggct    120

cctgggtaga actgcacttc agcaataatg ggaacggggg cagcgttcca gcctcggttt    180

ctatttataa tggagacatg gaaaaaatac tgctggacgc acagcatgag tctggacgga    240

gtagctccaa gagctctcac tgtgacagcc cacctcgctc gcagacacca caagatacca    300

acagggcttc tgaaacagat acccatagca ttggagagaa aaacagctca cagtctgagg    360

aagatgatat tgaaagaagg aaagaagttg aaagcatctt gaagaaaaac tcagattgga    420

tatgggattg gtcaagtcgg ccggaaaata ttccccccaa ggagttcctc tttaaacacc    480

cgaagcgcac ggccaccctc agcatgagga acacgagcgt catgaagaaa gggggcatat    540

tctctgcaga atttctgaaa gttttccttc catctctgct gctctctcat ttgctggcca    600

tcggattggg gatctatatt ggaaggcgtc tgacaacctc caccagcacc ttttgatgaa    660

gaactggagt ctgacttggt tcgttagtgg attacttctg agcttgcaac atagctcact    720

gaagagctgt tagatcctgg gccttcgtgg ctcgagagac tagaatcgca gatacgaaaa    780

ccccgcagc                                                            789
```

<210> SEQ ID NO 8
<211> LENGTH: 2251
<212> TYPE: DNA
<213> ORGANISM: Homo sapiens

<400> SEQUENCE: 8

```
ctgctgaagc gggaaggagg agctagggct gggggcggag ctttcacacg cgcaccctct     60

gttccctccc tccctccctc gacacaagca actgggtctc cagccgccac tccgggttta    120

tttgtttaca agcggattac gtcagctcct ccctctcttc cctatctctg gacccgcctc    180

ctgaactctt ttcccgcccc tttcggctcc gaaccggctt gcgtcacaat ggtgcgatat    240

tcggattggc tggagtcggc catcacgctc cagctacgcc acttcctttt cgtggcacta    300

taaagggtgc tgcacggcgc ttgcatctct tcgcctctcg gagctggaaa tgcagctatt    360

gagatcttcg aatgctgcgg agctggaggc ggaggcagct ggggaggtcc gagcgatgtg    420

accaggccgc catcgctcgt ctcttcctct ctcctgccgc ctcctgtctc gaaaataact    480

tttttagtct aaagaaagaa agacaaaagt agtcgtccgc ccctcacgcc ctctcttcct    540

ctcagccttc cgcccggtga ggaagcccgg ggtggctgct ccgccgtcgg ggccgcgccg    600

ccgagcccca gccgccccgg gccgcccccg cacgccgccc ccatgcatcc cttctacacc    660

cgggccgcca ccatgatagg cgagatcgcc gccgccgtgt ccttcatctc caagtttctc    720

cgcaccaagg ggctcacgag cgagcgacag ctgcagacct tcagccagag cctgcaggag    780
```

```
ctgctggcag gtgagcaggg gagtcctaag cgttgtttct ctgttcttct tttcttctat    840

agaacattat aaacatcact ggttcccaga aaagccatgc aagggatcgg gttaccgttg    900

tattcgcatc aaccataaaa tggatcctct gattggacag gcagcacagc ggattggact    960

gagcagtcag gagctgttca ggcttctccc aagtgaactc acactctggg ttgaccccta   1020

tgaagtgtcc tacagaattg gagaggatgg ctccatctgt gtgctgtatg aagcctcacc   1080

agcaggaggt agcactcaaa acagcaccaa cgtgcaaatg gtagacagcc gaatcagctg   1140

taaggaggaa cttctcttgg gcagaacgag cccttccaaa aactacaata tgatgactgt   1200

atcaggttaa gatatagtct gtggatggat catctgatga tgatggataa atttgatttt   1260

tgctttgggt gggctcctct tggggatgga ttatggaatt taaaccatgt cacagctgtg   1320

aagatctggc acaagataga atggtaaaaa aaaaaaaaaa ttttaagtga cagtgccata   1380

gtttggacag tacctttcaa tgattaattt taatagcctg tgagtccaag taaatgatca   1440

ctttatttgc tagggaggga agtcctaggg tggtttcagt ttctcccaga catacctaaa   1500

tttttacatc aatcctttta aagaaaatct gtatttcaaa gaatctttct ctgcagtaaa   1560

tctcgcaggg gaatttgcac tattacactt gaaagttgtt attgttaacc ttttcggcag   1620

cttttaatag gaaagttaaa cgttttaaac atggtagtac tggaaatttt acaagacttt   1680

tacctagcac ttaaatatgt ataaatgtac ataaagacaa actagtaagc atgacctggg   1740

gaaatggtca gaccttgtat tgtgtttttg gccttgaaag tagcaagtga ccagaatctg   1800

ccatggcaac aggctttaaa aaagaccctt aaaaagacac tgtctcaact gtggtgttag   1860

caccagccag ctctctgtac atttgctagc ttgtagtttt ctaagactga gtaaacttct   1920

tatttttaga aagtggaggt ctggtttgta actttccttg tacttaattg ggtaaaagtc   1980

ttttccacaa accaccatct attttgtgaa ctttgttagt catcttttat ttggtaaatt   2040

atgaactggt gtaaatttgt acagttcatg tatattgatt gtggcaaagt tgtacagatt   2100

tctatatttt ggatgagaaa tttttcttct ctctataata aatcgtttct tatcttggca   2160

ttttaatcaa tctctgtcat gatagaggtt gctaaagtat tttctagaga acggttctat   2220

aaactgaata tctgttgcac actggtcatg c                                  2251
```

<210> SEQ ID NO 9
<211> LENGTH: 2060
<212> TYPE: DNA
<213> ORGANISM: Homo sapiens

<400> SEQUENCE: 9

```
atttttggcc ctcgtgacag tgattgatag ctgctgggaa ggtataaaag cagcttgcct     60

gcgaaggttc ttcacactgc tcagggaaga gcctgctacg gtggactgtg agactcagtg    120

cactgtcctc ctcccagcga ccccacgctg gaccccctgc cggaccctcc acccttcggc    180

ccccaagctt cccaggggct tcctttggac tggactgtcc ctgctcatcc attctcctgc    240

cacccccaga cctcctcagc tccaggttgc cacctcctct cgccagagtg atgaggtccc    300

ggcttctgct ctccgtggcc catctgccca caattcggga gaccacggag gagatgctgc    360

ttgggggtcc tggacaggag cccccaccct ctcctagcct ggatgactac gtgaggtcta    420

tatctcgact ggcacagccc acctctgtgc tggacaaggc cacggcccag ggccaaccca    480

ggccacccca caggccagcc caggcctgcc ggaagggccg ccctgctgtg tccctgcgag    540

acatcaccgc acgtttcagt ggccagcagc ccacactgcc catggctgat actgtggacc    600
```

-continued

```
ccctggactg gctttttggg gagtcccagg aaaagcagcc aagccagagg gacctgccaa    660

ggaggactgg cccctctgct ggcctctggg gtccacatag acagatggac agcagcaagc    720

ccatggggc ccccagaggg aggctctgtg aagccaggat gcctgggcat tccctggcaa    780

gaccaccgca ggatgggcag cagagctctg acctaagaag ctggactttt gggcagtctg    840

cccaagccat ggcctcccgc caccgccccc gccccagcag tgtcctcaga acactctact    900

cgcacctccc ggtgatccat gaactctgac ccctccccag taaaggcttc tgtagagagc    960

atgctgggtc tgcatctcct ctcgtctcct ccatggtggt cactgcccct ggcaggtctc   1020

tgaaagggaa atgcttttct gcagaggccc ctgcttgggc agttcacagt gagaccgacc   1080

ccctctgaat atgataacag cctgtttcac atgaggagat gttaccaatc ccgttcgctc   1140

tgacccttgc tggctgatca ccttgagcaa cttacttaac atctgtgttc ctcagtttct   1200

catgggtaat atagggataa ttactggcac ctgcctccca ggccattctg acgtgtaacc   1260

gcatatagga gcccactggc tgagtagcta ccatcatcgc tggtggggaa actggtggta   1320

ggggtgtgag ggtagtgggg gtgtcagccc cccaggtgtt tcagaacaag gcctcgggca   1380

ctcccaagtc tgcctcttgg ctcccaccct caaagcccat gttctgtgag gcccaagaga   1440

acacatggag tcttagcaaa tgcactaatg tattccgggg gactgtcacc tggcaccact   1500

ggggcactct gctggctaca actcatacgt cctgtggtgg cattgggaga gttcccccat   1560

gatgagggcc aagatagaat ctgtaccact cagtgctacc atccccaccc ctacaccact   1620

tccacacagg ggcctcatgg catggtcagg gtcccagctg tgggtgagag cagggcactg   1680

tccagctgtc cactggggaa gtcaagatgt cctaaggccc aggtcagggc atctggagtc   1740

tgaaggaccc tagttcctag aggcatctgg cagcaagaag gtgaggcatc agggaacggg   1800

aatcaggctg ggactgatca gaggtgaagg gacagagaga ggagaggagg aagattgagc   1860

tgggggcaac agccaagctc acctgggcag gtctctgcca cctccttgct ctgtgagctg   1920

tcagtctagg ttattctctt tttttgtggc tatttttaat tgctttggat ttgttaaatg   1980

ttttctgtct tctgttaagt gtgttttctc tggagataga atgtaaacca tattaaaagg   2040

aaaaagtttc agacaagcaa                                                2060
```

<210> SEQ ID NO 10
<211> LENGTH: 2300
<212> TYPE: DNA
<213> ORGANISM: Homo sapiens

<400> SEQUENCE: 10

```
actcggggca acaggcagat ttgcctgctg agggtggaga cccacgagcc gaggcctcct     60

gcagtgttct gcacagcaaa ccgcacgcta tggctgacag ccgggatccc gccagcgacc    120

agatgcagca ctggaaggag cagcgggccg cgcagaaagc tgatgtcctg accactggag    180

ctggtaaccc agtaggagac aaacttaatg ttattacagt agggccccgt gggccccttc    240

ttgttcagga tgtggttttc actgatgaaa tggctcattt tgaccgagag agaattcctg    300

agagagttgt gcatgctaaa ggagcagggg cctttggcta ctttgaggtc acacatgaca    360

ttaccaaata ctccaaggca aaggtatttg agcatattgg aaagaagact cccatcgcag    420

ttcggttctc cactgttgct ggagaatcgg gttcagctga cacagttcgg gaccctcgtg    480

ggtttgcagt gaaattttac acagaagatg gtaactggga tctcgttgga aataacaccc    540

ccattttctt catcagggat cccatattgt ttccatcttt tatccacagc caaaagagaa    600

atcctcagac acatctgaag gatccggaca tggtctggga cttctggagc ctacgtcctg    660
```

```
agtctctgca tcaggtttct ttcttgttca gtgatcgggg gattccagat ggacatcgcc    720

acatgaatgg atatggatca catactttca agctggttaa tgcaaatggg gaggcagttt    780

attgcaaatt ccattataag actgaccagg gcatcaaaaa cctttctgtt gaagatgcgg    840

cgagactttc ccaggaagat cctgactatg gcatccggga tctttttaac gccattgcca    900

caggaaagta cccctcctgg actttttaca tccaggtcat gacatttaat caggcagaaa    960

cttttccatt taatccattc gatctcacca aggtttggcc tcacaaggac taccctctca   1020

tcccagttgg taaactggtc ttaaaccgga atccagttaa ttactttgct gaggttgaac   1080

agatagcctt cgacccaagc aacatgccac ctggcattga ggccagtcct gacaaaatgc   1140

ttcagggccg cctttttgcc tatcctgaca ctcaccgcca tcgcctggga cccaattatc   1200

ttcatatacc tgtgaactgt ccctaccgtg ctcgagtggc caactaccag cgtgacggcc   1260

cgatgtgcat gcaggacaat cagggtggtg ctccaaatta ctaccccaac agctttggtg   1320

ctccggaaca acagccttct gccctggagc acagcatcca atattctgga gaagtgcgga   1380

gattcaacac tgccaatgat gataacgtta ctcaggtgcg ggcattctat gtgaacgtgc   1440

tgaatgagga acagaggaaa cgtctgtgtg agaacattgc cggccacctg aaggatgcac   1500

aaattttcat ccagaagaaa gcggtcaaga acttcactga ggtccaccct gactacggga   1560

gccacatcca ggctcttctg gacaagtaca atgctgagaa gcctaagaat gcgattcaca   1620

cctttgtgca gtccggatct cacttggcgg caagggagaa ggcaaatctg tgaggccggg   1680

gccctgcacc tgtgcagcga agcttagcgt tcatccgtgt aacccgctca tcactggatg   1740

aagattctcc tgtgctagat gtgcaaatgc aagctagtgg cttcaaaata gagaatccca   1800

ctttctatag cagattgtgt aacaatttta atgctatttc cccaggggaa aatgaaggtt   1860

aggatttaac agtcatttaa aaaaaaaatt tgttttgacg gatgattgga ttattcattt   1920

aaaatgatta gaaggcaagt ttctagctag aaatatgatt ttatttgaca aaatttgttg   1980

aaattatgta tgtttacata tcacctcatg gcctattata ttaaaatatg gctataaata   2040

tataaaaaga aaagataaag atgatctact cagaaatttt tatttttcta aggttctcat   2100

aggaaaagta catttaatac agcagtgtca tcagaagata acttgagcac cgtcatggct   2160

taatgtttat tcctgataat aattgatcaa attcattttt ttcactggag ttacattaat   2220

gttaattcag cactgatttc acaacagatc aatttgtaat tgcttacatt tttacaataa   2280

ataatctgta cgtaagaaca                                                2300
```

<210> SEQ ID NO 11
<211> LENGTH: 2723
<212> TYPE: DNA
<213> ORGANISM: Homo sapiens

<400> SEQUENCE: 11

```
gggagaaacg ttctcactcg ctctctgctc gctgcgggcg ctccccgccc tctgctgcca     60

gaaccttggg gatgtgccta gacccggcgc agcacacgtc cgggccaacc gcgagcagaa    120

caaacctttg gcgggcggcc aggaggctcc ctcccagcca ccgccccccct ccagcgcctt    180

tttttccccc catacaatac aagatcttcc ttcctcagtt cccttaaagc acagcccagg    240

gaaacctcct cacagttttc atccagccac gggccagcat gtctgggggc aaatacgtag    300

actcggaggg acatctctac accgttccca tccgggaaca gggcaacatc tacaagccca    360

acaacaaggc catggcagac gagctgagcg agaagcaagt gtacgacgcg cacaccaagg    420
```

-continued

```
agatcgacct ggtcaaccgc gaccctaaac acctcaacga tgacgtggtc aagattgact    480

ttgaagatgt gattgcagaa ccagaaggga cacacagttt tgacggcatt tggaaggcca    540

gcttcaccac cttcactgtg acgaaatact ggttttaccg cttgctgtct gccctctttg    600

gcatcccgat ggcactcatc tggggcattt acttcgccat tctctctttc ctgcacatct    660

gggcagttgt accatgcatt aagagcttcc tgattgagat tcagtgcatc agccgtgtct    720

attccatcta cgtccacacc gtctgtgacc cactctttga agctgttggg aaaatattca    780

gcaatgtccg catcaacttg cagaaagaaa tataaatgac atttcaagga tagaagtata    840

cctgattttt tttcctttta attttcctgg tgccaatttc aagttccaag ttgctaatac    900

agcaacaatt tatgaattga attatcttgg ttgaaaataa aaagatcact ttctcagttt    960

tcataagtat tatgtctctt ctgagctatt tcatctattt ttggcagtct gaatttttaa   1020

aacccattta aatttttttc cttacctttt tatttgcatg tggatcaacc atcgctttat   1080

tggctgagat atgaacatat tgttgaaagg taatttgaga gaaatatgaa gaactgagga   1140

ggaaaaaaaa aaaaaagaaa agaaccaaca acctcaactg cctactccaa aatgttggtc   1200

attttatgtt aagggaagaa ttccagggta tggccatgga gtgtacaagt atgtgggcag   1260

attttcagca aactcttttc ccactgttta aggagttagt ggattactgc cattcacttc   1320

ataatccagt aggatccagt gatccttaca agttagaaaa cataatcttc tgccttctca   1380

tgatccaact aatgccttac tcttcttgaa attttaacct atgatatttt ctgtgcctga   1440

atatttgtta tgtagataac aagacctcag tgccttcctg tttttcacat tttccttttc   1500

aaatagggtc taactcagca actcgcttta ggtcagcagc ctccctgaag accaaaatta   1560

gaatatccat gacctagttt tccatgcgtg tttctgactc tgagctacag agtctggtga   1620

agctcacttc tgggcttcat ctggcaacat ctttatccgt agtgggtatg gttgacacta   1680

gcccaatgaa atgaattaaa gtggaccaat agggctgagc tctctgtggg ctggcagtcc   1740

tggaagccag ctttccctgc ctctcatcaa ctgaatgagg tcagcatgtc tattcagctt   1800

cgtttatttt caagaataat cacgctttcc tgaatccaaa ctaatccatc accggggtgg   1860

tttagtggct caacattgtg ttcccatttc agctgatcag tgggcctcca aggaggggct   1920

gtaaaatgga ggccattgtg tgagcctatc agagttgctg caaacctgac ccctgctcag   1980

taaagcactt gcaaccgtct gttatgctgt gacacatggc cctcccccct gccaggagct   2040

ttggacctaa tccaagcatc cctttgccca gaaagaagat gggggaggag gcagtaataa   2100

aaagattgaa gtattttgct ggaataagtt caaattcttc tgaactcaaa ctgaggaatt   2160

tcacctgtaa acctgagtcg tacagaaagc tgcctggtat atccaaaagc tttttattcc   2220

tcctgctcat attgtgattc tgcctttggg gacttttctt aaaccttcag ttatgatttt   2280

tttttcatac acttattgga actctgcttg atttttgcct cttccagtct tcctgacact   2340

ttaattacca acctgttacc tactttgact ttttgcattt aaaacagaca ctggcatgga   2400

tatagtttta cttttaaact gtgtacataa ctgaaaatgt gctatactgc atacttttta   2460

aatgtaaaga tatttttatc tttatatgaa gaaaatcact taggaaatgg ctttgtgatt   2520

caatctgtaa actgtgtatt ccaagacatg tctgttctac atagatgctt agtccctcat   2580

gcaaatcaat tactggtcca aaagattgct gaaattttat atgcttactg atatatttta   2640

caatttttta tcatgcatgt cctgtaaagg ttacaagcct gcacaataaa aatgtttaac   2700

ggttaaacag tcaaaaaaaa aaa                                           2723
```

<210> SEQ ID NO 12
<211> LENGTH: 3976
<212> TYPE: DNA
<213> ORGANISM: Homo sapiens

<400> SEQUENCE: 12

```
ctgggtcctg tgtgtgccac aggggtgggg tgtccagcga gcggtctcct cctcctgcta     60
gtgctgctgc ggcgtcccgc ggcctccccg agtcgggcgg gaggggagag cgggtgtgga    120
tttgtcttga cggtaattgt tgcgtttcca cgtctcggag gcctgcgcgc tgggttgctc    180
cttcttcggg agcgagctgt tctcagcgat cccactccca gccggggctc cccacacaca    240
ctgggctgcg tgcgtgtgga gtgggacccg cgcacacgcg tgtctctgga cagctacggc    300
gccgaaagaa ctaaaattcc agatggcaaa ctcaatgaat ggcagaaacc ctggtggtcg    360
aggaggaaat ccccgaaaag gtcgaatttt gggtattatt gatgctattc aggatgcagt    420
tggacccccct aagcaagctg ccgcagatcg caggaccgtg gagaagactt ggaagctcat    480
ggacaaagtg gtaagactgt gccaaaatcc caaacttcag ttgaaaaata gcccaccata    540
tatacttgat attttgcctg atacatatca gcatttacga cttatattga gtaaatatga    600
tgacaaccag aaacttgccc aactcagtga gaatgagtac tttaaaatct acattgatag    660
ccttatgaaa aagtcaaaac gggcaataag actctttaaa gaaggcaagg agagaatgta    720
tgaagaacag tcacaggaca gacgaaatct cacaaaactg tcccttatct tcagtcacat    780
gctggcagaa atcaaagcaa tctttcccaa tggtcaattc cagggagata actttcgtat    840
cacaaaagca gatgctgctg aattctggag aaagtttttt ggagacaaaa ctatcgtacc    900
atggaaagta ttcagacagt gccttcatga ggtccaccag attagctctg gcctggaagc    960
aatggctcta aaatcaacaa ttgatttaac ttgcaatgat tacatttcag tttttgaatt   1020
tgatattttt accaggctgt ttcagccttg gggctctatt ttgcggaatt ggaatttctt   1080
agctgtgaca catccaggtt acatggcatt tctcacatat gatgaagtta aagcacgact   1140
acagaaatat agcaccaaac ccggaagcta tattttccgg ttaagttgca ctcgattggg   1200
acagtgggcc attggctatg tgactgggga tgggaatatc ttacagacca tacctcataa   1260
caagccctta tttcaagccc tgattgatgg cagcagggaa ggattttatc tttatcctga   1320
tgggaggagt tataatcctg atttaactgg attatgtgaa cctacacctc atgaccatat   1380
aaaagttaca caggaacaat atgaattata ttgtgaaatg ggctccactt ttcagctctg   1440
taagatttgt gcagagaatg acaaagatgt caagattgag ccttgtgggc atttgatgtg   1500
cacctcttgc cttacggcat ggcaggagtc ggatggtcag ggctgccctt tctgtcgttg   1560
tgaaataaaa ggaactgagc ccataatcgt ggaccccttt gatccaagag atgaaggctc   1620
caggtgttgc agcatcattg accccctttgg catgccgatg ctagacttgg acgacgatga   1680
tgatcgtgag gagtccttga tgatgaatcg gttggcaaac gtccgaaagt gcactgacag   1740
gcagaactca ccagtcacat caccaggatc ctctcccctt gcccagagaa gaaagccaca   1800
gcctgaccca ctccagatcc cacatctaag cctgccaccc gtgcctcctc gcctggatct   1860
aattcagaaa ggcatagtta gatctccctg tggcagccca acgggttcac caaagtcttc   1920
tccttgcatg gtgagaaaac aagataaacc actcccagca ccacctcctc ccttaagaga   1980
tcctcctcca ccgccacctg aaagacctcc accaatccca ccagacaata gactgagtag   2040
acacatccat catgtggaaa gcgtgccttc cagagacccg ccaatgcctc ttgaagcatg   2100
gtgccctcgg gatgtgtttg ggactaatca gcttgtggga tgtcgactcc taggggaggg   2160
```

ctctccaaaa cctggaatca cagcgagttc aaatgtcaat ggaaggcaca gtagagtggg 2220
ctctgaccca gtgcttatgc ggaaacacag acgccatgat ttgcctttag aaggagctaa 2280
ggtcttttcc aatggtcacc ttggaagtga agaatatgat gttcctcccc ggctttctcc 2340
tcctcctcca gttaccaccc tcctccctag cataaagtgt actggtccgt tagcaaattc 2400
tctttcagag aaaacaagag acccagtaga ggaagatgat gatgaataca agattccttc 2460
atcccaccct gtttccctga attcacaacc atctcattgt cataatgtaa aacctcctgt 2520
tcggtcttgt gataatggtc actgtatgct gaatggaaca catggtccat cttcagagaa 2580
gaaatcaaac atccctgact taagcatata tttaaaggga gatgtttttg attcagcctc 2640
tgatcccgtg ccattaccac ctgccaggcc tccaactcgg gacaatccaa agcatggttc 2700
ttcactcaac aggacgccct ctgattatga tcttctcatc cctccattag gtgaagatgc 2760
ttttgatgcc ctccctccat ctctcccacc tcccccacct cctgcaaggc atagtctcat 2820
tgaacattca aaacctcctg gctccagtag ccggccatcc tcaggacagg atctttttct 2880
tcttccttca gatccctttg ttgatctagc aagtggccaa gttcctttgc ctcctgctag 2940
aaggttacca ggtgaaaatg tcaaaactaa cagaacatca caggactatg atcagcttcc 3000
ttcatgttca gatggttcac aggcaccagc cagaccccct aaaccacgac cgcgcaggac 3060
tgcaccagaa attcaccaca gaaaacccca tgggcctgag gcggcattgg aaaatgtcga 3120
tgcaaaaatt gcaaaactca tgggagaggg ttatgccttt gaagaggtga agagagcctt 3180
agagatagcc cagaataatg tcgaagttgc ccggagcatc ctccgagaat ttgccttccc 3240
tcctccagta tccccacgtc taaatctata gcagccagaa ctgtagacac caaaatggaa 3300
agcaatcgat gtattccaag agtgtggaaa taaagagaac tgagatggaa ttcaagagag 3360
aagtgtctcc tcctcgtgta gcagcttgag aagaggcttg ggagtgcagc ttctcaaagg 3420
agaccgatgc ttgctcagga tgtcgacagc tgtggcttcc ttgtttttgc tagccatatt 3480
tttaaatcag ggttgaactg acaaaaataa tttaaagacg tttacttccc ttgaactttg 3540
aacctgtgaa atgctttacc ttgtttacag tttggcaaag ttgcagtttg ttcttgtttt 3600
tagtttagtt ttgttttggt gttttgatac ctgtactgtg ttcttcacag accctttgta 3660
gcgtggtcag gtctgctgta acatttccca ccaactctct tgctgtccac atcaacagct 3720
aaatcattta ttcatatgga tctctaccat ccccatgcct tgcccaggtc cagttccatt 3780
tctctcattc acaagatgct ttgaaggttc tgattttcaa ctgatcaaac taatgcaaaa 3840
aaaaaaaagt atgtattctt cactactgag tttcttcttt ggaaaccatc actattgaga 3900
gatgggaaaa acctgaatgt ataaagcatt tatttgtcaa taaactgcct tttgtaaggg 3960
gttttcacat aacata 3976

<210> SEQ ID NO 13
<211> LENGTH: 4304
<212> TYPE: DNA
<213> ORGANISM: Homo sapiens

<400> SEQUENCE: 13
cacacggact acaggggagt tttgttgaag ttgcaaagtc ctggagcctc cagagggctg 60
tcggcgcagt agcagcgagc agcagagtcc gcacgctccg gcgaggggca gaagagcgcg 120
agggagcgcg gggcagcaga agcgagagcc gagcgcggac ccagccagga cccacagccc 180
tccccagctg cccaggaaga gccccagcca tggaacacca gctcctgtgc tgcgaagtgg 240
aaaccatccg ccgcgcgtac cccgatgcca acctcctcaa cgaccgggtg ctgcgggcca 300

```
tgctgaaggc ggaggagacc tgcgcgccct cggtgtccta cttcaaatgt gtgcagaagg    360
aggtcctgcc gtccatgcgg aagatcgtcg ccacctggat gctggaggtc tgcgaggaac    420
agaagtgcga ggaggaggtc ttcccgctgg ccatgaacta cctggaccgc ttcctgtcgc    480
tggagcccgt gaaaaagagc cgcctgcagc tgctgggggc cacttgcatg ttcgtggcct    540
ctaagatgaa ggagaccatc cccctgacgg ccgagaagct gtgcatctac accgacaact    600
ccatccggcc cgaggagctg ctgcaaatgg agctgctcct ggtgaacaag ctcaagtgga    660
acctggccgc aatgaccccg cacgatttca ttgaacactt cctctccaaa atgccagagg    720
cggaggagaa caaacagatc atccgcaaac acgcgcagac cttcgttgcc ctctgtgcca    780
cagatgtgaa gttcatttcc aatccgccct ccatggtggc agcggggagc gtggtggccg    840
cagtgcaagg cctgaacctg aggagcccca acaacttcct gtcctactac cgcctcacac    900
gcttcctctc cagagtgatc aagtgtgacc cggactgcct ccgggcctgc caggagcaga    960
tcgaagccct gctggagtca agcctgcgcc aggcccagca gaacatggac cccaaggccg   1020
ccgaggagga ggaagaggag gaggaggagg tggacctggc ttgcacaccc accgacgtgc   1080
gggacgtgga catctgaggg cgccaggcag gcgggcgcca ccgccacccg cagcgagggc   1140
ggagccggcc ccaggtgctc ccctgacagt ccctcctctc cggagcattt tgataccaga   1200
agggaaagct tcattctcct tgttgttggt tgtttttcc tttgctcttt ccccccttcca   1260
tctctgactt aagcaaaaga aaaagattac ccaaaaactg tctttaaaag agagagagag   1320
aaaaaaaaaa tagtatttgc ataaccctga gcggtggggg aggagggttg tgctacagat   1380
gatagaggat tttatacccc aataatcaac tcgtttttat attaatgtac ttgtttctct   1440
gttgtaagaa taggcattaa cacaaaggag gcgtctcggg agaggattag gttccatcct   1500
ttacgtgttt aaaaaaaagc ataaaaacat tttaaaaaca tagaaaaatt cagcaaacca   1560
tttttaaagt agaagagggt tttaggtaga aaaacatatt cttgtgcttt tcctgataaa   1620
gcacagctgt agtggggttc taggcatctc tgtactttgc ttgctcatat gcatgtagtc   1680
actttataag tcattgtatg ttattatatt ccgtaggtag atgtgtaacc tcttcacctt   1740
attcatggct gaagtcacct cttggttaca gtagcgtagc gtgcccgtgt gcatgtcctt   1800
tgcgcctgtg accaccaccc caacaaacca tccagtgaca aaccatccag tggaggtttg   1860
tcgggcacca gccagcgtag cagggtcggg aaaggccacc tgtcccactc ctacgatacg   1920
ctactataaa gagaagacga aatagtgaca taatatattc tatttttata ctcttcctat   1980
ttttgtagtg acctgtttat gagatgctgg ttttctaccc aacggccctg cagccagctc   2040
acgtccaggt tcaacccaca gctacttggt ttgtgttctt cttcatattc taaaaccatt   2100
ccatttccaa gcactttcag tccaataggt gtaggaaata gcgctgtttt tgttgtgtgt   2160
gcagggaggg cagttttcta atggaatggt ttgggaatat ccatgtactt gtttgcaagc   2220
aggactttga ggcaagtgtg ggccactgtg gtggcagtgg aggtggggtg tttgggaggc   2280
tgcgtgccag tcaagaagaa aaaggtttgc attctcacat tgccaggatg ataagttcct   2340
ttcctttttct ttaaagaagt tgaagtttag gaatcctttg gtgccaactg gtgtttgaaa   2400
gtagggacct cagaggttta cctagagaac aggtggtttt taagggttat cttagatgtt   2460
tcacaccgga aggtttttaa acactaaaat atataattta tagttaaggc taaaaagtat   2520
atttattgca gaggatgttc ataaggccag tatgatttat aaatgcaatc tccccttgat   2580
ttaaacacac agatacacac acacacacac acacacacaa accttctgcc tttgatgtta   2640
```

```
cagatttaat acagtttatt tttaaagata gatcctttta taggtgagaa aaaaacaatc   2700
tggaagaaaa aaaccacaca aagacattga ttcagcctgt ttggcgtttc ccagagtcat   2760
ctgattggac aggcatgggt gcaaggaaaa ttagggtact caacctaagt tcggttccga   2820
tgaattctta tcccctgccc cttcctttaa aaaacttagt gacaaaatag acaatttgca   2880
catcttggct atgtaattct tgtaattttt atttaggaag tgttgaaggg aggtggcaag   2940
agtgtggagg ctgacgtgtg agggaggaca ggcgggagga ggtgtgagga ggaggctccc   3000
gaggggaagg ggcggtgccc acaccgggga caggccgcag ctccattttc ttattgcgct   3060
gctaccgttg acttccaggc acggtttgga aatattcaca tcgcttctgt gtatctcttt   3120
cacattgttt gctgctattg gaggatcagt tttttgtttt acaatgtcat atactgccat   3180
gtactagttt tagttttctc ttagaacatt gtattacaga tgcctttttt gtagtttttt   3240
ttttttttat gtgatcaatt ttgacttaat gtgattactg ctctattcca aaaaggttgc   3300
tgtttcacaa tacctcatgc ttcacttagc catggtggac ccagcgggca ggttctgcct   3360
gctttggcgg gcagacacgc gggcgcgatc ccacacaggc tggcgggggc cggcccccgag   3420
gccgcgtgcg tgagaaccgc gccggtgtcc ccagagacca ggctgtgtcc ctcttctctt   3480
ccctgcgcct gtgatgctgg gcacttcatc tgatcggggg cgtagcatca tagtagtttt   3540
tacagctgtg ttattctttg cgtgtagcta tggaagttgc ataattatta ttattattat   3600
tataacaagt gtgtcttacg tgccaccacg gcgttgtacc tgtaggactc tcattcggga   3660
tgattggaat agcttctgga atttgttcaa gttttgggta tgtttaatct gttatgtact   3720
agtgttctgt ttgttattgt tttgttaatt acaccataat gctaatttaa agagactcca   3780
aatctcaatg aagccagctc acagtgctgt gtgccccggt cacctagcaa gctgccgaac   3840
caaaagaatt tgcaccccgc tgcgggccca cgtggttggg gccctgccct ggcagggtca   3900
tcctgtgctc ggaggccatc tcgggcacag gcccaccccg ccccacccct ccagaacacg   3960
gctcacgctt acctcaacca tcctggctgc ggcgtctgtc tgaaccacgc gggggccttg   4020
agggacgctt tgtctgtcgt gatggggcaa gggcacaagt cctggatgtt gtgtgtatcg   4080
agaggccaaa ggctggtggc aagtgcacgg ggcacagcgg agtctgtcct gtgacgcgca   4140
agtctgaggg tctgggcggc gggcggctgg gtctgtgcat ttctggttgc accgcggcgc   4200
ttcccagcac caacatgtaa ccggcatgtt tccagcagaa gacaaaaaga caaacatgaa   4260
agtctagaaa taaaactggt aaaaccccaa aaaaaaaaaa aaaa                    4304
```

<210> SEQ ID NO 14
<211> LENGTH: 6531
<212> TYPE: DNA
<213> ORGANISM: Homo sapiens

<400> SEQUENCE: 14

```
gcccagccag cttgcgtcac cgcttcagag cggagaagag cgagcagggg agagcgagac     60
cagttttaag gggaggaccg gtgcgagtga ggcagccccg aggctctgct cgcccaccac    120
ccaatcctcg cctcccttct gctccacctt ctctctctgc cctcacctct cccccgaaaa    180
ccccctattt agccaaagga aggaggtcag gggaacgctc tcccctcccc ttccaaaaaa    240
caaaaacaga aaaacccttt tccaggccgg ggaaagcagg agggagaggg gccgccgggc    300
tggccatgga gctgctgtgc cacgaggtgg acccggtccg cagggccgtg cgggaccgca    360
acctgctccg agacgaccgc gtcctgcaga acctgctcac catcgaggag cgctaccttc    420
cgcagtgctc ctacttcaag tgcgtgcaga aggacatcca accctacatg cgcagaatgg    480
```

```
tggccacctg gatgctggag gtctgtgagg aacagaagtg cgaagaagag gtcttccctc    540
tggccatgaa ttacctggac cgtttcttgg ctggggtccc gactccgaag tcccatctgc    600
aactcctggg tgctgtctgc atgttcctgg cctccaaact caaagagacc agcccgctga    660
ccgcggagaa gctgtgcatt tacaccgaca actccatcaa gcctcaggag ctgctggagt    720
gggaactggt ggtgctgggg aagttgaagt ggaacctggc agctgtcact cctcatgact    780
tcattgagca catcttgcgc aagctgcccc agcagcggga gaagctgtct ctgatccgca    840
agcatgctca gaccttcatt gctctgtgtg ccaccgactt taagtttgcc atgtacccac    900
cgtcgatgat cgcaactgga agtgtgggag cagccatctg tgggctccag caggatgagg    960
aagtgagctc gctcacttgt gatgccctga ctgagctgct ggctaagatc accaacacag   1020
acgtggattg tctcaaagct tgccaggagc agattgaggc ggtgctcctc aatagcctgc   1080
agcagtaccg tcaggaccaa cgtgacggat ccaagtcgga ggatgaactg gaccaagcca   1140
gcacccctac agacgtgcgg gatatcgacc tgtgaggatg ccagttgggc cgaaagagag   1200
agacgcgtcc ataatctggt ctcttcttct ttctggttgt ttttgttctt tgtgttttag   1260
ggtgaaactt aaaaaaaaaa ttctgccccc acctagatca tatttaaaga tcttttagaa   1320
gtgagagaaa aaggtcctac gaaaacggaa taataaaaag catttggtgc ctatttgaag   1380
tacagcataa gggaatccct tgtatatgcg aacagttatt gtttgattat gtaaaagtaa   1440
tagtaaaatg cttacaggaa aacctgcaga gtagttagag aatatgtatg cctgcaatat   1500
gggaacaaat tagaggagac tttttttttt catgttatga gctagcacat acaccccctt   1560
gtagtataat ttcaaggaac tgtgtacgcc atttatggca tgattagatt gcaaagcaat   1620
gaactcaaga aggaattgaa ataaggaggg acatgatggg gaaggagtac aaaacaatct   1680
ctcaacatga ttgaaccatt tgggatggag aagcaccttt gctctcagcc acctgttact   1740
aagtcaggag tgtagttgga tctctacatt aatgtcctct tgctgtctac agtagctgct   1800
acctaaaaaa agatgtttta ttttgccagt tggacacagg tgattggctc ctgggtttca   1860
tgttctgtga catcctgctt cttcttccaa atgcagttca ttgcagacac caccatattg   1920
ctatctaatg gggaaatgta gctatgggcc ataaccaaaa ctcacatgaa acggaggcag   1980
atggagacca agggtgggat ccagaatgga gtcttttctg ttattgtatt taaaagggta   2040
atgtggcctt ggcatttctt cttagaaaaa aactaatttt tggtgctgat tggcatgtct   2100
ggttcacagt ttagcattgt tataaaccat tccattcgaa aagcactttg aaaaattgtt   2160
cccgagcgat agatgggatg gtttatgcaa gtcatgctga atactcctcc cctcttctct   2220
tttgcccccct cccttcctgc ccccagtctg ggttactctt cgcttctggt atctggcgtt   2280
ctttggtaca cagttctggt gttcctacca ggactcaaga gacacccctt cctgctgaca   2340
ttcccatcac aacattcctc agacaagcct gtaaactaaa atctgttacc attctgatgg   2400
cacagaagga tcttaattcc catctctata cttctccttt ggacatggaa agaaaagtta   2460
ttgctggtgc aaagatagat ggctgaacat cagggtgtgg cattttgttc ccttttccgt   2520
tttttttttt ttattgttgt tgttaatttt attgcaaagt tgtattcagc gtacttgaat   2580
ttttcttcct ctccacttct tagaggcatt cagttagcaa agaggttgga gcaacaactt   2640
tttttttttt ttttgcacaa ttgtaattga caggtaatga agctatttgt taaaatattt   2700
gccttttttaa gtaaaaaaga aaaatcagaa cagggctatt tgaagaatta ttttatacac   2760
agattctgcc ttgtttcata gtatgagggt tgaagacgga aaacaatcta agggtctctc   2820
```

-continued

```
atttttttaa ttttgttttg ttcagtttgg tttttttttt tttttgcgct gctaagaagc   2880
taaagtcatc catccttatt cacgttgaca gtacctagct gtaatgtttc acagagtgtg   2940
ctgctatttt ataaacattt ttataatata ttattttact gcttaaattc caagtcctga   3000
agtagatggt tgagatatga gttcttcgta ctggaaaagc ccttccgtag tttgttttct   3060
tctggtagca tattcatggt tgtttttttt tttctttttt ggttttttgg tttttttttt   3120
ttcctctgat cacattcttc aaagacggag tattctttac ctcaggttta ctggacaaaa   3180
tcaataacta caaaaggcaa tgattcacgc ttttgttttc ataatacctc acaaccgtac   3240
agtttctgct tgggagccca ttcgcatgag gaatacagaa gcagtgtgag cagggctgac   3300
tccctctcag gtggaaggca gggcggtctc actcccaggg accttttttgg tcatggaggc   3360
catcgggctc ccagttagac cctggtatcc tcatcatgat ggaaaaaata cattgaacca   3420
agggatcctc cctccccttc aaggcagacg ttcagtacaa acatttatgc ggtaggctca   3480
gatgtcgtaa tttgcactta ggtaccaggt gtcaggaaac agactaaaaa gaattccacc   3540
aggctgtttg gagatcctca tcttggagct tttcaaaag cggggcttca tctgcaaagg   3600
gccctttcat cttgaagttt ttcccctccg tctttcccct cccctggcat ggacaccttg   3660
tgtttaggat catctctgca ggtttcctag gtctgaatct gcgagtagat gaacctgcag   3720
caagcagcgt ttatggtgct tccttctccc tcctctgtct caaactgcgc aggcaagcac   3780
tatgcaagcc caggccctct gctgagcggt actaaacggt cgggttttca atcacactga   3840
attggcagga taagaaaaat aggtcagata agtatgggat gatagttgaa gggaggtgaa   3900
gaggctgctt ctctacagag gtgaaattcc agatgagtca gtctcttggg aagtgtgttt   3960
agaagggttc aggactttgt gagttagcat gaccctaaaa ttctagggga tttctggtgg   4020
gacaatgggt ggtgaattct gaagttttgg agagggaagt ggagcagcca gcaagtaagc   4080
tagccagagt tttctcaaga gccagctttg ctcagcacac tctcctgggc cccaaggagt   4140
cccacggaat ggggaaagcg ggaaccctgg agttcttggg aatcttggag cctaaagaga   4200
aaccgaggtg caaattcatt tcatggtgac tgacccttga gcttaaacag aagcagcaaa   4260
tgaaagaacc ggacaaataa ggaagggcac aagcctaccc gactctattt acagtctgta   4320
actttccact cttcctgtag tcccgaggcc cctgggtcct tctagctttt ctctttccca   4380
tccttggggc cttgtgtgat gatgggtgtg gggctgccga tgggaaagtc gggggttgtt   4440
aggcttttct gcctgctcct gcttaaacac aagaaggaat cctggatttt gccctctcct   4500
tagctcttag tctctttggt aggagttttg ttccagagga gctctccccc ttggatttga   4560
acttgctctt tttgttgttg ttgttctttc tcttcttttt cttacctccc actaaagggg   4620
ttccaaatta tcctggtctt tttctacctt gttgtgtttc tatctcgtct ttacttccat   4680
ctgtttgttt ttttctccat cagtgggggc cgagttgttc ccccagcctg ccaaattttg   4740
atccttcccc tcttttggcc aaatcctagg gggaagaaat cctagtatgc caaaaatata   4800
tgctaagcat aattaaactc catgcgggtc cataacagcc aagaagcctg caggagaaag   4860
ccaagggcag ttccctccgc agaacacccc atgcgtgctg agaggcgagc tccttgaaga   4920
aggggctgtt cttccaggag gccttatttt gaactgcctc aggaccccac tggagagcac   4980
agcatgcctt actactgggt catccttggt ctatgtgctc tgtactggag gctctgttct   5040
gcctcttatc agccaggtca ggggcacaca tggcttaagt gacaaagcca gaggagaaga   5100
caaccctgac agcatcacgc tgcatcccat tgctagcagg attggcaact cttcagacgg   5160
agctgcgctt ccctgcagtc tagcacctct agggcctctc cagactgtgc cctgggagct   5220
```

```
ctgggactga aaggttaaga acataaggca ggatcagatg actctctcca agagggcagg   5280

ggaattttct ctccatgggc cacaggggac agggctggga gaagaaatag acttgcacct   5340

tatgtcatgt aaataattga ttttctagtt caagaagata atattggtag tgtgggaatt   5400

ggaggtagga aggggaggaa gtctgagtaa gccagttggc ttctaagcca aaaggattcc   5460

tctttgttta tctctgagac agtccaacct tgagaatagc tttaaaaggg aaattaatgc   5520

tgagatgata aagtcccctt aagccaacaa accctctgta gctatagaat gagtgcaggt   5580

ttctattggt gtggactcag agcaatttac aagagctgtt catgcagcca tccatttgtg   5640

caaaataggg taagaagatt caagaggata tttattactt cctcatacca catggctttt   5700

gatgattctg gattctaaac aacccagaat ggtcatttca ggcacaacga tactacattc   5760

gtgtgtgtct gcttttaaac ttggctgggc tatcagaccc tattctcggc tcaggttttg   5820

agaagccatc agcaaatgtg tacgtgcatg ctgtagctgc agcctgcatc ccttcgcctg   5880

cagcctactt tggggaaata aagtgcctta ctgactgtag ccattacagt atccaatgtc   5940

ttttgacagg tgcctgtcct tgaaaaacaa agtttctatt tttattttta attggtttag   6000

ttcttaactg ctggccaact cttacatccc cagcaaatca tcgggccatt ggattttttc   6060

cattatgttc atcaccctta tatcatgtac ctcagatctc tctctctctc ctctctctca   6120

gttatgtagt ttcttgtctt ggactttttt ttttcttttc tttttctttt tttttttgct   6180

ttaaaacaag tgtgatgcca tatcaagtcc atgttattct ctcacagtgt actctataag   6240

aggtgtgggt gtctgtttgg tcaggatgtt agaaagtgct gataagtagc atgatcagtg   6300

tatgcgaaaa ggtttttagg aagtatggca aaaatgttgt attggctatg atggtgacat   6360

gatatagtca gctgcctttt aagaggtctt atctgttcag tgttaagtga tttaaaaaaa   6420

taataacctg ttttctgact agtttaaaga tggatttgaa aatggttttg aatgcaatta   6480

ggttatgcta tttggacaat aaactcacct tgacctaaat taaaaaaaaa a            6531
```

<210> SEQ ID NO 15
<211> LENGTH: 5489
<212> TYPE: DNA
<213> ORGANISM: Homo sapiens

<400> SEQUENCE: 15

```
gaaactctta acaaaaacaa ggggctcggg gaggtttccg ctgaggcggc gggggtgcgg     60

cggtgggctg gtcttccgcg gccggcgttg cgccgcggcg gagggtgggc gcgcggggag    120

cgggatggag ccggggctgt gaggccgagg cggcggtgcc tgggaggaag ggtcggatgc    180

cggaccgggg gcaccgctga ggcggtgggt ccccgacctg cgagacaggt ttggaagccc    240

ccgctgcgcc cagtccgtgc ggaccgcgag gccgcgggcg ggtggaggcg cgtctccggc    300

acgatgaagg atttgggggc agagcacttg gcaggtcatg aaggggtcca acttctcggg    360

ttgttgaacg tctacctgga acaagaagag agattccaac ctcgagaaaa agggctgagt    420

ttgattgagg ctaccccgga gaatgataac actttgtgtc caggattgag aaatgccaaa    480

gttgaagatt taaggagttt agccaacttt tttggatctt gcactgaaac ttttgtcctg    540

gctgtcaata ttttggacag gttcttggct cttatgaagg tgaaacctaa acatttgtct    600

tgcattggag tctgttcttt tttgctggct gctagaatag ttgaagaaga ctgcaatatt    660

ccatccactc atgatgtgat ccggattagt cagtgtaaat gtactgcttc tgacataaaa    720

cggatggaaa aaataatttc agaaaaattg cactatgaat tggaagctac tactgcctta    780
```

```
aactttttgc acttatacca tactattata ctttgtcata cttcagaaag gaaagaaata    840
ctgagccttg ataaactaga agctcagctg aaagcttgca actgccgact catcttttca    900
aaagcaaaac catctgtatt agccttgtgc cttctcaatt tggaagtgga aactttgaaa    960
tctgttgaat tactggaaat tctcttgcta gttaaaaaac attccaagat taatgacact   1020
gagttcttct actggagaga gttggtttct aaatgcctag ccgagtattc ttctcctgaa   1080
tgttgcaaac cagatcttaa gaagttggtt tggatcgttt caaggcgcac agcccagaac   1140
ctccacaaca gctactatag tgttcctgag ctgccaacga tacctgaggg gggttgtttt   1200
gatgaaagtg aaagtgagga ctcttgtgaa gatatgagtt gtggagagga gagtctcagc   1260
agctctcctc ccagtgatca agagtgcacc ttctttttca acttcaaagt ggcacaaaca   1320
ctgtgctttc catcttagaa atctgattgt tctgtcagaa tttatattta caggtttcaa   1380
agcaataaat gggggaatag gtagtttcct ggtttagccc ccatctagtc aggaattaat   1440
atactggaat acctaccttc tatttgttat tcagatcaga tctggcctat tttcatattt   1500
atcctaagcc atcaaatggg gtagtgcctc ttaaaccatt aacagtactt tagacattgg   1560
cactttattt ttctcgtaga tctttagcta ctttggggag gagggaaggt gctgatacct   1620
tcaatttgtt acttttcaag atttttaaaa ataactagtg tagcttatct taaacatttt   1680
ataaaacctt cagatgtctt taagcagatt ggaagtatgc aagtgcttcc ttagcaggga   1740
cagtggataa tccttaatgg tttatcatag atttcaccct ccccccttct cagaagagtg   1800
agtatgctct taaatgtcaa acacattttt gttgttttgt tttttaaatg atcagtgtct   1860
atttgatgtg atgcagatct tataaatttg ggaattataa tattgacatt tctgtgattt   1920
ttatatatgt aatgtcttaa ttgagatttc tgttaaggca gaaataatta ggctagggct   1980
cttagttttc attcctattg cccaagtatt gtcaaactat ggtattattt taatgttact   2040
ttaaaaatcc ataatctgct agttttgcat gtacttatat gaaaacagtg cagtaagttg   2100
aaaactcagt atctatggaa ttgataaatg ttgatctggt gtagtatatt ttatcgcatt   2160
ttcttatatt aaaaaatgtc tgcatgatta cattttattt cctttgtaat ttacatttca   2220
gaatagtgta ttgctatatg ggtgccaaga ttgaatatga agaacccgag tgtttgtagt   2280
attatagttt taagcaaatc tgtgtggtga tacagccata agaatggggc ttatataaac   2340
tctgtacatg taagattttg tacagagaat ttttaacttt ataaattgta tatgaacatg   2400
taaatctttt aaaatgtaca taaaatactg tattttttta ccttgtgtgt gatagtctag   2460
tcattgcatg taaatataat ttattatgta ttctgtagta taaatcatac attgatgact   2520
tacattttta ctggtaagtc aacatccgtt ggatgttttc tgaagtggct ctttttgaag   2580
tgataataga ttgtaattca aaataaaatt attaatgaat tctccttgtt tgggatcaca   2640
tcttaatttt taatctgtta aaagttcttg atgtatttta atgagaagac tttaggtgag   2700
gctacagtga ttccagagtg agccttctaa ctggctagca gaagttctct aggtttggca   2760
tctgtgcctt ggagatactg aaagagaatc tgtcatttga caattgacct ctttgtggga   2820
tggactcatt aagtatgctc tcagagactg gtatattacc agaatgccta ttaattttca   2880
gtgagaggca acaggtatta agtagaacag aatgctcagg ttggcagatt agaacgatct   2940
ttcaggagac aaagcaagtt ttaatcagtt gtttggttaa taagtatggg gtgttcgctg   3000
tgatagggcc ccgccagctt ctggctcttg tggacctcaa aagtatcagg tggttttgca   3060
agtggtggtc ctttcccctg ccccacccca ataggttccc catctgtcta gtttgatttt   3120
tgtagacctt tgttttctct agttagaaaa tcaggtacac tgaatatggt tttcatgtaa   3180
```

```
cacctcttct ctggagatag gggtatgttt tcctaccctt ctagtggaga atcctacttg   3240
aggatgacct ttcctctctt actaaataat attagtaaat agtgggcaat atattctgct   3300
ttcagatttt gatttgttga gatgtaaaag ttgtttgggg cttaccaaat ctcaagactc   3360
tctttagctc ctgcaggatt gtattgcttt tcttactgga tatttttcct gggtaagcat   3420
ctttgtggct tcatctcttc cccctgtggt tttcagtgta tttagtcgag acctctctgc   3480
tgagcttgca acctgtttat tcacatggcc tgccatgcca cttggaggtt tctgattact   3540
cccaaacctg ctggttcttt atgtctttct cagcgaataa ttccatctat tcatgttgga   3600
aacttaggtg atatgctcat ctccttttgc ctgtttatgg aggtcaccag cctctatcat   3660
ttgtatgatt tcgtttacac tgtttatatc tctctgtccc cccttttttct gccattggca   3720
tggtttagac ctgtactctt tatcagcaga ggtactgtaa tatatttgtg atccctcagc   3780
ttccaggctt actcctggtc tctgccttcc tatctacata tccttttaaa ataaaatttt   3840
aactatctcc tgaaaaattg ttgagtaggt cacgcacaat caggagaaaa atctattcat   3900
gacatacaag tctctgtcta atctgaacac tgcacctgtc tctggccttt ttttcttgtc   3960
atttcctaga ccttaaaaaa tgtgtattga gaaagaactc tgttagctat acagaagatg   4020
aactgggcaa tatagagtag cagcatggag accagtctga ctgaactaag gcagtggaag   4080
tgtggatgag gaagagaggt gaaaattgag aagcgctatc ctttctcttt gggcattatt   4140
aggaggctca cagacaagtc caggagcctg gttataccct cctgtgccat tcaaccaggt   4200
ggctttccca tgactgtgat gaataaaatt gagaagcccc tgcccttttc agagcagagg   4260
gtgaggagaa agctaccatt ttgtcctcat ccttaccccc gttgacttgg cgagagattt   4320
gacctttcag gttttgatcc tgtcattttc taggatgtgg tgcacgcact ttgctgttgc   4380
gcatggtgaa gtattgtgcc taggtcctgg gtcttcatct gtttggctct gctactgttt   4440
cctcctccca ggaagtgtgg ttagacaaat aatgtgtttt aattacctgt cacactcagg   4500
attaatacat actcaggtta actgtagaga ggcattggct tcagaacact cctcgtgaca   4560
attttaacca ttttctttgt ctagagtctg cctttttctt ttttacaatt tcttttattt   4620
caacactagg tttcaatatg gtgttcctgc tacctcccac ctccctcctc cctcatcaca   4680
catgcaaatt gtcagcttat tgagacaacc cacttagatt catatatgga caaggacaag   4740
gtattttgca tttgttactg gaattcagtt ttcctaacta tttactacca gaaatggtca   4800
ataacttact ttgtgtttag caaatcaaat tgtgtgatag atagtttccc agtatgatgg   4860
ccagtcagtc tttccatccc tgtgcctaca tgctgctctt cccgtccaca agtggagtct   4920
gtttctcttg agttttggct ggccttatga atggctttgc ttactgaagt gcagcagaag   4980
aaatttagta tatgtccaag cctaggcttt aagagactgg cagctttcct tttatccttt   5040
ttggaagcta gccaccatgc tgcaaagaag ctcagctgga ttactgaaag atgagaggcc   5100
atgtggagag agactcttga ggatgagaga ttatcttgga tgttccagcc ttaagctccc   5160
agctgaatgt gggtgtatcc tcagctacac cacagaaaac agaggaacta ctcagtcgat   5220
cccaatcaac ccacagactc actagaaata acaaattatt gttttaagcc acgaggtttt   5280
gggggagggt tgttaaacag taatagataa gtgagacaga ttgcttgtta tttatggtca   5340
aatggtgatt atctctggtg agattacagg tgatgttttt tttaagttat gcctatctgt   5400
agtttccttt ttttcctaaa attgatttga attattagtg tattaacaga ataaagaatg   5460
aactttaaaa cacaaaaaaa aaaaaaaaa                                     5489
```

<210> SEQ ID NO 16
<211> LENGTH: 2122
<212> TYPE: DNA
<213> ORGANISM: Homo sapiens

<400> SEQUENCE: 16
ggtggctatt ttgtccttgg gctgcctgtt ttcagctgct gcaaccacag ggatttcttc 60
tgttcaggcg ccatgtcaga accggctggg gatgtccgtc agaacccatg cggcagcaag 120
gcctgccgcc gcctcttcgg cccagtggac agcgagcagc tgagccgcga ctgtgatgcg 180
ctaatggcgg gctgcatcca ggaggcccgt gagcgatgga acttcgactt tgtcaccgag 240
acaccactgg agggtgactt cgcctgggag cgtgtgcggg gccttggcct gcccaagctc 300
taccttccca cggggccccg gcgaggccgg gatgagttgg gaggaggcag gcggcctggc 360
acctcacctg ctctgctgca ggggacagca gaggaagacc atgtggacct gtcactgtct 420
tgtacccttg tgcctcgctc aggggagcag gctgaagggt ccccaggtgg acctggagac 480
tctcagggtc gaaaacggcg gcagaccagc atgacagatt tctaccactc caaacgccgg 540
ctgatcttct ccaagaggaa gccctaatcc gcccacagga agcctgcagt cctggaagcg 600
cgagggcctc aaaggcccgc tctacatctt ctgccttagt ctcagtttgt gtgtcttaat 660
tattatttgt gttttaattt aaacacctcc tcatgtacat accctggccg ccccctgccc 720
cccagcctct ggcattagaa ttatttaaac aaaaactagg cggttgaatg agaggttcct 780
aagagtgctg ggcattttta ttttatgaaa tactatttaa agcctcctca tcccgtgttc 840
tccttttcct ctctcccgga ggttgggtgg gccggcttca tgccagctac ttcctcctcc 900
ccacttgtcc gctgggtggt accctctgga ggggtgtggc tccttcccat cgctgtcaca 960
ggcggttatg aaattcaccc cctttcctgg acactcagac ctgaattctt tttcatttga 1020
gaagtaaaca gatggcactt tgaaggggcc tcaccgagtg ggggcatcat caaaaacttt 1080
ggagtcccct cacctcctct aaggttgggc agggtgaccc tgaagtgagc acagcctagg 1140
gctgagctgg ggacctggta ccctcctggc tcttgatacc cccctctgtc ttgtgaaggc 1200
agggggaagg tggggtcctg gagcagacca ccccgcctgc cctcatggcc cctctgacct 1260
gcactgggga gcccgtctca gtgttgagcc ttttccctct ttggctcccc tgtacctttt 1320
gaggagcccc agctaccctt cttctccagc tgggctctgc aattcccctc tgctgctgtc 1380
cctcccccttt gtcctttccc ttcagtaccc tctcagctcc aggtggctct gaggtgcctg 1440
tcccaccccc acccccagct caatggactg gaaggggaag ggacacacaa gaagaagggc 1500
accctagttc tacctcaggc agctcaagca gcgaccgccc cctcctctag ctgtgggggt 1560
gagggtccca tgtggtggca caggccccct tgagtggggt tatctctgtg ttaggggtat 1620
atgatggggg agtagatctt tctaggaggg agacactggc ccctcaaatc gtccagcgac 1680
cttcctcatc caccccatcc ctccccagtt cattgcactt tgattagcag cggaacaagg 1740
agtcagacat tttaagatgg tggcagtaga ggctatggac agggcatgcc acgtgggctc 1800
atatggggct gggagtagtt gtctttcctg gcactaacgt tgagcccctg gaggcactga 1860
agtgcttagt gtacttggag tattggggtc tgaccccaaa caccttccag ctcctgtaac 1920
atactggcct ggactgtttt ctctcggctc cccatgtgtc ctggttcccg tttctccacc 1980
tagactgtaa acctctcgag ggcagggacc acaccctgta ctgttctgtg tctttcacag 2040
ctcctcccac aatgctgaat atacagcagg tgctcaataa atgattctta gtgactttac 2100
ttgtaaaaaa aaaaaaaaaa aa 2122

<210> SEQ ID NO 17
<211> LENGTH: 2413
<212> TYPE: DNA
<213> ORGANISM: Homo sapiens

<400> SEQUENCE: 17

```
cttcttcgtc agcctccctt ccaccgccat attgggccac taaaaaaagg gggctcgtct     60
tttcggggtg tttttctccc cctcccctgt ccccgcttgc tcacggctct gcgactccga    120
cgccggcaag gtttggagag cggctgggtt cgcgggaccc gcgggcttgc acccgcccag    180
actcggacgg gctttgccac cctctccgct tgcctggtcc cctctcctct ccgccctccc    240
gctcgccagt ccatttgatc agcggagact cggcggccgg gccggggctt ccccgcagcc    300
cctgcgcgct cctagagctc gggccgtggc tcgtcggggt ctgtgtcttt tggctccgag    360
ggcagtcgct gggcttccga gaggggttcg ggctgcgtag ggcgctttg ttttgttcgg    420
ttttgttttt ttgagagtgc gagagaggcg gtcgtgcaga cccgggagaa agatgtcaaa    480
cgtgcgagtg tctaacggga gccctagcct ggagcggatg gacgccaggc aggcggagca    540
ccccaagccc tcggcctgca ggaacctctt cggcccggtg gaccacgaag agttaacccg    600
ggacttggag aagcactgca gagacatgga agaggcgagc cagcgcaagt ggaatttcga    660
ttttcagaat cacaaacccc tagagggcaa gtacgagtgg caagaggtgg agaagggcag    720
cttgcccgag ttctactaca gacccccgcg gccccccaaa ggtgcctgca aggtgccggc    780
gcaggagagc caggatgtca gcgggagccg cccggcggcg cctttaattg gggctccggc    840
taactctgag gacacgcatt tggtggaccc aaagactgat ccgtcggaca gccagacggg    900
gttagcggag caatgcgcag gaataaggaa gcgacctgca accgacgatt cttctactca    960
aaacaaaaga gccaacagaa cagaagaaaa tgtttcagac ggttccccaa atgccggttc   1020
tgtggagcag acgcccaaga agcctggcct cagaagacgt caaacgtaaa cagctcgaat   1080
taagaatatg tttccttgtt tatcagatac atcactgctt gatgaagcaa ggaagatata   1140
catgaaaatt ttaaaaatac atatcgctga cttcatggaa tggacatcct gtataagcac   1200
tgaaaaacaa caacacaata acactaaaat tttaggcact cttaaatgat ctgcctctaa   1260
aagcgttgga tgtagcatta tgcaattagg tttttcctta tttgcttcat tgtactacct   1320
gtgtatatag tttttacctt ttatgtagca cataaacttt ggggaaggga gggcagggtg   1380
gggctgagga actgacgtgg agcggggtat gaagagcttg ctttgattta cagcaagtag   1440
ataaatattt gacttgcatg aagagaagca attttgggga agggtttgaa ttgttttctt   1500
taaagatgta atgtcccttt cagagacagc tgatacttca tttaaaaaaa tcacaaaaat   1560
ttgaacactg gctaaagata attgctattt atttttacaa gaagtttatt ctcatttggg   1620
agatctggtg atctcccaag ctatctaaag tttgttagat agctgcatgt ggctttttta   1680
aaaaagcaac agaaacctat cctcactgcc ctccccagtc tctcttaaag ttggaattta   1740
ccagttaatt actcagcaga atggtgatca ctccaggtag tttggggcaa aaatccgagg   1800
tgcttgggag ttttgaatgt taagaattga ccatctgctt ttattaaatt tgttgacaaa   1860
attttctcat tttcttttca cttcgggctg tgtaaacaca gtcaaaataa ttctaaatcc   1920
ctcgatattt ttaaagatct gtaagtaact tcacattaaa aaatgaaata ttttttaatt   1980
taaagcttac tctgtccatt tatccacagg aaagtgttat ttttcaagga aggttcatgt   2040
agagaaaagc acacttgtag gataagtgaa atggatacta catctttaaa cagtatttca   2100
```

```
ttgcctgtgt atggaaaaac catttgaagt gtacctgtgt acataactct gtaaaaacac   2160

tgaaaaatta tactaactta tttatgttaa aagatttttt ttaatctaga caatatacaa   2220

gccaaagtgg catgttttgt gcatttgtaa atgctgtgtt gggtagaata ggttttcccc   2280

tcttttgtta aataatatgg ctatgcttaa aaggttgcat actgagccaa gtataatttt   2340

ttgtaatgtg tgaaaaagat gccaattatt gttacacatt aagtaatcaa taaagaaaac   2400

ttccatagct att                                                      2413
```

<210> SEQ ID NO 18
<211> LENGTH: 4372
<212> TYPE: DNA
<213> ORGANISM: Homo sapiens

<400> SEQUENCE: 18

```
ggtgcctccg gggcggggc ctccttcggt tggcggcctc gggcttcggg agtcctccaa     60

gaggccaggt gaggccgtcc cgtgatgccc cgcgccccgg ccgctctggc ctgcaacgtg    120

tctctggggc ggaggcagcg gcagtggagt tcgctgcgcg ctgttggggg ccacctgtct    180

tttcgcttgt gtccctcttt ctagtgtcgc gctcgagtcc cgacgggccg ctccaagcct    240

cgacatgtcg tacaactacg tggtaacggc ccagaagccc accgccgtga acggctgcgt    300

gaccggacac tttacttcgg ccgaagactt aaacctgttg attgccaaaa acacgagatt    360

agagatctat gtggtcaccg ccgaggggct tcggcccgtc aaagaggtgg gcatgtatgg    420

gaagattgcg gtcatggagc ttttcaggcc caagggggag agcaaggacc tgctgtttat    480

cttgacagcg aagtacaatg cctgcatcct ggagtataaa cagagtggcg agagcattga    540

catcattacg cgagcccatg gcaatgtcca ggaccgcatt ggccgcccct cagagaccgg    600

cattattggc atcattgacc ctgagtgccg gatgattggc ctgcgtctct atgatggcct    660

tttcaaggtt attccactag atcgcgataa taaagaactc aaggccttca acatccgcct    720

ggaggagctg catgtcattg atgtcaagtt cctatatggt tgccaagcac ctactatttg    780

ctttgtctac caggaccctc aggggcggca cgtaaaaacc tatgaggtgt ctctccgaga    840

aaaggaattc aataagggcc cttggaaaca ggaaaatgtc gaagctgaag cttccatggt    900

gatcgcagtc ccagagccct ttgggggggc catcatcatt ggacaggagt caatcaccta    960

tcacaatggt gacaaatacc tggctattgc ccctcctatc atcaagcaaa gcacgattgt   1020

gtgccacaat cgagtggacc ctaatggctc aagatacctg ctgggagaca tggaaggccg   1080

gctcttcatg ctgcttttgg agaaggagga acagatggat ggcaccgtca ctctcaagga   1140

tctccgtgta gaactccttg gagagacctc tattgctgag tgcttgacat accttgataa   1200

tggtgttgtg tttgtcgggt ctcgcctggg tgactcccag cttgtgaagc tcaacgttga   1260

cagtaatgaa caaggctcct atgtagtggc catggaaacc tttaccaact taggacccat   1320

tgtcgatatg tgcgtggtgg acctggagag gcaggggcag ggcagctgg tcacttgctc   1380

tggggctttc aaggaaggtt ctttgcggat catccggaat ggaattggaa tccacgagca   1440

tgccagcatt gacttaccag gcatcaaagg attatggcca ctgcggtctg accctaatcg   1500

tgagactgat gacactttgg tgctctcttt tgtgggccag acaagagttc tcatgttaaa   1560

tggagaggag gtagaagaaa ccgaactgat gggtttcgtg gatgatcagc agactttctt   1620

ctgtggcaac gtggctcatc agcagcttat ccagatcact tcagcatcgg tgaggttggt   1680

ctctcaagaa cccaaagctc tggtcagtga atggaaggag cctcaggcca agaacatcag   1740

tgtggcctcc tgcaatagca gccaggtggt ggtggctgta ggcagggccc tctactatct   1800
```

```
gcagatccat cctcaggagc tccggcagat cagccacaca gagatggaac atgaagtggc   1860
ttgcttggac atcaccccat taggagacag caatggactg tcccctcttt gtgccattgg   1920
cctctggacg gacatctcgg ctcgtatctt gaagttgccc tcttttgaac tactgcacaa   1980
ggagatgctg ggtggagaga tcattcctcg ctccatcctg atgaccacct ttgagagtag   2040
ccattacctc ctttgtgcct tgggagatgg agcgcttttc tactttgggc tcaacattga   2100
gacaggtctg ttgagcgacc gtaagaaggt gactttgggc acccagccca ccgtattgag   2160
gacttttcgt tctctttcta ccaccaacgt ctttgcttgt tctgaccgcc ccactgtcat   2220
ctatagcagc aaccacaaat tggtcttctc aaatgtcaac ctcaaggaag tgaactacat   2280
gtgtcccctc aattcagatg gctatcctga cagcctggcg ctggccaaca atagcaccct   2340
caccattggc accatcgatg agatccagaa gctgcacatt cgcacagttc cctctatga    2400
gtctccaagg aagatctgct accaggaagt gtcccagtgt ttcggggtcc tctccagccg   2460
cattgaagtc caagacacga gtgggggcac gacagccttg aggcccagcg ctagcaccca   2520
ggctctgtcc agcagtgtaa gctccagcaa gctgttctcc agcagcactg ctcctcatga   2580
gacctccttt ggagaagagg tggaggtgca caacctactt atcattgacc aacacacctt   2640
tgaagtgctt catgcccacc agtttctgca gaatgaatat gccctcagtc tggtttcctg   2700
caagctgggc aaagacccca acacttactt cattgtgggc acagcaatgg tgtatcctga   2760
agaggcagag cccaagcagg gtcgcattgt ggtctttcag tattcggatg gaaaactaca   2820
gactgtggct gaaaaggaag tgaaaggggc cgtgtactct atggtggaat ttaacgggaa   2880
gctgttagcc agcatcaata gcacggtgcg gctctatgag tggacaacag agaaggagct   2940
gcgcactgag tgcaaccact acaacaacat catggccctc tacctgaaga ccaagggcga   3000
cttcatcctg gtgggcgacc ttatgcgctc agtgctgctg cttgcctaca agcccatgga   3060
aggaaacttt gaagagattg ctcgagactt taatcccaac tggatgagtg ctgtggaaat   3120
cttggatgat gacaattttc tgggggctga aaatgccttt aacttgtttg tgtgtcaaaa   3180
ggatagcgct gccaccactg acgaggagcg gcagcacctc caggaggttg gtcttttcca   3240
cctgggcgag tttgtcaatg tcttttgcca cggctctctg gtaatgcaga atctgggtga   3300
gacttccacc cccacacaag gctcggtgct cttcggcacg gtcaacggca tgatagggct   3360
ggtgacctca ctgtcagaga gctggtacaa cctcctgctg gacatgcaga atcgactcaa   3420
taaagtcatc aaaagtgtgg ggaagatcga gcactccttc tggagatcct ttcacaccga   3480
gcggaagaca gaaccagcca caggtttcat cgacggtgac ttgattgaga gtttcctgga   3540
tattagccgc cccaagatgc aggaggtggt ggcaaaccta cagtatgacg atggcagcgg   3600
tatgaagcga gaggccactg cagacgacct catcaaggtt gtggaggagc taactcggat   3660
ccattagcca agggcagggg gcccctttgc tgaccctccc caaaggcttt gccctgctgc   3720
cctccccctc ctctccacca tcgtcttctt ggccatggga ggcctttccc taagccagct   3780
gcccccagag ccacagttcc cctatgtgga agtggggcgg gcttcataga gacttgggaa   3840
tgagctgaag gtgaaacatt ttctccctgg atttttacca gtctcacatg attccagcca   3900
tcaccttaga ccaccaagcc ttgattggtg ttgccagttg tcctccttcc ggggaaggat   3960
tttgcagttc tttggctgaa aggaagctgt gcgtgtgtgt gtgtgtatgt gtgtgtgtgt   4020
atgtgtatct cacactcatg cattgtcctc tttttattta gattggcagt gtagggagtt   4080
gtgggtagtg gggaagaggg ttaggagggt ttcattgtct gtgaagtgag accttccttt   4140
```

```
tacttttctt ctattgcctc tgagagcatc aggcctagag gcctgactgc caagccatgg   4200

gtagcctggg tgtaaaacct ggagatggtg gatgatcccc acgccacagc ccttttgtct   4260

ctgcaaactg ccttcttcgg aaagaagaag gtgggaggat gtgaattgtt agtttctgag   4320

ttttaccaaa taaagtagaa tataagaaga aaggtaaaaa aaaaaaaaaa aa           4372
```

<210> SEQ ID NO 19
<211> LENGTH: 827
<212> TYPE: DNA
<213> ORGANISM: Homo sapiens

<400> SEQUENCE: 19

```
gtgatccttg gggccaggta tggcatgccc attgatatgt ggagcctggg ctgcatttta     60

gcagagctcc tgacgggtta ccccctcttg cctggggaag atgaagggga ccagctggcc    120

tgtatgattg aactgttggg catgccctca cagaaactgc tggatgcatc caaacgagcc    180

aaaaatttg tgagctccaa gggttatccc cgttactgca ctgtcacgac tctctcagat    240

ggctctgtgg tcctaaacgg aggccgttcc cggagggggga aactgagggg cccaccggag    300

agcagagagt gggggaacgc gctgaagggg tgtgatgatc ccctttttcct tgacttctta    360

aaacagtgtt tagagtggga tcctgcagtg cgcatgaccc caggccaggc tttgcggcac    420

ccctggctga ggaggcggtt gccaaagcct cccaccgggg agaaaacgtc agtgaaaagg    480

ataactgaga gcaccggtgc tatcacatct atatccaagt tacctccacc ttctagctca    540

gcttccaaac tgaggactaa tttggcgcag atgacagatg ccaatgggaa tattcagcag    600

aggacagtgt tgccaaaact tgttagctga gctcacgtcc cctgatgctg gtaacctgaa    660

agatacgaca ttgctgagcc ttactgggtt gaaaaggagt agctcagacc tgtttttatt    720

tgctcaataa ctctactcat ttgtatcttt tcagcactta attttaatgt aagaaagttg    780

ttcattttgt ttttataaaa tacatgagga caatgaaaaa aaaaaaa                 827
```

<210> SEQ ID NO 20
<211> LENGTH: 4975
<212> TYPE: DNA
<213> ORGANISM: Homo sapiens

<400> SEQUENCE: 20

```
ctctcacaca cacacacccc tcccctgcca tccctccccg gactccggct ccggctccga     60

ttgcaatttg caacctccgc tgccgtcgcc gcagcagcca ccaattcgcc agcggttcag    120

gtggctcttg cctcgatgtc ctagcctagg ggcccccggg ccggacttgg ctgggctccc    180

ttcaccctct gcggagtcat gagggcgaac gacgctctgc aggtgctggg cttgcttttc    240

agcctggccc ggggctccga ggtgggcaac tctcaggcag tgtgtcctgg gactctgaat    300

ggcctgagtg tgaccggcga tgctgagaac caataccaga cactgtacaa gctctacgag    360

aggtgtgagg tggtgatggg gaaccttgag attgtgctca cgggacacaa tgccgacctc    420

tccttcctgc agtggattcg agaagtgaca ggctatgtcc tcgtggccat gaatgaattc    480

tctactctac cattgcccaa cctccgcgtg gtgcgaggga cccaggtcta cgatgggaag    540

tttgccatct tcgtcatgtt gaactataac accaactcca gccacgctct gcgccagctc    600

cgcttgactc agctcaccga gattctgtca gggggtgttt atattgagaa gaacgataag    660

ctttgtcaca tggacacaat tgactggagg gacatcgtga gggaccgaga tgctgagata    720

gtggtgaagg acaatggcag aagctgtccc ccctgtcatg aggtttgcaa ggggcgatgc    780

tggggtcctg gatcagaaga ctgccagaca ttgaccaaga ccatctgtgc tcctcagtgt    840
```

```
aatggtcact gctttgggcc caaccccaac cagtgctgcc atgatgagtg tgccgggggc    900
tgctcaggcc ctcaggacac agactgcttt gcctgccggc acttcaatga cagtggagcc    960
tgtgtacctc gctgtccaca gcctcttgtc tacaacaagc taactttcca gctggaaccc   1020
aatccccaca ccaagtatca gtatggagga gtttgtgtag ccagctgtcc ccataacttt   1080
gtggtggatc aaacatcctg tgtcagggcc tgtcctcctg acaagatgga agtagataaa   1140
aatgggctca agatgtgtga gccttgtggg ggactatgtc ccaaagcctg tgagggaaca   1200
ggctctggga gccgcttcca gactgtggac tcgagcaaca ttgatggatt tgtgaactgc   1260
accaagatcc tgggcaacct ggactttctg atcaccggcc tcaatggaga cccctggcac   1320
aagatccctg ccctggaccc agagaagctc aatgtcttcc ggacagtacg ggagatcaca   1380
ggttacctga acatccagtc ctggccgccc cacatgcaca acttcagtgt tttttccaat   1440
ttgacaacca ttggaggcag aagcctctac aaccggggct tctcattgtt gatcatgaag   1500
aacttgaatg tcacatctct gggcttccga tccctgaagg aaattagtgc tgggcgtatc   1560
tatataagtg ccaataggca gctctgctac caccactctt tgaactggac caaggtgctt   1620
cgggggccta cggaagagcg actagacatc aagcataatc ggccgcgcag agactgcgtg   1680
gcagagggca aagtgtgtga cccactgtgc tcctctgggg gatgctgggg cccaggccct   1740
ggtcagtgct tgtcctgtcg aaattatagc cgaggaggtg tctgtgtgac ccactgcaac   1800
tttctgaatg ggagcctcg agaatttgcc catgaggccg aatgcttctc ctgccacccg    1860
gaatgccaac ccatgggggg cactgccaca tgcaatggct cgggctctga tacttgtgct   1920
caatgtgccc attttcgaga tggccccac tgtgtgagca gctgccccca tggagtccta    1980
ggtgccaagg gcccaatcta caagtaccca gatgttcaga atgaatgtcg gccctgccat   2040
gagaactgca cccaggggtg taaaggacca gagcttcaag actgtttagg acaaacactg   2100
gtgctgatcg gcaaaaccca tctgacaatg gctttgacag tgatagcagg attggtagtg   2160
attttcatga tgctgggcgg cacttttctc tactggcgtg ggcgccggat tcagaataaa   2220
agggctatga ggcgatactt ggaacggggt gagagcatag agcctctgga ccccagtgag   2280
aaggctaaca aagtcttggc cagaatcttc aaagagacag agctaaggaa gcttaaagtg   2340
cttggctcgg gtgtctttgg aactgtgcac aaaggagtgt ggatccctga gggtgaatca   2400
atcaagattc cagtctgcat taaagtcatt gaggacaaga gtggacggca gagttttcaa   2460
gctgtgacag atcatatgct ggccattggc agcctggacc atgcccacat tgtaaggctg   2520
ctgggactat gcccagggtc atctctgcag cttgtcactc aatatttgcc tctgggttct   2580
ctgctggatc atgtgagaca acaccggggg gcactggggc cacagctgct gctcaactgg   2640
ggagtacaaa ttgccaaggg aatgtactac cttgaggaac atggtatggt gcatagaaac   2700
ctggctgccc gaaacgtgct actcaagtca cccagtcagg ttcaggtggc agattttggt   2760
gtggctgacc tgctgcctcc tgatgataag cagctgctat acagtgaggc caagactcca   2820
attaagtgga tggcccttga gagtatccac tttgggaaat acacacacca gagtgatgtc   2880
tggagctatg gtgtgacagt ttgggagttg atgaccttcg gggcagagcc ctatgcaggg   2940
ctacgattgg ctgaagtacc agacctgcta gagaaggggg agcggttggc acagccccag   3000
atctgcacaa ttgatgtcta catggtgatg gtcaagtgtt ggatgattga tgagaacatt   3060
cgcccaacct ttaaagaact agccaatgag ttcaccagga tggcccgaga cccaccacgg   3120
tatctggtca taaagagaga gagtgggcct ggaatagccc ctgggccaga gccccatggt   3180
```

```
ctgacaaaca agaagctaga ggaagtagag ctggagccag aactagacct agacctagac   3240
ttggaagcag aggaggacaa cctggcaacc accacactgg gctccgccct cagcctacca   3300
gttggaacac ttaatcggcc acgtgggagc cagagccttt taagtccatc atctggatac   3360
atgcccatga accagggtaa tcttgggggg tcttgccagg agtctgcagt ttctgggagc   3420
agtgaacggt gcccccgtcc agtctctcta cacccaatgc cacggggatg cctggcatca   3480
gagtcatcag aggggcatgt aacaggctct gaggctgagc tccaggagaa agtgtcaatg   3540
tgtagaagcc ggagcaggag ccggagccca cggccacgcg gagatagcgc ctaccattcc   3600
cagcgccaca gtctgctgac tcctgttacc ccactctccc cacccgggtt agaggaagag   3660
gatgtcaacg gttatgtcat gccagataca cacctcaaag gtactccctc ctcccgggaa   3720
ggcacccttt cttcagtggg tctcagttct gtcctgggta ctgaagaaga agatgaagat   3780
gaggagtatg aatacatgaa ccggaggaga aggcacagtc cacctcatcc ccctaggcca   3840
agttcccttg aggagctggg ttatgagtac atggatgtgg ggtcagacct cagtgcctct   3900
ctgggcagca cacagagttg cccactccac cctgtaccca tcatgcccac tgcaggcaca   3960
actccagatg aagactatga atatatgaat cggcaacgag atggaggtgg tcctgggggt   4020
gattatgcag ccatgggggc ctgcccagca tctgagcaag ggtatgaaga gatgagagct   4080
tttcaggggc ctggacatca ggccccccat gtccattatg cccgcctaaa aactctacgt   4140
agcttagagg ctacagactc tgcctttgat aaccctgatt actggcatag caggcttttc   4200
cccaaggcta atgcccagag aacgtaactc ctgctccctg tggcactcag ggagcattta   4260
atggcagcta gtgcctttag agggtaccgt cttctcccta ttccctctct ctcccaggtc   4320
ccagcccctt ttccccagtc ccagacaatt ccattcaatc tttggaggct tttaaacatt   4380
ttgacacaaa attcttatgg tatgtagcca gctgtgcact ttcttctctt tcccaacccc   4440
aggaaaggtt ttccttattt tgtgtgcttt cccagtccca ttcctcagct tcttcacagg   4500
cactcctgga gatatgaagg attactctcc atatcccttc ctctcaggct cttgactact   4560
tggaactagg ctcttatgtg tgcctttgtt tcccatcaga ctgtcaagaa gaggaaaggg   4620
aggaaaccta gcagaggaaa gtgtaatttt ggtttatgac tcttaacccc ctagaaagac   4680
agaagcttaa aatctgtgaa gaaagaggtt aggagtagat attgattact atcataattc   4740
agcacttaac tatgagccag gcatcatact aaacttcacc tacattatct cacttagtcc   4800
tttatcatcc ttaaaacaat tctgtgacat acatattatc tcattttaca caaagggaag   4860
tcgggcatgg tggctcatgc ctgtaatctc agcactttgg gaggctgagg cagaaggatt   4920
acctgaggca aggagtttga gaccagctta gccaacatag taagaccccc atctc        4975
```

<210> SEQ ID NO 21
<211> LENGTH: 4627
<212> TYPE: DNA
<213> ORGANISM: Homo sapiens

<400> SEQUENCE: 21

```
tcacttgcct gatatttcca gtgtcagagg gacacagcca acgtggggtc ccttctaggc     60
tgacagccgc tctccagcca ctgccgcgag cccgtctgct cccgccctgc ccgtgcactc    120
tccgcagccg ccctccgcca agccccagcg cccgctccca tcgccgatga ccgcggggag    180
gaggatggag atgctctgtg ccggcagggt ccctgcgctg ctgctctgcc tgggtttcca    240
tcttctacag gcagtcctca gtacaactgt gattccatca tgtatcccag gagagtccag    300
tgataactgc acagctttag ttcagacaga agacaatcca cgtgtggctc aagtgtcaat    360
```

```
aacaaagtgt agctctgaca tgaatggcta ttgtttgcat ggacagtgca tctatctggt    420
ggacatgagt caaaactact gcaggtgtga agtgggttat actggtgtcc gatgtgaaca    480
cttcttttta accgtccacc aacctttaag caaagagtat gtggctttga ccgtgattct    540
tattattttg tttcttatca cagtcgtcgg ttccacatat tatttctgca gatggtacag    600
aaatcgaaaa agtaaagaac caaagaagga atatgagaga gttacctcag ggatccaga    660
gttgccgcaa gtctgaatgg cgccatcaaa cttatgggca gggataacag tgtgcctggt    720
taatattaat attccatttt attaataata tttatgttgg gtcaagtgtt aggtcaataa    780
cactgtattt taatgtactt gaaaaatgtt tttatttttg ttttattttt gacagactat    840
ttgctaatgt ataatgtgca gaaaatattt aatatcaaaa gaaaattgat atttttatac    900
aagtaatttc ctgagctaaa tgcttcattg aaagcttcaa agtttatatg cctggtgcac    960
agtgcttaga agtaagcaat tcccaggtca tagctcaaga attgttagca aatgacagat   1020
ttctgtaagc ctatatatat agtcaaatcg atttagtaag tatgtttttt atgttcctca   1080
aatcagtgat aattggtttg actgtaccat ggtttgatat gtagttggca ccatggtatc   1140
atatattaaa acaataatgc aattagaatt tgggagaagc aaatataggt cctgtgttaa   1200
acactacaca tttgaaacaa gctaaccctg gggagtctat ggtctcttca ctcaggtctc   1260
agctataatt ctgttatatg aggggcagtg gacagttccc tatgccaact cacgactcct   1320
acaggtacta gtcactcatc taccagattc tgcctatgta aaatgaattg aaaaacaatt   1380
ttctgtaatc ttttatttaa gtagtgggca tttcatagct tcacaatgtt cctttttttgt   1440
atattacaac atttatgtga ggtaattatt gctcaacaga caattagaaa aaagtccaca   1500
cttgaagcct aaatttgtgc tttttaagaa tatttttaga ctatttcttt ttatagggggc   1560
tttgctgaat tctaacatta aatcacagcc caaaatttga tggactaatt attattttaa   1620
aatatatgaa gacaataatt ctacatgttg tcttaagatg gaaatacagt tatttcatct   1680
tttattcaag gaagttttaa ctttaataca gctcagtaaa tggcttcttc tagaatgtaa   1740
agttatgtat ttaaagttgt atcttgacac aggaaatggg aaaaaactta aaaattaata   1800
tggtgtattt ttccaaatga aaaatctcaa ttgaaagctt ttaaaatgta gaaacttaaa   1860
cacaccttcc tgtggaggct gagatgaaaa ctagggctca ttttcctgac atttgtttat   1920
tttttggaag agacaaagat ttcttctgca ctctgagccc ataggtctca gagagttaat   1980
aggagtattt ttgggctatt gcataaggag ccactgctgc caccactttt ggattttatg   2040
ggaggctcct tcatcgaatg ctaaaccttt gagtagagtc tccctggatc acataccagg   2100
tcagggagga tctgttcttc ctctacgttt atcctggcat gtgctagggt aaacgaaggc   2160
ataataagcc atggctgacc tctggagcac caggtgccag gacttgtctc catgtgtatc   2220
catgcattat ataccctggt gcaatcacac gactgtcatc taaagtcctg gccctggccc   2280
ttactattag gaaaataaac agacaaaaac aagtaaatat atatggtcct atacatattg   2340
tatatatatt catatacaaa catgtatgta tacatgacct taatggatca tagaattgca   2400
gtcatttggt gctctgctaa ccatttatat aaaacttaaa aacaagagaa aagaaaaatc   2460
aattagatct aaacagttat ttctgtttcc tatttaatat agctgaagtc aaaatatgta   2520
agaacacatt ttaaatactc tacttacagt tggccctctg tggttagttc cacatctgtg   2580
gattcaacca accaaggacg gaaaatgctt aaaaaaataat acaacaacaa caaaaaaatac   2640
attataacaa ctatttactt tttttttttt ctttttgaga tggagtctcg ctctgttgcc   2700
```

```
caggttggag tgcagtggca cgatctcggc tcactgcaac ctcacctccc gggttcaaga   2760
gatcctcctg cctcagcctc ctgagcagct gggactacag gcgcatgcca ccatgcccag   2820
ctaatttttg tatttttagt agaggcgggg tttcaccatg ttggccagga tggtctcaat   2880
ctcctaacct tgagatccac cctccacagc ctcccaaact gctgggatta caggcgtgag   2940
ccaccgcacg tagcatttac attaggtatt acaagtaatg taaagatgat ttaagtatac   3000
aggaggatgt gaataggtta tatgcaagca ctatgccctt ttatataagt gacttgaaca   3060
tctgtgcccg attttagtat gtgcaggggg gcgatctggg aatcagtccc ctgtggatac   3120
caaggtacaa ctgtatttat taacgcttac tagatgtgag gagagtctga atattttcag   3180
tgatcttggc tgtttcaaaa aaatctattg acttttcaat aaatcagctg caatccattt   3240
atttcattta caaaagattt attgtaagcc tctcaatctt ggtttttcag ttgatcttaa   3300
gcatgtcaat tcataaaaac aagtcatttt tgtatttttc atctttaaga atgcttaaaa   3360
aagctaatcc ctaaaatagt tagatctttg taaatgcata ttaaataata aagtatgacc   3420
cacattactt tttatgggtg aaaataagac aaaaataata gttttagtga ggatggtgct   3480
gagtaaacat aaaaactgat ttgctctcag ctgatgtgtc ctgtacacag tgggaagatt   3540
ttagttcaca cttagtctaa ctcccccatt ttacagattt ctcactatat atatttctag   3600
aaggggctat gcatattcaa tgtattgaga accaaagcaa ccacaaatgc ataaatgcat   3660
aatttatggt cttcaaccaa ggccacataa taacccagtt aacttactct ttaaccagga   3720
atattaagtt ctataactag tactcaaggt ttaaccttaa aattaagatt tccttaacct   3780
taaccttaaa attgatatta tattaaacat acataataca atgtaactcc actgttctcc   3840
tgaatatttt ttgctctaat ctctctgccg aaagtcaaag tgatgggaga attggtatac   3900
tggtatgact acgtcttaag tcagattttt atttatgagt ctttgagact aaattcaatc   3960
accaccaggt atcaaatcaa cttttatgca gcaaatatat gattctagtg tctgactttt   4020
gttaaattca gtaatgcagt ttttaaaaac ctgtatctga cccactttgt aatttttgct   4080
ccaatatcca ttctgtagac ttttgaaaaa aaagttttta atttgatgcc caatatattc   4140
tgaccgttaa aaaattcttg ttcatatggg agaaggggga gtaatgactt gtacaaacag   4200
tatttctggt gtatatttta atgtttttaa aaagagtaat ttcatttaaa tatctgttat   4260
tcaaatttga tgatgttaaa tgtaatataa tgtattttct ttttattttg cactctgtaa   4320
ttgcactttt taagtttgaa gagccatttt ggtaaacggt ttttattaaa gatgctatgg   4380
aacataaagt tgtattgcat gcaatttaaa gtaacttatt tgactatgaa tattatcgga   4440
ttactgaatt gtatcaattt gtttgtgttc aatatcagct ttgataattg tgtaccttaa   4500
gatattgaag gagaaaatag ataatttaca agatattatt aatttttatt tatttttctt   4560
gggaattgaa aaaaattgaa ataaataaaa atgcattgaa catcttgcat tcaaaatctt   4620
cactgac                                                             4627
```

<210> SEQ ID NO 22
<211> LENGTH: 6450
<212> TYPE: DNA
<213> ORGANISM: Homo sapiens

<400> SEQUENCE: 22

```
gagttgtgcc tggagtgatg tttaagccaa tgtcagggca aggcaacagt ccctggccgt     60
cctccagcac ctttgtaatg catatgagct cgggagacca gtacttaaag ttggaggccc    120
gggagcccag gagctggcgg agggcgttcg tcctgggagc tgcacttgct ccgtcgggtc    180
```

```
gccggcttca ccggaccgca ggctcccggg gcagggccgg ggccagagct cgcgtgtcgg    240
cgggacatgc gctgcgtcgc ctctaacctc gggctgtgct ctttttccag gtggcccgcc    300
ggtttctgag ccttctgccc tgcggggaca cggtctgcac cctgcccgcg gccacggacc    360
atgaccatga ccctccacac caaagcatct gggatggccc tactgcatca gatccaaggg    420
aacgagctgg agcccctgaa ccgtccgcag ctcaagatcc ccctggagcg gcccctgggc    480
gaggtgtacc tggacagcag caagcccgcc gtgtacaact accccgaggg cgccgcctac    540
gagttcaacg ccgcggccgc cgccaacgcg caggtctacg gtcagaccgg cctcccctac    600
ggccccgggt ctgaggctgc ggcgttcggc tccaacggcc tggggggttt ccccccactc    660
aacagcgtgt ctccgagccc gctgatgcta ctgcacccgc cgccgcagct gtcgcctttc    720
ctgcagcccc acggccagca ggtgccctac tacctggaga acgagcccag cggctacacg    780
gtgcgcgagg ccggcccgcc ggcattctac aggccaaatt cagataatcg acgccagggt    840
ggcagagaaa gattggccag taccaatgac aagggaagta tggctatgga atctgccaag    900
gagactcgct actgtgcagt gtgcaatgac tatgcttcag gctaccatta tggagtctgg    960
tcctgtgagg gctgcaaggc cttcttcaag agaagtattc aaggacataa cgactatatg   1020
tgtccagcca ccaaccagtg caccattgat aaaaacagga ggaagagctg ccaggcctgc   1080
cggctccgca aatgctacga agtgggaatg atgaaaggtg ggatacgaaa agaccgaaga   1140
ggagggagaa tgttgaaaca caagcgccag agagatgatg gggagggcag gggtgaagtg   1200
gggtctgctg gagacatgag agctgccaac ctttggccaa gcccgctcat gatcaaacgc   1260
tctaagaaga acagcctggc cttgtccctg acggccgacc agatggtcag tgccttgttg   1320
gatgctgagc cccccatact ctattccgag tatgatccta ccagaccctt cagtgaagct   1380
tcgatgatgg gcttactgac caacctggca gacagggagc tggttcacat gatcaactgg   1440
gcgaagaggg tgccaggctt tgtggatttg accctccatg atcaggtcca ccttctagaa   1500
tgtgcctggc tagagatcct gatgattggt ctcgtctggc gctccatgga gcacccagtg   1560
aagctactgt ttgctcctaa cttgctcttg gacaggaacc agggaaaatg tgtagagggc   1620
atggtggaga tcttcgacat gctgctggct acatcatctc ggttccgcat gatgaatctg   1680
cagggagagg agtttgtgtg cctcaaatct attattttgc ttaattctgg agtgtacaca   1740
tttctgtcca gcaccctgaa gtctctggaa gagaaggacc atatccaccg agtcctggac   1800
aagatcacag acactttgat ccacctgatg gccaaggcag gcctgaccct gcagcagcag   1860
caccagcggc tggcccagct cctcctcatc ctctcccaca tcaggcacat gagtaacaaa   1920
ggcatggagc atctgtacag catgaagtgc aagaacgtgg tgcccctcta tgacctgctg   1980
ctggagatgc tggacgccca ccgcctacat gcgcccacta gccgtggagg ggcatccgtg   2040
gaggagacgg accaaagcca cttggccact gcgggctcta cttcatcgca ttccttgcaa   2100
aagtattaca tcacgggggga ggcagagggt ttccctgcca cagtctgaga gctccctggc   2160
tcccacacgg ttcagataat ccctgctgca ttttaccctc atcatgcacc actttagcca   2220
aattctgtct cctgcataca ctccggcatg catccaacac caatggcttt ctagatgagt   2280
ggccattcat ttgcttgctc agttcttagt ggcacatctt ctgtcttctg ttgggaacag   2340
ccaaagggat tccaaggcta aatctttgta acagctctct ttcccccttg ctatgttact   2400
aagcgtgagg attcccgtag ctcttcacag ctgaactcag tctatgggtt ggggctcaga   2460
taactctgtg catttaagct acttgtagag acccaggcct ggagagtaga cattttgcct   2520
```

```
ctgataagca ctttttaaat ggctctaaga ataagccaca gcaaagaatt taaagtggct   2580

cctttaattg gtgacttgga gaaagctagg tcaagggttt attatagcac cctcttgtat   2640

tcctatggca atgcatcctt ttatgaaagt ggtacacctt aaagctttta tatgactgta   2700

gcagagtatc tggtgattgt caattcactt ccccctatag gaatacaagg ggccacacag   2760

ggaaggcaga tcccctagtt ggccaagact tattttaact tgatacactg cagattcaga   2820

gtgtcctgaa gctctgcctc tggctttccg gtcatgggtt ccagttaatt catgcctccc   2880

atggacctat ggagagcaac aagttgatct tagttaagtc tccctatatg agggataagt   2940

tcctgatttt tgtttttatt tttgtgttac aaaagaaagc cctccctccc tgaacttgca   3000

gtaaggtcag cttcaggacc tgttccagtg ggcactgtac ttggatcttc ccggcgtgtg   3060

tgtgccttac acaggggtga actgttcact gtggtgatgc atgatgaggg taaatggtag   3120

ttgaaaggag caggggccct ggtgttgcat ttagccctgg ggcatggagc tgaacagtac   3180

ttgtgcagga ttgttgtggc tactagagaa caagagggaa agtagggcag aaactggata   3240

cagttctgag cacagccaga cttgctcagg tggccctgca caggctgcag ctacctagga   3300

acattccttg cagaccccgc attgcctttg gggtgccct gggatccctg gggtagtcca   3360

gctcttattc atttcccagc gtggccctgg ttggaagaag cagctgtcaa gttgtagaca   3420

gctgtgttcc tacaattggc ccagcaccct ggggcacggg agaagggtgg ggaccgttgc   3480

tgtcactact caggctgact ggggcctggt cagattacgt atgcccttgg tggtttagag   3540

ataatccaaa atcagggttt ggtttgggga agaaaatcct ccccccttcct cccccgcccc   3600

gttccctacc gcctccactc ctgccagctc atttccttca atttcctttg acctataggc   3660

taaaaaagaa aggctcattc cagccacagg gcagccttcc ctgggccttt gcttctctag   3720

cacaattatg ggttacttcc tttttcttaa caaaaaagaa tgtttgattt cctctgggtg   3780

accttattgt ctgtaattga aaccctattg agaggtgatg tctgtgttag ccaatgaccc   3840

aggtagctgc tcgggcttct cttggtatgt cttgtttgga aaagtggatt tcattcattt   3900

ctgattgtcc agttaagtga tcaccaaagg actgagaatc tgggagggca aaaaaaaaaa   3960

aaaaagtttt tatgtgcact taaatttggg gacaatttta tgtatctgtg ttaaggatat   4020

gcttaagaac ataattcttt tgttgctgtt tgtttaagaa gcaccttagt ttgtttaaga   4080

agcaccttat atagtataat atatattttt ttgaaattac attgcttgtt tatcagacaa   4140

ttgaatgtag taattctgtt ctggatttaa tttgactggg ttaacatgca aaaaccaagg   4200

aaaaatattt agtttttttt tttttttttg tatacttttc aagctacctt gtcatgtata   4260

cagtcattta tgcctaaagc ctggtgatta ttcatttaaa tgaagatcac atttcatatc   4320

aacttttgta tccacagtag acaaaatagc actaatccag atgcctattg ttggatattg   4380

aatgacagac aatcttatgt agcaaagatt atgcctgaaa aggaaaatta ttcagggcag   4440

ctaattttgc ttttaccaaa atatcagtag taatattttt ggacagtagc taatgggtca   4500

gtgggttctt tttaatgttt atacttagat tttcttttaa aaaaattaaa ataaaacaaa   4560

aaaaatttct aggactagac gatgtaatac cagctaaagc caaacaatta tacagtggaa   4620

ggttttacat tattcatcca atgtgtttct attcatgtta agatactact acatttgaag   4680

tgggcagaga acatcagatg attgaaatgt tcgcccaggg gtctccagca actttggaaa   4740

tctctttgta tttttacttg aagtgccact aatggacagc agatattttc tggctgatgt   4800

tggtattggg tgtaggaaca tgatttaaaa aaaaaactct tgcctctgct ttcccccact   4860

ctgaggcaag ttaaaatgta aaagatgtga tttatctggg gggctcaggt atggtgggga   4920
```

agtggattca ggaatctggg gaatggcaaa tatattaaga agagtattga aagtatttgg 4980
aggaaaatgg ttaattctgg gtgtgcacca aggttcagta gagtccactt ctgccctgga 5040
gaccacaaat caactagctc catttacagc catttctaaa atggcagctt cagttctaga 5100
gaagaaagaa caacatcagc agtaaagtcc atggaatagc tagtggtctg tgtttctttt 5160
cgccattgcc tagcttgccg taatgattct ataatgccat catgcagcaa ttatgagagg 5220
ctaggtcatc caaagagaag accctatcaa tgtaggttgc aaaatctaac ccctaaggaa 5280
gtgcagtctt tgatttgatt tccctagtaa ccttgcagat atgtttaacc aagccatagc 5340
ccatgccttt tgagggctga acaaataagg gacttactga taatttactt ttgatcacat 5400
taaggtgttc tcaccttgaa atcttataca ctgaaatggc cattgattta ggccactggc 5460
ttagagtact ccttcccctg catgacactg attacaaata ctttcctatt catactttcc 5520
aattatgaga tggactgtgg gtactgggag tgatcactaa caccatagta atgtctaata 5580
ttcacaggca gatctgcttg gggaagctag ttatgtgaaa ggcaaataaa gtcatacagt 5640
agctcaaaag gcaaccataa ttctctttgg tgcaagtctt gggagcgtga tctagattac 5700
actgcaccat tcccaagtta atcccctgaa aacttactct caactggagc aaatgaactt 5760
tggtcccaaa tatccatctt ttcagtagcg ttaattatgc tctgtttcca actgcatttc 5820
ctttccaatt gaattaaagt gtggcctcgt ttttagtcat ttaaaattgt tttctaagta 5880
attgctgcct ctattatggc acttcaattt tgcactgtct tttgagattc aagaaaaatt 5940
tctattcatt tttttgcatc caattgtgcc tgaactttta aaatatgtaa atgctgccat 6000
gttccaaacc catcgtcagt gtgtgtgttt agagctgtgc accctagaaa caacatactt 6060
gtcccatgag caggtgcctg agacacagac ccctttgcat tcacagagag gtcattggtt 6120
atagagactt gaattaataa gtgacattat gccagtttct gttctctcac aggtgataaa 6180
caatgctttt tgtgcactac atactcttca gtgtagagct cttgttttat gggaaaaggc 6240
tcaaatgcca aattgtgttt gatggattaa tatgcccttt tgccgatgca tactattact 6300
gatgtgactc ggttttgtcg cagctttgct ttgtttaatg aaacacactt gtaaacctct 6360
tttgcacttt gaaaaagaat ccagcgggat gctcgagcac ctgtaaacaa ttttctcaac 6420
ctatttgatg ttcaaataaa gaattaaact 6450

<210> SEQ ID NO 23
<211> LENGTH: 3376
<212> TYPE: DNA
<213> ORGANISM: Homo sapiens

<400> SEQUENCE: 23
ggcgaccgaa cgcggcggtc ggcagcgttc gcgcgggggc ctgcgaagcg ctgctcgggg 60
ccggcactgc ccgcggggag gacgcgccgc cgccgccacc cagcgccgcc gccgccgccg 120
cctccagccg ggccgccgcg cgtcccgggg gccggccccg cgagcgcagg agtaaacacc 180
gccggagtct tggagccgct gcagaaggga ataaagagag atgcagggat ttgtgaggtt 240
acggcgcccc agctgcaaga tgcactagcc ggctgaaccc gggatcggct gacttgttgg 300
aaccggagtg ctctgcacgg agagtggtgg atgagttgaa gttgccttcc cggggctcat 360
tttccacgct gccgagagga atccgagagg caaggcaatc acttcgtctt gccattgatt 420
gggtatcggg agcttttttt ttctcccctc tctctttctt ttcctccgtc ttgttgcatg 480
caagaaaatt acagtccgct gctcgcccgc cctgggtgcg agatattcag ccccgctctc 540

```
tcccgtgcat tgtgcaaccc aaagatgaaa gaccgaaggg gagaaagtta aagaaatcgc    600
ccacatgcgc tggatcagtc cacggcttgg ggaaaggcat ccagagaagg tgggagcgga    660
gagtttgaag tctttacagg cgggaagatg gcggactgga gctgaaagtg ttgattggga    720
aacttgggtg attcttgtgt ttatttacaa tcctcttgac ccaggcagga cacatgcagg    780
ccaaaaaacg ctatttcatc ctgctctcag ctggctcttg tctcgccctt ttgttttatt    840
tcggaggctt gcagtttagg gcatcgagga gccacagccg gagagaagaa cacagcggta    900
ggaatggctt gcaccacccc agtccggatc atttctggcc ccgcttcccg gacgctctgc    960
gccccttcgt tccttgggat caattggaaa acgaggattc cagcgtgcac atttcccccc   1020
ggcagaagcg agatgccaac tccagcatct acaaaggcaa gaagtgccgc atggagtcct   1080
gcttcgattt caccctttgc aagaaaaacg gcttcaaagt ctacgtatac ccacagcaaa   1140
aaggggagaa aatcgccgaa agttaccaaa acattctagc ggccatcgag ggctccaggt   1200
tctacacctc ggaccccagc caggcgtgcc tctttgtcct gagtctggat actttagaca   1260
gagaccagtt gtcacctcag tatgtgcaca atttgagatc caaagtgcag agtctccact   1320
tgtggaacaa tggtaggaat catttaattt ttaatttata ttccggcact tggcctgact   1380
acaccgagga cgtggggttt gacatcggcc aggcgatgct ggccaaagcc agcatcagta   1440
ctgaaaactt ccgacccaac tttgatgttt ctattcccct cttttctaag gatcatccca   1500
ggacaggagg ggagaggggg tttttgaagt tcaacaccat ccctcctctc aggaagtaca   1560
tgctggtatt caaggggaag aggtacctga cagggatagg atcagacacc aggaatgcct   1620
tatatcacgt ccataacggg gaggacgttg tgctcctcac cacctgcaag catggcaaag   1680
actggcaaaa gcacaaggat tctcgctgtg acagagacaa caccgagtat gagaagtatg   1740
attatcggga aatgctgcac aatgccactt tctgtctggt tcctcgtggt cgcaggcttg   1800
ggtccttcag attcctggag gctttgcagg ctgcctgcgt ccctgtgatg ctcagcaatg   1860
gatgggagtt gccattctct gaagtgatta attggaacca agctgccgtc ataggcgatg   1920
agagattgtt attacagatt ccttctacaa tcaggtctat tcatcaggat aaaatcctag   1980
cacttagaca gcagacacaa ttcttgtggg aggcttattt ttcttcagtt gagaagattg   2040
tattaactac actagagatt attcaggaca gaatattcaa gcacatatca cgtaacagtt   2100
taatatggaa caaacatcct ggaggattgt tcgtactacc acagtattca tcttatctgg   2160
gagattttcc ttactactat gctaatttag gtttaaagcc cccctccaaa ttcactgcag   2220
tcatccatgc ggtgaccccc ctggtctctc agtcccagcc agtgttgaag cttctcgtgg   2280
ctgcagccaa gtcccagtac tgtgcccaga tcatagttct atggaattgt gacaagcccc   2340
taccagccaa acaccgctgg cctgccactg ctgtgcctgt cgtcgtcatt gaaggagaga   2400
gcaaggttat gagcagccgt tttctgccct acgacaacat catcacagac gccgtgctca   2460
gccttgacga ggacacggtg ctttcaacaa cagaggtgga tttcgccttc acagtgtggc   2520
agagcttccc tgagaggatt gtggggtacc ccgcgcgcag ccacttctgg gataactcta   2580
aggagcggtg gggatacaca tcaaagtgga cgaacgacta ctccatggtg ttgacaggag   2640
ctgctattta ccacaaatat tatcactacc tatactccca ttacctgcca gccagcctga   2700
agaacatggt ggaccaattg gccaattgtg aggacattct catgaacttc ctggtgtctg   2760
ctgtgacaaa attgcctcca atcaaagtga cccagaagaa gcagtataag gagacaatga   2820
tgggacagac ttctcgggct tcccgttggg ctgaccctga ccactttgcc cagcgacaga   2880
gctgcatgaa tacgtttgcc agctggtttg gctacatgcc gctgatccac tctcagatga   2940
```

```
ggctcgaccc cgtcctcttt aaagaccagg tctctatttt gaggaagaaa taccgagaca   3000

ttgagcgact ttgaggaatc cggctgagtg ggggaggggga agcaagaagg gatgggggtc   3060

aagctgctct ctcttcccag tgcagatcca ctcatcagca gagccagatt gtgccaacta   3120

tccaaaaact tagatgagca gaatgacaaa aaaaaaaagg ccaatgagaa ctcaactcct   3180

ggctcctggg actgcaccag actgctccaa actcacctca ctggcttctg tgtcccaaga   3240

ctaggttgtg tacagtttaa ttatggaaca ttaaataatt atttttgaaa tgattgctat   3300

gcaggtttaa actttttttaa tgatcaaaac tattaaaaac cagagttctt tgtttaatca   3360

aaaaaaaaaa aaaaaa                                                    3376
```

<210> SEQ ID NO 24
<211> LENGTH: 972
<212> TYPE: DNA
<213> ORGANISM: Homo sapiens

<400> SEQUENCE: 24

```
tctagactca ggactgagaa gaagtaaaac cgtttgctgg ggctggcctg actcaccagc     60

tgccatgcag cagcccttca attacccata tccccagatc tactgggtgg acagcagtgc    120

cagctctccc tgggcccctc caggcacagt tcttccctgt ccaacctctg tgcccagaag    180

gcctggtcaa aggaggccac caccaccacc gccaccgcca ccactaccac ctccgccgcc    240

gccgccacca ctgcctccac taccgctgcc acccctgaag aagagaggga accacagcac    300

aggcctgtgt ctccttgtga tgtttttcat ggttctggtt gccttggtag gattgggcct    360

ggggatgttt cagctcttcc acctacagaa ggagctggca gaactccgag agtctaccag    420

ccagatgcac acagcatcat ctttggagaa gcaaataggc caccccagtc caccccctga    480

aaaaaaggag ctgaggaaag tggcccattt aacaggcaag tccaactcaa ggtccatgcc    540

tctggaatgg gaagacacct atggaattgt cctgctttct ggagtgaagt ataagaaggg    600

tggccttgtg atcaatgaaa ctgggctgta ctttgtatat tccaaagtat acttccgggg    660

tcaatcttgc aacaacctgc ccctgagcca caaggtctac atgaggaact ctaagtatcc    720

ccaggatctg gtgatgatgg aggggaagat gatgagctac tgcactactg ggcagatgtg    780

ggcccgcagc agctacctgg gggcagtgtt caatcttacc agtgctgatc atttatatgt    840

caacgtatct gagctctctc tggtcaattt tgaggaatct cagacgtttt tcggcttata    900

taagctctaa gagaagcact ttgggattct ttccattatg attctttgtt acaggcaccg    960

agatgttcta ga                                                        972
```

<210> SEQ ID NO 25
<211> LENGTH: 1391
<212> TYPE: DNA
<213> ORGANISM: Homo sapiens

<400> SEQUENCE: 25

```
tgcaccccga gcatccgccc cgggtggcac gtccccgagc ccaccaggcc ggccccgtct     60

ccccatccgt ctagtccgct cgcggtgcca tgccattcct cgggcaggac tggcggtccc    120

ccgggcagaa ctgggtgaag acggccgacg gctggaagcg cttcctggat gagaagagcg    180

gcagtttcgt gagcgacctc agcagttact gcaacaagga ggtatacaat aaggagaatc    240

ttttcaacag cctgaactat gatgttgcag ccaagaagag aaagaaggac atgctgaata    300

gcaaaaccaa aactcagtat ttccaccaag aaaaatggat ctatgttcac aaaggaagta    360
```

```
ctaaagagcg ccatggatat tgcaccctgg gggaagcttt caacagactg gacttctcaa    420
ctgccattct ggattccaga agatttaact acgtggtccg gctgttggag ctgatagcaa    480
agtcacagct cacatccctg agtggcatcg cccaaaagaa cttcatgaat attttggaaa    540
aagtggtact gaaagtcctt gaagaccagc aaaacattag actaataagg gaactactcc    600
agaccctcta cacatcctta tgtacactgg tccaaagagt cggcaagtct gtgctggtcg    660
ggaacattaa catgtgggtg tatcggatgg agacgattct ccactggcag cagcagctga    720
acaacattca gatcaccagg cctgccttca aaggcctcac cttcactgac ctgcctttgt    780
gcctacaact gaacatcatg cagaggctga gcgacgggcg ggacctggtc agcctgggcc    840
aggctgcccc cgacctgcac gtgctcagcg aagaccggct gctgtggaag aaactctgcc    900
agtaccactt ctccgagcgg cagatccgca aacgattaat tctgtcagac aaagggcagc    960
tggattggaa gaagatgtat ttcaaacttg tccgatgtta ccccaaggaaa gagcagtatg   1020
gagataccct tcagctctgc aaacactgtc acatcctttc ctggaagggc actgaccatc   1080
cgtgcactgc caataaccca gagagctgct ccgtttcact ttcaccccag gactttatca   1140
acttgttcaa gttctgaatc ccagcacatg acaacacttc agaagggtcc ccctgctgac   1200
tggagagctg ggaatatggc atttggacac ttcatttgta aatagtgtac attttaaaca   1260
ttggctcgaa acttcagaga taagtcatgg agaggacatt ggaggggaga aatgcagttg   1320
ctgactggga atttaagaat gtgaacttct cactagaatt ggtatggaaa agcaaaatac   1380
tgtaaataaa c                                                         1391
```

```
<210> SEQ ID NO 26
<211> LENGTH: 4654
<212> TYPE: DNA
<213> ORGANISM: Homo sapiens

<400> SEQUENCE: 26

ggcggcggct ggaggagagc gcggtggaga gccgagcggg cgggcggcgg gtgcggagcg     60
ggcgagggag cgcgcgcggc cgccacaaag ctcgggcgcc gcggggctgc atgcggcgta    120
cctggcccgg cgcggcgact gctctccggg ctggcggggg ccggccgcga gccccggggg    180
ccccgaggcc gcagcttgcc tgcgcgctct gagccttcgc aactcgcgag caaagtttgg    240
tggaggcaac gccaagcctg agtcctttct tcctctcgtt ccccaaatcc gagggcagcc    300
cgcgggcgtc atgcccgcgc tcctccgcag cctggggtac gcgtgaagcc cgggaggctt    360
ggcgccggcg aagacccaag gaccactctt ctgcgtttgg agttgctccc cgcaaccccg    420
ggctcgtcgc tttctccatc ccgacccacg cggggcgcgg ggacaacaca ggtcgcggag    480
gagcgttgcc attcaagtga ctgcagcagc agcggcagcg cctcggttcc tgagcccacc    540
gcaggctgaa ggcattgcgc gtagtccatg cccgtagagg aagtgtgcag atgggattaa    600
cgtccacatg gagatatgga agaggaccgg ggattggtac cgtaaccatg gtcagctggg    660
gtcgtttcat ctgcctggtc gtggtcacca tggcaacctt gtccctggcc cggccctcct    720
tcagtttagt tgaggatacc acattagagc cagaagagcc accaaccaaa taccaaatct    780
ctcaaccaga agtgtacgtg gctgcgccag gggagtcgct agaggtgcgc tgcctgttga    840
aagatgccgc cgtgatcagt tggactaagg atggggtgca cttggggccc aacaatagga    900
cagtgcttat tggggagtac ttgcagataa agggcgccac gcctagagac tccggcctct    960
atgcttgtac tgccagtagg actgtagaca gtgaaacttg gtacttcatg gtgaatgtca   1020
cagatgccat ctcatccgga gatgatgagg atgacaccga tggtgcggaa gattttgtca   1080
```

```
gtgagaacag taacaacaag agagcaccat actggaccaa cacagaaaag atggaaaagc   1140
ggctccatgc tgtgcctgcg gccaacactg tcaagtttcg ctgcccagcc ggggggaacc   1200
caatgccaac catgcggtgg ctgaaaaacg ggaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaaggccg ccggtgttaa caccacggac aaagagattg   1620
aggttctcta tattcggaat gtaacttttg aggacgctgg ggaatatacg tgcttggcgg   1680
gtaattctat tgggatatcc tttcactctg catggttgac agttctgcca gcgcctggaa   1740
gagaaaagga gattacagct tccccagact acctggagat agccatttac tgcatagggg   1800
tcttcttaat cgcctgtatg gtggtaacag tcatcctgtg ccgaatgaag aacacgacca   1860
agaagccaga cttcagcagc cagccggctg tgcacaagct gaccaaacgt atcccctgc   1920
ggagacaggt aacagtttcg gctgagtcca gctcctccat gaactccaac accccgctgg   1980
tgaggataac aacacgcctc tcttcaacgg cagacacccc catgctggca ggggtctccg   2040
agtatgaact tccagaggac ccaaaatggg agtttccaag agataagctg acactgggca   2100
agcccctggg agaaggttgc tttgggcaag tggtcatggc ggaagcagtg ggaattgaca   2160
aagacaagcc caaggaggcg gtcaccgtgg ccgtgaagat gttgaaagat gatgccacag   2220
agaaagacct ttctgatctg gtgtcagaga tggagatgat gaagatgatt gggaaacaca   2280
agaatatcat aaatcttctt ggagcctgca cacaggatgg gcctctctat gtcatagttg   2340
agtatgcctc taaaggcaac ctccgagaat acctccgagc ccggaggcca cccgggatgg   2400
agtactccta tgacattaac cgtgttcctg aggagcagat gaccttcaag gacttggtgt   2460
catgcaccta ccagctggcc agaggcatgg agtacttggc ttcccaaaaa tgtattcatc   2520
gagatttagc agccagaaat gttttggtaa cagaaaacaa tgtgatgaaa atagcagact   2580
ttggactcgc cagagatatc aacaatatag actattacaa aaagaccacc aatgggcggc   2640
ttccagtcaa gtggatggct ccagaagccc tgtttgatag agtatacact catcagagtg   2700
atgtctggtc cttcggggtg ttaatgtggg agatcttcac tttagggggc tcgccctacc   2760
cagggattcc cgtggaggaa ctttttaagc tgctgaagga aggacacaga atggataagc   2820
cagccaactg caccaacgaa ctgtacatga tgatgaggga ctgttggcat gcagtgccct   2880
cccagagacc aacgttcaag cagttggtag aagacttgga tcgaattctc actctcacaa   2940
ccaatgagga atacttggac ctcagccaac ctctcgaaca gtattcacct agttaccctg   3000
acacaagaag ttcttgttct tcaggagatg attctgtttt ttctccagac cccatgcctt   3060
acgaaccatg ccttcctcag tatccacaca taaacggcag tgttaaaaca tgaatgactg   3120
tgtctgcctg tccccaaaca ggacagcact gggaacctag ctacactgag cagggagacc   3180
atgcctccca gagcttgttg tctccacttg tatatatgga tcagaggagt aaataattgg   3240
aaaagtaatc agcatatgtg taaagattta tacagttgaa aacttgtaat cttccccagg   3300
aggagaagaa ggtttctgga gcagtggact gccacaagcc accatgtaac ccctctcacc   3360
tgccgtgcgt actggctgtg gaccagtagg actcaaggtg gacgtgcgtt ctgccttcct   3420
```

```
tgttaatttt gtaataattg gagaagattt atgtcagcac acacttacag agcacaaatg   3480
cagtatatag gtgctggatg tatgtaaata tattcaaatt atgtataaat atatattata   3540
tatttacaag gagttatttt ttgtattgat tttaaatgga tgtcccaatg cacctagaaa   3600
attggtctct cttttttttaa tagctatttg ctaaatgctg ttcttacaca taatttctta   3660
attttcaccg agcagaggtg gaaaaatact tttgctttca gggaaaatgg tataacgtta   3720
atttattaat aaattggtaa tatacaaaac aattaatcat ttatagtttt ttttgtaatt   3780
taagtggcat ttctatgcag gcagcacagc agactagtta atctattgct tggacttaac   3840
tagttatcag atcctttgaa aagagaatat ttacaatata tgactaattt ggggaaaatg   3900
aagttttgat ttatttgtgt ttaaatgctg ctgtcagacg attgttctta gacctcctaa   3960
atgccccata ttaaaagaac tcattcatag gaaggtgttt cattttggtg tgcaaccctg   4020
tcattacgtc aacgcaacgt ctaactggac ttcccaagat aaatggtacc agcgtcctct   4080
taaaagatgc cttaatccat tccttgagga cagaccttag ttgaaatgat agcagaatgt   4140
gcttctctct ggcagctggc cttctgcttc tgagttgcac attaatcaga ttagcctgta   4200
ttctcttcag tgaattttga taatggcttc cagactcttt ggcgttggag acgcctgtta   4260
ggatcttcaa gtcccatcat agaaaattga aacacagagt tgttctgctg atagttttgg   4320
ggatacgtcc atctttttaa gggattgctt tcatctaatt ctggcaggac ctcaccaaaa   4380
gatccagcct catacctaca tcagacaaaa tatcgccgtt gttccttctg tactaaagta   4440
ttgtgttttg ctttggaaac acccactcac tttgcaatag ccgtgcaaga tgaatgcaga   4500
ttacactgat cttatgtgtt acaaaattgg agaaagtatt taataaaacc tgttaatttt   4560
tatactgaca ataaaaatgt ttctacagat attaatgtta acaagacaaa ataaatgtca   4620
cgcaacttat ttttttaata aaaaaaaaaa aaaa                               4654
```

<210> SEQ ID NO 27
<211> LENGTH: 1398
<212> TYPE: DNA
<213> ORGANISM: Homo sapiens

<400> SEQUENCE: 27

```
ggagagcggg gccctttgtc ctccagtggc tggtaggcag tggctgggag gcagcggccc     60
aattagtgtc gtgcggcccg tggcgaggcg aggtccgggg agcgagcgag caagcaaggc    120
gggaggggtg gccggagctg cggcggctgg cacaggagga ggagcccggg cgggcgaggg    180
gcggccggag agcgccaggg cctgagctgc cggagcggcg cctgtgagtg agtgcagaaa    240
gcaggcgccc gcgcgctagc cgtggcagga gcagcccgca cgccgcgctc tctccctggg    300
cgacctgcag tttgcaatat gactttggag gaattctcgg ctggagagca gaagaccgaa    360
aggatggata aggtggggga tgccctggag gaagtgctca gcaaagccct gagtcagcgc    420
acgatcactg tcggggtgta cgaagcggcc aagctgctca acgtcgaccc cgataacgtg    480
gtgttgtgcc tgctggcggc ggacgaggac gacgacagag atgtggctct gcagatccac    540
ttcaccctga tccaggcgtt ttgctgcgag aacgacatca acatcctgcg cgtcagcaac    600
ccgggccggc tggcggagct cctgctcttg gagaccgacg ctggccccgc ggcgagcgag    660
ggcgccgagc agcccccgga cctgcactgc gtgctggtga cgaatccaca ttcatctcaa    720
tggaaggatc ctgccttaag tcaacttatt tgtttttgcc gggaaagtcg ctacatggat    780
caatgggttc cagtgattaa tctccctgaa cggtgatggc atctgaatga aaataactga    840
accaaattgc actgaagttt ttgaaatacc tttgtagtta ctcaagcagt tactccctac    900
```

```
actgatgcaa ggattacaga aactgatgcc aaggggctga gtgagttcaa ctacatgttc    960

tgggggcccg gagatagatg actttgcaga tggaaagagg tgaaaatgaa gaaggaagct   1020

gtgttgaaac agaaaaataa gtcaaaagga acaaaaatta caaagaacca tgcaggaagg   1080

aaaactatgt attaatttag aatggttgag ttacattaaa ataaaccaaa tatgttaaag   1140

tttaagtgtg cagccatagt ttgggtattt ttggtttata tgccctcaag taaaagaaaa   1200

gccgaaaggg ttaatcatat ttgaaaacca tattttattg tattttgatg agatattaaa   1260

ttctcaaagt tttattataa attctactaa gttattttat gacatgaaaa gttatttatg   1320

ctataaattt tttgaaacac aatacctaca ataaactggt atgaataatt gcatcatttc   1380

aaaaaaaaaa aaaaaaaa                                                 1398
```

<210> SEQ ID NO 28
<211> LENGTH: 11242
<212> TYPE: DNA
<213> ORGANISM: Homo sapiens

<400> SEQUENCE: 28

```
ttttttttt ttttttttga gaaaggggaa tttcatccca aataaaagga atgaagtctg     60

gctccggagg agggtccccg acctcgctgt gggggctcct gtttctctcc gccgcgctct    120

cgctctggcc gacgagtgga gaaatctgcg ggccaggcat cgacatccgc aacgactatc    180

agcagctgaa gcgcctggag aactgcacgg tgatcgaggg ctacctccac atcctgctca    240

tctccaaggc cgaggactac cgcagctacc gcttccccaa gctcacggtc attaccgagt    300

acttgctgct gttccgagtg gctggcctcg agagcctcgg agacctcttc cccaacctca    360

cggtcatccg cggctggaaa ctcttctaca actacgccct ggtcatcttc gagatgacca    420

atctcaagga tattgggctt tacaacctga ggaacattac tcgggggggcc atcaggattg    480

agaaaaatgc tgacctctgt tacctctcca ctgtggactg gtccctgatc ctggatgcgg    540

tgtccaataa ctacattgtg gggaataagc cccaaagga atgtggggac ctgtgtccag    600

ggaccatgga ggagaagccg atgtgtgaga agaccaccat caacaatgag tacaactacc    660

gctgctggac cacaaaccgc tgccagaaaa tgtgcccaag cacgtgtggg aagcgggcgt    720

gcaccgagaa caatgagtgc tgccaccccg agtgcctggg cagctgcagc gcgcctgaca    780

acgacacggc ctgtgtagct tgccgccact actactatgc cggtgtctgt gtgcctgcct    840

gcccgcccaa cacctacagg tttgagggct ggcgctgtgt ggaccgtgac ttctgcgcca    900

acatcctcag cgccgagagc agcgactccg aggggtttgt gatccacgac ggcgagtgca    960

tgcaggagtg cccctcgggc ttcatccgca acggcagcca gagcatgtac tgcatccctt   1020

gtgaaggtcc ttgcccgaag gtctgtgagg aagaaaagaa aacaaagacc attgattctg   1080

ttacttctgc tcagatgctc caaggatgca ccatcttcaa gggcaatttg ctcattaaca   1140

tccgacgggg gaataacatt gcttcagagc tggagaactt catggggctc atcgaggtgg   1200

tgacgggcta cgtgaagatc cgccattctc atgccttggt ctccttgtcc ttcctaaaaa   1260

accttcgcct catcctagga gaggagcagc tagaagggaa ttactccttc tacgtcctcg   1320

acaaccagaa cttgcagcaa ctgtgggact gggaccaccg caacctgacc atcaaagcag   1380

ggaaaatgta ctttgctttc aatcccaaat tatgtgtttc cgaaatttac cgcatggagg   1440

aagtgacggg gactaaaggg cgccaaagca aaggggacat aaacaccagg aacaacgggg   1500

agagagcctc ctgtgaaagt gacgtcctgc atttcacctc caccaccacg tcgaagaatc   1560
```

-continued

```
gcatcatcat aacctggcac cggtaccggc cccctgacta cagggatctc atcagcttca   1620
ccgtttacta caaggaagca ccctttaaga atgtcacaga gtatgatggg caggatgcct   1680
gcggctccaa cagctggaac atggtggacg tggacctccc gcccaacaag gacgtggagc   1740
ccggcatctt actacatggg ctgaagccct ggactcagta cgccgtttac gtcaaggctg   1800
tgaccctcac catggtggag aacgaccata tccgtggggc caagagtgag atcttgtaca   1860
ttcgcaccaa tgcttcagtt ccttccattc ccttggacgt tctttcagca tcgaactcct   1920
cttctcagtt aatcgtgaag tggaaccctc cctctctgcc caacggcaac ctgagttact   1980
acattgtgcg ctggcagcgg cagcctcagg acggctacct ttaccggcac aattactgct   2040
ccaaagacaa aatccccatc aggaagtatg ccgacggcac catcgacatt gaggaggtca   2100
cagagaaccc caagactgag gtgtgtggtg gggagaaagg gccttgctgc gcctgcccca   2160
aaactgaagc cgagaagcag gccgagaagg aggaggctga ataccgcaaa gtctttgaga   2220
atttcctgca caactccatc ttcgtgccca gacctgaaag gaagcggaga gatgtcatgc   2280
aagtggccaa caccaccatg tccagccgaa gcaggaacac cacggccgca gacacctaca   2340
acatcaccga cccggaagag ctggagacag agtacccttt ctttgagagc agagtggata   2400
acaaggagag aactgtcatt tctaaccttc ggcctttcac attgtaccgc atcgatatcc   2460
acagctgcaa ccacgaggct gagaagctgg gctgcagcgc ctccaacttc gtctttgcaa   2520
ggactatgcc cgcagaagga gcagatgaca ttcctgggcc agtgacctgg gagccaaggc   2580
ctgaaaactc catcttttta aagtggccgg aacctgagaa tcccaatgga ttgattctaa   2640
tgtatgaaat aaaatacgga tcacaagttg aggatcagcg agaatgtgtg tccagacagg   2700
aatacaggaa gtatggaggg gccaagctaa accggctaaa cccggggaac tacacagccc   2760
ggattcaggc cacatctctc tctgggaatg ggtcgtggac agatcctgtg ttcttctatg   2820
tccaggccaa aacaggatat gaaaacttca tccatctgat catcgctctg cccgtcgctg   2880
tcctgttgat cgtgggaggg ttggtgatta tgctgtacgt cttccataga aagagaaata   2940
acagcaggct ggggaatgga gtgctgtatg cctctgtgaa cccggagtac ttcagcgctg   3000
ctgatgtgta cgttcctgat gagtgggagg tggctcggga gaagatcacc atgagccggg   3060
aacttgggca ggggtcgttt gggatggtct atgaaggagt tgccaagggt gtggtgaaag   3120
atgaacctga aaccagagtg gccattaaaa cagtgaacga ggccgcaagc atgcgtgaga   3180
ggattgagtt tctcaacgaa gcttctgtga tgaaggagtt caattgtcac catgtggtgc   3240
gattgctggg tgtggtgtcc caaggccagc caacactggt catcatggaa ctgatgacac   3300
ggggcgatct caaaagttat ctccggtctc tgaggccaga aatggagaat aatccagtcc   3360
tagcacctcc aagcctgagc aagatgattc agatggccgg agagattgca gacggcatgg   3420
catacctcaa cgccaataag ttcgtccaca gagaccttgc tgcccggaat tgcatggtag   3480
ccgaagattt cacagtcaaa atcggagatt ttggtatgac gcgagatatc tatgagacag   3540
actattaccg gaaaggaggg aaagggctgc tgcccgtgcg ctggatgtct cctgagtccc   3600
tcaaggatgg agtcttcacc acttactcgg acgtctggtc cttcggggtc gtcctctggg   3660
agatcgccac actggccgag cagccctacc agggcttgtc caacgagcaa gtccttcgct   3720
tcgtcatgga gggcggcctt ctggacaagc cagacaactg tcctgacatg ctgtttgaac   3780
tgatgcgcat gtgctggcag tataacccca agatgaggcc ttccttcctg gagatcatca   3840
gcagcatcaa agaggagatg gagcctggct tccgggaggt ctccttctac tacagcgagg   3900
agaacaagct gcccgagccg gaggagctgg acctggagcc agagaacatg gagagcgtcc   3960
```

```
ccctggaccc ctcggcctcc tcgtcctccc tgccactgcc cgacagacac tcaggacaca   4020
aggccgagaa cggccccggc cctggggtgc tggtcctccg cgccagcttc gacgagagac   4080
agccttacgc ccacatgaac gggggccgca agaacgagcg ggccttgccg ctgccccagt   4140
cttcgacctg ctgatccttg gatcctgaat ctgtgcaaac agtaacgtgt gcgcacgcgc   4200
agcggggtgg ggggggagag agagttttaa caatccattc acaagcctcc tgtacctcag   4260
tggatcttca gaactgccct tgctgcccgc gggagacagc ttctctgcag taaaacacat   4320
ttgggatgtt cctttttttca atatgcaagc agctttttat tccctgccca aacccttaac   4380
tgacatgggc ctttaagaac cttaatgaca acacttaata gcaacagagc acttgagaac   4440
cagtctcctc actctgtccc tgtccttccc tgttctccct ttctctctcc tctctgcttc   4500
ataacggaaa aataattgcc acaagtccag ctgggaagcc ctttttatca gtttgaggaa   4560
gtggctgtcc ctgtggcccc atccaaccac tgtacacacc cgcctgacac cgtgggtcat   4620
tacaaaaaaa cacgtggaga tggaaatttt taccttttatc tttcaccttt ctagggacat   4680
gaaatttaca aagggccatc gttcatccaa ggctgttacc attttaacgc tgcctaattt   4740
tgccaaaatc ctgaactttc tccctcatcg gcccggcgct gattcctcgt gtccggaggc   4800
atgggtgagc atggcagctg gttgctccat ttgagagaca cgctggcgac acactccgtc   4860
catccgactg cccctgctgt gctgctcaag gccacaggca cacaggtctc attgcttctg   4920
actagattat tatttggggg aactggacac aataggtctt tctctcagtg aaggtgggga   4980
gaagctgaac cggcttccct gccctgcctc cccagccccc tgcccaaccc ccaagaatct   5040
ggtggccatg ggccccgaag cagcctggcg gacaggcttg gagtcaaggg gccccatgcc   5100
tgcttctctc ccagccccag ctcccccgcc cgcccccaag gacacagatg ggaaggggtt   5160
tccagggact cagccccact gttgatgcag gtttgcaagg aaagaaattc aaacaccaca   5220
acagcagtaa gaagaaaagc agtcaatgga ttcaagcatt ctaagctttg ttgacatttt   5280
ctctgttcct aggacttctt catgggtctt acagttctat gttagaccat gaaacatttg   5340
catacacatc gtctttaatg tcacttttat aactttttta cggttcagat attcatctat   5400
acgtctgtac agaaaaaaaa aagctgctat tttttttgtt cttgatcttt gtggatttaa   5460
tctatgaaaa ccttcaggtc caccctctcc cctttctgct cactccaaga aacttcttat   5520
gctttgtact agagtgcgtg actttcttcc tcttttcccg gtaatggata cttctatcac   5580
ataatttgcc atgaactgtt ggatgccttt ttataaatac atcccccatc cctgctccca   5640
cctgcccctt tagttgtttt ctaacccgta ggctctctgg gcacgaggca gaaagcaggc   5700
cgggcaccca tcctgagagg gccgcgctcc tctccccagc ctgccctcac agcattggag   5760
cctgttacag tgcaagacat gatacaaact caggtcagaa aaacaaaggt taaatatttc   5820
acacgtcttt gttcagtgtt tccactcacc gtggttgaga agcctcaccc tctctttccc   5880
ttgcctttgc ttaggttgtg acacacatat atatatattt ttttaattct tgggtacaac   5940
agcagtgtta accgcagaca ctaggcattt ggattactat ttttcttaat ggctatttaa   6000
tccttccatc ccacgaaaaa cagctgctga gtccaaggga gcagcagagc gtggtccggc   6060
agggcctgtt gtggccctcg ccaccccccct caccggaccg actgacctgt ctttggaacc   6120
agaacatccc aagggaactc cttcgcactg gcgttgagtg ggaccccggg atccaggctg   6180
gcccagggcg gcaccctcag ggctgtgccc gctggagtgc taggtggagg cagcacagac   6240
gccacggtgg cccaagagcc cctttgcttc ttgctggggg accagggctg tggtgctggc   6300
```

```
ccactttccc tcggccagga atccaggtcc ttggggccca ggggtcttgt cttgtttcat   6360
ttttagcact tctcaccaga gagatgacag cacaagagtt gcttctggga tagaaatgtt   6420
taggagtaag aacaaagctg ggatacggtg attgctagtt gtgactgaag attcaacaca   6480
gaaaagaaag tttatacggc ttttttgctg gtcagcagtt tgtcccactg ctttctctag   6540
tctctatccc atagcgtgtt ccctttaaaa aaaaaaaaaa ggtattatat gtaggagttt   6600
tcttttaatt tattttgtga taaattacca gtttcaatca ctgtagaaaa gccccattat   6660
gaatttaaat ttcaaggaaa gggtgtgtgt gtgtgtatgt gtggggtgtg tgtgtgtgag   6720
agtgatggga cagttcttga tttttgggt tttttttccc ccaaacattt atctacctca   6780
ctcttatttt ttatatgtgt atatagacaa aagaatacat ctcacctttc tcagcacctg   6840
acaataggcc gttgatactg gtaacctcat ccacgccaca ggcgccacac ccaggtgatg   6900
cagggggaag ccaggctgta ttccggggtc aaagcaacac taactcacct ctctgctcat   6960
ttcagacagc ttgccttttt ctgagatgtc ctgttttgtg ttgctttttt tgttttgttt   7020
tctatcttgg tttccaccaa ggtgttagat ttctcctcct cctagccagg tggccctgtg   7080
aggccaacga gggcaccaga gcacacctgg gggagccacc aggctgtccc tggctggttg   7140
tctttggaac aaactgcttc tgtgcagatg gaatgaccaa cacatttcgt ccttaagaga   7200
gcagtggttc ctcaggttct gaggagagga aggtgtccag gcagcaccat ctctgtgcga   7260
atccccaggg taaaggcgtg gggcattggg tttgctcccc ttgctgctgc tccatccctg   7320
caggaggctc gcgctgaggc aggaccgtgc ggccatggct gctgcattca ttgagcacaa   7380
aggtgcagct gcagcagcag ctggagagca agagtcaccc agcctgtgcg ccagaatgca   7440
gaggctcctg acctcacagc cagtccctga tagaacacac gcaggagcag agtcccctcc   7500
ccctccaggc tgccctctca acttctccct cacctccttc cctaggggta gacagagatg   7560
taccaaacct tccggctgga aagcccagtg gccggcgccg aggctcgtgg cgtcacgccc   7620
cccccgccag ggctgtacct ccgtctccct ggtcctgctg ctcacaggac agacggctcg   7680
ctcccctctt ccagcagctg ctcttacagg cactgatgat ttcgctggga agtgtggcgg   7740
gcagctttgc ctaagcgtgg atggctcctc ggcaattcca gcctaagtga aggcgctcag   7800
gagcctcctg ctggaacgcg acccatctct cccaggaccc cggggatctt aaggtcattg   7860
agaaatactg ttggatcagg gttttgttct tccacactgt aggtgacccc ttggaataac   7920
ggcctctcct ctcgtgcaca tacctaccgg tttccacaac tggatttcta cagatcattc   7980
agctggttat aagggttttg tttaaactgt ccgagttact gatgtcattt tgtttttgtt   8040
ttatgtaggt agcttttaag tagaaaacac taacagtgta gtgcccatca tagcaaatgc   8100
ttcagaaaca cctcaataaa agagaaaact tggcttgtgt gatggtgcag tcactttact   8160
ggaccaaccc acccaccttg actataccaa ggcatcatct atccacagtt ctagcctaac   8220
ttcatgctga tttctctgcc tcttgatttt tctctgtgtg ttccaaataa tcttaagctg   8280
agttgtggca ttttccatgc aacctccttc tgccagcagc tcacactgct tgaagtcata   8340
tgaaccactg aggcacatca tggaattgat gtgagcatta agacgttctc ccacacagcc   8400
cttccctgag gcagcaggag ctggtgtgta ctggagacac tgttgaactt gatcaagacc   8460
cagaccaccc caggtctcct tcgtgggatg tcatgacgtt tgacatacct ttggaacgag   8520
cctcctcctt ggaagatgga agaccgtgtt cgtggccgac ctggcctctc ctggcctgtt   8580
tcttaagatg cggagtcaca tttcaatggt acgaaaagtg gcttcgtaaa atagaagagc   8640
agtcactgtg gaactaccaa atggcgagat gctcggtgca cattggggtg ctttgggata   8700
```

```
aaagatttat gagccaacta ttctctggca ccagattcta ggccagtttg ttccactgaa   8760
gcttttccca cagcagtcca cctctgcagg ctggcagccg aatggcttgc cagtggctct   8820
gtggcaagat cacactgaga tcgatgggtg agaaggctag gatgcttgtc tagtgttctt   8880
agctgtcacg ttggctcctt ccagggtggc cagacggtgt tggccactcc cttctaaaac   8940
acaggcgccc tcctggtgac agtgacccgc cgtggtatgc cttggcccat tccagcagtc   9000
ccagttatgc atttcaagtt tggggtttgt tcttttcgtt aatgttcctc tgtgttgtca   9060
gctgtcttca tttcctgggc taagcagcat tgggagatgt ggaccagaga tccactcctt   9120
aagaaccagt ggcgaaagac actttctttc ttcactctga agtagctggt ggtacaaatg   9180
agaacttcaa gagaggatgt tatttagact gaacctctgt tgccagagat gctgaagata   9240
cagaccttgg acaggtcaga gggtttcatt tttggccttc atcttagatg actggttgcg   9300
tcatttggag aagtgagtgc tccttgatgg tggaatgacc gggtggtggg tacagaacca   9360
ttgtcacagg gatcctggca cagagaagag ttacgagcag cagggtgcag ggcttggaag   9420
gaatgtgggc aaggttttga acttgattgt tcttgaagct atcagaccac atcgaggctc   9480
agcagtcatc cgtgggcatt tggtttcaac aaagaaacct aacatcctac tctggaaact   9540
gatctcggag ttaaggcgaa ttgttcaaga acacaaacta catcgcactc gtcagttgtc   9600
agttctgggg catgacttta gcgttttgtt tctgcgagaa cataacgatc actcattttt   9660
atgtcccacg tgtgtgtgtc cgcatctttc tggtcaacat tgttttaact agtcactcat   9720
tagcgttttc aatagggctc ttaagtccag tagattacgg gtagtcagtt gacgaagatc   9780
tggtttacaa gaactaatta aatgtttcat tgcatttttg taagaacaga ataattttat   9840
aaaatgtttg tagtttataa ttgccgaaaa taatttaaag acactttttt tttctctgtg   9900
tgtgcaaatg tgtgtttgtg atccattttt tttttttttt tttaggacac ctgtttacta   9960
gctagcttta caatatgcca aaaaaggatt tctccctgac cccatccgtg gttcaccctc  10020
ttttcccccc atgctttttg ccctagttta taacaaagga atgatgatga tttaaaaagt  10080
agttctgtat cttcagtatc ttggtcttcc agaaccctct ggttgggaag ggggatcattt  10140
tttactggtc atttcccttt ggagtgtagc tactttaaca gatggaaaga acctcattgg  10200
ccatggaaac agccgaggtg ttggagccca gcagtgcatg gcaccgttcg gcatctggct  10260
tgattggtct ggctgccgtc attgtcagca cagtgccatg gacatgggaa gacttgactg  10320
cacagccaat ggttttcatg atgattacag catacacagt gatcacataa acgatgacag  10380
ctatggggca cacaggccat ttgcttacat gcctcgtatc atgactgatt actgctttgt  10440
tagaacacag aagagaccct attttattta aggcagaacc ccgaagatac gtatttccaa  10500
tacagaaaag aatttttaat aaaaactata acatacacaa aaattggttt taaagttgac  10560
tccacttcct ctaactccag tggattgttg gccatgtctc cccaactcca caatatctct  10620
atcatgggaa acacctgggg tttttgcgct acataggaga aagatctgga aactatttgg  10680
gttttgtttt caacttttca tttggatgtt tggcgttgca cacacacatc caccggtgga  10740
agagacgccc ggtgaaaaca cctgtctgct ttctaagcca gtgaggttga ggtgagaggt  10800
ttgccagagt ttgtctacct ctgggtatcc ctttgtctgg gataaaaaaa atcaaaccag  10860
aaggcgggat ggaatggatg caccgcaaat aatgcatttt ctgagttttc ttgttaaaaa  10920
aaaatttttt taagtaagaa aaaaaaaggt aataacatgg ccaatttgtt acataaaatg  10980
actttctgtg tataaattat tcctaaaaaa tcctgtttat ataaaaaatc agtagatgaa  11040
```

```
aaaaatttca aaatgttttt gtatattctg ttgtaagaat ttattcctgt tattgcgata  11100

tactctggat tctttacata atggaaaaaa gaaactgtct attttgaatg gctgaagcta  11160

aggcaacgtt agtttctctt actctgcttt tttctagtaa agtactacat ggtttaagtt  11220

aaataaaata attctgtatg ca                                           11242
```

<210> SEQ ID NO 29
<211> LENGTH: 1660
<212> TYPE: DNA
<213> ORGANISM: Homo sapiens

<400> SEQUENCE: 29

```
ggtgcactag caaaacaaac ttattttgaa cactcagctc ctagcgtgcg gcgctgccaa     60

tcattaacct cctggtgcaa gtggcgcggc ctgtgccctt tataaggtgc gcgctgtgtc    120

cagcgagcat cggccaccgc catcccatcc agcgagcatc tgccgccgcg ccgccgccac    180

cctcccagag agcactggcc accgctccac catcacttgc ccagagtttg ggccaccgcc    240

cgccgccacc agcccagaga gcatcggccc ctgtctgctg ctcgcgcctg gagatgtcag    300

aggtccccgt tgctcgcgtc tggctggtac tgctcctgct gactgtccag gtcggcgtga    360

cagccggcgc tccgtggcag tgcgcgccct gctccgccga gaagctcgcg ctctgcccgc    420

cggtgtccgc ctcgtgctcg gaggtcaccc ggtccgccgg ctgcggctgt tgcccgatgt    480

gcgccctgcc tctgggcgcc gcgtgcggcg tggcgactgc acgctgcgcc cggggactca    540

gttgccgcgc gctgccgggg gagcagcaac ctctgcacgc cctcacccgc ggccaaggcg    600

cctgcgtgca ggagtctgac gcctccgctc cccatgctgc agaggcaggg agccctgaaa    660

gcccagagag cacggagata actgaggagg agctcctgga taatttccat ctgatggccc    720

cttctgaaga ggatcattcc atcctttggg acgccatcag tacctatgat ggctcgaagg    780

ctctccatgt caccaacatc aaaaaatgga aggagccctg ccgaatagaa ctctacagag    840

tcgtagagag tttagccaag gcacaggaga catcaggaga agaaatttcc aaattttacc    900

tgccaaactg caacaagaat ggattttatc acagcagaca gtgtgagaca tccatggatg    960

gagaggcggg actctgctgg tgcgtctacc cttggaatgg gaagaggatc cctgggtctc   1020

cagagatcag gggagacccc aactgccaga tatattttaa tgtacaaaac tgaaaccaga   1080

tgaaataatg ttctgtcacg tgaaatattt aagtatatag tatatttata ctctagaaca   1140

tgcacattta tatatatatg tatatgtata tatatatagt aactactttt tatactccat   1200

acataacttg atatagaaag ctgtttattt attcactgta agtttatttt ttctacacag   1260

taaaaacttg tactatgtta ataacttgtc ctatgtcaat ttgtatatca tgaaacactt   1320

ctcatcatat tgtatgtaag taattgcatt tctgctcttc caaagctcct gcgtctgttt   1380

ttaaagagca tggaaaaata ctgcctagaa aatgcaaaat gaaataagag agagtagttt   1440

ttcagctagt ttgaaggagg acggttaact tgtatattcc accattcaca tttgatgtac   1500

atgtgtaggg aaagttaaaa gtgttgatta cataatcaaa gctacctgtg gtgatgttgc   1560

cacctgttaa aatgtacact ggatatgttg ttaaacacgt gtctataatg gaaacattta   1620

caataaatat tctgcatgga aatactgtta aaaaaaaaaa                         1660
```

<210> SEQ ID NO 30
<211> LENGTH: 2638
<212> TYPE: DNA
<213> ORGANISM: Homo sapiens

<400> SEQUENCE: 30

```
agatgcgagc actgcggctg ggcgctgagg atcagccgct tcctgcctgg attccacagc     60
ttcgcgccgt gtactgtcgc cccatccctg cgcgcccagc ctgccaagca gcgtgccccg    120
gttgcaggcg tcatgcagcg ggcgcgaccc acgctctggg ccgctgcgct gactctgctg    180
gtgctgctcc gcgggccgcc ggtggcgcgg gctggcgcga gctcggcggg cttgggtccc    240
gtggtgcgct gcgagccgtg cgacgcgcgt gcactggccc agtgcgcgcc tccgcccgcc    300
gtgtgcgcgg agctggtgcg cgagccgggc tgcggctgct gcctgacgtg cgcactgagc    360
gagggccagc cgtgcggcat ctacaccgag cgctgtggct ccggccttcg ctgccagccg    420
tcgcccgacg aggcgcgacc gctgcaggcg ctgctggacg gccgcgggct ctgcgtcaac    480
gctagtgccg tcagccgcct gcgcgcctac ctgctgccag cgccgccagc tccaggtgag    540
ccgcccgcgc caggaaatgc tagtgagtcg gaggaagacc gcagcgccgg cagtgtggag    600
agcccgtccg tctccagcac gcaccgggtg tctgatccca agttccaccc cctccattca    660
aagataatca tcatcaagaa agggcatgct aaagacagcc agcgctacaa agttgactac    720
gagtctcaga gcacagatac ccagaacttc tcctccgagt ccaagcggga gacagaatat    780
ggtccctgcc gtagagaaat ggaagacaca ctgaatcacc tgaagttcct caatgtgctg    840
agtcccaggg gtgtacacat tcccaactgt gacaagaagg gattttataa gaaaaagcag    900
tgtcgccctt ccaaaggcag gaagcggggc ttctgctggt gtgtggataa gtatgggcag    960
cctctcccag gctacaccac caaggggaag gaggacgtgc actgctacag catgcagagc   1020
aagtagacgc ctgccgcaag gttaatgtgg agctcaaata tgccttattt tgcacaaaag   1080
actgccaagg acatgaccag cagctggcta cagcctcgat ttatatttct gtttgtggtg   1140
aactgatttt ttttaaacca aagtttagaa agaggttttt gaaatgccta tggtttcttt   1200
gaatggtaaa cttgagcatc ttttcacttt ccagtagtca gcaaagagca gtttgaattt   1260
tcttgtcgct tcctatcaaa atattcagag actcgagcac agcacccaga cttcatgcgc   1320
ccgtggaatg ctcaccacat gttggtcgaa gcggccgacc actgactttg tgacttaggc   1380
ggctgtgttg cctatgtaga gaacacgctt cacccccact ccccgtacag tgcgcacagg   1440
ctttatcgag aataggaaaa cctttaaacc ccggtcatcc ggacatccca acgcatgctc   1500
ctggagctca cagccttctg tggtgtcatt tctgaaacaa gggcgtggat ccctcaacca   1560
agaagaatgt ttatgtcttc aagtgacctg tactgcttgg ggactattgg agaaaataag   1620
gtggagtcct acttgtttaa aaaatatgta tctaagaatg ttctagggca ctctgggaac   1680
ctataaaggc aggtatttcg ggccctcctc ttcaggaatc ttcctgaaga catggcccag   1740
tcgaaggccc aggatggctt ttgctgcggc cccgtggggt aggagggaca gagagacagg   1800
gagagtcagc ctccacattc agaggcatca caagtaatgg cacaattctt cggatgactg   1860
cagaaaatag tgttttgtag ttcaacaact caagacgaag cttatttctg aggataagct   1920
ctttaaaggc aaagctttat tttcatctct catcttttgt cctccttagc acaatgtaaa   1980
aaagaatagt aatatcagaa caggaaggag gaatggcttg ctggggagcc catccaggac   2040
actgggagca catagagatt cacccatgtt tgttgaactt agagtcattc tcatgctttt   2100
ctttataatt cacacatata tgcagagaag atatgttctt gttaacattg tatacaacat   2160
agccccaaat atagtaagat ctatactaga taatcctaga tgaaatgtta gagatgctat   2220
atgatacaac tgtggccatg actgaggaaa ggagctcacg cccagagact gggctgctct   2280
cccggaggcc aaacccaaga aggtctggca aagtcaggct cagggagact ctgccctgct   2340
```

```
gcagacctcg gtgtggacac acgctgcata gagctctcct tgaaaacaga ggggtctcaa   2400

gacattctgc ctacctatta gcttttcttt atttttttaa ctttttgggg ggaaaagtat   2460

ttttgagaag tttgtcttgc aatgtattta taaatagtaa ataaagtttt taccattaaa   2520

aaaatatctt tccctttgtt attgaccatc tctgggcttt gtatcactaa ttattttatt   2580

ttattatata ataattattt tattataata aaatcctgaa aggggaaaat aaaaaaaa     2638


<210> SEQ ID NO 31
<211> LENGTH: 4723
<212> TYPE: DNA
<213> ORGANISM: Homo sapiens

<400> SEQUENCE: 31

gggggctgc gcggccgggt cggtgcgcac acgagaagga cgcgcggccc ccagcgctct     60

tgggggccgc ctcggagcat gacccccgcg ggccagcgcc gcgcgcctga tccgaggaga    120

ccccgcgctc ccgcagccat gggcaccggg ggccggcggg gggcggcggc cgcgccgctg    180

ctggtggcgg tggccgcgct gctactgggc gccgcgggcc acctgtaccc cggagaggtg    240

tgtcccggca tggatatccg gaacaacctc actaggttgc atgagctgga gaattgctct    300

gtcatcgaag gacacttgca gatactcttg atgttcaaaa cgaggcccga agatttccga    360

gacctcagtt tccccaaact catcatgatc actgattact tgctgctctt ccgggtctat    420

gggctcgaga gcctgaagga cctgttcccc aacctcacgg tcatccgggg atcacgactg    480

ttctttaact acgcgctggt catcttcgag atggttcacc tcaaggaact cggcctctac    540

aacctgatga acatcacccg gggttctgtc cgcatcgaga agaacaatga gctctgttac    600

ttggccacta tcgactggtc ccgtatcctg gattccgtgg aggataatca catcgtgttg    660

aacaaagatg acaacgagga gtgtggagac atctgtccgg gtaccgcgaa gggcaagacc    720

aactgccccg ccaccgtcat caacgggcag tttgtcgaac gatgttggac tcatagtcac    780

tgccagaaag tttgcccgac catctgtaag tcacacggct gcaccgccga aggcctctgt    840

tgccacagcg agtgcctggg caactgttct cagcccgacg accccaccaa gtgcgtggcc    900

tgccgcaact tctacctgga cggcaggtgt gtggagacct gcccgccccc gtactaccac    960

ttccaggact ggcgctgtgt gaacttcagc ttctgccagg acctgcacca caaatgcaag   1020

aactcgcgga ggcagggctg ccaccaatac gtcattcaca acaacaagtg catccctgag   1080

tgtccctccg ggtacacgat gaattccagc aacttgctgt gcaccccatg cctgggtccc   1140

tgtcccaagg tgtgccacct cctagaaggc gagaagacca tcgactcggt gacgtctgcc   1200

caggagctcc gaggatgcac cgtcatcaac gggagtctga tcatcaacat tcgaggaggc   1260

aacaatctgg cagctgagct agaagccaac ctcggcctca ttgaagaaat ttcagggtat   1320

ctaaaaatcc gccgatccta cgctctggtg tcactttcct tcttccggaa gttacgtctg   1380

attcgaggag agaccttgga aattgggaac tactccttct atgccttgga caaccagaac   1440

ctaaggcagc tctgggactg gagcaaacac aacctcacca ccactcaggg gaaactcttc   1500

ttccactata accccaaact ctgcttgtca gaaatccaca agatggaaga agtttcagga   1560

accaaggggc gccaggagag aaacgacatt gccctgaaga ccaatgggga caaggcatcc   1620

tgtgaaaatg agttacttaa attttcttac attcggacat cttttgacaa gatcttgctg   1680

agatgggagc cgtactggcc ccccgacttc cgagacctct tggggttcat gctgttctac   1740

aaagaggccc cttatcagaa tgtgacggag ttcgatgggc aggatgcgtg tggttccaac   1800

agttggacgg tggtagacat tgacccaccc ctgaggtcca acgaccccaa atcacagaac   1860
```

```
cacccagggt ggctgatgcg gggtctcaag ccctggaccc agtatgccat ctttgtgaag   1920
accctggtca ccttttcgga tgaacgccgg acctatgggg ccaagagtga catcatttat   1980
gtccagacag atgccaccaa cccctctgtg cccctggatc caatctcagt gtctaactca   2040
tcatcccaga ttattctgaa gtggaaacca ccctccgacc ccaatggcaa catcacccac   2100
tacctggttt tctgggagag gcaggcggaa gacagtgagc tgttcgagct ggattattgc   2160
ctcaaagggc tgaagctgcc ctcgaggacc tggtctccac cattcgagtc tgaagattct   2220
cagaagcaca accagagtga gtatgaggat tcggccggcg aatgctgctc ctgtccaaag   2280
acagactctc agatcctgaa ggagctggag gagtcctcgt ttaggaagac gtttgaggat   2340
tacctgcaca acgtggtttt cgtccccaga aaaacctctt caggcactgg tgccgaggac   2400
cctaggccat ctcggaaacg caggtccctt ggcgatgttg ggaatgtgac ggtggccgtg   2460
cccacggtgg cagctttccc caacacttcc tcgaccagcg tgcccacgag tccggaggag   2520
cacaggcctt ttgagaaggt ggtgaacaag gagtcgctgg tcatctccgg cttgcgacac   2580
ttcacgggct atcgcatcga gctgcaggct tgcaaccagg acacccctga ggaacggtgc   2640
agtgtggcag cctacgtcag tgcgaggacc atgcctgaag ccaaggctga tgacattgtt   2700
ggccctgtga cgcatgaaat ctttgagaac aacgtcgtcc acttgatgtg gcaggagccg   2760
aaggagccca atggtctgat cgtgctgtat gaagtgagtt atcggcgata tggtgatgag   2820
gagctgcatc tctgcgtctc ccgcaagcac ttcgctctgg aacggggctg caggctgcgt   2880
gggctgtcac cggggaacta cagcgtgcga atccgggcca cctcccttgc gggcaacggc   2940
tcttggacgg aacccaccta tttctacgtg acagactatt tagacgtccc gtcaaatatt   3000
gcaaaaatta tcatcggccc cctcatcttt gtctttctct tcagtgttgt gattggaagt   3060
atttatctat tcctgagaaa gaggcagcca gatgggccgc tgggaccgct ttacgcttct   3120
tcaaaccctg agtatctcag tgccagtgat gtgtttccat gctctgtgta cgtgccggac   3180
gagtgggagg tgtctcgaga gaagatcacc ctccttcgag agctggggca gggctccttc   3240
ggcatggtgt atgagggcaa tgccagggac atcatcaagg gtgaggcaga gacccgcgtg   3300
gcggtgaaga cggtcaacga gtcagccagt ctccgagagc ggattgagtt cctcaatgag   3360
gcctcggtca tgaagggctt cacctgccat cacgtggtgc gcctcctggg agtggtgtcc   3420
aagggccagc ccacgctggt ggtgatggag ctgatggctc acggagacct gaagagctac   3480
ctccgttctc tgcggccaga ggctgagaat aatcctggcc gccctccccc tacccttcaa   3540
gagatgattc agatggcggc agagattgct gacgggatgg cctacctgaa cgccaagaag   3600
tttgtgcatc gggacctggc agcgagaaac tgcatggtcg cccatgattt tactgtcaaa   3660
attggagact ttggaatgac cagagacatc tatgaaacgg attactaccg gaaagggggc   3720
aagggtctgc tccctgtacg gtggatggca ccggagtccc tgaaggatgg ggtcttcacc   3780
acttcttctg acatgtggtc ctttggcgtg gtcctttggg aaatcaccag cttggcagaa   3840
cagccttacc aaggcctgtc taatgaacag gtgttgaaat ttgtcatgga tggagggtat   3900
ctggatcaac ccgacaactg tccagagaga gtcactgacc tcatgcgcat gtgctggcaa   3960
ttcaacccca agatgaggcc aaccttcctg gagattgtca acctgctcaa ggacgacctg   4020
caccccagct ttccagaggt gtcgttcttc cacagcgagg agaacaaggc tcccgagagt   4080
gaggagctgg agatggagtt tgaggacatg gagaatgtgc ccctggaccg ttcctcgcac   4140
tgtcagaggg aggaggcggg gggccgggat ggagggtcct cgctgggttt caagcggagc   4200
```

```
tacgaggaac acatccctta cacacacatg aacggaggca agaaaaacgg gcggattctg   4260

accttgcctc ggtccaatcc ttcctaacag tgcctaccgt ggcgggggcg ggcaggggtt   4320

cccattttcg ctttcctctg gtttgaaagc ctctggaaaa ctcaggattc tcacgactct   4380

accatgtcca gtggagttca gagatcgttc ctatacattt ctgttcatct taaggtggac   4440

tcgtttggtt accaatttaa ctagtcctgc agaggattta actgtgaacc tggagggcaa   4500

ggggtttcca cagttgctgc tcctttgggg caacgacggt ttcaaaccag gattttgtgt   4560

tttttcgttc cccccacccg cccccagcag atggaaagaa agcacctgtt tttacaaatt   4620

cttttttttt tttttttttt ttttttttg ctggtgtctg agcttcagta taaaagacaa   4680

aacttcctgt ttgtggaaca aaatttcgaa agaaaaaacc aaa                    4723
```

```
<210> SEQ ID NO 32
<211> LENGTH: 3017
<212> TYPE: DNA
<213> ORGANISM: Homo sapiens

<400> SEQUENCE: 32

ggatccctga gcgtcacgcc gctgttgtgg agcgcgtgtt gacaacgtcg ccggggagac     60

gggcgggggc ggggcccggg agagggggag gcgcggccct ggcggcgcgc gaggggccgg    120

gctgtcagcg caaggcccag gccgccgcag tggccacggc cgctgccgcc cgccggctta    180

tataccgcgg ctaaatttag gctgcgcccg gagctcgtcc ccatccggga cgcgtttccg    240

ccgccgccgc tttggcccgg cccccgcgcg cgccgcgcct ataaggcttg ggcgggcccg    300

gccgcggccc acagagccgt ccccgcccgc ccgcgccccg accagcccgg cctcgggcag    360

ccactcaccg gtgtccccgt ccgcgtcctt cctccccggg tcccggccat ggcgctgagt    420

gaacccatcc tgccgtcctt ttccactttc gccagcccgt gccgcgagcg cggcctgcag    480

gaggtgaggg cggcggggac ggcggggcga ccgggaccgt gggcggcggg ctcggggtag    540

tagaacgtgg gctgcggggt gacaggacgc gaaggcgggg actgcagact caggagagga    600

ggatgcgggc cacggggatc gcggacttag ggtggtaaaa ggcaagcagc gccccccgag    660

ccccgccgcc cgctcacgcc cattgccctg tcgcccgcag cgctggccgc gcgccgaacc    720

cgagtccggc ggcaccgacg acgacctcaa cagcgtgctg gacttcatcc tgtccatggg    780

gctggatggc ctgggcgccg aggccgcccc ggagccgccg ccgccgcccc cgccgcctgc    840

gttctattac cccgaacccg gcgcgccccc gccctacagc gcccccgcgg gtggcctggt    900

gtctgagctg ctgcgacccg agctggatgc gccgccgggg cccgcactgc acggccgctt    960

tctgctggcg ccgcccggcc gcctggtcaa ggccgagccc cctgaagcgg acggcggcgg   1020

cggctacggc tgcgcccccg ggctgacccg tggaccgcgc ggcctcaagc gcgagggcgc   1080

cccaggcccg gcggcttcgt gcatgcgagg tcccgggggc cgcccccgc cgccgcccga   1140

cacaccgccg ctcagccccg acggccccgc gcgcctgccc gcgcccggtc cgcgcgcctc   1200

cttcccgccg cctttcggtg gccctggttt cggcgcgccc gggcccggcc tgcattacgc   1260

gccgcctgcg cccccagcct tcggtctttt cgacgacgcg gccgccgccg cggcagccct   1320

gggcctggcg ccccccgccg cccgcggtct cctcacgccg cctgcgtccc cgctggagct   1380

gctggaggcc aagccaaagc gcggccgccg ctcttggccc cgcaaacgca ccgccactca   1440

cacctgcagc tacgcgggct gcggcaagac ctacaccaag agttcgcatc tgaaggcgca   1500

tctgcgcacg cacacaggtg ggcggcacgc acgagccagg agcgcaggcg gggggacgcg   1560

ggaggagagg tcggattccc agcgcgcgcc agaaaatgaa tttaggacct cccttggggc   1620
```

```
gtggctcagg gggatctggc agtggtgcac gcttaggact ccccaggagc gtggctcggg   1680
aggttggttg ggggggcaca caggaacact ccctaaggaa gtgtgatccg agaggttggg   1740
gtgggggctt gcacgcttag gacgaggggg gcctccggag gttgggaaga gcacttagaa   1800
aacctcctgg aggcgtggct agggagacag tctcagaaag ttggggaggg ggagcaggtt   1860
taggagccgc tgggcacttg gctcagaatc cccggggctg aggctcaggt agttggggag   1920
taggtgcgcg tttaggaacc ccggggagat gctgcgtctc aggaagttgg ggagggcgct   1980
caggcttggg actcctctgg ggacaaggct caggaccttg ggagggagt gttcgctggg   2040
aaaccttgag agattccgtg tcttagaatg ctggagagag gtgcatgctt aggaccgtcg   2100
gggagcgtgg ctgacaacag tggggagtgg accttgcgct cctccgaccc cctgggggtg   2160
aggatccgga ttgtgggggg agttggggat gtagggcaag gatccctcag ggcgcaaca   2220
ctaccgcggg gagcgcgtca aggccctggt tagggatagg ttgcgctcgc cggggtagcc   2280
atacgtgccc tgtcctggga ggggaactga cgcttactct cgccccctcc ctgcaggtga   2340
gaagccctac cactgcaact gggacggctg cggctggaag tttgcgcgct cagacgagct   2400
cacgcgccac taccgaaagc acacgggcca ccggccattc cagtgccatc tgtgcgatcg   2460
tgccttctcg cgctccgatc acctggcgct gcacatgaaa cggcacatgt agccgggacg   2520
cccccgccca cctgcgcgcg gccgtggcgg gtcccacgcg ccgggcgcgg ccccctccca   2580
aactgtgact ggtatttatt ggacccagag aaccgggccg ggcacagcgt ggctacagag   2640
ggtctccctc gatgacgacg acgacgacgc caccacccca gcccccgtct gtgactgaag   2700
gcccggtggg aaaagaccac gatcctcctt gacgagtttt gtttttcaaa atggtgcaat   2760
aatttaagtg gcatcttctc tcccaccggg tctacactag aggatcgagg cttgtgatgc   2820
cttgtaagaa ataagggcct taatttgtac tgtctgcggc atttttata atattgtata   2880
tagtgactga caaatattgt attactgtac atagagagac aggtgggcat ttttgggcta   2940
cctggttcgt ttttataaga ttttgctggg ttggtttttt tttttattaa aaagttttgc   3000
atcttttaaa aaaaaaa                                                 3017
```

<210> SEQ ID NO 33
<211> LENGTH: 2949
<212> TYPE: DNA
<213> ORGANISM: Homo sapiens

<400> SEQUENCE: 33

```
agtttcccga ccagagagaa cgaacgtgtc tgcgggcgcg cggggagcag aggcggtggc     60
gggcggcggc ggcaccggga gccgccgagt gaccctcccc cgcccctctg gccccccacc    120
ctcccacccg cccgtggccc gcgcccatgg ccgcgcgcgc tccacacaac tcaccggagt    180
ccgcgccttg cgccgccgac cagttcgcag ctccgcgcca cggcagccag tctcacctgg    240
cggcaccgcc cgcccaccgc cccggccaca gcccctgcgc ccacggcagc actcgaggcg    300
accgcgacag tggtgggggga cgctgctgag tggaagagag cgcagcccgg ccaccggacc    360
tacttactcg ccttgctgat tgtctatttt tgcgtttaca acttttctaa gaacttttgt    420
atacaaagga actttttaaa aaagacgctt ccaagttata tttaatccaa agaagaagga    480
tctcggccaa tttggggttt tgggttttgg cttcgtttct tctcttcgtt gactttgggg    540
ttcaggtgcc ccagctgctt cgggctgccg aggaccttct gggcccccac attaatgagg    600
cagccacctg gcgagtctga catggctgtc agcgacgcgc tgctcccatc tttctccacg    660
```

```
ttcgcgtctg gcccggcggg aagggagaag acactgcgtc aagcaggtgc cccgaataac    720
cgctggcggg aggagctctc ccacatgaag cgacttcccc cagtgcttcc cggccgcccc    780
tatgacctgg cggcggcgac cgtggccaca gacctggaga gcggcggagc cggtgcggct    840
tgcggcggta gcaacctggc gcccctacct cggagagaga ccgaggagtt caacgatctc    900
ctggacctgg actttattct ctccaattcg ctgacccatc ctccggagtc agtggccgcc    960
accgtgtcct cgtcagcgtc agcctcctct tcgtcgtcgc cgtcgagcag cggccctgcc   1020
agcgcgccct ccacctgcag cttcacctat ccgatccggg ccgggaacga cccgggcgtg   1080
gcgccgggcg gcacgggcgg aggcctcctc tatggcaggg agtccgctcc ccctccgacg   1140
gctcccttca acctggcgga catcaacgac gtgagcccct cgggcggctt cgtggccgag   1200
ctcctgcggc cagaattgga cccggtgtac attccgccgc agcagccgca gccgccaggt   1260
ggcgggctga tgggcaagtt cgtgctgaag gcgtcgctga gcgcccctgg cagcgagtac   1320
ggcagcccgt cggtcatcag cgtcagcaaa ggcagccctg acggcagcca cccggtggtg   1380
gtggcgccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620
cacccggggc ccaattaccc atccttcctg cccgatcaga tgcagccgca agtcccgccg   1680
ctccattacc aagagctcat gccacccggt tcctgcatgc cagaggagcc caagccaaag   1740
aggggaagac gatcgtggcc ccggaaaagg accgccaccc acacttgtga ttacgcgggc   1800
tgcggcaaaa cctacacaaa gagttcccat ctcaaggcac acctgcgaac ccacacaggt   1860
gagaaacctt accactgtga ctgggacggc tgtggatgga aattcgcccg ctcagatgaa   1920
ctgaccaggc actaccgtaa acacacgggg caccgcccgt tccagtgcca aaaatgcgac   1980
cgagcatttt ccaggtcgga ccacctcgcc ttacacatga agaggcattt ttaaatccca   2040
gacagtggat atgacccaca ctgccagaag agaattcagt atttttttact tttcacactg   2100
tcttcccgat gagggaagga gcccagccag aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaagggggt gactggaagt tgtggatatc agggtataaa   2340
ttatatccgt gagttggggg agggaagacc agaattccct tgaattgtgt attgatgcaa   2400
tataagcata aaagatcacc ttgtattctc tttaccttct aaaagccatt attatgatgt   2460
tagaagaaga ggaagaaatt caggtacaga aaacatgttt aaatagccta aatgatggtg   2520
cttggtgagt cttggttcta aaggtaccaa acaaggaagc caaagttttc aaactgctgc   2580
atactttgac aaggaaaatc tatatttgtc ttccgatcaa catttatgac ctaagtcagg   2640
taatatacct ggtttacttc tttagcattt ttatgcagac agtctgttat gcactgtggt   2700
ttcagatgtg caataatttg tacaatggtt tattcccaag tatgccttaa gcagaacaaa   2760
tgtgtttttc tatatagttc cttgccttaa taaatatgta atataaattt aagcaaacgt   2820
ctattttgta tatttgtaaa ctacaaagta aaatgaacat tttgtggagt ttgtattttg   2880
catactcaag gtgagaatta agttttaaat aaacctataa tattttatct gaaaaaaaaa   2940
aaaaaaaaa                                                            2949
```

<210> SEQ ID NO 34
<211> LENGTH: 2073
<212> TYPE: DNA
<213> ORGANISM: Homo sapiens

<400> SEQUENCE: 34

```
agatgccacg ccccatagct ccaccagtca ccgcggcaca gtggccctta agcgaggagc     60
ggcggcgccc gcagcaatca cagcagtgcc gacgtcgtgg gtgtttggtg tgaggctgcg    120
agccgccgcg agttctcacg gtcccgccgg cgccaccacc gcggtcactc accgccgccg    180
ccgccaccac tgccaccacg gtcgcctgcc acaggtgtct gcaattgaac tccaaggtgc    240
agaatggttt ggaaagtagc tgtattcctc agtgtggccc tgggcattgg tgccgttcct    300
atagatgatc ctgaagatgg aggcaagcac tgggtggtga tcgtggcagg ttcaaatggc    360
tggtataatt ataggcacca ggcagacgcg tgccatgcct accagatcat tcaccgcaat    420
gggattcctg acgaacagat cgttgtgatg atgtacgatg acattgctta ctctgaagac    480
aatcccactc caggaattgt gatcaacagg cccaatggca cagatgtcta tcagggagtc    540
ccgaaggact acactggaga ggatgttacc ccacaaaatt tccttgctgt gttgagaggc    600
gatgcagaag cagtgaaggg cataggatcc ggcaaagtcc tgaagagtgg cccccaggat    660
cacgtgttca tttacttcac tgaccatgga tctactggaa tactggtttt tcccaatgaa    720
gatcttcatg taaaggacct gaatgagacc atccattaca tgtacaaaca caaaatgtac    780
cgaaagatgg tgttctacat tgaagcctgt gagtctgggt ccatgatgaa ccacctgccg    840
gataacatca atgtttatgc aactactgct gccaacccca gagagtcgtc ctacgcctgt    900
tactatgatg agaagaggtc cacgtacctg gggggactggt acagcgtcaa ctggatggaa    960
gattcggacg tggaagatct gactaaagag accctgcaca agcagtacca cctggtaaaa   1020
tcgcacacca acaccagcca cgtcatgcag tatggaaaca aaacaatctc caccatgaaa   1080
gtgatgcagt ttcagggtat gaaacgcaaa gccagttctc ccgtccccct acctccagtc   1140
acacaccttg acctcacccc cagccctgat gtgcctctca ccatcatgaa aaggaaactg   1200
atgaacacca atgatctgga ggagtccagg cagctcacgg aggagatcca gcggcatctg   1260
gatgccaggc acctcattga gaagtcagtg cgtaagatcg tctccttgct ggcagcgtcc   1320
gaggctgagg tggagcagct cctgtccgag agagccccgc tcacggggca cagctgctac   1380
ccagaggccc tgctgcactt ccggacccac tgcttcaact ggcactcccc cacgtacgag   1440
tatgcgttga gacatttgta cgtgctggtc aacctttgtg agaagccgta tccgcttcac   1500
aggataaaat tgtccatgga ccacgtgtgc cttggtcact actgaagagc tgcctcctgg   1560
aagcttttcc aagtgtgagc gccccaccga ctgtgtgctg atcagagact ggagaggtgg   1620
agtgagaagt ctccgctgct cgggccctcc tggggagccc ccgctccagg gctcgctcca   1680
ggaccttctt cacaagatga cttgctcgct gttacctgct tccccagtct tttctgaaaa   1740
actacaaatt agggtgggaa aagctctgta ttgagaaggg tcatatttgc tttctaggag   1800
gtttgttgtt ttgcctgtta gttttgagga gcaggaagct catgggggct tctgtagccc   1860
ctctcaaaag gagtctttat tctgagaatt tgaagctgaa acctctttaa atcttcagaa   1920
tgattttatt gaagagggcc gcaagcccca aatggaaaac tgtttttaga aaatatgatg   1980
atttttgatt gcttttgtat ttaattctgc aggtgttcaa gtcttaaaaa ataaagattt   2040
ataacagaac ccaaataaaa aaaaaaaaaa aaa                                2073
```

<210> SEQ ID NO 35

```
<211> LENGTH: 3470
<212> TYPE: DNA
<213> ORGANISM: Homo sapiens

<400> SEQUENCE: 35

atacacacag actcacagcg agaccgacac acactcccat acactcacac acacaactgc     60
aggcagcgag gctcgggaag tcaggccggc ttttcgcccc ggcgccttct ctgctccagc    120
cggccgggtc tccctggggg cccggagctc ggccgggccg cgcagccccg ttagaggacg    180
agctcggcgg acccccgctc ctccatgggc aaacgcgggc ggccgcgcaa ggaggcgcgc    240
tgcgagggcg cggggctggc ccccgccgcg cccccggctg tgccccccgc cgtggccgcg    300
ccccagcccc cggccctgcc cgaggacccc gctggggcca agcccaggtg cccccttctca    360
gacattttca acaccagcga gaactcgatg gagaagcaca tcaacacttt tctgcagaac    420
gtgcagattc tgctcgaggc cgccagctac ctggagcaga tcgagaaaga aaacaaaaag    480
tgtgaacatg gctacgcctc ttcattcccg tccatgccga gcccccgact gcagcattca    540
aagcccccac ggaggttgag ccgggcacag aaacacagca gcgggagcag caacaccagc    600
actgccaaca gatctacaca caatgagctg gaaaagaatc gacgagctca tctgcgcctt    660
tgtttagaac gcttaaaagt tctgattcca ctaggaccag actgcacccg gcacacaaca    720
cttggtttgc tcaacaaagc caaagcacac atcaagaaac ttgaagaagc tgaaagaaaa    780
agccagcacc agctcgagaa tttggaacga gaacagagat tttaaagtg gcgactggaa    840
cagctgcagg gtcctcagga gatggaacga atacgaatgg acagcattgg atcaactatt    900
tcttcagatc gttctgattc agagcgagag gagattgaag tggatgttga aagcacagag    960
ttctcccatg gagaagtgga caatataagt accaccagca tcagtgacat tgatgaccac   1020
agcagcctgc cgagtattgg gagtgacgag ggttactcca gtgccagtgt caaactttca   1080
ttcacttcat agaacccagc atgacataac agtgcagggc aaaatattca ctgggccaat   1140
tcaatacaaa caatctctta aattgggttc atgatgcagt ctcctcttta aaacaaaaca   1200
aaacaaaaca aaactatact tgaacaaaag ggtcagagga cctgtattta agcaaatact   1260
tagcaaaaag tggggcagag cctcccaagg agaacaaata ttcagaatat tcatattgga   1320
aaaatcacaa tttttaatgg cagcagaaaa cttgtgtgaa attttcttga tttgagttga   1380
ttgagaagag gacattggag atgccatcct ctttctcttt tctagtttgc tcatactaca   1440
ttgagtagac acatttaagg atggggttat gaacccttcc tgagctttat ggtcctaaaa   1500
gcaaaataaa aactattcga atgaaaagac aagaaaatca ggtattaatc ttggatagct   1560
aataatgagc tattaaaact cagcctggga cagtttatca tgaagcctgt ggatgatcaa   1620
tcctttatta ttattttttt tttttgaaaa aagctcattt catgctctgc aaaaggagag   1680
actcccatga agccttttga aagggatcat catgcagctc aactttctgt tggattccat   1740
gctaagcaag ctaaccttat cctgcattgt tagcactagg cacccagctg ccacctctcc   1800
atcctgctgc ccttaggcca catgggagca gtccatgcat gacagcctct atcctacaag   1860
gcctatgagt atggattggg ggggccaaaa ggaaaaagct ccatgtgcct ctttgtctgc   1920
gtgggtcaga agagttgtgc acgcagatta gcaggccaag gtctgagcca cagcagcatt   1980
tttatttcag attttgataa ctgtttatat gtgttgaaaa ccaaaatgac atctttttaa   2040
agcttatcca taaaaaaaaa tagatgtctt ttatagtgga aaaacacatg gggaaaaaaa   2100
tcatctattt tgatgcagca tttgataatg ataaaacacc tcacacctca ctctttatag   2160
tgcacaaaat gaatgaggtc tgggctaggt agaaaaaggg tcaatgctat ttttgttttt   2220
```

```
agaatcatta ccttttacca gcttttaacc atctgatatc tatagtagac acactatcat   2280

agttaacata gtaagttcag cacttgtctc attttaatgt aaagatttgc ttccattttc   2340

ctacaggcag tctctctctt cctcacagtc ccactgtgca ggtgctattg ttactcttac   2400

gaatattttc agtaatgtta ttttcttcta agtgaaattt ctagcctgca ctttgatgtc   2460

atgtgttccc tttgtctttc aaactccaag gttcccttgt ggccctctcc cttaccctgg   2520

gaaggcctct tggagacctt accccctggct gtttggactt tgtatacttt aaataattta   2580

actaccctta attacttaaa aaaaaaaaaa agctttatga ttttcataac ttattgctga   2640

ttttaatgga ttgttaattt cagtcctgta gttttatttt atgtttagat agggctgggc   2700

aaggaaaaag aaaataaaga caaccatatt tagcagtgca gttgagttgt gtgttaatgt   2760

tagactatcc ctttgtgagt gacactttaa cagcattcac tgcttctata tatagtgtac   2820

catcttggtc atacattacg cctcaacata tacttgtgct cttcctttgc ctccagaaga   2880

agtttttcct tgattgtgct atgtttcagt ggaagaaatt ctttgaagta gatgtgagtg   2940

aaaaactgca tgcctttaga agcccagtat cagaacttgc tacgtttcag gtgctaggga   3000

cttaatgaaa aacaggacaa aacaattcct ttttgtggcc caggtaaatt atttctggtt   3060

tcacttataa ttactaatgg ctgagtcaag atgttgtctc tgtgtttgct tactcttgat   3120

caagtgtgag acagtttgaa gactgtgcta ccatacaaag tgaatgaagc cagtgactaa   3180

gcttctgttt gttttgttat tctcatggcc ttcgcttgca ttatttgggc cttcattcag   3240

atgaacttga ggtgccattt tgttgcatat gtacaggatt atgggctgga aagcatttgt   3300

tataaaccta tagtgcacat tttaactgcc ccctaaatta cccttccctg ggtttgtttt   3360

ccttggggtg gtgtagattg tatgagtaag aagtattaat tttttaaaag acaaatcaac   3420

tttgaagaca caaaagttaa ttggaagaaa taaaaactgt gaacgaagaa              3470
```

<210> SEQ ID NO 36
<211> LENGTH: 1823
<212> TYPE: DNA
<213> ORGANISM: Homo sapiens

<400> SEQUENCE: 36

```
gagaagctag ggtgaggaa gccctggggc gctgccgccg ctttccttaa ccacaaatca     60

ggccggacag gagagggagg ggtgggggac agtgggtggg cattcagact gccagcactt    120

tgctatctac agccggggct cccgagcggc agaaagttcc ggccactctc tgccgcttgg    180

gttgggcgaa gccaggaccg tgccgcgcca ccgccaggat atggagctac tgtcgccacc    240

gctccgcgac gtagacctga cggcccccga cggctctctc tgctcctttg ccacaacgga    300

cgacttctat gacgacccgt gtttcgactc cccggacctg cgcttcttcg aagacctgga    360

cccgcgcctg atgcacgtgg gcgcgctcct gaaacccgaa gagcactcgc acttccccgc    420

ggcggtgcac ccggccccgg gcgcacgtga ggacgagcat gtgcgcgcgc ccagcgggca    480

ccaccaggcg ggccgctgcc tactgtgggc ctgcaaggcg tgcaagcgca agaccaccaa    540

cgccgaccgc cgcaaggccg ccaccatgcg cgagcggcgc cgcctgagca aagtaaatga    600

ggcctttgag acactcaagc gctgcacgtc gagcaatcca aaccagcggt tgcccaaggt    660

ggagatcctg cgcaacgcca tccgctatat cgagggcctg caggctctgc tgcgcgacca    720

ggacgccgcg ccccctggcg ccgcagccgc cttctatgcg ccgggcccgc tgcccccggg    780

ccgcggcggc gagcactaca gcggcgactc cgacgcgtcc agcccgcgct ccaactgctc    840
```

```
cgacggcatg atggactaca gcggccccccc gagcggcgcc cggcggcgga actgctacga     900

aggcgcctac tacaacgagg cgcccagcga acccaggccc gggaagagtg cggcggtgtc     960

gagcctagac tgcctgtcca gcatcgtgga gcgcatctcc accgagagcc ctgcggcgcc    1020

cgccctcctg ctggcggacg tgccttctga gtcgcctccg cgcaggcaag aggctgccgc    1080

cccagcgag ggagagagca gcggcgaccc cacccagtca ccggacgccg ccccgcagtg    1140

ccctgcgggt gcgaacccca acccgatata ccaggtgctc tgaggggatg gtggccgccc    1200

acccgcccga gggatggtgc ccctagggtc cctcgcgccc aaaagattga acttaaatgc    1260

ccccctccca acagcgcttt aaaagcgacc tctcttgagg taggagaggc gggagaactg    1320

aagtttccgc ccccgcccca cagggcaagg acacagcgcg gttttttcca cgcagcaccc    1380

ttctcggaga cccattgcga tggccgctcc gtgttcctcg gtgggccaga gctgaacctt    1440

gaggggctag gttcagcttt ctcgcgccct cccccatggg ggtgagaccc tcgcagacct    1500

aagccctgcc ccgggatgca ccggttattt ggggggggcgt gagacccagt gcactccggt    1560

cccaaatgta gcaggtgtaa ccgtaaccca cccccaaccc gtttcccggt tcaggaccac    1620

tttttgtaat acttttgtaa tctattcctg taaataagag ttgctttgcc agagcaggag    1680

cccctggggc tgtatttatc tctgaggcat ggtgtgtggt gctacaggga atttgtacgt    1740

ttataccgca ggcgggcgag ccgcgggcgc tcgctcaggt gatcaaaata aaggcgctaa    1800

tttataaaaa aaaaaaaaaa aaa                                            1823
```

<210> SEQ ID NO 37
<211> LENGTH: 4345
<212> TYPE: DNA
<213> ORGANISM: Homo sapiens

<400> SEQUENCE: 37

```
actgaaacta ggggcaagga gacgaagaga acatgaaagt taaactttaa gatgaagaac      60

aaagctgaac atactgatgc attggatctt tggagaggat ctcagaactc attgtactta     120

atttacaggc taaaacctta gaagaggaat ttattatatc ctacacaaga ctccagggaa     180

gcacatggcc ttggactgaa ggctggcatc tggaagctgt cagccaccag caccttctgc     240

agcaggaaaa ggccagggct ctgctggagc aggcagcaga gtggacgcac agtaacatgg     300

gcaacttgaa gagcgtggcc caggagcctg ggccaccctg cggcctgggg ctggggctgg     360

gccttgggct gtgcggcaag cagggcccag ccaccccggc ccctgagccc agccgggccc     420

cagcatccct actcccacca gcgccagaac acagcccccc gagctccccg ctaacccagc     480

cccagaggg gcccaagttc cctcgtgtga agaactggga ggtggggagc atcacctatg     540

acaccctcag cgcccaggcg cagcaggatg ggccctgcac cccaagacgc tgcctgggct     600

ccctggtatt tccacggaaa ctacagggcc ggccctcccc cggccccccg gcccctgagc     660

agctgctgag tcaggcccgg gacttcatca accagtacta cagctccatt aagaggagcg     720

gctcccaggc ccacgaacag cggcttcaag aggtggaagc cgaggtggca gccacaggca     780

cctaccagct tagggagagc gagctggtgt tcggggctaa gcaggcctgg cgcaacgctc     840

cccgctgcgt gggccggatc cagtggggga agctgcaggt gttcgatgcc cgggactgca     900

ggtctgcaca ggaaatgttc acctacatct gcaaccacat caagtatgcc accaaccggg     960

gcaaccttcg ctcggccatc acagtgttcc cgcagcgctg ccctggccga ggagacttcc    1020

gaatctggaa cagccagctg gtgcgctacg cgggctaccg gcagcaggat ggctctgtgc    1080

gggggggaccc agccaacgtg gagatcaccg agctctgcat tcagcacggc tggaccccag    1140
```

```
gaaacggtcg cttcgacgtg ctgcccctgc tgctgcaggc cccagatgat cccccagaac   1200
tcttccttct gccccccgag ctggtccttg aggtgcccct ggagcacccc acgctggagt   1260
ggtttgcagc cctgggcctg cgctggtacg ccctcccggc agtgtccaac atgctgctgg   1320
aaattggggg cctggagttc cccgcagccc ccttcagtgg ctggtacatg agcactgaga   1380
tcggcacgag gaacctgtgt gaccctcacc gctacaacat cctggaggat gtggctgtct   1440
gcatggacct ggatacccgg accacctcgt ccctgtggaa agacaaggca gcagtggaaa   1500
tcaacgtggc cgtgctgcac agttaccagc tagccaaagt caccatcgtg gaccaccacg   1560
ccgccacggc ctctttcatg aagcacctgg agaatgagca gaaggccagg gggggctgcc   1620
ctgcagactg ggcctggatc gtgccccccca tctcgggcag cctcactcct gttttccatc   1680
aggagatggt caactatttc ctgtccccgg ccttccgcta ccagccagac ccctggaagg   1740
ggagtgccgc caagggcacc ggcatcacca ggaagaagac ctttaaagaa gtggccaacg   1800
ccgtgaagat ctccgcctcg ctcatgggca cggtgatggc gaagcgagtg aaggcgacaa   1860
tcctgtatgg ctccgagacc ggccgggccc agagctacgc acagcagctg gggagactct   1920
tccggaaggc ttttgatccc cgggtcctgt gtatggatga gtatgacgtg gtgtccctcg   1980
aacacgagac gctggtgctg gtggtaacca gcacatttgg gaatggggat cccccggaga   2040
atggagagag ctttgcagct gccctgatgg agatgtccgg cccctacaac agctcccctc   2100
ggccggaaca gcacaagagt tataagatcc gcttcaacag catctcctgc tcagacccac   2160
tggtgtcctc ttggcggcgg aagaggaagg agtccagtaa cacagacagt gcaggggccc   2220
tgggcaccct caggttctgt gtgttcgggc tcggctcccg ggcataccccc cacttctgcg   2280
cctttgctcg tgccgtggac acacggctgg aggaactggg cggggagcgg ctgctgcagc   2340
tgggccaggg cgacgagctg tgcggccagg aggaggcctt ccgaggctgg gcccaggctg   2400
ccttccaggc cgcctgtgag accttctgtg tgggagagga tgccaaggcc gccgcccgag   2460
acatcttcag ccccaaacgg agctggaagc gccagaggta ccggctgagc gcccaggccg   2520
agggcctgca gttgctgcca ggtctgatcc acgtgcacag gcggaagatg ttccaggcta   2580
caatccgctc agtggaaaac ctgcaaagca gcaagtccac gagggccacc atcctggtgc   2640
gcctggacac cggaggccag gaggggctgc agtaccagcc gggggaccac ataggtgtct   2700
gcccgcccaa ccggcccggc cttgtggagg cgctgctgag ccgcgtggag gacccgccgg   2760
cgcccactga gcccgtggca gtagagcagc tggagaaggg cagccctggt ggccctcccc   2820
ccggctgggt gcgggacccc cggctgcccc cgtgcacgct gcgccaggct ctcaccttct   2880
tcctggacat cacctcccca cccagccctc agctcttgcg gctgctcagc accttggcag   2940
aagagcccag ggaacagcag gagctggagg ccctcagcca ggatccccga cgctacgagg   3000
agtggaagtg gttccgctgc cccacgctgc tggaggtgct ggagcagttc ccgtcggtgg   3060
cgctgcctgc cccactgctc ctcacccagc tgcctctgct ccagccccgg tactactcag   3120
tcagctcggc acccagcacc cacccaggag agatccacct cactgtagct gtgctggcat   3180
acaggactca ggatgggctg ggccccctgc actatggagt ctgctccacg tggctaagcc   3240
agctcaagcc cggagaccct gtgccctgct tcatccgggg ggctccctcc ttccggctgc   3300
cacccgatcc cagcttgccc tgcatcctgg tgggtccagg cactggcatt gccccccttcc   3360
ggggattctg gcaggagcgg ctgcatgaca ttgagagcaa agggctgcag cccactccca   3420
tgactttggt gttcggctgc cgatgctccc aacttgacca tctctaccgc gacgaggtgc   3480
```

```
agaacgccca gcagcgcggg gtgtttggcc gagtcctcac cgccttctcc cgggaacctg   3540

acaaccccaa gacctacgtg caggacatcc tgaggacgga gctggctgcg gaggtgcacc   3600

gcgtgctgtg cctcgagcgg ggccacatgt ttgtctgcgg cgatgttacc atggcaacca   3660

acgtcctgca gaccgtgcag cgcatcctgg cgacggaggg cgacatggag ctggacgagg   3720

ccggcgacgt catcggcgtg ctgcgggatc agcaacgcta ccacgaagac attttcgggc   3780

tcacgctgcg cacccaggag gtgacaagcc gcatacgcac ccagagcttt tccttgcagg   3840

agcgtcagtt gcggggcgca gtgccctggg cgttcgaccc tcccggctca gacaccaaca   3900

gcccctgaga gccgcctggc tttcccttcc agttccggga gagcggctgc ccgactcagg   3960

tccgcccgac caggatcagc cccgctcctc ccctcttgag gtggtgcctt ctcacatctg   4020

tccagaggct gcaaggattc agcattattc ctccaggaag gagcaaaacg cctcttttcc   4080

ctctctaggc ctgttgcctc gggcctgggt ccgccttaat ctggaaggcc cctcccagca   4140

gcggtacccc agggcctact gccacccgct tcctgtttct tagtcgaatg ttagattcct   4200

cttgcctctc tcaggagtat cttacctgta aagtctaatc tctaaatcaa gtatttatta   4260

ttgaagattt accataaggg actgtgccag atgttaggag aactactaaa gtgcctaccc   4320

cagctcatgt ggattacaaa aaaaa                                         4345
```

<210> SEQ ID NO 38
<211> LENGTH: 2692
<212> TYPE: DNA
<213> ORGANISM: Homo sapiens

<400> SEQUENCE: 38

```
tttaaagctg ggaggttctg ccaccaagca cggccttccc actgggaaca caaacttgct     60

ggcgggaaga gcccggaaag aaacctgtgg atctcccttc gagatcatcc aaagagaaga    120

aaggtgacct cacattcgtg ccccttagca gcactctgca gaaatgcctc ctcagctgca    180

aaacggcctg aacctctcgg ccaaagttgt ccagggaagc ctggacagcc taccccaggc    240

agtgagggag tttctcgaga ataacgctga gctgtgtcag cctgatcaca tccacatctg    300

tgacggctct gaggaggaga atgggcggct tctgggccag atggaggaag agggcatcct    360

caggcggctg aagaagtatg acaactgctg gttggctctc actgacccca gggatgtggc    420

caggatcgaa agcaagacgg ttatcgtcac ccaagagcaa agagacacag tgcccatccc    480

caaaacaggc ctcagccagc tcggtcgctg gatgtcagag gaggattttg agaaagcgtt    540

caatgccagg ttcccagggt gcatgaaagg tcgcaccatg tacgtcatcc cattcagcat    600

ggggccgctg ggctcgcctc tgtcaaagat cggcatcgag ctgacggatt caccctacgt    660

ggtggccagc atgcggatca tgacgcggat gggcacgccc gtcctggaag cagtgggcga    720

tggggagttt gtcaaatgcc tccattctgt ggggtgccct ctgcctttac aaaagccttt    780

ggtcaacaac tggccctgca acccggagct gacgctcatc gcccacctgc ctgaccgcag    840

agagatcatc tcctttggca gtgggtacgg cgggaactcg ctgctcggga agaagtgctt    900

tgctctcagg atggccagcc ggctggccaa ggaggaaggg tggctggcag agcacatgct    960

gattctgggt ataaccaacc ctgagggtga gaagaagtac ctggcggccg catttcccag   1020

cgcctgcggg aagaccaacc tggccatgat gaaccccagc ctccccgggt ggaaggttga   1080

gtgcgtcggg gatgacattg cctggatgaa gtttgacgca caaggtcatt taagggccat   1140

caacccagaa aatggctttt tcggtgtcgc tcctgggact tcagtgaaga ccaaccccaa   1200

tgccatcaag accatccaga agaacacaat ctttaccaat gtggccgaga ccagcgacgg   1260
```

```
gggcgtttac tgggaaggca ttgatgagcc gctagcttca ggtgtcacca tcacgtcctg   1320

gaagaataag gagtggagct cagaggatgg ggaaccttgt gcccacccca actcgaggtt   1380

ctgcacccct gccagccagt gccccatcat tgatgctgcc tgggagtctc cggaaggtgt   1440

tcccattgaa ggcattatct ttggaggccg tagacctgct ggtgtccctc tagtctatga   1500

agctctcagc tggcaacatg gagtctttgt gggggcggcc atgagatcag aggccacagc   1560

ggctgcagaa cataaaggca aaatcatcat gcatgacccc tttgccatgc ggcccttctt   1620

tggctacaac ttcggcaaat acctggccca ctggcttagc atggcccagc acccagcagc   1680

caaactgccc aagatcttcc atgtcaactg gttccggaag gacaaggaag gcaaattcct   1740

ctggccaggc tttggagaga actccagggt gctggagtgg atgttcaacc ggatcgatgg   1800

aaaagccagc accaagctca cgcccatagg ctacatcccc aaggaggatg ccctgaacct   1860

gaaaggcctg gggcacatca acatgatgga gcttttcagc atctccaagg aattctggga   1920

gaaggaggtg gaagacatcg agaagtatct ggaggatcaa gtcaatgccg acctcccctg   1980

tgaaatcgag agagagatcc ttgccttgaa gcaaagaata agccagatgt aatcagggcc   2040

tgagtgcttt acctttaaaa tcattccctt tcccatccat aaggtgcagt aggagcaaga   2100

gagggcaagt gttcccaaat tgacgccacc ataataatca tcaccacacc gtgagcagat   2160

ctgaaaggca cactttgatt tttttaagga taagaaccac agaacactgg gtagtagcta   2220

atgaaattga gaagggaaat cttagcatgc ctccaaaaat tcacatccaa tgcatagttt   2280

gttcaaattt aaggttactc aggcattgat cttttcagtg ttttttcact ttagctatgt   2340

ggattagcta gaatgcacac caaaaaaata cttgagctgt atatatatat gtgtgtgtgt   2400

gtgtgtgtgt gtgtgtgtgt gtgtgcatgt atgtgcacat gtgtctgtgt ggtatatttg   2460

tgtatgtgta tttgtatgta ctgttattga aaatatattt aatacctttg gaaaaatctt   2520

gggcaagatg acctactagt tttccttgaa aaaaagttgc tttgttatta atattgtgct   2580

taaattattt ttatacacca ttgttcctta cctttacata attgcaatat ttcccccttta   2640

ctacttcttg gaaaaaaatt acaaaatgaa gttttataga aaagaaaaaa aa           2692
```

<210> SEQ ID NO 39
<211> LENGTH: 3710
<212> TYPE: DNA
<213> ORGANISM: Homo sapiens

<400> SEQUENCE: 39

```
aggacgcgtt tccaagttcc agtgactcct cctgtttggg actcgggggg agagtgcggg     60

gagacaaata aaacctcggg cggcggcggc tggtgggaag acttgaactt gaatctcgaa    120

ccactgcatc tccgactctg cccagactct tcactccgcg gcaccctcaa accccagccc    180

aggccggggc gcacaagcca gccagcgcac ctgcagtcct cgcccggacg cgccgcgccc    240

cctcggaacc aggctctgct ccgagcagcc ttcgcccctc aagccagcca cagtccccgc    300

caggccgggt gggcgtcaag atgaaggcgg cccgcttcgt gctgcgcagc gctggctcgc    360

tcaacggcgc cggcctggtg ccccgagagg tggagcattt ctcgcgctac agcccgtccc    420

cgctgtccat gaagcagcta ctggactttg gttcagaaaa tgcatgtgaa agaacttctt    480

ttgcattttt gcgacaagaa ttgcctgtga gactcgccaa cattctgaag gaaattgata    540

tcctcccgac ccaattagta aatacctctt cagtgcaatt ggttaaaagc tggtatatac    600

agagcctgat ggatttggtg gaattccatg agaaaagccc agatgaccag aaagcattat    660
```

```
cagactttgt agatacactc atcaaagttc gaaatagaca ccataatgta gtccctacaa    720
tggcacaagg aatcatagag tataaagatg cctgtacagt tgacccagtc accaatcaaa    780
atcttcaata tttcttggat cgattttaca tgaaccgtat ttctactcgg atgctgatga    840
accagcacat tcttatattt agtgactcac agacaggaaa cccaagccac attggaagca    900
ttgatcctaa ctgtgatgtg gtagcagtgg tccaagatgc ctttgagtgt tcaaggatgc    960
tctgtgatca gtattattta tcatctccag aattaaagct tacacaagtg aatggaaaat   1020
ttccagacca accaattcac atcgtgtatg ttccttctca cctccatcat atgctctttg   1080
aactatttaa gaatgcaatg cgggcaacag ttgaacacca ggaaaatcag ccttccctta   1140
caccaataga ggttattgtt gtcttgggaa aagaagacct taccattaag atttcagaca   1200
gaggaggtgg tgttcccctg agaattattg accgcctctt tagttataca tactccactg   1260
caccaacgcc tgtgatggat aattcccgga atgctccttt ggctggtttt ggttacggct   1320
tgccaatttc tcgtctgtat gcaaagtact ttcaaggaga tctgaatctc tactctttat   1380
caggatatgg aacagatgct atcatctact taaaggcttt gtcttctgag tctatagaaa   1440
aacttccagt tttaacaag tcagccttca aacattatca gatgagctct gaggctgatg   1500
actggtgtat cccaagcagg gaaccaaaga acctggcaaa agaagtggcc atgtgaagag   1560
ggacactcag gacactttac gggatcaaag tgggtctaca ccagtgctgc ttcctgaatg   1620
tttgtgtgtg aacccttgtt tcctccaaaa caaacgacag caacgaaaac tccttaatca   1680
gaacactgat ccaatgagga atggagcttg tttctgtgac ccaggagaac ttagtgcaag   1740
actacaggag ttaacagatg gccagctcct tattttttaa tgtagaataa ctcctgagtt   1800
tatatcaaat cctgaagaaa taagcctcag ttttccatct gtttttgata agaataagaa   1860
agggagtgag tgtgaagatg gtggttagca gtttcactaa gactgatatt ttaggcctct   1920
tgttcacatc aaaagatatt ggtgtcagaa taccagcatt ttcctgccat gcaaaggatt   1980
aaaacttagt ttacactatg tggttacaaa tatatgtcaa tgtacatttt gaacatattt   2040
atgtgctatg gaaggaaatg ctggtgacta aaataaggtt tactctgaaa gaggaggaat   2100
tttattcaaa gcattcaaac attttattca agtgtttcaa aattcaaagc attgtattca   2160
aagttgcagt gaaggcatca acttatgtaa aaactcagaa ggaaggctcc tctgataaaa   2220
acacagctcc tttattatgc tgcttttctt gttcacttta cacactaagt aaacacttat   2280
tgtcaggtgc ctagtcttga gtgaattgtt agatgtgcac tgaactcggg atgttgggga   2340
ttggagagag agaattgcca aagtaacagc aaaaatatct cttactttgc tttgtttata   2400
aataaattag tagattggaa aaactagtgt tagggaaaga aatcacatgt tcagagccta   2460
attcagtagg aagggctttt ctctaccctg aaatgaaggt aatccaaagg catccatttt   2520
ctaggcttaa aagatatatt tttgatatat ttaattatat tctctacact ccagcattaa   2580
tatgtctgtt taaaaattac taattctcaa atggctcaag aacattagaa tttaagtacc   2640
ttttagagta attattttaa gcaaatagcc tggacgtaag agattctcat gccagcatgc   2700
tttcatttgt cagttgttgt gactgagaga taatgaatga cacctgaaat gcatatggta   2760
tttttgggag agttaaggta taatttgaag gttggcagac cagttgcgct gattactctt   2820
agagaagaag aaatggaaaa atgaaagaag gcaggaagga aagaaaggat ataggaagag   2880
agggaagcag aaggcaggca tttttctatt ttccccacaa attatttcaa aaaaaatctg   2940
tattttctgg gatatgtcat tggcaagagg aagaactggt gttttgaaag cagtatggat   3000
tctttaaatg cctctcactc ttacaagata gtaggctttg agataataaa cttacccgtg   3060
```

```
tcaattaaca tttaaactgg catatagaaa aaaaggagga tttttctgca ttgtaaaata   3120

atcagtatgg tttatatgtt gaatttgaca tttgtgtgta atttcatggt ggcctagtgt   3180

tgtggtgctt ctggtaatgg taatagaagc tcaactattt ttttgtggat ttcagttttt   3240

atcatcagaa gtcctagaca gtgacatttc ttaatggtgg gagtccagct catgcatttc   3300

tgattataca aaacagtttg cagtaggtta tttgtcattt cagtttttta ctgaaatttg   3360

agctaaacat ttttacatgt aaatacttgt atttaccaaa gatttaaatc agttgattaa   3420

ttaattaact caaatactgt gaactatctc taaaacacta gaaaaaaagaa atgttagtat   3480

ctcaattaca ccaactgtgc aaatgaactt tgataaaaata gaaataatct acattggcct   3540

ttgtgaaatc tggggaagag ctttaggatt ctagtagatg gatactgaat actcaggccc   3600

acttaaatta ttaatgtata cattgtgttt ttgtctttat gctatgtaca gagaaatgtg   3660

ataatttttt ataataaata tttttatgta tgataaaaga aaaaaaaaaa              3710
```

<210> SEQ ID NO 40
<211> LENGTH: 1295
<212> TYPE: DNA
<213> ORGANISM: Homo sapiens

<400> SEQUENCE: 40

```
ccttcccctg gcccggggag ctgctccttg tgctgccggg aaggtcaaag tcccgcgccc     60

accaggagag ctcggcaagt atataaggac agaggagcgc gggaccaagc ggcggcgaag    120

gaggggaaga agagccgcga ccgagagagg ccgccgagcg tccccgccct cagagagcag    180

cctcccgaga caggcacttg ctggattctc caaaagtatc tgcagtggct gttccaccag    240

gagagcctca gcctgcctgg aagatgccga gatcgtgctg cagccgctcg gggccctgt    300

tgctggcctt gctgcttcag gcctccatgg aagtgcgtgg ctggtgcctg gagagcagcc    360

agtgtcagga cctcaccacg gaaagcaacc tgctggagtg catccgggcc tgcaagcccg    420

acctctcggc cgagactccc atgttcccgg gaaatggcga cgagcagcct ctgaccgaga    480

acccccggaa gtacgtcatg ggccacttcc gctgggaccg attcggccgc cgcaacagca    540

gcagcagcgg cagcagcggc gcagggcaga agcgcgagga cgtctcagcg ggcgaagact    600

gcggcccgct gcctgagggc ggccccgagc cccgcagcga tggtgccaag ccgggcccgc    660

gcgagggcaa gcgctcctac tccatggagc acttccgctg gggcaagccg gtgggcaaga    720

agcggcgccc agtgaaggtg taccctaacg gcgccgagga cgagtcggcc gaggccttcc    780

ccctggagtt caagagggag ctgactggcc agcgactccg ggagggagat ggccccgacg    840

gccctgccga tgacggcgca ggggcccagg ccgacctgga gcacagcctg ctggtggcgg    900

ccgagaagaa ggacgagggc ccctacagga tggagcactt ccgctggggc agcccgccca    960

aggacaagcg ctacggcggt ttcatgacct ccgagaagag ccagacgccc ctggtgacgc   1020

tgttcaaaaa cgccatcatc aagaacgcct acaagaaggg cgagtgaggg cacagcgggg   1080

ccccagggct accctccccc aggaggtcga ccccaaagcc ccttgctctc ccctgccctg   1140

ctgccgcctc ccagcctggg gggtcgtggc agataatcag cctcttaaag ctgcctgtag   1200

ttaggaaata aaacctttca aatttcacat ccacctctga ctttgaatgt aaactgtgtg   1260

aataaagtaa aaatacgtag ccgtcaaata acagc                              1295
```

<210> SEQ ID NO 41
<211> LENGTH: 6318
<212> TYPE: DNA

<213> ORGANISM: Homo sapiens

<400> SEQUENCE: 41

```
tagtaagaca ggtgccttca gttcactctc agtaaggggc tggttgcctg catgagtgtg     60
tgctctgtgt cactgtggat tggagttgaa aaagcttgac tggcgtcatt caggagctgg    120
atggcgtggg acatgtgcaa ccaggactct gagtctgtat ggagtgacat cgagtgtgct    180
gctctggttg gtgaagacca gcctctttgc ccagatcttc ctgaacttga tctttctgaa    240
ctagatgtga acgacttgga tacagacagc tttctgggtg gactcaagtg gtgcagtgac    300
caatcagaaa taatatccaa tcagtacaac aatgagcctt caaacatatt tgagaagata    360
gatgaagaga atgaggcaaa cttgctagca gtcctcacag agacactaga cagtctccct    420
gtggatgaag acggattgcc ctcatttgat gcgctgacag atggagacgt gaccactgac    480
aatgaggcta gtccttcctc catgcctgac ggcacccctc caccccagga ggcagaagag    540
ccgtctctac ttaagaagct cttactggca ccagccaaca ctcagctaag ttataatgaa    600
tgcagtggtc tcagtaccca gaaccatgca aatcacaatc acaggatcag aacaaaccct    660
gcaattgtta agactgagaa ttcatggagc aataaagcga agagtatttg tcaacagcaa    720
aagccacaaa gacgtccctg ctcggagctt ctcaaatatc tgaccacaaa cgatgaccct    780
cctcacacca aacccacaga gaacagaaac agcagcagag acaaatgcac ctccaaaaag    840
aagtcccaca cacagtcgca gtcacaacac ttacaagcca aaccaacaac tttatctctt    900
cctctgaccc cagagtcacc aaatgacccc aagggttccc catttgagaa caagactatt    960
gaacgcacct taagtgtgga actctctgga actgcaggcc taactccacc caccactcct   1020
cctcataaag ccaaccaaga taaccctttt agggcttctc caaagctgaa gtcctcttgc   1080
aagactgtgg tgccaccacc atcaaagaag cccaggtaca gtgagtcttc tggtacacaa   1140
ggcaataact ccaccaagaa agggccggag caatccgagt tgtatgcaca actcagcaag   1200
tcctcagtcc tcactggtgg acacgaggaa aggaagacca agcggcccag tctgcggctg   1260
tttggtgacc atgactattg ccagtcaatt aattccaaaa cagaaatact cattaatata   1320
tcacaggagc tccaagactc tagacaacta gaaaataaag atgtctcctc tgattggcag   1380
gggcagattt gttcttccac agattcagac cagtgctacc tgagagagac tttggaggca   1440
agcaagcagg tctctccttg cagcacaaga aaacagctcc aagaccagga aatccgagcc   1500
gagctgaaca agcacttcgg tcatcccagt caagctgttt ttgacgacga agcagacaag   1560
accggtgaac tgagggacag tgatttcagt aatgaacaat tctccaaact acctatgttt   1620
ataaattcag gactagccat ggatggcctg tttgatgaca gcgaagatga aagtgataaa   1680
ctgagctacc cttgggatgg cacgcaatcc tattcattgt tcaatgtgtc tccttcttgt   1740
tcttctttta actctccatg tagagattct gtgtcaccac ccaaatcctt attttctcaa   1800
agaccccaaa ggatgcgctc tcgttcaagg tccttttctc gacacaggtc gtgttcccga   1860
tcaccatatt ccaggtcaag atcaaggtct ccaggcagta gatcctcttc aagatcctgc   1920
tattactatg agtcaagcca ctacagacac cgcacgcacc gaaattctcc cttgtatgtg   1980
agatcacgtt caagatcgcc ctacagccgt cggcccaggt atgacagcta cgaggaatat   2040
cagcacgaga ggctgaagag ggaagaatat cgcagagagt atgagaagcg agagtctgag   2100
agggccaagc aaagggagag gcagaggcag aaggcaattg aagagcgccg tgtgatttat   2160
gtcggtaaaa tcagacctga cacaacacgg acagaactga gggaccgttt tgaagttttt   2220
ggtgaaattg aggagtgcac agtaaatctg cgggatgatg gagacagcta tggtttcatt   2280
```

```
acctaccgtt atacctgtga tgcttttgct gctcttgaaa atggatacac tttgcgcagg   2340
tcaaacgaaa ctgactttga gctgtacttt tgtggacgca agcaattttt caagtctaac   2400
tatgcagacc tagattcaaa ctcagatgac tttgaccctg cttccaccaa gagcaagtat   2460
gactctctgg attttgatag tttactgaaa gaagctcaga gaagcttgcg caggtaacat   2520
gttccctagc tgaggatgac agagggatgg cgaatacctc atgggacagc gcgtccttcc   2580
ctaaagacta ttgcaagtca tacttaggaa tttctcctac tttacactct ctgtacaaaa   2640
acaaaacaaa acaacaacaa tacaacaaga acaacaacaa caataacaac aatggtttac   2700
atgaacacag ctgctgaaga ggcaagagac agaatgatat ccagtaagca catgtttatt   2760
catgggtgtc agctttgctt ttcctggagt ctcttggtga tggagtgtgc gtgtgtgcat   2820
gtatgtgtgt gtgtatgtat gtgtgtggtg tgtgtgcttg gtttagggga agtatgtgtg   2880
ggtacatgtg aggactgggg gcacctgacc agaatgcgca agggcaaacc atttcaaatg   2940
gcagcagttc catgaagaca cgcttaaaac ctagaacttc aaaatgttcg tattctattc   3000
aaaaggaaat atatatatat atatatatat atatatatat atatataaat taaaaaggaa   3060
agaaaactaa caaccaacca accaaccaac caaccacaaa ccaccctaaa atgacagccg   3120
ctgatgtctg ggcatcagcc tttgtactct gtttttttaa gaaagtgcag aatcaacttg   3180
aagcaagctt tctctcataa cgtaatgatt atatgacaat cctgaagaaa ccacaggttc   3240
catagaacta atatcctgtc tctctctctc tctctctctc tctctttttt ttttcttttt   3300
ccttttgcca tggaatctgg gtgggagagg atactgcggg caccagaatg ctaaagtttc   3360
ctaacatttt gaagtttctg tagttcatcc ttaatcctga cacccatgta aatgtccaaa   3420
atgttgatct tccactgcaa atttcaaaag ccttgtcaat ggtcaagcgt gcagcttgtt   3480
cagcggttct ttctgaggag cggacaccgg gttacattac taatgagagt tgggtagaac   3540
tctctgagat gtgttcagat agtgtaattg ctacattctc tgatgtagtt aagtatttac   3600
agatgttaaa tggagtattt ttattttatg tatatactat acaacaatgt tctttttttgt   3660
tacagctatg cactgtaaat gcagccttct tttcaaaact gctaaatttt tcttaatcaa   3720
gaatattcaa atgtaattat gaggtgaaac aattattgta cactaacata tttagaagct   3780
gaacttactg cttatatata tttgattgta aaaacaaaaa gacagtgtgt gtgtctgttg   3840
agtgcaacaa gagcaaaatg atgctttccg cacatccatc ccttaggtga gcttcaatct   3900
aagcatcttg tcaagaaata tcctagtccc ctaaaggtat taaccacttc tgcgatattt   3960
ttccacattt tcttgtcgct tgtttttctt tgaagtttta tacactggat ttgttagggg   4020
aatgaaattt tctcatctaa aatttttcta gaagatatca tgattttatg taaagtctct   4080
caatgggtaa ccattaagaa atgtttttat tttctctatc aacagtagtt ttgaaactag   4140
aagtcaaaaa tctttttaaa atgctgtttt gttttaattt ttgtgatttt aatttgatac   4200
aaaatgctga ggtaataatt atagtatgat ttttacaata attaatgtgt gtctgaagac   4260
tatctttgaa gccagtattt ctttcccttg gcagagtatg acgatggtat ttatctgtat   4320
tttttacagt tatgcatcct gtataaatac tgatatttca ttcctttgtt tactaaagag   4380
acatatttat cagttgcaga tagcctattt attataaatt atgagatgat gaaaataata   4440
aagccagtgg aaattttcta cctaggatgc atgacaattg tcaggttgga gtgtaagtgc   4500
ttcatttggg aaattcagct tttgcagaag cagtgtttct acttgcacta gcatggcctc   4560
tgacgtgacc atggtgttgt tcttgatgac attgcttctg ctaaatttaa taaaaacttc   4620
```

-continued

```
agaaaaacct ccattttgat catcaggatt tcatctgagt gtggagtccc tggaatggaa   4680

ttcagtaaca tttggagtgt gtattcaagt ttctaaattg agattcgatt actgtttggc   4740

tgacatgact tttctggaag acatgataca cctactactc aattgttctt ttcctttctc   4800

tcgcccaaca cgatcttgta agatggattt cacccccagg ccaatgcagc taattttgat   4860

agctgcattc atttatcacc agcatattgt gttctgagtg aatccactgt ttgtcctgtc   4920

ggatgcttgc ttgatttttt ggcttcttat ttctaagtag atagaaagca ataaaaatac   4980

tatgaaatga aagaacttgt tcacaggttc tgcgttacaa cagtaacaca tctttaatcc   5040

gcctaattct tgttgttctg taggttaaat gcaggtattt taactgtgtg aacgccaaac   5100

taaagtttac agtctttctt tctgaatttt gagtatcttc tgttgtagaa taataataaa   5160

aagactatta agagcaataa attattttta agaaatcgag atttagtaaa tcctattatg   5220

tgttcaagga ccacatgtgt tctctatttt gcctttaaat ttttgtgaac caattttaaa   5280

tacattctcc tttttgccct ggattgttga catgagtgga atacttggtt tcttttctta   5340

cttatcaaaa gacagcacta cagatatcat attgaggatt aatttatccc ccctaccccc   5400

agcctgacaa atattgttac catgaagata gttttcctca atggacttca aattgcatct   5460

agaattagtg gagcttttgt atcttctgca gacactgtgg gtagcccatc aaaatgtaag   5520

ctgtgctcct ctcattttta tttttatttt tttgggagag aatatttcaa atgaacacgt   5580

gcaccccatc atcactggag gcaaatttca gcatagatct gtaggatttt tagaagaccg   5640

tgggccattg ccttcatgcc gtggtaagta ccacatctac aattttggta accgaactgg   5700

tgctttagta atgtggattt ttttcttttt taaaagagat gtagcagaat aattcttcca   5760

gtgcaacaaa atcaattttt tgctaaacga ctccgagaac aacagttggg ctgtcaacat   5820

tcaaagcagc agagagggaa ctttgcacta ttggggtatg atgtttgggt cagttgataa   5880

aaggaaacct tttcatgcct ttagatgtga gcttccagta ggtaatgatt atgtgtcctt   5940

tcttgatggc tgtaatgaga acttcaatca ctgtagtcta agacctgatc tatagatgac   6000

ctagaatagc catgtactat aatgtgatga ttctaaattt gtacctatgt gacagacatt   6060

ttcaataatg tgaactgctg atttgatgga gctactttaa gatttgtagg tgaaagtgta   6120

atactgttgg ttgaactatg ctgaagaggg aaagtgagcg attagttgag cccttgccgg   6180

gcctttttc cacctgccaa ttctacatgt attgttgtgg ttttattcat tgtatgaaaa   6240

ttcctgtgat tttttttaaa tgtgcagtac acatcagcct cactgagcta ataaagggaa   6300

acgaatgttt caaatcta                                                 6318
```

<210> SEQ ID NO 42
<211> LENGTH: 4790
<212> TYPE: DNA
<213> ORGANISM: Homo sapiens

<400> SEQUENCE: 42

```
ggggaagcgc agtgcgcagg cgcaactgcc tggctctgct cgctccggcg ctccggccca     60

gctctcgcgg acaagtccag acatcgcgcg ccccccttc tccgggtccg ccccctcccc    120

cttctcggcg tcgtcgaaga taaacaatag ttggccggcg agcgcctagt gtgtctcccg    180

ccgccggatt cggcgggctg cgtgggaccg gcgggatccc ggccagccgg ccatggcggg    240

gctgtactcg ctgggagtga gcgtcttctc cgaccagggc gggaggaagt acatggagga    300

cgttactcaa atcgttgtgg agcccgaacc gacggctgaa gaaaagccct cgccgcggcg    360

gtcgctgtct cagccgttgc ctccgcggcc gtcgccggcc gcccttcccg gcggcgaagt    420
```

```
ctcggggaaa ggcccagcgg tggcagcccg agaggctcgc gaccctctcc cggacgccgg    480
ggcctcgccg gcacctagcc gctgctgccg ccgccgttcc tccgtggcct ttttcgccgt    540
gtgcgacggg cacggcgggc gggaggcggc acagtttgcc cgggagcact tgtggggttt    600
catcaagaag cagaagggtt tcacctcgtc cgagccggct aaggtttgcg ctgccatccg    660
caaaggcttt ctcgcttgtc accttgccat gtggaagaaa ctggcggaat ggccaaagac    720
tatgacgggt cttcctagca catcagggac aactgccagt gtggtcatca ttcggggcat    780
gaagatgtat gtagctcacg taggtgactc aggggtggtt cttggaattc aggatgaccc    840
gaaggatgac tttgtcagag ctgtggaggt gacacaggac cataagccag aacttcccaa    900
ggaaagagaa cgaatcgaag gacttggtgg gagtgtaatg aacaagtctg ggtgaatcg    960
tgtagtttgg aaacgacctc gactcactca caatggacct gttagaagga gcacagttat   1020
tgaccagatt ccttttctgg cagtagcaag agcacttggt gatttgtgga gctatgattt   1080
cttcagtggt gaatttgtgg tgtcacctga accagacaca agtgtccaca ctcttgaccc   1140
tcagaagcac aagtatatta tattggggag tgatggactt tggaatatga ttccaccaca   1200
agatgccatc tcaatgtgcc aggaccaaga ggagaaaaaa tacctgatgg gtgagcatgg   1260
acaatcttgt gccaaaatgc ttgtgaatcg agcattgggc cgctggaggc agcgtatgct   1320
ccgagcagat aacactagtg ccatagtaat ctgcatctct ccagaagtgg acaatcaggg   1380
aaactttacc aatgaagatg agttatacct gaacctgact gacagccctt cctataatag   1440
tcaagaaacc tgtgtgatga ctccttcccc atgttctaca ccaccagtca agtcactgga   1500
ggaggatcca tggccaaggg tgaattctaa ggaccatata cctgccctgg ttcgtagcaa   1560
tgccttctca gagaattttt tagaggtttc agctgagata gctcgagaga atgtccaagg   1620
tgtagtcata ccctcaaaag atccagaacc acttgaagaa aattgcgcta aagccctgac   1680
tttaaggata catgattctt tgaataatag ccttccaatt ggccttgtgc ctactaattc   1740
aacaaacact gtcatggacc aaaaaaattt gaagatgtca actcctggcc aaatgaaagc   1800
ccaagaaatt gaaagaaccc ctccaacaaa ctttaaaagg acattagaag agtccaattc   1860
tggcccccctg atgaagaagc atagacgaaa tggcttaagt cgaagtagtg gtgctcagcc   1920
tgcaagtctc cccacaacct cacagcgaaa gaactctgtt aaactcacca tgcgacgcag   1980
acttaggggc cagaagaaaa ttggaaatcc tttacttcat caacacagga aaactgtttg   2040
tgtttgctga aatgcatctg ggaaatgagg tttttccaaa cttaggatat aagagggctt   2100
tttaaatttg gtgccgatgt tgaacttttt ttaaggggag aaaattaaaa gaaatataca   2160
gtttgacttt ttggaattca gcagttttat cctggccttg tacttgcttg tattgtaaat   2220
gtggattttg tagatgttag ggtataagtt gctgtaaaat ttgtgtaaat ttgtatccac   2280
acaaattcag tctctgaata cacagtattc agagtctctg atacacagta attgtgacaa   2340
tagggctaaa tgtttaaaga aatcaaaaga atctattaga ttttagaaaa acatttaaac   2400
tttttaaaat acttattaaa aaatttgtat aagccacttg tcttgaaaac tgtgcaactt   2460
tttaaagtaa attattaagc agactggaaa agtgatgtat tttcatagtg acctgtgttt   2520
cacttaatgt ttcttagagc caagtgtctt ttaaacatta ttttttattt ctgatttcat   2580
aattcagaac taaatttttc atagaagtgt tgagccatgc tacagttagt cttgtcccaa   2640
ttaaaatact atgcagtatc tcttacatca gtagcatttt tctaaaacct tagtcatcag   2700
atatgcttac taaatcttca gcatagaagg aagtgtgttt gcctaaaaca atctaaaaca   2760
```

```
attcccttct ttttcatccc agaccaatgg cattattagg tcttaaagta gttactccct   2820
tctcgtgttt gcttaaaata tgtgaagttt tccttgctat ttcaataaca gatggtgctg   2880
ctaattccca acatttctta aattatttta tatcatacag ttttcattga ttatatgggt   2940
atatattcat ctaataaatc agtgaactgt tcctcatgtt gctgaatttg tagttgttgg   3000
tttattttaa tggtatgtac aagttgagta tcccttatcc aaaatgcttg ggaccagaag   3060
tgtttcagat tttttaaaat tttggaatat ttgctttata ctgagctttt gagtgttccc   3120
aatctgaaat tcaaaatgct ctaatgagca tttcctttga gcatcatgcc tgctctgaaa   3180
aagtttctga ttctggagca ttttggattt tggattttca gattagggat gcttaacctg   3240
gattaacatt ctgttgtgcc atgatcatgc tttacagtga gtgtatttta tttatttatt   3300
attttgtttg tttgtttgag atggagtctc actctgtcat ccaggctaga gtgcagtggc   3360
gtgatctcgg ctgactgcaa cctctgcctc ccgggttcaa gtgattctcc tgcctcaatc   3420
tctctcccca gaagctggga ttacaggtgt gtgccaccac acccggctaa tttttttttt   3480
tttttttgag atggagtcta gctctgtcat ccaggctgga gtgcagtggt gtgatctcgg   3540
ctccctgcaa cctctgcctt ctgggttcct gcgattctcc tgcctcagcc tcctgagtag   3600
ctgagattac aggcacgcgc cactgtgccc agccaatttt tgtattttta gtagagatgg   3660
ggtttcacat gtcagtcatg ctggtcttga tctcctgacc tcgtgatcca cccgcctcga   3720
cctcccaaag tactgggatt acaggcgtga gccaccgcat ccggcctgag ttttatgctt   3780
tcaatgtatt tcttacattt cagttcaagt gattttcatg tctcagcctc ctgagtagct   3840
ggaactacag gtgcgtgcca ccatgcctgg ctaagttttg tatttttagt agagatgggt   3900
tttcatcatg ttggccaaga tggtcttgat ctcttgacct catgatccac cagcctaggc   3960
ctcccaaagt gctgggatta caggtgtgag ccaccgtgcc cagccaacta tgccattatt   4020
taaccatgtc cacacattct ggttattttc aatattttgc agaagataat tcttgatcgg   4080
tgtgtcttat gccacaagga ttaaaatatg tattcattgc tacaaaacaa tatctcgaaa   4140
tttagcagtt taaaacaaca aatattatct ccagtttctg agcctcagaa atctgagagt   4200
ggtttagctg ggtgatagtc tcgtggtttt ggtcaagcta ccaaccaggg ctacaatctt   4260
tcgaaggtgt cattggggct agaagatctg cttcccgcaa gactcacagc tgttggcagg   4320
agacctcagt ttgttgccac atgttcccct ccagagggcc tctcacaaca tggcagttat   4380
ttgtccccag agcaagcaac accggagggc aaggaagaag ccatgatgtt ttttgtaacc   4440
tagcctctga aagtgtcata ccaattctgt attttgttgg tcacacagac caagtcaact   4500
acaacgtggg agactcctac acaaggcatg aattctagga ggtgggcatt tttaagtgtc   4560
atctggaagg aggctgtcac aacctggaag ttaaaagcat tgatattctg aaatacagcg   4620
tgtataacat tgttttagta gggtgtgcaa tagttatgtt ttggtaatag cattaatgaa   4680
caatgttatt ttcatcttcc agacatctgg aagattgctc tagtggagta aaacatctta   4740
atgtattttg tccctaaata aactatctca ctaacaaaaa aaaaaaaaaa              4790
```

<210> SEQ ID NO 43
<211> LENGTH: 1637
<212> TYPE: DNA
<213> ORGANISM: Homo sapiens

<400> SEQUENCE: 43

```
agagggcccg ctcaccaccc cgtaggcccc gcccctgcgt ctctgcccgc cccgtggcgc     60
ccgagtgcac tgaagatggc ggctgctgta ggacggttgc tccgagcgtc ggttgcccga    120
```

```
catgtgagtg ccattccttg gggcatttct gccactgcag ccctcaggcc tgctgcatgt    180

ggaagaacga gcttgacaaa tttattgtgt tctggttcca gtcaagcaaa attattcagc    240

accagttcct catgccatgc acctgctgtc acccagcatg caccctattt taagggtaca    300

gccgttgtca atggagagtt caaagaccta agccttgatg actttaaggg gaaatatttg    360

gtgcttttct tctatccttt ggatttcacc tttgtgtgtc ctacagaaat tgttgctttt    420

agtgacaaag ctaacgaatt tcacgacgtg aactgtgaag ttgtcgcagt ctcagtggat    480

tcccacttta gccatcttgc ctggataaat acaccaagaa agaatggtgg tttgggccac    540

atgaacatcg cactcttgtc agacttaact aagcagattt cccgagacta cggtgtgctg    600

ttagaaggtt ctggtcttgc actaagaggt ctcttcataa ttgaccccaa tggagtcatc    660

aagcatttga gcgtcaacga tctcccagtg ggccgaagcg tggaagaaac cctccgcttg    720

gtgaaggcgt tccagtatgt agaaacacat ggagaagtct gcccagcgaa ctggacaccg    780

gattctccta cgatcaagcc aagtccagct gcttccaaag agtactttca gaaggtaaat    840

cagtagatca cccatgtgta tctgcacctt ctcaactgag agaagaacca cagttgaaac    900

ctgcttttat cattttcaag atggttattt gtagaaggca aggaaccaat tatgcttgta    960

ttcataagta ttactctaaa tgttttgttt ttgtaattct ggctaagacc ttttaaacat   1020

ggttagttgc tagtacaagg aatcctttat tggtaacatc ttggtggctg gctagctagt   1080

ttctacagaa cataatttgc ctctatagaa ggctattctt agatcatgtc tcaatggaaa   1140

cactcttctt tcttagcctt acttgaatct tgcctataat aaagtagagc aacacacatt   1200

gaaagcttct gatcaacggt cctgaaattt tcatcttgaa tgtctttgta ttaaactgaa   1260

ttttctttta agctaacaaa gatcataatt ttcaatgatt agccgtgtaa ctcctgcaat   1320

gaatgtttat gtgattgaag caaatgtgaa tcgtattatt ttaaaaagtg gcagagtgac   1380

ttaactgatc atgcatgatc cctcatccct gaaattgagt ttatgtagtc attttactta   1440

ttttattcat tagctaactt tgtctatgta tatttctaga tattgattag tgtaatcgat   1500

tataaaggat atttatcaaa tccagggatt gcattttgaa attataatta ttttctttgc   1560

tgaagtattc attgtaaaac atacaaaata aacatatttt aaaacatttg cattttacca   1620

ccaaaaaaaa aaaaaaa                                                   1637
```

<210> SEQ ID NO 44
<211> LENGTH: 6582
<212> TYPE: DNA
<213> ORGANISM: Homo sapiens

<400> SEQUENCE: 44

```
agagggcaag gagagagcag agaacacact ttgccttctc tttggtattg agtaatatca     60

accaaattgc agacatctca acactttggc caggcagcct gctgagcaag gtacctcagc    120

cagcatggca gcctctttcc cacccacctt gggactcagt tctgccccag atgaaattca    180

gcacccacat attaaatttt cagaatggaa atttaagctg ttccgggtga gatcctttga    240

aaagacacct gaagaagctc aaaaggaaaa gaaggattcc tttgagggga aaccctctct    300

ggagcaatct ccagcagtcc tggacaaggc tgatggtcag aagccagtcc caactcagcc    360

attgttaaaa gcccacccta agttttcaaa gaaatttcac gacaacgaga aagcaagagg    420

caaagcgatc catcaagcca accttcgaca tctctgccgc atctgtggga attcttttag    480

agctgatgag cacaacagga gatatccagt ccatggtcct gtggatggta aaaccctagg    540
```

```
ccttttacga aagaaggaaa agagagctac ttcctggccg gacctcattg ccaaggtttt    600
ccggatcgat gtgaaggcag atgttgactc gatccacccc actgagttct gccataactg    660
ctggagcatc atgcacagga agtttagcag tgccccatgt gaggtttact tcccgaggaa    720
cgtgaccatg gagtggcacc cccacacacc atcctgtgac atctgcaaca ctgcccgtcg    780
gggactcaag aggaagagtc ttcagccaaa cttgcagctc agcaaaaaac tcaaaactgt    840
gcttgaccaa gcaagacaag cccgtcagcg caagagaaga gctcaggcaa ggatcagcag    900
caaggatgtc atgaagaaga tcgccaactg cagtaagata catcttagta ccaagctcct    960
tgcagtggac ttcccagagc actttgtgaa atccatctcc tgccagatct gtgaacacat   1020
tctggctgac cctgtggaga ccaactgtaa gcatgtcttt tgccgggtct gcattctcag   1080
atgcctcaaa gtcatgggca gctattgtcc ctcttgccga tatccatgct tccctactga   1140
cctggagagt ccagtgaagt cctttctgag cgtcttgaat tccctgatgg tgaaatgtcc   1200
agcaaaagag tgcaatgagg aggtcagttt ggaaaaatat aatcaccaca tctcaagtca   1260
caaggaatca aaagagattt ttgtgcacat taataaaggg ggccggcccc gccaacatct   1320
tctgtcgctg actcggagag ctcagaagca ccggctgagg gagctcaagc tgcaagtcaa   1380
agcctttgct gacaaagaag aaggtggaga tgtgaagtcc gtgtgcatga ccttgttcct   1440
gctggctctg agggcgagga atgagcacag gcaagctgat gagctggagg ccatcatgca   1500
gggaaagggc tctggcctgc agccagctgt ttgcttggcc atccgtgtca acaccttcct   1560
cagctgcagt cagtaccaca agatgtacag gactgtgaaa gccatcacag ggagacagat   1620
ttttcagcct ttgcatgccc ttcggaatgc tgagaaggta cttctgccag gctaccacca   1680
ctttgagtgg cagccacctc tgaagaatgt gtcttccagc actgatgttg gcattattga   1740
tgggctgtct ggactatcat cctctgtgga tgattaccca gtggacacca ttgcaaagag   1800
gttccgctat gattcagctt tggtgtctgc tttgatggac atggaagaag acatcttgga   1860
aggcatgaga tcccaagacc ttgatgatta cctgaatggc cccttcactg tggtggtgaa   1920
ggagtcttgt gatggaatgg gagacgtgag tgagaagcat gggagtgggc ctgtagttcc   1980
agaaaaggca gtccgttttt cattcacaat catgaaaatt actattgccc acagctctca   2040
gaatgtgaaa gtatttgaag aagccaaacc taactctgaa ctgtgttgca agccattgtg   2100
ccttatgctg gcagatgagt ctgaccacga gacgctgact gccatcctga gtcctctcat   2160
tgctgagagg gaggccatga agagcagtga attaatgctt gagctgggag gcattctccg   2220
gactttcaag ttcatcttca ggggcaccgg ctatgatgaa aaacttgtgc gggaagtgga   2280
aggcctcgag gcttctggct cagtctacat ttgtactctt tgtgatgcca cccgtctgga   2340
agcctctcaa aatcttgtct tccactctat aaccagaagc catgctgaga acctggaacg   2400
ttatgaggtc tggcgttcca acccttacca tgagtctgtg gaagaactgc gggatcgggt   2460
gaaaggggtc tcagctaaac ctttcattga gacagtccct tccatagatg cactccactg   2520
tgacattggc aatgcagctg agttctacaa gatcttccag ctagagatag gggaagtgta   2580
taagaatccc aatgcttcca aagaggaaag gaaaaggtgg caggccacac tggacaagca   2640
tctccggaag aagatgaacc tcaaaccaat catgaggatg aatggcaact ttgccaggaa   2700
gctcatgacc aaagagactg tggatgcagt ttgtgagtta attccttccg aggagaggca   2760
cgaggctctg agggagctga tggatcttta cctgaagatg aaaccagtat ggcgatcatc   2820
atgccctgct aaagagtgcc cagaatccct ctgccagtac agtttcaatt cacagcgttt   2880
tgctgagctc ctttctacga agttcaagta taggtatgag ggaaaaatca ccaattattt   2940
```

```
tcacaaaacc ctggcccatg ttcctgaaat tattgagagg gatggctcca ttggggcatg   3000
ggcaagtgag ggaaatgagt ctggtaacaa actgtttagg cgcttccgga aaatgaatgc   3060
caggcagtcc aaatgctatg agatggaaga tgtcctgaaa caccactggt tgtacacctc   3120
caaatacctc cagaagttta tgaatgctca taatgcatta aaaacctctg ggtttaccat   3180
gaaccctcag gcaagcttag gggacccatt aggcatagag gactctctgg aaagccaaga   3240
ttcaatggaa ttttaagtag ggcaaccact tatgagttgg tttttgcaat tgagtttccc   3300
tctgggttgc attgagggct tctcctagca ccctttactg ctgtgtatgg ggcttcacca   3360
tccaagaggt ggtaggttgg agtaagatgc tacagatgct ctcaagtcag gaatagaaac   3420
tgatgagctg attgcttgag gcttttagtg agttccgaaa agcaacagga aaaatcagtt   3480
atctgaaagc tcagtaactc agaacaggag taactgcagg ggaccagaga tgagcaaaga   3540
tctgtgtgtg ttggggagct gtcatgtaaa tcaaagccaa ggttgtcaaa gaacagccag   3600
tgaggccagg aaagaaattg gtcttgtggt tttcattttt ttccccttg attgattata   3660
ttttgtattg agatatgata agtgccttct atttcatttt tgaataattc ttcattttta   3720
taattttaca tatcttggct tgctatataa gattcaaaag agctttttaa atttttctaa   3780
taatatctta catttgtaca gcatgatgac ctttacaaag tgctctcaat gcatttaccc   3840
attcgttata taaatatgtt acatcaggac aactttgaga aaatcagtcc tttttatgt   3900
ttaaattatg tatctattgt aaccttcaga gtttaggagg tcatctgctg tcatggattt   3960
ttcaataatg aatttagaat acacctgtta gctacagtta gttattaaat cttctgataa   4020
tatatgttta cttagctatc agaagccaag tatgattctt tatttttact ttttcatttc   4080
aagaaattta gagtttccaa atttagagct tctgcataca gtcttaaagc cacagaggct   4140
tgtaaaaata taggttagct tgatgtctaa aaatatattt catgtcttac tgaaacattt   4200
tgccagactt tctccaaatg aaacctgaat caatttttct aaatctaggt ttcatagagt   4260
cctctcctct gcaatgtgtt attctttcta taatgatcag tttactttca gtggattcag   4320
aattgtgtag caggataacc ttgtattttt ccatccgcta agtttagatg gagtccaaac   4380
gcagtacagc agaagagtta acatttacac agtgcttttt accactgtgg aatgttttca   4440
cactcatttt tccttacaac aattctgagg agtaggtgtt gttattatct ccatttgatg   4500
ggggtttaaa tgatttgctc aaagtcattt aggggtaata aatacttggc ttggaaattt   4560
aacacagtcc ttttgtctcc aaagcccttc ttctttccac cacaaattaa tcactatgtt   4620
tataaggtag tatcagaatt tttttaggat tcacaactaa tcactatagc acatgacctt   4680
gggattacat ttttatgggg caggggtaag caagttttta aatcatttgt gtgctctggc   4740
tcttttgata gaagaaagca acacaaaagc tccaaagggc cccctaaccc tcttgtggct   4800
ccagttattt ggaaactatg atctgcatcc ttaggaatct gggatttgcc agttgctggc   4860
aatgtagagc aggcatggaa ttttatatgc tagtgagtca taatgatatg ttagtgttaa   4920
ttagtttttt cttcctttga ttttattggc cataattgct actcttcata cacagtatat   4980
caaagagctt gataatttag ttgtcaaaag tgcatcggcg acattatctt taattgtatg   5040
tatttggtgc ttcttcaggg attgaactca gtatctttca ttaaaaaaca cagcagtttt   5100
ccttgctttt tatatgcaga atatcaaagt catttctaat ttagttgtca aaaacatata   5160
catattttaa cattagtttt tttgaaaact cttggttttg tttttttgga aatgagtggg   5220
ccactaagcc acactttccc ttcatcctgc ttaatccttc cagcatgtct ctgcactaat   5280
```

```
aaacagctaa attcacataa tcatcctatt tactgaagca tggtcatgct ggtttataga   5340

tttttaccc atttctactc tttttctcta ttggtggcac tgtaaatact ttccagtatt   5400

aaattatcct tttctaacac tgtaggaact attttgaatg catgtgacta agagcatgat   5460

ttatagcaca acctttccaa taatccctta atcagatcac attttgataa accctgggaa   5520

catctggctg caggaatttc aatatgtaga aacgctgcct atggtttttt gcccttactg   5580

ttgagactgc aatatcctag accctagttt tatactagag ttttattttt agcaatgcct   5640

attgcaagtg caattatata ctccagggaa attcaccaca ctgaatcgag catttgtgtg   5700

tgtatgtgtg aagtatatac tgggacttca gaagtgcaat gtatttttct cctgtgaaac   5760

ctgaatctac aagttttcct gccaagccac tcaggtgcat tgcagggacc agtgataatg   5820

gctgatgaaa attgatgatt ggtcagtgag gtcaaaagga gccttgggat taataaacat   5880

gcactgagaa gcaagaggag gagaaaaaga tgtctttttc ttccaggtga actggaattt   5940

agttttgcct cagatttttt tcccacaaga tacagaagaa gataaagatt tttttggttg   6000

agagtgtggg tcttgcatta catcaaacag agttcaaatt ccacacagat aagaggcagg   6060

atatataagc gccagtggta gttgggagga ataaaccatt atttggatgc aggtggtttt   6120

tgattgcaaa tatgtgtgtg tcttcagtga ttgtatgaca gatgatgtat tcttttgatg   6180

ttaaaagatt ttaagtaaga gtagatacat tgtacccatt ttacattttc ttattttaac   6240

tacagtaatc tacataaata tacctcagaa atcatttttg gtgattattt tttgttttgt   6300

agaattgcac ttcagtttat tttcttacaa ataaccttac attttgttta atggcttcca   6360

agagcctttt tttttttgt atttcagaga aaattcaggt accaggatgc aatggattta   6420

tttgattcag gggacctgtg tttccatgtc aaatgttttc aaataaaatg aaatatgagt   6480

ttcaatactt tttatatttt aatatttcca ttcattaata ttatggttat tgtcagcaat   6540

tttatgtttg aatatttgaa ataaaagttt aagatttgaa aa                      6582
```

<210> SEQ ID NO 45
<211> LENGTH: 2457
<212> TYPE: DNA
<213> ORGANISM: Homo sapiens

<400> SEQUENCE: 45

```
attagatcag tgttcataag aacatctgta ggcacacata cacactctct ttacagtcag     60

ccttctgctt gccacagtca tagtgggcag tcagtgaatc ttccccaagt gctgacaatt    120

aatacctggt ttagcggcaa agattcagag aggcgtgagc agcccctctg gccttcagac    180

aaaaatctac gtaccatcag aaactatgtc tctgcagatg gtaacagtca gtaataacat    240

agccttaatt cagccaggct tctcactgat gaattttgat ggacaagttt tcttctttgg    300

acaaaaaggc tggcccaaaa gatcctgccc cactggagtt ttccatctgg atgtaaagca    360

taaccatgtc aaactgaagc ctacaatttt ctctaaggat tcctgctacc tccctcctct    420

tcgctaccca gccacttgca cattcaaagg cagcttggag tctgaaaagc atcaatacat    480

catccatgga gggaaaacac caaacaatga ggtttcagat aagatttatg tcatgtctat    540

tgtttgcaag aacaacaaaa aggttacttt tcgctgcaca gagaaagact tggtaggaga    600

tgttcctgaa gccagatatg gtcattccat taatgtggtg tacagccgag ggaaaagtat    660

gggtgttctc tttggaggac gctcatacat gccttctacc cacagaacca cagaaaaatg    720

gaatagtgta gctgactgcc tgccctgtgt tttcctggtg gattttgaat ttgggtgtgc    780

tacatcatac attcttccag aacttcagga tgggctatct tttcatgtct ctattgccaa    840
```

```
aaatgacacc atctatattt taggaggaca ttcacttgcc aataatatcc ggcctgccaa    900

cctgtacaga ataagggttg atcttcccct gggtagccca gctgtgaatt gcacagtctt    960

gccaggagga atctctgtct ccagtgcaat cctgactcaa actaacaatg atgaatttgt   1020

tattgttggt ggctatcagc ttgaaaatca aaaaagaatg atctgcaaca tcatctcttt   1080

agaggacaac aagatagaaa ttcgtgagat ggagacccca gattggaccc cagacattaa   1140

gcacagcaag atatggtttg gaagcaacat gggaaatgga actgtttttc ttggcatacc   1200

aggagacaat aaacaagttg tttcagaagg attctatttc tatatgttga aatgtgctga   1260

agatgatact aatgaagagc agacaacatt cacaaacagt caaacatcaa cagaagatcc   1320

aggggattcc actccctttg aagactctga agaattttgt ttcagtgcag aagcaaatag   1380

ttttgatggt gatgatgaat ttgacaccta taatgaagat gatgaagaag atgagtctga   1440

gacaggctac tggattacat gctgccctac ttgtgatgtg gatatcaaca cttgggtacc   1500

attctattca actgagctca acaaacccgc catgatctac tgctctcatg ggatgggca    1560

ctgggtccat gctcagtgca tggatctggc agaacgcaca ctcatccatc tgtcagcagg   1620

aagcaacaag tattactgca atgagcatgt ggagatagca agagctctac acactcccca   1680

aagagtccta cccttaaaaa agcctccaat gaaatccctc cgtaaaaaag gttctggaaa   1740

aatcttgact cctgccaaga aatcctttct tagaaggttg tttgattagt tttgcaaaag   1800

cctttcagat tcaggtgtat ggaatttttg aatctatttt taaaatcata acattgattt   1860

taaaaataca tttttgttta tttaaaatgc ctatgttttc ttttagttac atgaattaag   1920

ggccagaaaa aagtgtttat aatgcaatga taaataaagt cattctagac cctatacatt   1980

ttgaaaatat tttacccaaa tactcaattt actaatttat tcttcactga ggatttctga   2040

tctgattttt tattcaacaa accttaaaca cccagaagca gtaataatca tcgaggtatg   2100

tttatattta ttatataagt cttggtaaca aataacctat aaagtgttta tgacaaattt   2160

agccaataaa gaaattaaca cccaaaagaa ttaaattgat tattttgtgc aacataacaa   2220

ttcggcagtt ggccaaaact taaaagcaag atctactaca tcccacatta gtgttcttta   2280

tataccttca agcaaccctt tggattatgc ccatgaacaa gttagtttct catagcttta   2340

cagatgtaga tataaatata aatatatgta tacatataga tagataatgt tctccactga   2400

cacaaaagaa gaaataaata atctacatca aaaaaaaaaa aaaaaaaaaa aaaaaaa      2457
```

<210> SEQ ID NO 46
<211> LENGTH: 4903
<212> TYPE: DNA
<213> ORGANISM: Homo sapiens

<400> SEQUENCE: 46

```
gtcgtttgcg gcggcgcagg cgcggtgcgg gcggcggacg ggcgggcgct tcgccgtttg     60

aatggctgcg ggcccgggcc ctcacctcac ctgaggtccg gccgcccagg ggtgcgctat    120

gccgtcggga ggtgaccagt cgccaccgcc cccgcctccc cctccggcgg cggcagcctc    180

ggatgaggag gaggaggacg acggcgaggc ggaagacgcc gcgccgcctg ccgagtcgcc    240

caccccctcag atccagcagc ggttcgacga gctgtgcagc cgcctcaaca tggacgaggc   300

ggcgcgggcc gaggcctggg acagctaccg cagcatgagc gaaagctaca cgctggaggg    360

aaatgatctt cattggttag catgtgcctt atatgtggct tgcagaaaat ctgttccaac    420

tgtaagcaaa gggacagtgg aaggaaacta tgtatcttta actagaatcc tgaaatgttc    480
```

```
agagcagagc ttaatcgaat tttttaataa gatgaagaag tgggaagaca tggcaaatct    540
acccccacat ttcagagaac gtactgagag attagaaaga aacttcactg tttctgctgt    600
aatttttaag aaatatgaac ccatttttca ggacatcttt aaataccctc aagaggagca    660
acctcgtcag cagcgaggaa ggaaacagcg gcgacagccc tgtactgtgt ctgaaatttt    720
ccatttttgt tgggtgcttt ttatatatgc aaaaggtaat ttccccatga ttagtgatga    780
tttggtcaat tcttatcacc tgctgctgtg tgctttggac ttagtttatg gaaatgcact    840
tcagtgttct aatcgtaaag aacttgtgaa ccctaatttt aaaggcttat ctgaagattt    900
tcatgctaaa gattctaaac cttcctctga cccccccttgt atcattgaga aactgtgttc    960
cttacatgat ggcctagttt tggaagcaaa ggggataaag gaacatttct ggaaaccccta   1020
tattaggaaa ctttatgaaa aaaagctcct taagggaaaa gaagaaaatc tcactgggtt   1080
tctagaacct gggaactttg gagagagttt taaagccatc aataaggcct atgaggagta   1140
tgttttatct gttgggaatt tagatgagcg gatatttctt ggagaggatg ctgaggagga   1200
aattgggact ctctcaaggt gtctgaacgc tggttcagga acagagactg ctgaaagggt   1260
gcagatgaaa aacatcttac agcagcattt tgacaagtcc aaagcactta gaatctccac   1320
accactaact ggtgttaggt acattaagga gaatagccct tgtgtgactc cagtttctac   1380
agctacgcat agcttgagtc gtcttcacac catgctgaca ggcctcagga atgcaccaag   1440
tgagaaactg gaacagattc tcaggacatg ttccagagat ccaacccagg ctattgctaa   1500
cagactgaaa gaaatgtttg aaatatattc tcagcatttc cagccagacg aggatttcag   1560
taattgtgct aaagaaattg ccagcaaaca ttttcgtttt gcggagatgc tttactataa   1620
agtattagaa tctgttattg agcaggaaca aaaaagacta ggagacatgg atttatctgg   1680
tattctggaa caagatgcgt tccacagatc tctcttggcc tgctgccttg aggtcgtcac   1740
tttttcttat aagcctcctg ggaattttcc atttattact gaaatatttg atgtgcctct   1800
ttatcatttt tataaggtga tagaagtatt cattagagca gaagatggcc tttgtagaga   1860
ggtggtaaaa caccttaatc agattgaaga acagatctta gatcatttgg catggaaacc   1920
agagtctcca ctctgggaaa aaattagaga caatgaaaac agagttccta catgtgaaga   1980
ggtcatgcca cctcagaacc tggaaagggc agatgaaatt tgcattgctg gctcccccttt   2040
gactcccaga agggtgactg aagttcgtgc tgatactgga ggacttggaa ggagcataac   2100
atctccaacc acattatacg ataggtacag ctccccacca gccagcacta ccagaaggcg   2160
gctatttgtt gagaatgata gccccctctga tggagggacg cctgggcgca tgcccccaca   2220
gcccctagtc aatgctgtcc ctgtgcagaa tgtatctggg gagactgttt ctgtcacacc   2280
agttcctgga cagactttgg tcaccatggc aaccgccact gtcacagcca acaatgggca   2340
aacggtaacc attcctgtgc aaggtattgc caatgaaaat ggagggataa cattcttccc   2400
tgtccaagtc aatgttgggg ggcaggcaca agctgtgaca ggctccatcc agcccctcag   2460
tgctcaggcc ctggctggaa gtctgagctc tcaacaggtg acaggaacaa ctttgcaagt   2520
ccctggtcaa gtggccattc aacagatttc cccaggtggc caacagcaga agcaaggcca   2580
gtctgtaacc agcagtagta atagacccag gaagaccagc tctttatcgc ttttctttag   2640
aaaggtatac catttagcag ctgtccgcct tcgggatctc tgtgccaaac tagatatttc   2700
agatgaattg aggaaaaaaa tctggacctg ctttgaattc tccataattc agtgtcctga   2760
acttatgatg gacagacatc tggaccagtt attaatgtgt gccatttatg tgatggcaaa   2820
ggtcacaaaa gaagataagt ccttccagaa cattatgcgt tgttatagga ctcagccgca   2880
```

```
ggcccggagc caggtgtata gaagtgtttt gataaaaggg aaaagaaaaa gaagaaattc   2940
tggcagcagt gatagcagaa gccatcagaa ttctccaaca gaactaaaca aagatagaac   3000
cagtagagac tccagtccag ttatgaggtc aagcagcacc ttgccagttc cacagcccag   3060
cagtgctcct cccacaccta ctcgcctcac aggtgccaac agtgacatgg aagaagagga   3120
gaggggagac ctcattcagt tctacaacaa catctacatc aaacagatta agacatttgc   3180
catgaagtac tcacaggcaa atatggatgc tcctccactc tctccctatc catttgtaag   3240
aacaggctcc cctcgccgaa tacagttgtc tcaaaatcat cctgtctaca tttccccaca   3300
taaaaatgaa acaatgcttt ctcctcgaga aaagattttc tattacttca gcaacagtcc   3360
ttcaaagaga ctgagagaaa ttaatagtat gatacgcaca ggagaaactc ctactaaaaa   3420
gagaggaatt cttttggaag atggaagtga atcacctgca aaaagaattt gcccagaaaa   3480
tcattctgcc ttattacgcc gtctccaaga tgtagctaat gaccgtggtt cccactgagg   3540
ttagtctctt gtattaaact cttcacaaaa tctgtttagc agcagccttt aatgcatcta   3600
gattatggag ctttttttcct taatccagct gatgagttac agcctgttag taacatgagg   3660
ggacattttg gtgagaaatg ggacttaact ccttccagtg tccttagaac attttaattc   3720
atcccaactg tcttttttttc cctaccattc agtgattact gtcaaggctg cttagaatcc   3780
aaacttggat tttgactct ggcaaagctt ttagaaatac tgcaagaaaa tgatgtgtac   3840
ccaaacgtga gcataggagg cttctgttga cgtactccaa cagaagaact gtgtttcaag   3900
ttcaatccta cctgttttgt ggtcagctgt agtcctcata aaaagcaaaa caaaaattag   3960
gtattttgtc ctaaaacacc tggtaggagt gtgtgatttt ttgcattcct gacaaaggag   4020
agcacaccca ggtttggagg tcctaggtca ttagccctcg tctcccgttc cctttgtgca   4080
catcttccct ctccccattc ggtgtggtgc agtgtgaaaa gtccttgatt gttcgggtgt   4140
gcaatgtctg agtgaacctg tataagtgga ggcactttag ggctgtaaaa tgcatgattt   4200
tgtaacccag attttgctgt atatttgtga tagcactttc tacaatgtga actttattaa   4260
atacaaaact tccaggctaa acatccaata ttttctttaa tgcttttata tttttttaaa   4320
atgttaaaac ccctatagcc accttttggg aatgttttaa attctccagt tttttgttat   4380
atagggatca accagctaag aaaagatttt aatcaagttg aattgagggg attaatatga   4440
aaacttatga cctcttcctt taggagggag ttatctaaaa gaaatgtcta ttaaggtgat   4500
atatttaaaa atatttttgg gtgttcctgg cagtttaaaa aaattggttg gagaatttag   4560
gtttttatta gtaccatagt accatttata caaattagaa aatgttattt aacagctgaa   4620
ttatctatac atatctttat taatcactat tgttccagca gttttcaagt caaattaata   4680
atcttattag ggagaaaatt caattgtaaa ttgaatcagt ataaacaaag ttactaggta   4740
acttcatatt gctgagagaa atatggaact tacattgttc aattagaata gtgttctgca   4800
aaaatattta taaaacttct caagatactg ctactgtaat tttatatgaa gataagtgta   4860
tttttcaata aagcatttat aaattaaaaa aaaaaaaaaa aaa                     4903
```

<210> SEQ ID NO 47
<211> LENGTH: 5189
<212> TYPE: DNA
<213> ORGANISM: Homo sapiens

<400> SEQUENCE: 47

```
ggactgcgaa aggagcaggg ttgcggagct agggctccag cctgcggccg cgcattcttg     60
```

```
cgtctggcca gccgcgagct ctaagggtcg gccccgcccg gtccgccccc gcggctccct    120
gccaggctct cgcgggcgcg ctcggggtgg ggcctcgcgg ctggcggaga tgcggccggg    180
gctgcgcggt ggtgatgcga gcctgctggg cggcgcgccg gggcagccgg agccgcgcgc    240
cgcggcgctg taatcggaca ccaagagcgc tcgcccccgg cctccggcca ctttccattc    300
actccgaggt gcttgattga gcgacgcgga gaagagctcc gggtgccgcg gcactgcagc    360
gctgagattc ctttacaaag aaactcagag gaccgggaag aaagaatttc acctttgcga    420
cgtgctagaa aataaggtcg tctgggaaaa ggactggaga cacaagcgca tccaaccccg    480
gtagcaaact gatgactttt ccgtgctgat ttctttcaac ctcggtattt tcccttggat    540
attaacttgc atatctgaag aaatggcatt ccggacaatt tgcgtgttgg ttggagtatt    600
tatttgttct atctgtgtga aaggatcttc ccagccccaa gcaagagttt atttaacatt    660
tgatgaactt cgagaaacca agacctctga atacttcagc ctttcccacc atcctttaga    720
ctacaggatt ttattaatgg atgaagatca ggaccggata tatgtgggaa gcaaagatca    780
cattctttcc ctgaatatta acaatataag tcaagaagct ttgagtgttt tctggccagc    840
atctacaatc aaagttgaag aatgcaaaat ggctggcaaa gatcccacac acggctgtgg    900
gaactttgtc cgtgtaattc agactttcaa tcgcacacat ttgtatgtct gtgggagtgg    960
cgctttcagt cctgtctgta cttacttgaa cagagggagg agatcagagg accaagtttt   1020
catgattgac tccaagtgtg aatctggaaa aggacgctgc tctttcaacc ccaacgtgaa   1080
cacggtgtct gttatgatca atgaggagct tttctctgga atgtatatag atttcatggg   1140
gacagatgct gctatttttc gaagtttaac caagaggaat gcggtcagaa ctgatcaaca   1200
taattccaaa tggctaagtg aacctatgtt tgtagatgca catgtcatcc cagatggtac   1260
tgatccaaat gatgctaagg tgtacttctt cttcaaagaa aaactgactg acaataacag   1320
gagcacgaaa cagattcatt ccatgattgc tcgaatatgt cctaatgaca ctggtggact   1380
gcgtagcctt gtcaacaagt ggaccacttt cttaaaggcg aggctggtgt gctcggtaac   1440
agatgaagac ggcccagaaa cacactttga tgaattagag gatgtgtttc tgctggaaac   1500
tgataacccg aggacaacac tagtgtatgg catttttaca acatcaagct cagttttcaa   1560
aggatcagcc gtgtgtgtgt atcatttatc tgatatacag actgtgttta atgggccttt   1620
tgcccacaaa gaagggccca atcatcagct gatttcctat cagggcagaa ttccatatcc   1680
tcgccctgga acttgtccag gaggagcatt tacacccaat atgcgaacca ccaaggagtt   1740
cccagatgat gttgtcactt ttattcggaa ccatcctctc atgtacaatt ccatctaccc   1800
aatccacaaa aggcctttga ttgttcgtat tggcactgac tacaagtata caaagatagc   1860
tgtggatcga gtgaacgctg ctgatgggag ataccatgtc ctgtttctcg gaacagatcg   1920
gggtactgtg caaaaagtgg ttgttcttcc tactaacaac tctgtcagtg gcgagctcat   1980
tctggaggag ctggaagtct ttaagaatca tgctcctata acaacaatga aaatttcatc   2040
taaaaagcaa cagttgtatg tgagttccaa tgaaggggtt tcccaggtat ctctgcaccg   2100
ctgccacatc tatggtacag cctgtgctga ctgctgcctg gcgcgggacc cttattgcgc   2160
ctgggatggc cattcctgtt ccagattcta cccaactggg aaacggagga gccgaagaca   2220
agatgtgaga catggaaacc cactgactca atgcagagga tttaatctaa aagcatacag   2280
aaatgcagct gaaattgtcc agtatggagt aaaaaataac accacttttc tggagtgtgc   2340
cccaagtct ccgcaggcat ctatcaagtg gctgttacag aaagacaaag acaggaggaa   2400
agaggttaag ctgaatgaac gaataatagc cacttcacag ggactcctga tccgctctgt   2460
```

```
tcagggttct gaccaaggac tttatcactg cattgctaca gaaaatagtt tcaagcagac   2520
catagccaag atcaacttca aagttttaga ttcagaaatg gtggctgttg tgacggacaa   2580
atggtcccca tggacctggg ccagctctgt gagggcttta cccttccacc cgaaggacat   2640
catgggggca ttcagccact cagaaatgca gatgattaac caatattgca aagacactcg   2700
gcagcaacat cagcagggag atgaatcaca gaaaatgaga ggggactatg gcaagttaaa   2760
ggccctcatc aatagtcgga aaagtagaaa caggaggaat cagttgccag agtcataata   2820
ttttcttatg tgggtcttat gcttccatta acaaatgctc tgtcttcaat gatcaaattt   2880
tgagcaaaga aacttgtgct ttaccaaggg gaattactga aaaaggtgat tactcctgaa   2940
gtgagtttta cacgaactga aatgagcatg cattttcttg tatgatagtg actagcacta   3000
gacatgtcat ggtcctcatg gtgcatataa atatatttaa cttaacccag attttattta   3060
tatctttatt caccttttct tcaaaatcga tatggtggct gcaaaactag aattgttgca   3120
tccctcaatt gaatgagggc catatccctg tggtattcct ttcctgcttt ggggctttag   3180
aattctaatt gtcagtgatt ttgtatatga aaacaagttc caaatccaca gcttttacgt   3240
agtaaaagtc ataaatgcat atgacagaat ggctatcaaa agaaatagaa aaggaagaca   3300
gcatttaaag ttgtataaaa acatgagtta ttcataaaga gaaaatgatg agtttttatg   3360
gttccaatga aatatgttgg ggttttttta agattgtaaa aataatcagt tactggtatc   3420
tgtcactgac ctttgtttcc ttattcagga agataaaaat cagtaaccta ccccatgaag   3480
atatttggtg ggagttatat cagtgaagca gtttggttta tattcttatg ttatcacctt   3540
ccaaacaaaa gcacttactt tttttggaag ttatttattt tagactcaaa gaatataatc   3600
tggcactact cagttattac tgtttgttct cttattccct agtctgtgtg gcaaattaaa   3660
caatataaga aggaaaaatt tgaagtatta gacttctaaa taaggtgtga aatcatcaaa   3720
aagaaaaatc aaagtagaaa ctactaattt tttaagagga atttataaca aatatggcta   3780
gttttcaact tcagtactca aattcaatga ttcttccttt tattaaaacc agtctcagat   3840
atcatactga tttttaagtc aacactatat attttatgat cttttcagtg tgatggcaag   3900
gtgcttgtta tgtctagaaa gtaagaaaac aatatgagga gacattctgt ctttcaaaag   3960
gtaatggtac atacgttcac tggtctctaa gtgtaaaagt agtaaatttt gtgatgaata   4020
aaataattat ctcctaattg tatgttagaa taattttatt agaataattt catactgaaa   4080
ttattttctc caaataaaaa ttagatggaa aaatgtgaaa aaaattattc atgctctcat   4140
atatatttta aaaacactac ttttgctttt ttatttacct tttaagacat tttcatgctt   4200
ccaggtaaaa acagatattg taccatgtac ctaatccaaa tatcatataa acattttatt   4260
tatagttaat aatctatgat gaaggtaatt aaagtagatt atggcctttt taagtattgc   4320
agtctaaaac ttcaaaaact aaaatcattg tcaaaattaa tatgattatt aatcagaata   4380
tcagaatatg attcactatt taaactatga taaattatga taatatatga ggaggcctcg   4440
ctatagcaaa aatagttaaa atgctgacat aacaccaaac ttcatttttt aaaaaatctg   4500
ttgttccaaa tgtgtataat tttaaagtaa tttctaaagc agtttattat aatggtttgc   4560
ctgcttaaaa ggtataatta aacttctttt ctcttctaca ttgacacaca gaaatgtgtc   4620
aatgtaaagc caaaaccatc ttctgtgttt atggccaatc tattctcaaa gttaaaagta   4680
aaattgtttc agagtcacag ttccctttat ttcacataag cccaaactga tagacagtaa   4740
cggtgtttag ttttatacta tatttgtgct atttaattct ttctattttc acaattatta   4800
```

-continued

```
aattgtgtac actttcatta cttttaaaaa tgtagaaatt cttcatgaac ataactctgc   4860

tgaatgtaaa agaaaatttt ttttcaaaaa tgctgttaat gtatactact ggtggttgat   4920

tggttttatt ttatgtagct tgacaattca gtgacttaat atctattcca tttgtattgt   4980

acataaaatt ttctagaaat acactttttt ccaaagtgta agtttgtgaa tagattttag   5040

catgatgaaa ctgtcataat ggtgaatgtt caatctgtgt aagaaaacaa actaaatgta   5100

gttgtcacac taaaatttaa ttggatattg atgaaatcat tggcctggca aaataaaaca   5160

tgttgaattc cccaaaaaaa aaaaaaaaa                                      5189
```

```
<210> SEQ ID NO 48
<211> LENGTH: 2164
<212> TYPE: DNA
<213> ORGANISM: Homo sapiens

<400> SEQUENCE: 48

ataaatatca gagtgtgctg ctgtggcttt gtggagctgc cagagtaaag caaagagaaa     60

ggaagcaggc ccgttggaag tggttgtgac aaccccagca atgtggagaa gcctggggct    120

tgccctggct ctctgtctcc tcccatcggg aggaacagag agccaggacc aaagctcctt    180

atgtaagcaa cccccagcct ggagcataag agatcaagat ccaatgctaa actccaatgg    240

ttcagtgact gtggttgctc ttcttcaagc cagctgatac ctgtgcatac tgcaggcatc    300

taaattagaa gacctgcgag taaaactgaa gaaagaagga tattctaata tttcttatat    360

tgttgttaat catcaaggaa tctcttctcg attaaaatac acacatctta agaataaggt    420

ttcagagcat attcctgttt atcaacaaga agaaaaccaa acagatgtct ggactctttt    480

aaatggaagc aaagatgact tcctcatata tgatagatgt ggccgtcttg tatatcatct    540

tggtttgcct tttccttcc taactttccc atatgtagaa gaagccatta agattgctta    600

ctgtgaaaag aaatgtggaa actgctctct cacgactctc aaagatgaag acttttgtaa    660

acgtgtatct ttggctactg tggataaaac agttgaaact ccatcgcctc attaccatca    720

tgagcatcat cacaatcatg gacatcagca ccttggcagc agtgagcttt cagagaatca    780

gcaaccagga gcaccaaatg ctcctactca tcctgctcct ccaggccttc atcaccacca    840

taagcacaag ggtcagcata ggcagggtca cccagagaac cgagatatgc cagcaagtga    900

agatttacaa gatttacaaa agaagctctg tcgaaagaga tgtataaatc aattactctg    960

taaattgccc acagattcag agttggctcc taggagctga tgctgccatt gtcgacatct   1020

gatatttgaa aaaacagggt ctgcaatcac ctgacagtgt aaagaaaacc tcccatcttt   1080

atgtagctga cagggacttc gggcagagga gaacataact gaatcttgtc agtgacgttt   1140

gcctccagct gcctgacaaa taagtcagca gcttataccc acagaagcca gtgccagttg   1200

acgctgaaag aatcaggcaa aaaagtgaga atgaccttca aactaaatat ttaaaatagg   1260

acatactccc caatttagtc tagacacaat ttcatttcca gcatttttat aaactaccaa   1320

attagtgaac caaaaataga aattagattt gtgcaaacat ggagaaatct actgaattgg   1380

cttccagatt ttaaatttta tgtcatagaa atattgactc aaaccatatt ttttatgatg   1440

gagcaactga aaggtgattg cagcttttgg ttaatatgtc tttttttttc tttttccagt   1500

gttctatttg ctttaatgag aatagaaacg taaactatga cctaggggtt tctgttggat   1560

aattagcagt ttagaatgga ggaagaacaa caaagacatg ctttccattt ttttctttac   1620

ttatctctca aaacaatatt actttgtctt ttcaatcttc tacttttaac taataaaata   1680

agtggatttt gtattttaag atccagaaat acttaacacg tgaatatttt gctaaaaaag   1740
```

```
catatataac tattttaaat atccatttat cttttgtata tctaagactc atcctgattt   1800

ttactatcac acatgaataa agcctttgta tctttctttc tctaatgttg tatcatactc   1860

ttctaaaact tgagtggctg tcttaaaaga tataagggga aagataatat tgtctgtctc   1920

tatattgctt agtaagtatt tccatagtca atgatggttt aataggtaaa ccaaacccta   1980

taaacctgac ctcctttatg gttaatacta ttaagcaaga atgcagtaca gaattggata   2040

cagtacggat ttgtccaaat aaattcaata aaaaccttaa agctgaaaaa aaaaaaaaaa   2100

aaaaaaaaaa aaaaaaaaaa aaaaaaaaaa aaaaaaaaaa aaaaaaaaaa aaaaaaaaaa   2160

aaaa                                                                2164
```

<210> SEQ ID NO 49
<211> LENGTH: 3212
<212> TYPE: DNA
<213> ORGANISM: Homo sapiens

<400> SEQUENCE: 49

```
gaacccggtg gctgcacaga caaaaaagcc ccgaatggct ggagggcgtt cagctgttaa     60

cagccttttg gggcagagca cggatttgac agctccacaa cgtgaggata tccactgacc    120

ccgcgagacg gaggagaacg cttccccgaa attctctgcc caccaaagcc agcgctgcaa    180

ggttgcaact ttcaaacttt gtttttccag aaagaagact gccctttcgt gtacaaggag    240

agggtgagag ggtgacctag cttgtagatc ggctgaaggc accagtggtt ccaaatgtca    300

cccagatgtg tgttttcatg acgatttgat ttctctgatt ttatttttac atttttcatt    360

ttaaaaatac aaagcaattt ttttggggca tgctgaaagg taactgaaga ccgcaaagga    420

aaaactattg tcatggctga aggagagaat gaagtgagat gggatggact ctgcagcaga    480

gattcaacta ctagggagac agcattggaa aacattaggc aaaccatttt gaggaaaacc    540

gagtatcttc gttcggtgaa agaaacacct catcgtccat cagacgggct ttcaaatacc    600

gagtcttcgg atgggttgaa taagctactt gctcatctgc ttatgctttc taagaggtgt    660

cccttcaaag atgtgagaga gaaaagtgag tttattctga agagcatcca ggaacttggc    720

attagaattc ctcgaccact aggacaggga ccaagcagat tcatcccaga aaaggagatc    780

ctccaagtgg ggagtgaaga cgcacagatg catgctttat ttgcagattc ttttgctgct    840

ttgggccgtt tggataacat tacgttagtg atggttttcc acccacaata tttagaaagt    900

ttcttaaaaa ctcagcacta tctactgcaa atggatgggc cgttacccct acattatcgt    960

cactacattg gaataatggc tgcggcaaga catcagtgct cctacttagt gaacctgcat   1020

gtaaatgatt tccttcatgt tggtggggac cccaagtggc tcaatggttt agagaatgct   1080

cctcaaaaac tacagaattt aggagaactt aacaaagtgt tagcccatag accttggctt   1140

attaccaaag aacacattga gggactttta aaagctgaag agcacagctg gtcccttgcg   1200

gaattggtac atgcagtagt tttactcaca cactatcatt ctcttgcctc attcacattc   1260

ggctgtggaa tcagtccaga aattcattgt gatggtggcc acacattcag acctccttct   1320

gttagcaact actgcatctg tgacattaca aatggcaatc acagtgtgga tgagatgccg   1380

gtcaactcag cagaaaatgt ttctgtaagt gattctttct ttgaggttga agccctcatg   1440

gaaaagatga ggcagttaca ggaatgtcga gatgaagaag aggcaagtca ggaagagatg   1500

gcttcacgtt ttgaaataga aaaaagagag agtatgtttg tcttctcttc agatgatgaa   1560

gaagttacac cagcaagagc tgtatctcgt cattttgagg atactagtta tggctataaa   1620
```

```
gatttctcta gacatgggat gcatgttcca acatttcgtg tccaggacta ttgctgggaa   1680
gatcatggtt attctttggt aaatcgcctt tatccagatg tgggacagtt gattgatgaa   1740
aaatttcaca ttgcttacaa tcttacttat aatacaatgg caatgcacaa agatgttgat   1800
acctcaatgc ttagacgggc aatttggaac tatattcact gcatgtttgg aataagatat   1860
gatgattatg actatggtga aattaaccag ctattggatc gtagctttaa agtttatatc   1920
aaaactgttg tttgcactcc tgaaaaggtt accaaaagaa tgtatgatag cttctggagg   1980
cagttcaagc actctgagaa ggttcatgtt aatctgcttc ttatagaagc taggatgcaa   2040
gcagaactcc tttatgctct gagagccatt acccgctata tgacctgatg cctttccttc   2100
attaaagatg attctggaat gatcagcaga tatagtctac aagggggaag gtactaagcc   2160
ccaggaccaa tggtagacaa aataattcag aaatccattg tgccatgatt cctttagttt   2220
ctgctatttt tctgtggaaa accactgctg gcacaagcag tgactgtttg gcagcttcaa   2280
gtttagagct gtgaagacag gctgccattc acagtatttt gctttttgac agtacaagat   2340
gctgtgtaac tgttttaata cagcaaatag taactctcca aatcctgttg cttttatgtt   2400
aaataagata acaagaattg gagcatgcaa agaatgggac ttggataatg acttaagctt   2460
tatatgtaaa gaattttaga agatcttggt gctgctattc ctgctggagg aatgaataga   2520
tggctgtttc agttaagcta ttagtaataa aagtgaacat tgctactatc tgagcctaca   2580
tacataactt gtgtgatttc aaattaaact tgcattatgt gttaattttc ttgcatctaa   2640
aaaagcatag aattcctact cacacagctc agcaacaacc attttgatgg taacagttaa   2700
tttctttcat tagtttttta aattcagggt tctggatatt aaattaaaat ggcattctta   2760
aagatttttct tcaaaaagca atcctaaatg aaagtgtgta aattataaga agctggcgat   2820
cttttgatat gctgtttcac aggatcctga cactggaggg cagctgtctt gtgcattact   2880
tgtgtttcca gcaccaaagt tgtgggacat gttgctgtag actgctgcgc agtcctgggt   2940
gcattcagtc tctctgcctc tgcctgcctc ctggtcccca ctttaaaggc tgtgcagctc   3000
cttaaataat aaagctggaa aatattttta gtcgggttat caaatttgat ttacaaaaac   3060
gctaactttg tttgaaatgc aaacaggttt gaaaatatgt attaagtact ttgtattctg   3120
gaagcgtgaa ttgcttttga agtctgtcag tattactggt atttttaaat aaagaagaat   3180
ttttctccaa ttttaaaaaa aaaaaaaaaa aa                                 3212
```

```
<210> SEQ ID NO 50
<211> LENGTH: 4086
<212> TYPE: DNA
<213> ORGANISM: Homo sapiens

<400> SEQUENCE: 50

gtcgagcggg agcagaggag gcgagggagg agggccagag aggcagttgg aagatggcgg     60
acgaggcggc cctcgccctt cagcccggcg gctccccctc ggcggcgggg gccgacaggg    120
aggccgcgtc gtcccccgcc ggggagccgc tccgcaagag gccgcggaga gatggtcccg    180
gcctcgagcg gagcccgggc gagcccggtg gggcggcccc agagcgtgag gtgccggcgg    240
cggccagggg ctgcccgggt gcggcggcgg cggcgctgtg gcgggaggcg gaggcagagg    300
cggcggcggc aggcggggag caagaggccc aggcgactgc ggcggctggg gaaggagaca    360
atgggccggg cctgcagggc ccatctcggg agccaccgct ggccgacaac ttgtacgacg    420
aagacgacga cgacgagggc gaggaggagg aagaggcggc ggcggcggcg attgggtacc    480
gagataacct tctgttcggt gatgaaatta tcactaatgg ttttcattcc tgtgaaagtg    540
```

```
atgaggagga tagagcctca catgcaagct ctagtgactg gactccaagg ccacggatag    600
gtccatatac ttttgttcag caacatctta tgattggcac agatcctcga acaattctta    660
aagatttatt gccggaaaca atacctccac ctgagttgga tgatatgaca ctgtggcaga    720
ttgttattaa tatcctttca gaaccaccaa aaaggaaaaa aagaaaagat attaatacaa    780
ttgaagatgc tgtgaaatta ctgcaagagt gcaaaaaaat tatagttcta actggagctg    840
gggtgtctgt ttcatgtgga atacctgact tcaggtcaag ggatggtatt tatgctcgcc    900
ttgctgtaga cttcccagat cttccagatc ctcaagcgat gtttgatatt gaatatttca    960
gaaaagatcc aagaccattc ttcaagtttg caaaggaaat atatcctgga caattccagc   1020
catctctctg tcacaaattc atagccttgt cagataagga aggaaaacta cttcgcaact   1080
atacccagaa catagacacg ctggaacagg ttgcgggaat ccaaaggata attcagtgtc   1140
atggttcctt tgcaacagca tcttgcctga tttgtaaata caaagttgac tgtgaagctg   1200
tacgaggaga tatttttaat caggtagttc ctcgatgtcc taggtgccca gctgatgaac   1260
cgcttgctat catgaaacca gagattgtgt tttttggtga aaatttacca gaacagtttc   1320
atagagccat gaagtatgac aaagatgaag ttgacctcct cattgttatt gggtcttccc   1380
tcaaagtaag accagtagca ctaattccaa gttccatacc ccatgaagtg cctcagatat   1440
taattaatag agaacctttg cctcatctgc attttgatgt agagcttctt ggagactgtg   1500
atgtcataat taatgaattg tgtcataggt taggtggtga atatgccaaa ctttgctgta   1560
accctgtaaa gctttcagaa attactgaaa aacctccacg aacacaaaaa gaattggctt   1620
atttgtcaga gttgccaccc acacctcttc atgtttcaga agactcaagt tcaccagaaa   1680
gaacttcacc accagattct tcagtgattg tcacactttt agaccaagca gctaagagta   1740
atgatgattt agatgtgtct gaatcaaaag gttgtatgga agaaaaacca caggaagtac   1800
aaacttctag gaatgttgaa agtattgctg aacagatgga aaatccggat ttgaagaatg   1860
ttggttctag tactggggag aaaaatgaaa gaacttcagt ggctggaaca gtgagaaaat   1920
gctggcctaa tagagtggca aaggagcaga ttagtaggcg gcttgatggt aatcagtatc   1980
tgtttttgcc accaaatcgt tacattttcc atggcgctga ggtatattca gactctgaag   2040
atgacgtctt atcctctagt tcttgtggca gtaacagtga tagtgggaca tgccagagtc   2100
caagtttaga agaacccatg gaggatgaaa gtgaaattga agaattctac aatggcttag   2160
aagatgagcc tgatgttcca gagagagctg gaggagctgg atttgggact gatggagatg   2220
atcaagaggc aattaatgaa gctatatctg tgaaacagga agtaacagac atgaactatc   2280
catcaaacaa atcatagtgt aataattgtg caggtacagg aattgttcca ccagcattag   2340
gaactttagc atgtcaaaat gaatgtttac ttgtgaactc gatagagcaa ggaaaccaga   2400
aaggtgtaat atttataggt tggtaaaata gattgttttt catggataat ttttaacttc   2460
attatttctg tacttgtaca aactcaacac taactttttt tttttaaaa aaaaaaaggt   2520
actaagtatc ttcaatcagc tgttgggtca agactaactt tcttttaaag gttcatttgt   2580
atgataaatt catatgtgta tatataattt tttttgtttt gtctagtgag tttcaacatt   2640
tttaaagttt tcaaaaagcc atcggaatgt taaattaatg taaagggaca gctaatctag   2700
accaaagaat ggtattttca cttttctttg taacattgaa tggtttgaag tactcaaaat   2760
ctgttacgct aaacttttga ttctttaaca caattatttt taaacactgg cattttccaa   2820
aactgtggca gctaactttt taaaatctca aatgacatgc agtgtgagta gaaggaagtc   2880
```

```
aacaatatgt ggggagagca ctcggttgtc tttactttta aaagtaatac ttggtgctaa   2940

gaatttcagg attattgtat ttacgttcaa atgaagatgg cttttgtact tcctgtggac   3000

atgtagtaat gtctatattg gctcataaaa ctaacctgaa aaacaaataa atgctttgga   3060

aatgtttcag ttgctttaga aacattagtg cctgcctgga tccccttagt tttgaaatat   3120

ttgccattgt tgtttaaata cctatcactg tggtagagct tgcattgatc ttttccacaa   3180

gtattaaact gccaaaatgt gaatatgcaa agcctttctg aatctataat aatggtactt   3240

ctactgggga gagtgtaata ttttggactg ctgttttcca ttaatgagga gagcaacagg   3300

cccctgatta tacagttcca aagtaataag atgttaattg taattcagcc agaaagtaca   3360

tgtctcccat tgggaggatt tggtgttaaa taccaaactg ctagccctag tattatggag   3420

atgaacatga tgatgtaact tgtaatagca gaatagttaa tgaatgaaac tagttcttat   3480

aatttatctt tatttaaaag cttagcctgc cttaaaacta gagatcaact ttctcagctg   3540

caaaagcttc tagtctttca agaagttcat actttatgaa attgcacagt aagcatttat   3600

ttttcagacc atttttgaac atcactccta aattaataaa gtattcctct gttgctttag   3660

tatttattac aataaaaagg gtttgaaata tagctgttct ttatgcataa aacacccagc   3720

taggaccatt actgccagag aaaaaaatcg tattgaatgg ccatttccct acttataaga   3780

tgtctcaatc tgaatttatt tggctacact aaagaatgca gtatatttag ttttccattt   3840

gcatgatgtt tgtgtgctat agatgatatt ttaaattgaa aagtttgttt taaattattt   3900

ttacagtgaa gactgttttc agctcttttt atattgtaca tagtctttta tgtaatttac   3960

tggcatatgt tttgtagact gtttaatgac tggatatctt ccttcaactt ttgaaataca   4020

aaaccagtgt tttttacttg tacactgttt taaagtctat taaaattgtc atttgacttt   4080

tttctg                                                              4086
```

<210> SEQ ID NO 51
<211> LENGTH: 11579
<212> TYPE: DNA
<213> ORGANISM: Homo sapiens

<400> SEQUENCE: 51

```
cggaccgtgc tttcgccgcc tgggagccgt ccggcgcagc agtttctagg tccccactgt     60

ccccgccgtc ccgccccttc gcgtcccggg aaccggctgg cttccgagcc gcactcgccg    120

atcctccagg catgccccgc tacgagctgg ctttaatcct gaaagccatg cagcggggtt    180

ggtacagtag gcttcactag acttagctgc aactcagaat ttctcctcca gcacctgagt    240

aaatgctgat ggtcttgtgg agagtggatt aagagtacga gctaagttct caatcccaat    300

taagaagcgg aaaatttaaa ctgtcttctt caaagtttat cacaaccacc accatcaaga    360

cagcaaacca aaggacaaag actttgaccc tgctgtgttg ctctgtgtag tccagttcac    420

gtatggttta cagacttggc tggggttact aaaaataaat aaaaagttgg acacttctgt    480

cattggagcg ctattattca caagttacca gaatgagagc tgtactggac acagcagaca    540

ttgccatagt ggccctgtat tttatcctgg tcatgtgcat tggtttttt gccatgtgga     600

aatctaatag aagcaccgtg agtggatact tcctggcggg gcgctctatg acctgggtaa    660

caattggtgc ctctctgttt gtgagcaata ttgggagtga gcacttcatt gggctggcag    720

gatctggagc tgcaagtgga tttgcagtgg gcgcatggga attcaatgcc ttactgcttt    780

tacaacttct gggatgggtt ttcatcccaa tttacatccg gtcaggggta tataccatgc    840

ctgaatactt gtccaagcga tttggtggcc ataggattca ggtctatttt gcagccttgt    900
```

```
ctctgattct ctatattttc accaagctct cggtggatct gtattcgggt gcccttttta    960
tccaggagtc tttgggttgg aatctttatg tgtctgtcat cctgctcatt ggcatgactg   1020
ctttgctgac tgtcaccgga ggccttgttg cagtgatcta cacagacact ctgcaggctc   1080
tgctcatgat cattggggca cttacactta tgattattag cataatggag attggcgggt   1140
ttgaggaagt taagagaagg tacatgttgg cctcacccga tgtcacttcc atcttattga   1200
catacaacct ttccaacaca aattcttgta atgtctcccc taagaaagaa gccctgaaaa   1260
tgctgcggaa tccaacagat gaagatgttc cttggcctgg attcattctt gggcagaccc   1320
cagcttcagt atggtactgg tgtgctgacc aagtcatcgt gcagagggtc cttgcagcca   1380
aaaacattgc tcatgccaaa ggctctactc ttatggctgg cttcttaaag ctcctgccaa   1440
tgtttatcat agttgtccca ggaatgattt ccaggatact gtttactgat gatatagctt   1500
gcatcaaccc agagcactgc atgctggtgt gtggaagcag agctggttgc tccaatattg   1560
cttacccacg cctggtgatg aagctggttc ctgtgggcct tcggggttta atgatggcag   1620
tgatgattgc agctctgatg agtgacttag actctatctt taacagtgcc agtaccatat   1680
tcaccctcga tgtgtacaaa cttatccgca agagcgcaag ctcccgggag ttaatgattg   1740
tggggaggat atttgtggca tttatggtgg tgatcagcat agcatgggtg ccaatcatcg   1800
tggagatgca aggaggccag atgtaccttt acattcagga ggtagcagat tacctgacac   1860
cccagtggc agccttgttc ctgctggcaa ttttctggaa gcgctgcaat gaacaagggg   1920
ctttctatgg tggaatggct ggctttgttc ttggagcagt ccgtttgata ctggcctttg   1980
cctaccgtgc cccagaatgt gaccaacctg ataataggcc gggcttcatc aaagacatcc   2040
attatatgta tgtggccaca ggattgtttt gggtcacggg actcattact gtaattgtga   2100
gccttctcac accacctccc acaaaggaac agattcgaac caccaccttt tggtctaaga   2160
agaacctggt ggtgaaggag aactgctccc caaaagagga accataccaa atgcaagaaa   2220
agagcattct gagatgcagt gagaataatg agaccatcaa ccacatcatt cccaacggga   2280
aatctgaaga cagcattaag ggccttcagc ctgaagatgt taatctgttg gtaacctgca   2340
gagaggaggg caacccagtg gcatccttag gtcattcaga ggcagaaaca ccagttgacg   2400
cttactccaa tgggcaagca gctctcatgg gtgagaaaga gagaaagaaa gaaacggatg   2460
atggaggtcg gtactggaag ttcatagact ggttttgtgg ctttaaaagt aagagcctca   2520
gcaagaggag tctcagagac ctgatggaag aggaggctgt ttgtttacag atgctagaag   2580
agactcggca agttaaagta atactaaata ttggactttt tgctgtgtgt tcacttggaa   2640
ttttcatgtt tgtttatttc tccttatgaa cttaaggata tggtgagaca ctaacttaag   2700
acaatactga ctggtctttg gggaaaaaag ttatgtaact gtgcatctct caggcattgt   2760
ttacgctgta ggttttagcc aaattttact tagcagaaaa tcatctaatt acaagacttt   2820
attttcccag agatggatta aagtaaatct tcaacttaag tgaagccaaa cctaacagac   2880
tgaattgtgc aaatgtggtt ttaaattttg cataccaaag taagaagaga ccaattattc   2940
tcacagagca cttagagcag aatatatgtt aagttaccat gaattaaggt atactgtctg   3000
cactgccaag tcttggcaga ccttaccctg aagtagaaga tttgctcatt tctaaagttt   3060
tttttctgtc tctgtaatcc ctcctaccat taagaaaaac ttatttctta gacattgtac   3120
aatcagttat gtactgaaaa tcgaatgtgc ttgtgtgata cttgtttcag gacaagttca   3180
tttgccaggt tcattttgtt agcatgagcc tacggattct gatttcccaa agaaagaatg   3240
```

```
ttttcctgta ggtatttttg taccaccagt atatggaatg ttagggaaaa actttgttcc   3300
agttcctttt tttttttctt tctactttca agtttaagtg aaccatactg aaatgaccaa   3360
caagtctgcc tgtaaagtta catgtcatga ttgtgttgtt aaatgattat gggggagaaa   3420
atgaagtaaa tgttgctgat gatccccata tttattgatc atattaaggt tgtttatata   3480
gtttggaaat gaccagcccc ctaagcagtg tttgattaac ttatgctaat cagatgatta   3540
ctcatatatt ctgctaattt tctagcttta ttcttgttat ttggaaaaat tattagccaa   3600
atgccttcct aggtggatcc agttggaaga tatgtccaga aacctgaaga aaaattgacg   3660
ctgcctttgt gtgctggatt gctctacttg attagatcat gatatatcaa ggttgaattt   3720
ttagagggaa aatttaattc tgatatctta ttgcatcctt gataagtttt tccctgattt   3780
ttttttcct caaaagactt tccatctgta cacagcctct acatttttgt tgtagtgact   3840
tagagcataa ggatgtttca gtgcaaactg gccgtcggta acagaaaact cagtgcatac   3900
tttgctgttg ttaggttgtc aatatagtct ttctgtagga tggatagcat gtttgagagg   3960
tgccaaacaa gaacttttgg ggttagtagt gtgtcttgtg gagggtatta caggactgtg   4020
taattatagg actctaactt gacatggctt ggcacccact tgcagctagt gggtacaggg   4080
tacaaaagat gttagagaaa agctctacag attacgtact tctgtgtctt cgtatgctca   4140
acactgtcct ttgtcctcca tgaaagatga aggaagcaaa ttatgtatgt actttctttg   4200
accttcttta atctctgata ctttttagat tgcatgattt tactaggctt gtatttaggg   4260
aaattacttt cataaatact tttgtagatt ttgaatcaaa actcagtctt tttaattttt   4320
ttgtagtcta taaactagtt tcattatgat ggacttgatt agtccaaagt taattttaga   4380
aattgtcagg tagcatagtg tcttcccatg atcaggaggc tttctgaagg actgagtctg   4440
taaatgaaaa aataatttat gtatgaatag catgtatttc tgaagagctt agagtgcctt   4500
gtagaatttt tttctcaatt ttattcttga ggtttataat ttgggggcca aatagataga   4560
gctcatcatt ttcttgtttg gaagttgagg ctgcgacatg tccaaggtta tgaagtctct   4620
tttgggaaga acagaaacca ggtctccaaa tctggactca tggtttgttc agatgtgtct   4680
ggacaaatgg ttgtcaatgt tttgtcctgt tttttcaaag gaactgttct tcctttggga   4740
caacctttttg gtgtttggga aagtaataag atcttggatt tttcaaatta acattaagtt   4800
gtaagaacta aaattttctt tgaaccacat tactgtgtaa ttcactgata attgacatat   4860
tggctgggca gcctatctct tccatatcca gcgtaaatga ataggaggtg tttgtgattt   4920
tttttttctc cctttattta acattgagtc ctagtagttt ggagaattag ggtccctcta   4980
ccttctttct gctcttgtct tagtaagata cataaggtac atcatcttgt gtctgtgtgt   5040
atatagcagt aggtcaagtt tagagtacta aagtctgtaa ataaggaatg actattagca   5100
tattcattag aattgtttat tcttgccagt ataaacatca ttttatttag actaaagtcc   5160
ctgaagcttg tctttcttat tgcttcccag taatagataa tgtgctcgag taagtttgtg   5220
aattgctgat tgcaacttaa ttcagggacc agtcttcaat ctatatttca ttagaatgat   5280
tgttcctgga atgatcatac atggactgtc ttaagctagc aaaatgttca tactttacac   5340
tgactaaatg ggtcctaaat gatgacattg gtctttagac attaacatgt gtatattttt   5400
atattagctc aagctaaggt tcagaattga agcttgatat tgactagaat agctaaaagt   5460
caaaatgagg tgaggacact ggtcttggaa ggtagagaaa aataaatgtc ttaccaggtg   5520
ttaatggtat ccccagttct tagacttttg tcttctcagg caattttcat ctcaagatct   5580
gatgagaagg gcatattaca ttggtatgca ggatgattat tgcatatttt gtgggacctc   5640
```

```
taatttccct ggtcatcttt cagaatattc tgttctgcca cccccagaga gtaaacactt   5700
gagccgattt cttcttcccc agctattctt tcctgggggt aattatgctt tgtctttaga   5760
ttagagaagc atcaagcaat agcaatggtg ctgtgtcctt cggcctaaat tcaatagatc   5820
tcatctccta gggcttcctt ttcacttggc tcaaaggatc cattgtattt tggcacaaag   5880
agcctggcca gggtcatgta gccatagctc ttagggatga tacctcaaga aattagctgg   5940
gacccatcac tctgtgaaac ttcacatttt aagaactgag ttgagggggt tgttatgcac   6000
ttctgtaact tgaggctaag caaggggtta actcttgtga gagccaatag agtgtgtctg   6060
tattcgcagt ccatggctca ttttctttat agtaggcata tggatcttcc cctctgactt   6120
tgaatatcat ttggtgtggc ctgtgggtta ttttcattct ttaccaccaa ataaagcggc   6180
ttattagcta ctcagttact tgctactcaa aggttaggtc ttccctgttc ctgcttggca   6240
gtgttaaagc ttacagggtt aacttatgat gattctcctg gctcattttc atcagaggca   6300
tgatgactgg aaagggatca catgggtcgt tggtggtgac acctcactgt ttcctaggtt   6360
tggatagaga gatgtataca agacctttcc tgttaaatta cgtgactaca gagacttgcc   6420
aggacaaaat tttcctaaga aatcagaaaa atgattaagt gagataagta cctgggtgac   6480
acagatatta gcccgttggt aaaagacaac aaatattagc ttaaaatctg catatgtaga   6540
atcattttca ttagatttag agcttgaagc accttggctc tcagctactt taaactcctc   6600
cccatataaa tcagggcacc aataaataag tttcagcttt ttaaaccctg gtttgatgtt   6660
aagcattata aagtacgaag tttgttacca cagtagagat aatttagtag aaaaatgctt   6720
tgaggcttca gtatttgtaa gattttgcat tagccagatg ctaggttgtt gaaggcattt   6780
cagtgttgat aatagcctga gcagacttct ttacaaatgg gatctgtttc tatatgtgta   6840
tatgcccact taccattcag agagactggt ctttctcttt gtcttccttc acattgctgt   6900
gtcagttcta cacctagtct tttcagcact tagcaaattc aaattttgat ttttttgtca   6960
gcttagttca ctttaaggca tattggcatg gtgtgtgaaa gtgatgtttt gccccagtat   7020
tgaggacttt tagatccaaa taatgactca ttaaatataa ttatgtttta agtatactga   7080
atttctgtta gcttaaaatg ttaattctca ggaatgattt tctcacactt tgtgttggct   7140
aataataaaa gcactgtttt attctcaaaa ctccttttttc aaaaattagg gagagagcag  7200
tagtgatcat ttatgtgagc ccctttgaaa tgatggtgtc agagtgcaga gaaacaatgg   7260
agttttgatg ccaaaaaggt ttttttgcag taaaagtaaa aatttggaat tagttggcat   7320
atagaggaac ccttttgtac tggaacgtat gaggctggat tgtgaaaagg taatctttcg   7380
attgctagac ttggttaact tagggctgca aatctttttc ttctgtcaag gtcacttaat   7440
atggaatgtt tttgtcagac tgtcctttgt tggaatactt tagctgttca gctactttga   7500
ctcctaggag agaatttagt taaggttcaa agtaattaac tggctttgcc agtggtgagt   7560
cccacaccat tattcactta gtagtcatat aaatgttttt atttaaactt ctctctcttc   7620
aatgctgaga ataaggcttt aaattactga ttcaccttta aaggaatgtt gtgagaattg   7680
atgtaatttc tgtttctgtt tccatctaaa cttctttata aaaagaggga ttagtttttt   7740
tgttttgggg taagcaccta atttatccag taaccaacaa ccctaaccat tggcatatat   7800
agtctttcac tcagaaataa acaaaaactg tttggtatat ctgtatcatt gctaatcttg   7860
tgcactttac tttttgggca gtaccataca tagtctgagg ctattgactt aaaccaataa   7920
ctgtacttta tgtaatgact cttaaatttg gttacctggg ttcacagctt gcttgaagag   7980
```

```
aaaggatgct agaataaagt aagcagctga agagcgagca aatcaagaca aaacacagtg   8040
gtctcagatt tttcgtagtg tgggaacagt ggttttgctc tataccactg aaaagcacta   8100
taacataatt gttgtccatg atactgaagc ttttcccctc acttctaggt tgtttacatt   8160
cagagctcta tcaataagag gaatacatat tacagtgaat tcgacaaccg cacaagttgg   8220
cagtaggtat ccccaaccta atttatcttg gtaaattcac cctgtttcct agtgctgctg   8280
gataaaagag tgtttacttt ttattgctct tagacagagt agtctagata agttttcaat   8340
ttatcaacat agcctagact tctgtaagtg gaatgttcat tagtaactca tctttttgtt   8400
gttataattg gaaacagaaa cgaggcttat tgctattgca gaaatcccaa actggcaaag   8460
gccagtatat atggtattcc ataatataac cagcttttga aatttatgtg tttggattag   8520
tgccttctgg ttaccagtat tgactctgct agtttgcacc tttccgttct taacagaaaa   8580
tttgtatttg ttattcctct taaattttgt cgtaactagt gaaggaagta aaaaaaaaaa   8640
aaaaacatgc attacattga catactttat gtgcagcctt tatttaggtt cagtgaaacc   8700
aggtagttct gtatttgtgt tgtagcctaa atgttgtttc ttttatatcc attaaaaact   8760
taaagttact tatgttctgt gatcttaatt ttgttgtgtt tccattgtag gttgataggt   8820
atatcgagaa caggtacgtg acaacagttt atattccatg atagaaagct aaagtccata   8880
gaaagcacaa aatcgtgttc acacattagt gtacccacac atagaaagca caagactaat   8940
agtattctct gtatcccaca agtgccagtc ataaaggcca ccaggtattt gtctcagagt   9000
tgctatgagc actacagtat tgataagccc aagacaatgc ggtatctaaa ctggtcctaa   9060
tggtaaggga cccaaaggaa taatctcaat aagtttgtac cacattgatg gagggagaga   9120
atataaatgt caagaatgcc aaaattatat ttgggggtta ctagctaaaa tggggtttga   9180
gggcttttta ctgcaacttg aaactggaga aatagggaca gatgtctagg tttttggtgg   9240
gtggaacagg tgacatattt ctgttttaag ctgtagtgtg attggggttt tttgtaaaaa   9300
atcttaaatc ttttaggaaa tattacctct taacagtgcc cccccaaaca tgcagaaagt   9360
catactttaa cagggcaaat actacttgtc tttgattttt tttgtgtacg tttgtatgtg   9420
agagatgaag ttacctttat ttttttccta tacttgactg tgcttcattt taataaagga   9480
taatttgatc tgagtgttct gagcatcaga ctaattctga agcatatttg ctagaggagc   9540
tactttgctt ttcacaatgg ggtggagagg attctttcac ttgtcccatt aaccctcttc   9600
tagtctagat gagatgaaat ctgttaatgt gtgtgtagaa gaaaacgtat gttcttctac   9660
tcagcattgc ccttttccac ctcctcactt cacctccgag tagcttgttt atcaagaatg   9720
aatgaatgtc tttgtcttaa attttgccca tgtgttaaaa gatgtaattc tcagaatggg   9780
agagaaatga ctacctttgt tcctactctt ttatataatt atccttttag ggaaagactt   9840
ggtcaactct aatatatcta gaaggaagac tatatctggt gtagactaat atgagatgtt   9900
ttagaagagt taacctgaac actttgaggg agagattatt cttgccagca aaaagctagc   9960
caggaatgag cctaccacat tatttgagaa tatcaaacct caggcctggg gggatgaggg  10020
gaagaagatt accagaagtg caggaaagag aagtttgagg aacacccttg gcttagcaac  10080
atgtgataat gcaaagctgt tataacctgt taatcctacg tactatgtgt tctgtacctt  10140
tacatgtttt taaatttaag atagtttgta agaactgtac aaaaaaatgc ttctggagat  10200
ttctttggca gaaatgcctt tcatctataa tttcatggag aactgcttta attagcctag  10260
gtgaaaagta gtcctagcag tgtaaatatg tataattaga gttttctaat ttcactgtga  10320
gatctctaac ttttgagtgg caaacagatc aagtcttttg ctcatagact tttctgtggg  10380
```

```
gttattaaaa tgcaaaagct ttattttttt taataatgcc atactccatt agtgtcagat  10440
gatggtatgg aatttgttcc cttgctttcc cccactgtta ctgcttcagt ttatagattg  10500
ccagcagagt tcagaaatag agcagggatt tacccgttct ttgcttggac atcccatttt  10560
cttttgtcca gacccatgtt ggcaatcatg tatgaactgt gttatacttc tcagtgcttt  10620
ctttttctt tttgataaga tggatatcaa aaatagttgc tgtgcaaaag ttagtagtct  10680
tcttcaagaa gaaaaccaat tctttttcta ataatatcct gtgaaattgc ttcattcatt  10740
catttatttt taagccaaat gtcagcagag tgctgctgct tttatctagt aattttgata  10800
tgtaagtatt aatgcatttt taaaagatgt ctacattgaa acatgttctt cccagtgtcc  10860
tgcttatgat gctttgttca gattttttgt aagagaccag ttagtacact gggggtgtat  10920
attgtgtaca tgtgtcattt tagttaggca ttgtaggcca aatgtgatta taaatgaagt  10980
tgatgaacat taattttgtt attagtgagt tttttgaatt gtaaatggat ttccagttta  11040
ccttctgttg tctacagctt ttttaatttt aaggtttgac taattgtatc catctcattg  11100
tacagtgttt tagttgcaag cagaaagtag aatttggtat aaagcaggtt atttctatat  11160
tgaaaggagt acagttgaaa ttgtagattt aagattgtta aaatcatgac aattctaact  11220
tgtctattct aacctattgt gtacaatctg attttttaaa attgtaaaca tgtatgatct  11280
tggtttcatg tgtttttgaa agtgttattg tttaaaaaat gaaaaaagca tatctgctaa  11340
agagctgtca gttttcatta ctgactctgt aaaatacact gttctttgtg tactgtgtgt  11400
tattttgcca gctgctgcat tagccttcaa aagtatttgg aaacttaaga tgaactacat  11460
ttcttgcaaa gtacattcct ttctgtggta ttttgtcctg taactgaagt atagtaatta  11520
ttttatggaa atgttagcaa ttctgtacca actttgaata aaatgaaaaa tttataaaa   11579
```

<210> SEQ ID NO 52
<211> LENGTH: 8789
<212> TYPE: DNA
<213> ORGANISM: Homo sapiens

<400> SEQUENCE: 52

```
atgctcagtg gcttctcgac aagttggcag caacaacacg gccctggtcg tcgtcgccgc     60
tgcggtaacg gagcggtttg ggtggcggag cctgcgttcg cgccttcccg ctctcctcgg    120
gaggcccttc ctgctctccc ctaggctccg cggccgccca gggggtggga gcgggtgagg    180
ggagccaggc gcccagcgag agaggccccc cgccgcaggg cggcccggga gctcgaggcg    240
gtccggcccg cgcgggcagc ggcgcggcgc tgaggagggg cggcctggcc gggacgcctc    300
ggggcggggg ccgaggagct ctccgggccg ccggggaaag ctacgggccc ggtgcgtccg    360
cggaccagca gcgcgggaga gcggactccc ctcgccaccg cccgagccca ggttatcctg    420
aatacatgtc taacaatttt ccttgcaacg ttagctgttg tttttcactg tttccaaagg    480
atcaaaattg cttcagaaat tggagacata tttgatttaa aaggaaaaac ttgaacaaat    540
ggacaatatg tctattacga atacaccaac aagtaatgat gcctgtctga gcattgtgca    600
tagtttgatg tgccatagac aaggtggaga gagtgaaaca tttgcaaaaa gagcaattga    660
aagtttggta aagaagctga aggagaaaaa agatgaattg gattctttaa taacagctat    720
aactacaaat ggagctcatc ctagtaaatg tgttaccata cagagaacat tggatgggag    780
gcttcaggtg gctggtcgga aaggatttcc tcatgtgatc tatgcccgtc tctggaggtg    840
gcctgatctt cacaaaaatg aactaaaaca tgttaaatat tgtcagtatg cgtttgactt    900
```

```
aaaatgtgat agtgtctgtg tgaatccata tcactacgaa cgagttgtat cacctggaat    960
tgatctctca ggattaacac tgcagagtaa tgctccatca agtatgatgg tgaaggatga   1020
atatgtgcat gactttgagg gacagccatc gttgtccact gaaggacatt caattcaaac   1080
catccagcat ccaccaagta atcgtgcatc gacagagaca tacagcaccc cagctctgtt   1140
agccccatct gagtctaatg ctaccagcac tgccaacttt cccaacattc ctgtggcttc   1200
cacaagtcag cctgccagta tactgggggg cagccatagt gaaggactgt tgcagatagc   1260
atcagggcct cagccaggac agcagcagaa tggatttact ggtcagccag ctacttacca   1320
tcataacagc actaccacct ggactggaag taggactgca ccatacacac ctaatttgcc   1380
tcaccaccaa aacggccatc ttcagcacca cccgcctatg ccgccccatc ccggacatta   1440
ctggcctgtt cacaatgagc ttgcattcca gcctcccatt tccaatcatc ctgctcctga   1500
gtattggtgt tccattgctt actttgaaat ggatgttcag gtaggagaga catttaaggt   1560
tccttcaagc tgccctattg ttactgttga tggatacgtg gacccttctg gaggagatcg   1620
cttttgtttg ggtcaactct ccaatgtcca caggacagaa gccattgaga gagcaaggtt   1680
gcacataggc aaaggtgtgc agttggaatg taaaggtgaa ggtgatgttt gggtcaggtg   1740
ccttagtgac cacgcggtct ttgtacagag ttactactta gacagagaag ctgggcgtgc   1800
acctggagat gctgttcata agatctaccc aagtgcatat ataaaggtct ttgatttgcg   1860
tcagtgtcat cgacagatgc agcagcaggc ggctactgca caagctgcag cagctgccca   1920
ggcagcagcc gtggcaggaa acatccctgg cccaggatca gtaggtggaa tagctccagc   1980
tatcagtctg tcagctgctg ctggaattgg tgttgatgac cttcgtcgct tatgcatact   2040
caggatgagt tttgtgaaag gctggggacc ggattaccca agacagagca tcaaagaaac   2100
accttgctgg attgaaattc acttacaccg ggccctccag ctcctagacg aagtacttca   2160
taccatgccg attgcagacc cacaaccttt agactgaggt cttttaccgt tggggccctt   2220
aaccttatca ggatggtgga ctacaaaata caatcctgtt tataatctga agatatattt   2280
cacttttgtt ctgctttatc ttttcataaa gggttgaaaa tgtgtttgct gccttgctcc   2340
tagcagacag aaactggatt aaaacaattt tttttttcct cttcagaact tgtcaggcat   2400
ggctcagagc ttgaagatta ggagaaacac attcttatta attcttcacc tgttatgtat   2460
gaaggaatca ttccagtgct agaaaattta gccctttaaa acgtcttaga gccttttatc   2520
tgcagaacat cgatatgtat atcattctac agaataatcc agtattgctg attttaaagg   2580
cagagaagtt ctcaaagtta attcacctat gttattttgt gtacaagttg ttattgttga   2640
acatacttca aaaataatgt gccatgtggg tgagttaatt ttaccaagag taactttact   2700
ctgtgtttaa aaagtaagtt aataatgtat tgtaatcttt catccaaaat attttttgca   2760
agttatatta gtgaagatgg tttcaattca gattgtcttg caacttcagt tttatttttg   2820
ccaaggcaaa aaactcttaa tctgtgtgta tattgagaat cccttaaaat taccagacaa   2880
aaaaatttaa aattacgttt gttattccta gtggatgact gttgatgaag tatacttttc   2940
ccctgttaaa cagtagttgt attcttctgt atttctaggc acaaggttgg ttgctaagaa   3000
gcctataaga ggaatttctt ttccttcatt catagggaaa ggttttgtat tttttaaaac   3060
actaaaagca gcgtcactct acctaatgtc tcactgttct gcaaaggtgg caatgcttaa   3120
actaaataat gaataaactg aatattttgg aaactgctaa attctatgtt aaatactgtg   3180
cagaataatg gaaacattac agttcataat aggtagtttg gatatttttg tacttgattt   3240
gatgtgactt tttttggtat aatgtttaaa tcatgtatgt tatgatattg tttaaaattc   3300
```

```
agtttttgta tcttggggca agactgcaaa ctttttttata tcttttggtt attctaagcc   3360
ctttgccatc aatgatcata tcaattggca gtgactttgt atagagaatt taagtagaaa   3420
agttgcagat gtattgactg taccacagac acaatatgta tgctttttac ctagctggta   3480
gcataaataa aactgaatct caacatacaa agttgaattc taggtttgat ttttaagatt   3540
ttttttttct tttgcacttt tgagtccaat ctcagtgatg aggtaccttc tactaaatga   3600
caggcaacag ccagttctat tgggcagctt tgtttttttc cctcacactc taccgggact   3660
tccccatgga cattgtgtat catgtgtaga gttggttttt ttttttttta atttttattt   3720
tactatagca gaaatagacc tgattatcta caagatgata aatagattgt ctacaggata   3780
aatagtatga aataaaatca aggattatct ttcagatgtg tttacttttg cctggagaac   3840
ttttagctat agaaacactt gtgtgatgat agtcctcctt atatcacctg gaatgaacac   3900
agcttctact gccttgctca gaaggtcttt taaatagacc atcctagaaa ccactgagtt   3960
tgcttatttc tgtgatttaa acatagatct tgatccaagc tacatgactt ttgtctttaa   4020
ataacttatc taccacctca tttgtactct tgattactta caaattcttt cagtaaacac   4080
ctaattttct tctgtaaaag tttggtgatt taagttttat tggcagtttt ataaaaagac   4140
atcttctcta gaaattgcta actttaggtc catttttactg tgaatgagga ataggagtga   4200
gttttagaat aacagatttt taaaaatcca gatgatttga ttaaaacctt aatcatacat   4260
tgacataatt cattgcttct tttttttgag atatggagtc ttgctgtgtt gcccaggcag   4320
gagtgcagtg gtatgatctc agctcactgc aacctctgcc tcccgggttc aactgattct   4380
cctgcctcag cctccctggt agctaggatt acaggtgccc gccaccatgc ctggctaact   4440
tttgtagttt tagtagagac ggggttttgc ctgttggcca ggctggtctt gaactcctga   4500
cctcaagtga tccatccacc ttggcctccc aaagtgctgg gattacgggc gtgagccact   4560
gtccctggcc tcattgttcc cttttctact ttaaggaaag ttttcatgtt taatcatctg   4620
gggaaagtat gtgaaaaata tttgttaaga agtatctctt tggagccaag ccacctgtct   4680
tggtttcttt ctactaagag ccataaagta tagaaatact tctagttgtt aagtgcttat   4740
atttgtacct agatttagtc acacgctttt gagaaaacat ctagtatgtt atgatcagct   4800
attcctgaga gcttggttgt taatctatat ttctatttct tagtggtagt catctttgat   4860
gaataagact aaagattctc acaggtttaa aattttatgt ctactttaag ggtaaaatta   4920
tgaggttatg gttctgggtg ggttttctct agctaattca tatctcaaag agtctcaaaa   4980
tgttgaattt cagtgcaagc tgaatgagag atgagccatg tacacccacc gtaagacctc   5040
attccatgtt tgtccagtgc ctttcagtgc attatcaaag ggaatccttc atggtgttgc   5100
ctttatttttc cggggagtag atcgtgggat atagtctatc tcatttttaa tagtttaccg   5160
cccctggtat acaaagataa tgacaataaa tcactgccat ataaccttgc tttttccaga   5220
aacatggctg ttttgtattg ctgtaaccac taaataggtt gcctatacca ttcctcctgt   5280
gaacagtgca gatttacagg ttgcatggtc tggcttaagg agagccatac ttgagacatg   5340
tgagtaaact gaactcatat tagctgtgct gcatttcaga cttaaaatcc atttttgtgg   5400
ggcagggtgt ggtgtgtaaa ggggggtgtt tgtaatacaa gttgaaggca aaataaaatg   5460
tcctgtctcc cagatgatat acatcttatt atttttaaag tttattgcta attgtaggaa   5520
ggtgagttgc aggtatcttt gactatggtc atctggggaa ggaaaatttt acattttact   5580
attaatgctc cttaagtgtc tatggaggtt aaagaataaa atggtaaatg tttctgtgcc   5640
```

```
tggtttgatg gtaactggtt aatagttact caccatttta tgcagagtca cattagttca   5700
cacccttttct gagagccttt tgggagaagc agttttattc tctgagtgga acagagttct   5760
ttttgttgat aatttctagt ttgctccctt cgttattgcc aactttactg gcattttatt   5820
taatgatagc agattgggaa aatggcaaat ttaggttacg gaggtaaatg agtatatgaa   5880
agcaattacc tctaaagcca gttaacaatt attttgtagg tggggtacac tcagcttaaa   5940
gtaatgcatt ttttttccc gtaaaggcag aatccatctt gttgcagata gctatctaaa   6000
taatctcata tcctcttttg caaagactac agagaatagg ctatgacaat cttgttcaag   6060
cctttccatt tttttccctg ataactaagt aatttctttg aacataccaa gaagtatgta   6120
aaaagtccat ggccttattc atccacaaag tggcatccta ggcccagcct tatccctagc   6180
agttgtccca gtgctgctag gttgcttatc ttgtttatct ggaatcactg tggagtgaaa   6240
ttttccacat catccagaat tgccttattt aagaagtaaa acgttttaat ttttagcctt   6300
tttttggtgg agttatttaa tatgtatatc agaggatata ctagatggta acatttcttt   6360
ctgtgcttgg ctatctttgt ggacttcagg ggcttctaaa acagacagga ctgtgttgcc   6420
tttactaaat ggtctgagac agctatggtt ttgaattttt agtttttttt ttttaaccca   6480
cttcccctcc tggtctcttc cctctctgat aattaccatt catatgtgag tgttagtgtg   6540
cctcctttta gcattttctt cttctctttc tgattcttca tttctgactg cctaggcaag   6600
gaaaccagat aaccaaactt actagaacgt tctttaaaac acaagtacaa actctgggac   6660
aggacccaag acactttcct gtgaagtgct gaaaaagacc tcattgtatt ggcatttgat   6720
atcagtttga tgtagcttag agtgcttcct gattcttgct gagtttcagg tagttgagat   6780
agagagaagt gagtcatatt catattttcc cccttagaat aatattttga aaggtttcat   6840
tgcttccact tgaatgctgc tcttacaaaa actggggtta caagggttac taaattagca   6900
tcagtagcca gaggcaatac cgttgtctgg aggacaccag caaacaacac acaacaaagc   6960
aaaacaaacc ttgggaaact aaggccattt gttttgtttt ggtgtcccct ttgaagccct   7020
gccttctggc cttactcctg tacagatatt tttgacctat aggtgccttt atgagaattg   7080
agggtctgac atcctgcccc aaggagtagc taaagtaatt gctagtgttt tcagggattt   7140
taacatcaga ctggaatgaa tgaatgaaac tttttgtcct tttttttct gttttttttt   7200
ttctaatgta gtaaggacta aggaaaacct ttggtgaaga caatcatttc tctctgttga   7260
tgtggatact tttcacaccg tttatttaaa tgctttctca ataggtccag agccagtgtt   7320
cttgttcaac ctgaaagtaa tggctctggg ttgggccaga cagttgcact ctctagtttg   7380
ccctctgcca caaatttgat gtgtgacctt tgggcaagtc atttatcttc tctgggcctt   7440
agttgcctca tctgtaaaat gagggagttg gagtagatta attattccag ctctgaaatt   7500
ctaagtgacc ttggctacct tgcagcagtt ttggatttct tccttatctt tgttctgctg   7560
tttgaggggg ctttttactt atttccatgt tattcaaagg agactaggct tgatatttta   7620
ttactgttct tttatggaca aaaggttaca tagtatgccc ttaagactta attttaacca   7680
aaggcctagc accaccttag ggctgcaat aaacacttaa cgcgcgtgcg cacgcgcgcg   7740
cgcacacaca cacacacaca cacacacaca cacaggtcag agtttaaggc tttcgagtca   7800
tgacattcta gcttttgaat tgcgtgcaca cacacacgca cgcacacact ctggtcagag   7860
tttattaagg ctttcgagtc atgacattat agcttttgag ttggtgtgtg tgacaccacc   7920
ctcctaagtg gtgtgtgctt gtaatttttt ttttcagtga aaatggattg aaaacctgtt   7980
gttaatgctt agtgatatta tgctcaaaac aaggaaattc ccttgaaccg tgtcaattaa   8040
```

```
actggtttat atgactcaag aaaacaatac cagtagatga ttattaactt tattcttggc   8100

tctttttagg tccattttga ttaagtgact tttggctgga tcattcagag ctctcttcta   8160

gcctaccctt ggatgagtac aattaatgaa attcatattt tcaaggacct gggagccttc   8220

cttggggctg ggttgagggt ggggggttgg ggagtcctgg tagaggccag ctttgtggta   8280

gctggagagg aagggatgaa accagctgct gttgcaaagg ctgcttgtca ttgatagaag   8340

gactcacggg cttggattga ttaagactaa acatggagtt ggcaaacttt cttcaagtat   8400

tgagttctgt tcaatgcatt ggacatgtga tttaagggaa aagtgtgaat gcttatagat   8460

gatgaaaacc tggtgggctg cagagcccag tttagaagaa gtgagttggg ggttggggac   8520

agatttggtg gtggtatttc ccaactgttt cctcccctaa attcagagga atgcagctat   8580

gccagaagcc agagaagagc cactcgtagc ttctgctttg gggacaactg gtcagttgaa   8640

agtcccagga gttcctttgt ggctttctgt atacttttgc ctggttaaag tctgtggcta   8700

aaaaatagtc gaacctttct tgagaactct gtaacaaagt atgtttttga ttaaaagaga   8760

aagccaacta aaaaaaaaaa aaaaaaaaa                                     8789
```

<210> SEQ ID NO 53
<211> LENGTH: 1593
<212> TYPE: DNA
<213> ORGANISM: Homo sapiens

<400> SEQUENCE: 53

```
gcggtgccct tgcggcgcag ctggggtcgc ggccctgctc cccgcgcttt cttaaggccc     60

gcgggcggcg caggagcggc actcgtggct gtggtggctt cggcagcggc ttcagcagat    120

cggcggcatc agcggtagca ccagcactag cagcatgttg agccgggcag tgtgcggcac    180

cagcaggcag ctggctccgg ttttggggta tctgggctcc aggcagaagc acagcctccc    240

cgacctgccc tacgactacg gcgccctgga acctcacatc aacgcgcaga tcatgcagct    300

gcaccacagc aagcaccacg cggcctacgt gaacaacctg aacgtcaccg aggagaagta    360

ccaggaggcg ttggccaagg gagatgttac agcccagata gctcttcagc ctgcactgaa    420

gttcaatggt ggtggtcata tcaatcatag cattttctgg acaaacctca gccctaacgg    480

tggtggagaa cccaaagggg agttgctgga agccatcaaa cgtgactttg gttcctttga    540

caagtttaag gagaagctga cggctgcatc tgttggtgtc caaggctcag gttggggttg    600

gcttggtttc aataaggaac ggggacactt acaaattgct gcttgtccaa atcaggatcc    660

actgcaagga acaacaggcc ttattccact gctggggatt gatgtgtggg agcacgctta    720

ctaccttcag tataaaaatg tcaggcctga ttatctaaaa gctatttgga atgtaatcaa    780

ctgggagaat gtaactgaaa gatacatggc ttgcaaaaag taaaccacga tcgttatgct    840

gagtatgtta agctctttat gactgttttt gtagtggtat agagtactgc agaatacagt    900

aagctgctct attgtagcat ttcttgatgt tgcttagtca cttatttcat aaacaactta    960

atgttctgaa taatttctta ctaaacattt tgttattggg caagtgattg aaaatagtaa   1020

atgctttgtg tgattgaatc tgattggaca ttttcttcag agagctaaat tacaattgtc   1080

atttataaaa ccatcaaaaa tattccatcc atatactttg gggacttgta gggatgcctt   1140

tctagtccta ttctattgca gttatagaaa atctagtctt ttgccccagt tacttaaaaa   1200

taaaatatta acactttccc aagggaaaca ctcggctttc tatagaaaat tgcacttttt   1260

gtcgagtaat cctctgcagt gatacttctg gtagatgtca cccagtggtt tttgttaggt   1320
```

caaatgttcc tgtatagttt ttgcaaatag agctgtatac tgtttaaatg tagcaggtga 1380
actgaactgg ggtttgctca cctgcacagt aaaggcaaac ttcaacagca aaactgcaaa 1440
aaggtggttt ttgcagtagg agaaaggagg atgtttattt gcagggcgcc aagcaaggag 1500
aattgggcag ctcatgcttg agacccaatc tccatgatga cctacaagct agagtattta 1560
aaggcagtgg taaatttcag gaaagcagaa gtt 1593

<210> SEQ ID NO 54
<211> LENGTH: 3286
<212> TYPE: DNA
<213> ORGANISM: Homo sapiens

<400> SEQUENCE: 54
gcgtgtcggg cgcggaaggg ggaggcggcc cggggcgccc gcgagtgagg cgcggggcgg 60
cgaagggagc gcgggtggcg gcacttgctg ccgcggcctt ggatgggctg ggccccccctc 120 gccgctccgc ctcctccaca cgcgcggcgg ccgcggcgag ggggacgcgc cgcccggggc 180
ccggcacctt cgggaacccc ccggcccgga gcctgcggcc tgcgccgcct cggccgccgg 240
gagccccgtg gagcccccgc cgccgcgccg ccccgcggac cggacgctga gggcactcgg 300
ggcggggcgc gcgctcgggc agacgtttgc ggggaggggg gcgcctgccg ggccccggcg 360
accaccttgg gggtcgcggg ccggctcggg gggcgcccag tgcgggccct cgcgggcgcc 420
gggcagcgac cagccctgag cggagctgtt ggccgcggcg ggaggcctcc cggacgcccc 480 cagcccccccg aacgctcgcc cgggccggcg ggagtcggcg ccccccggga ggtccgctcg 540
gtcgtccgcg gcggagcgtt tgctcctggg acaggcggtg ggaccggggc gtcgccggag 600
acgcccccag cgaagttggg ctctccaggt gtgggggtcc cgggggggtag cgacgtcgcg 660 gacccggcct gtgggatggg cggcccggag aagactgcgc tcggccgtgt tcatacttgt 720
ccgtgggcct gaggtccccg gaggatgacc tagcactgaa aagccccggc cggcctcccc 780
agggtccccg aggacgaagt tgaccctgac cgggccgtct cccagttctg aggcccgggt 840
cccactggaa ctcgcgtctg agccgccgtc ccggaccccc ggtgcccgcc ggtccgcaga 900
ccctgcaccg ggcttggact cgcagccggg actgacgtgt agaacaatcg tttctgttgg 960
aagaagggtt tttcccttcc ttttggggtt tttgttgcct ttttttttc ttttttcttt 1020 gtaaaatttt ggagaaggga agtcggaaca caaggaagga ccgctcaccc gcggactcag 1080
ggctggcggc gggactccag gaccctgggt ccagcatgga ggtggtggac ccgcagcagc 1140
tgggcatgtt cacggagggc gagctgatgt cggtgggtat ggacacgttc atccaccgca 1200
tcgactccac cgaggtcatc taccagccgc gccgcaagcg ggccaagctc atcggcaagt 1260
acctgatggg ggacctgctg ggggaaggct cttacggcaa ggtgaaggag gtgctggact 1320
cggagacgct gtgcaggagg gccgtcaaga tcctcaagaa gaagaagttg cgaaggatcc 1380
ccaacgggga ggccaacgtg aagaaggaaa ttcaactact gaggaggtta cggcacaaaa 1440
atgtcatcca gctggtggat gtgttataca acgaagagaa gcagaaaatg tatatggtga 1500
tggagtactg cgtgtgtggc atgcaggaaa tgctggacag cgtgccggag aagcgtttcc 1560
cagtgtgcca ggcccacggg tacttctgtc agctgattga cggcctggag tacctgcata 1620
gccagggcat tgtgcacaag gacatcaagc cggggaacct gctgctcacc accggtggca 1680
ccctcaaaat ctccgacctg ggcgtggccg aggcactgca cccgttcgcg gcggacgaca 1740
cctgccggac cagccagggc tccccggctt tccagccgcc cgagattgcc aacggcctgg 1800
acaccttctc cggcttcaag gtggacatct ggtcggctgg ggtcaccctc tacaacatca 1860

```
ccacgggtct gtaccccttc gaaggggaca acatctacaa gttgtttgag aacatcggga   1920

aggggagcta cgccatcccg ggcgactgtg gcccccgct ctctgacctg ctgaaaggga   1980

tgcttgagta cgaaccggcc aagaggttct ccatccggca gatccggcag cacagctggt   2040

tccggaagaa acatcctccg gctgaagcac cagtgcccat cccaccgagc ccagacacca   2100

aggaccggtg gcgcagcatg actgtggtgc cgtacttgga ggacctgcac ggcgcggacg   2160

aggacgagga cctcttcgac atcgaggatg acatcatcta cactcaggac ttcacggtgc   2220

ccggacaggt cccagaagag gaggccagtc acaatggaca gcgccggggc ctccccaagg   2280

ccgtgtgtat gaacggcaca gaggcggcgc agctgagcac caaatccagg gcggagggcc   2340

gggcccccaa ccctgcccgc aaggcctgct ccgccagcag caagatccgc cggctgtcgg   2400

cctgcaagca gcagtgaggc tggccgcctg cagcccgtgt ccaggagccc cgccaggtgc   2460

ccgcgccagg ccctcagtct tcctgccggt tccgcccgcc ctcccggaga ggtggccgcc   2520

atgcttctgt gccgaccacg ccccaggacc tccggagcgc cctgcagggc cgggcagggg   2580

gacagcaggg accgggcgca gccctccccc ctcggccgcc cggcagtgca cgcggcttgt   2640

tgacttcgca gccccgggcg gagccttccc gggcgggcgt gggaggaggg aggcggcctc   2700

catgcacttt atgtggagac tactggcccc gcccgtggcc tcgtgctccg cagggcgccc   2760

agcgccgtcc ggcggccccg ccgcagacca gctggcgggt gtggagacca ggctcctgac   2820

cccgccatgc atgcagcgcc acctggaagc cgcgcggccg ctttggtttt ttgtttggtt   2880

ggttccattt tcttttttc ttttttttt taagaaaaaa taaaaggtgg atttgagctg   2940

tggctgtgag ggtgtttgg gagctgctgg gtggcagggg ggctgtgggg tcgggctcac   3000

gtcgcggccg cctttgcgct ctcgggtcac cctgctttgg cggcccggcc ggagggcagg   3060

accctcacct ctcccccaag gccactgcgc tcttgggacc ccagagaaaa cccggagcaa   3120

gcaggagtgt gcggtcaata tttatatcat ccagaaaaga aaaacacgag aaacgccatc   3180

gcgggatggt gcagacgcgg cggggactcg gagggtgccg tgcgggcgag gccgcccaaa   3240

tttggcaata aataaagctt gggaagcttg gacctgaaaa aaaaaa                 3286
```

<210> SEQ ID NO 55
<211> LENGTH: 5174
<212> TYPE: DNA
<213> ORGANISM: Homo sapiens

<400> SEQUENCE: 55

```
ggagagctcg ccagagcgct cgcatggcgg gccggtgatt gtagtcaatc tggccgtatt     60

ctcaggcagg gtcgcccggg gcggactaca tctcccggga tgctgcgcgg ccgccccgcg    120

gaagattgtg aatatgtatc agaatgttaa tgattagctg ctgctaaatt tggtcaaaga    180

agtcacctac acagagcgtg ttgttagagc tgtgctgagc gggtgtttgg gttgttggct    240

gctttcttcc ccctttctca cacacttgta tattattttg aggtggtgtt cgcagagttt    300

gaaaggagag agaattaaaa aaaaaagccg caagcgtttc actcttttat ttttataatc    360

cccttcaatt tggggttaaa aaaaagacaa gaaaacagga aggaagagaa ataaggaaat    420

gagatgtggt aaaagaagct aaaaggtgcc ttttaaaaga tcgttgctgt gaagtgaaaa    480

aaatctccag agaaaccaaa aagcaccgcc gagacctctt ccgaaccaaa ggagtttgtg    540

tttgctttta gggaagaaga aagatcattc attcggagga ataacaacca attaaaagac    600

aaataaaaaa agtttggagt gggacgcaga gcgagcgaga ggagctgccg gcgggcggtg    660
```

```
gggcgcggag cccgcacttt cccggccggg tgagcggcgg ccgcggcgcc gggctcggcg    720
ggtgcgcctc ggcggagcga acgtcggagc gttgccttgg gagacgcgcg ccggacaatg    780
cccgcggcgg gccagtgacg cccgcgggga atgcggagcg gcccggcagc cggcacccag    840
ccgccgccgc gcgttcctgc cgcccgtgtc acgcgagacc cggcgggggc cgggaccgcc    900
cgagccgccc ctcagaccga gccggccgcc tccgctgccg cggccgcctc ctcttcgggg    960
tcattaaagc caatgagccg cgcgcctctg ccgagcgcag ccaactaaat cggcttggat   1020
gattcgcgac ctgagcaaga tgtacccgca gaccagacac ccggcaccgc atcagcctgc   1080
tcaacccttt aaatttacaa tttccgaatc ctgtgatcgg attaaggaag agtttcagtt   1140
tttacaggct caataccaca gtctgaagct ggaatgtgag aaactcgcca gtgagaagac   1200
agagatgcag cggcattatg tcatgtatta tgaaatgtcc tatgggttga atatagaaat   1260
gcacaagcag gcagagattg tcaagaggct gaatgctatc tgtgcacaag tcattccttt   1320
cctgtcccaa gagcaccagc aacaagtggt gcaggctgtg gaacgggcca agcaggtgac   1380
catggcagaa ctgaacgcca tcattgggca acaactccag gcccagcatt tatcacatgg   1440
acatggtctc cccgtacctc tgactccaca cccttcaggg ctccagcccc ctgccattcc   1500
acccatcggt agcagtgccg ggcttctggc cctctccagt gctctaggag gtcagtccca   1560
tcttccaatt aaagatgaga agaagcacca tgacaatgat caccaaagag acagagactc   1620
catcaagagc tcttcagtat ccccatcagc cagtttccga ggtgctgaga agcacagaaa   1680
ctccgcagac tactcctcag agagcaaaaa gcagaaaact gaagaaaagg aaattgcagc   1740
tcgttatgac agcgatggtg agaaaagtga tgacaacttg gtggttgacg tttccaatga   1800
ggatccatct tcccctcgag ggagcccagc acattccccc agagagaatg gcctagacaa   1860
gacacgcctg ctcaagaaag atgccccgat tagtccagcc tctattgcat cttccagcag   1920
tactccctcc tccaaatcca aagaacttag ccttaagagg gatatgggga aattgagtga   1980
aacacgtctt agcgaagatg aacaatgcac attggggtta cagagatggt tttgtcgcct   2040
gtggtttatg aatgaaaaat ctactactcc cgtctcaaag tccaataccc ctactccacg   2100
aactgatgcg cccaccccag gcagtaactc tactcccgga ttgaggcctg tacctggaaa   2160
accaccagga gttgaccctt tggcctcaag cctaaggacc ccaatggcag taccttgtcc   2220
atatccaact ccatttggga ttgtgcccca tgctggaatg aacggagagc tgaccagccc   2280
cggagcggcc tacgctgggc tccacaacat ctcccctcag atgagcgcag ctgctgccgc   2340
cgccgctgct gctgctgcct atgggagatc accagtggtg ggatttgatc cacaccatca   2400
catgcgtgtg ccagcaatac ctccaaacct gacaggcatt ccaggaggaa aaccagcata   2460
ctccttccat gttagcgcag atggtcagat gcagcctgtc ccttttccac ccgacgccct   2520
catcggacct ggaatccccc ggcatgctcg ccagatcaac accctcaacc acggggaggt   2580
ggtgtgcgcg gtgaccatca gcaaccccac gagacacgtg tacacgggtg ggaagggctg   2640
cgtcaaggtc tgggacatca gccacccagg caataagagt cctgtctccc agctcgactg   2700
tctgaacagg gataactaca tccgttcctg cagattgctc cctgatggtc gcaccctaat   2760
tgttggaggg gaagccagta ctttgtccat ttgggacctg gcggctccaa ccccacgcat   2820
caaggcagag ctgacatcct cggcccccgc ctgctatgcc ctggccatca gccccgattc   2880
caaggtctgc ttctcatgct gcagcgacgg caacatcgct gtgtgggatc tgcacaacca   2940
gaccttggtg aggcaattcc agggccacac agatggagcc agctgtattg acatttctaa   3000
tgatggcacc aagctctgga caggtggttt ggacaacacg gtcaggtcct gggacctgcg   3060
```

```
cgaggggcgg cagctgcagc agcacgactt cacctcccag atcttttctc tgggctactg   3120
cccaactgga gagtggcttg cagtggggat ggagaacagc aatgtggaag ttttgcatgt   3180
caccaagcca gacaaatacc aactacatct tcatgagagc tgtgtgctgt cgctcaagtt   3240
tgcccattgt ggcaaatggt ttgtaagcac tggaaaggac aaccttctga atgcctggag   3300
aacaccttat ggggccagta tattccagtc caaagaatcc tcatcggtgc ttagctgtga   3360
catctccgtg gacgacaaat acattgtcac tggctctggg gataagaagg ccacagttta   3420
tgaagttatt tattaaagac aaatcttcat gcagactgga cttctcctcc tggtagcact   3480
ttgctctgtc atccttttg ttcaccccca tccccgcatc taaaaccaag gatttcagat   3540
actcattgca gttgtggagt ttaatcccct ttcttaacct cacttcccac ttgctattga   3600
attgtgaata gtcattaaaa acctgtgata ccaaatcttc agctgtctac ttggaagaac   3660
atggaataag catacttaac agtgaaaaga atctttaatt atgtattata tctgtaatat   3720
atttattttg tttaaagaag gctttctaac aatgactgac taaataaagc tgtctgctcc   3780
tgcattgata atgaaggtgc gttgtatttg ataccccctcc ccccctttt ttggcaaagg   3840
aggggaaagg aaggtttaaa ataattgatt taaaatgtca ctaagtgtag actgatgact   3900
gtatagagat gtgaaatgta taattacaca tggaagcaat atgttgctgt gttgttatta   3960
ggtttttttt gtttttgttt tctacatctt ttaaagactt ttggaaattt ggctgaacaa   4020
ttagaacaca acaggccaac tcatactcat ttggatctat ttagacaacg ttaaccaata   4080
tatctatagc tttagattat attcgataaa agtaattgga cttttttttct tttttgact   4140
cgttgacaag tgtctttgta atatgttttt agttcccttt ttttgttgta ttataggcag   4200
atgaacaaat taaatttggc ctcaaagaga gaacttactc ccttctggat atttttgcca   4260
catttctttg caaaaggaga tatatatatc tttagtcagt tttgttgtta tgagaaatta   4320
tgggttattt tgtggcatgc tctttgggag ctgcacagtt atggggagga ctcccactgc   4380
tgtgcaagtt aagtctttta caaaacaagg acagcagagg agggtttgca gagacctccc   4440
tctgaaaaac acaaagaatg gactctctcc tgggatgagg acttgctttc tttacctccg   4500
gttctttcca tgtcttagtt ggatgtccct gaaatggaca caggctgtgc cattgtgcca   4560
gaaacattgt gttatctttt atgttgttgt tgttgctgtt aaactataat atgtgacttc   4620
ttttttttatt attttttgtt tgaatgcttt aaaaatcttt taagtctgtg gatctgctga   4680
tgtacagtgc ctttgctgct atggatcaaa atcaaaagaa ccgtgtagat atactttatt   4740
gtataagtag aaaattactt aatttcatac tagaaatgga tggatgctgc aagttgaaat   4800
ggactgtcca ttgacgttcc taatgtggta gcagaaaaaa aaaaatggtg tcttaagtgc   4860
ttagtgtttg atgtcattaa cagtttcgta aaactctaca gtgtagaaag attttgatac   4920
taaactgtgc gttgtacata gttctaatgc attgtattga ccaccagtac ttctataatg   4980
gtagattgtt tgtgaattca gacttttaag cattaaacat aaataacttc tagtatgctt   5040
atttttctaa ttctttgtct tgatgacatt agtttatttt ttatctttgg ctgtgccact   5100
cctatatatt aaaaatgcct agttttttca agggagattg ttgttaaagt aaagtggttt   5160
tttttgttgt taaa                                                      5174
```

<210> SEQ ID NO 56
<211> LENGTH: 1769
<212> TYPE: DNA
<213> ORGANISM: Homo sapiens

<400> SEQUENCE: 56
cctcactgac tataaaagaa tagagaagga agggcttcag tgaccggctg cctggctgac 60
ttacagcagt cagactctga caggatcatg gctatgatgg aggtccaggg gggacccagc 120
ctgggacaga cctgcgtgct gatcgtgatc ttcacagtgc tcctgcagtc tctctgtgtg 180
gctgtaactt acgtgtactt taccaacgag ctgaagcaga tgcaggacaa gtactccaaa 240
agtggcattg cttgtttctt aaaagaagat gacagttatt gggaccccaa tgacgaagag 300
agtatgaaca gcccctgctg gcaagtcaag tggcaactcc gtcagctcgt tagaaagatg 360
attttgagaa cctctgagga aaccatttct acagttcaag aaaagcaaca aaatatttct 420
cccctagtga gagaaagagg tcctcagaga gtagcagctc acataactgg gaccagagga 480
agaagcaaca cattgtcttc tccaaactcc aagaatgaaa aggctctggg ccgcaaaata 540
aactcctggg aatcatcaag gagtgggcat tcattcctga gcaacttgca cttgaggaat 600
ggtgaactgg tcatccatga aaaagggttt tactacatct attcccaaac atactttcga 660
tttcaggagg aaataaaaga aaacacaaag aacgacaaac aaatggtcca atatatttac 720
aaatacacaa gttatcctga ccctatattg ttgatgaaaa gtgctagaaa tagttgttgg 780
tctaaagatg cagaatatgg actctattcc atctatcaag gggaatattt tgagcttaag 840
gaaaatgaca gaatttttgt ttctgtaaca aatgagcact tgatagacat ggaccatgaa 900
gccagttttt tcggggcctt tttagttggc taactgacct ggaaagaaaa agcaataacc 960
tcaaagtgac tattcagttt tcaggatgat acactatgaa gatgtttcaa aaaatctgac 1020
caaaacaaac aaacagaaaa cagaaaacaa aaaaacctct atgcaatctg agtagagcag 1080
ccacaaccaa aaaattctac aacacacact gttctgaaag tgactcactt atcccaagaa 1140
aatgaaattg ctgaaagatc tttcaggact ctacctcata tcagtttgct agcagaaatc 1200
tagaagactg tcagcttcca aacattaatg caatggttaa catcttctgt ctttataatc 1260
tactccttgt aaagactgta gaagaaagcg caacaatcca tctctcaagt agtgtatcac 1320
agtagtagcc tccaggtttc cttaagggac aacatcctta agtcaaaaga gagaagaggc 1380
accactaaaa gatcgcagtt tgcctggtgc agtggctcac acctgtaatc ccaacatttt 1440
gggaacccaa ggtgggtaga tcacgagatc aagagatcaa gaccatagtg accaacatag 1500
tgaaacccca tctctactga aagtgcaaaa attagctggg tgtgttggca catgcctgta 1560
gtcccagcta cttgagaggc tgaggcagga gaatcgtttg aacccgggag gcagaggttg 1620
cagtgtggtg agatcatgcc actacactcc agcctggcga cagagcgaga cttggtttca 1680
aaaaaaaaaa aaaaaaaaaa cttcagtaag tacgtgttat ttttttcaat aaaattctat 1740
tacagtatgt caaaaaaaaa aaaaaaaaa 1769

<210> SEQ ID NO 57
<211> LENGTH: 2979
<212> TYPE: DNA
<213> ORGANISM: Homo sapiens

<400> SEQUENCE: 57
gtggctcttc tggcccgggc tactatatag agacgtttcc gcctcctgct tgaaactaac 60
ccctcttttt ctccaaagga gtgcttgtgg agatcggatc ttttctccag caattggggg 120
aaagaaggct ttttctctga attagcttag tgtaaccagc ggcgtatatt ttttaggcgc 180
cttttcgaaa acctagtagt taatattcat ttgtttaaat cttattttat ttttaagctc 240
aaactgctta agaatacctt aattccttaa agtgaaataa ttttttgcaa aggggtttcc 300

```
tcgatttgga gctttttttt tcttccaccg tcatttctaa ctcttaaaac caactcagtt    360
ccatcatggt gatgttcaag aagatcaagt cttttgaggt ggtctttaac gaccctgaaa    420
aggtgtacgg cagtggcgag aaggtggctg gccgggtgat agtggaggtg tgtgaagtta    480
ctcgtgtcaa agccgttagg atcctggctt gcggagtggc taaagtgctt tggatgcagg    540
gatcccagca gtgcaaacag acttcggagt acctgcgcta tgaagacacg cttcttctgg    600
aagaccagcc aacaggtgag aatgagatgg tgatcatgag acctggaaac aaatatgagt    660
acaagttcgg ctttgagctt cctcaggggc ctctgggaac atccttcaaa ggaaaatatg    720
ggtgtgtaga ctactgggtg aaggcttttc ttgaccgccc gagccagcca actcaagaga    780
caaagaaaaa ctttgaagta gtggatctgg tggatgtcaa tacccctgat ttaatggcac    840
ctgtgtctgc taaaaaagaa aagaaagttt cctgcatgtt cattcctgat gggcgggtgt    900
ctgtctctgc tcgaattgac agaaaaggat tctgtgaagg tgatgagatt tccatccatg    960
ctgactttga gaatacatgt tcccgaattg tggtccccaa agctgccatt gtggcccgcc   1020
acacttacct tgccaatggc cagaccaagg tgctgactca gaagttgtca tcagtcagag   1080
gcaatcatat tatctcaggg acatgcgcat catggcgtgg caagagcctt cgggttcaga   1140
agatcaggcc ttctatcctg ggctgcaaca tccttcgagt tgaatattcc ttactgatct   1200
atgttagcgt tcctggatcc aagaaggtca tccttgacct gcccctggta attggcagca   1260
gatcaggtct aagcagcaga acatccagca tggccagccg aaccagctct gagatgagtt   1320
gggtagatct gaacatccct gataccccag aagctcctcc ctgctatatg gatgtcattc   1380
ctgaagatca ccgattggag agcccaacca ctcctctgct agatgacatg gatggctctc   1440
aagacagccc tatctttatg tatgcccctg agttcaagtt catgccacca ccgacttata   1500
ctgaggtgga tccctgcatc ctcaacaaca atgtgcagtg agcatgtgga agaaaagaag   1560
cagctttacc tacttgtttc tttttgtctc tcttcctgga cactcacttt ttcagagact   1620
caacagtctc tgcaatggag tgtgggtcca ccttagcctc tgacttccta atgtaggagg   1680
tggtcagcag gcaatctcct gggccttaaa ggatgcggac tcatcctcag ccagcgccca   1740
tgttgtgata caggggtgtt tgttggatgg gtttaaaaat aactagaaaa actcaggccc   1800
atccatttc tcagatctcc ttgaaaattg aggccttttc gatagtttcg ggtcaggtaa   1860
aaatggcctc ctggcgtaag cttttcaagg tttttggag gcttttgta aattgtgata   1920
ggaactttgg accttgaact tacgtatcat gtggagaaga gccaatttaa caaactagga   1980
agatgaaaag ggaaattgtg gccaaaactt tgggaaaagg aggttcttaa aatcagtgtt   2040
tcccctttgt gcacttgtag aaaaaaaaga aaaaccttct agagctgatt tgatggacaa   2100
tggagagagc tttccctgtg attataaaaa aggaagctag ctgctctacg gtcatctttg   2160
cttagagtat actttaacct ggcttttaaa gcagtagtaa ctgccccacc aaaggtctta   2220
aaagccattt ttggagccta ttgcactgtg ttctcctact gcaaatattt tcatatggga   2280
ggatggtttt ctcttcatgt aagtccttgg aattgattct aaggtgatgt tcttagcact   2340
ttaattcctg tcaaattttt tgttctcccc ttctgccatc ttaaatgtaa gctgaaactg   2400
gtctactgtg tctctagggt taagccaaaa gacaaaaaaa attttactac ttttgagatt   2460
gccccaatgt acagaattat ataattctaa cgcttaaatc atgtgaaagg gttgctgctg   2520
tcagccttgc ccactgtgac ttcaaaccca aggaggaact cttgatcaag atgcccaacc   2580
ctgtgatcag aacctccaaa tactgccatg agaaactaga gggcaggtct tcataaaagc   2640
```

-continued

```
cctttgaacc cccttcctgc cctgtgttag gagataggga tattggcccc tcactgcagc   2700

tgccagcact tggtcagtca ctctcagcca tagcactttg ttcactgtcc tgtgtcagag   2760

cactgagctc cacccttttc tgagagttat tacagccaga aagtgtgggc tgaagatggt   2820

tggtttcatg tttttgtatt atgtatcttt ttgtatggta aagactatat tttgtactta   2880

accagatata tttttacccc agatggggat attctttgta aaaaatgaaa ataaagtttt   2940

tttaatggaa aaaaaaaaaa aaaaaaaaaa aaaaaaaaa                          2979
```